US 8,236,513 B2

(12) United States Patent
Atassi

(10) Patent No.: US 8,236,513 B2
(45) Date of Patent: Aug. 7, 2012

(54) DETERMINING AND REDUCING IMMUNORESISTANCE TO BOTULINUM TOXIN THERAPY USING BOTULINUM TOXIN A PEPTIDES

(75) Inventor: M. Zouhair Atassi, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 679 days.

(21) Appl. No.: 12/192,955

(22) Filed: Aug. 15, 2008

(65) Prior Publication Data
US 2009/0004680 A1    Jan. 1, 2009

Related U.S. Application Data

(63) Continuation of application No. 12/028,633, filed on Feb. 8, 2008, now abandoned, and a continuation-in-part of application No. 10/821,669, filed on Apr. 9, 2004, now Pat. No. 7,341,843.

(60) Provisional application No. 60/462,754, filed on Apr. 11, 2003.

(51) Int. Cl.
*G01N 33/53* (2006.01)

(52) U.S. Cl. .......... 435/7.92; 435/7.1; 435/7.9; 436/501

(58) Field of Classification Search .................. None
See application file for complete search history.

(56) References Cited

U.S. PATENT DOCUMENTS

| | | | |
|---|---|---|---|
| 4,551,435 A | 11/1985 | Liberti et al. | |
| 4,643,718 A | 2/1987 | Marten | |
| 6,048,529 A | 4/2000 | Atassi et al. | |
| 6,667,158 B1 | 12/2003 | Bavari et al. | |
| 6,676,622 B2 | 1/2004 | Strahilevitz | |
| 7,341,843 B2 * | 3/2008 | Atassi | 435/7.32 |
| 7,462,699 B2 * | 12/2008 | Atassi | 530/390.1 |
| 7,531,179 B2 * | 5/2009 | Atassi | 424/197.11 |
| 7,635,484 B2 * | 12/2009 | Atassi | 424/197.11 |
| 7,670,788 B2 * | 3/2010 | Atassi | 435/7.1 |
| 7,691,587 B2 * | 4/2010 | Atassi | 435/7.1 |
| 7,855,268 B2 * | 12/2010 | Atassi | 530/300 |
| 2002/0155114 A1 | 10/2002 | Marks et al. | |
| 2002/0197278 A1 | 12/2002 | Allison | |

(Continued)

FOREIGN PATENT DOCUMENTS

WO    94/21684    9/1994

(Continued)

OTHER PUBLICATIONS

Amersdorfer et al., "Genetic and immunological comparison of anti-botulinum type A antibodies from immune and non-immune human phage libraries," *Vaccine* 20:1640-1648 (2002).

(Continued)

*Primary Examiner* — Albert Navarro
*Assistant Examiner* — Ginny Portner
(74) *Attorney, Agent, or Firm* — Kenton Abel; Debra Condino

(57) ABSTRACT

The present invention provides BoNT/A peptide compositions, tolerogizing compositions, BoNT/A immune response inducing compositions and antibody compositions, as well as methods of determining immunoresistance to botulinum toxin therapy in an individual, methods of preventing or reducing immunoresistance to botulinum toxin therapy in an individual, methods of vaccinating an individual against botulinum toxin, methods of preparing anti-BoNT/A antibodies, methods of treating botulinum toxicity in an individual and methods of reducing anti-botulinum toxin antibodies in an individual.

12 Claims, 28 Drawing Sheets

Synthetic BoNT/A Peptides

| Peptide Number | Sequence Position | Amino acid sequence |
|---|---|---|
| L-Peptide | 218–231 | A V T L A H E L I H A G H R |
| H_N-domain Peptides | | |
| N1 | 449–467 | A L N D L C I K V N N W D L F F S P S |
| N2 | 463–481 | F F S P S E D N F T N D L N K G E E I |
| N3 | 477–495 | K G E E I T S D T N I E A A S E N I S |
| N4 | 491–509 | S E N I S L D L I Q Q Y Y L T F N F D |
| N5 | 505–523 | T F N F D N E P E N I S I E N L S S D |
| N6 | 519–537 | N L S S D I I G Q L E L M P N I E R F |
| N7 | 533–551 | N I E R F P N G K K Y E L D K Y T M F |
| N8 | 547–565 | K Y T M F H Y L R A Q E F E H G K S R |
| N9 | 561–579 | H G K S R I A L T N S V N E A L L N P |
| N10 | 575–593 | A L L N P S R V Y T F F S S D Y V K K |
| N11 | 589–607 | D Y V K K V N K A T E A A M F L G W V |
| N12 | 603–621 | F L G W V E Q L V Y D F T D E T S E V |
| N13 | 617–635 | E T S E V S T T D K I A D I T I I I P |
| N14 | 631–649 | T I I I P Y I G P A L N I G N M L Y K |
| N15 | 645–663 | N M L Y K D D F V G A L I F S G A V I |
| N16 | 659–677 | S G A V I L L E F I P E I A I P V L G |
| N17 | 673–691 | I P V L G T F A L V S Y I A N K V L T |
| N18 | 687–705 | N K V L T V Q T I D N A L S K R N E K |
| N19 | 701–719 | K R N E K W D E V Y K Y I V T N N L A |
| N20 | 715–733 | T N N L A K V N T Q I D L I R K K M K |
| N21 | 729–747 | R K K M K E A L E N Q A E A T K A I I |
| N22 | 743–761 | T K A I I N Y Q Y N Q Y T E E E K N N |
| N23 | 757–775 | E E K N N I N F N I D D L S S K L N E |
| N24 | 771–789 | S K L N E S I N K A M I N I N K F L N |
| N25 | 785–803 | N K F L N Q C S V S Y L M N S M I P Y |
| N26 | 799–817 | S M I P Y G V K R L E D F D A S L K D |
| N27 | 813–831 | A S L K D A L L K Y I Y D N R G T L I |
| N28 | 827–845 | R G T L I G Q V D R L K D K V N N T L |
| N29 | 841–859 | V N N T L S T D I P F Q L S K Y V D N |

U.S. PATENT DOCUMENTS

| | | | |
|---|---|---|---|
| 2004/0101534 A1 | 5/2004 | Diamond | |
| 2004/0110284 A1* | 6/2004 | Bavari et al. | 435/326 |
| 2004/0175385 A1 | 9/2004 | Marks et al. | |
| 2004/0265935 A1 | 12/2004 | Atassi | |
| 2005/0106182 A1 | 5/2005 | Li et al. | |

FOREIGN PATENT DOCUMENTS

| | | |
|---|---|---|
| WO | 2005/014798 | 2/2005 |
| WO | 2005/030119 | 4/2005 |

OTHER PUBLICATIONS

Amersdorfer et al., "Molecular characterization of murine humoral immune response to botulinum neurotoxin type A binding domain as assessed by using phage antibody libraries," *Infect. Immun.* 65:3743-3752 (1997).

Aoki, "Pharmacology and immunology of botulinum toxin serotypes," *J. Neurol.* 248 Suppl. 1:3-10 (2001).

Atassi and Dolimbek, "Mapping of the antibody-binding regions on the HN-domain (residues 449-859) of botulinum neurotoxin A with antitoxin antibodies from four host species. Full profile of the continuous antigenic regions of the H-chain of botulinum neurotoxin A," *Protein J.* 23:39-52 (2004).

Atassi and Oshima, "Structure, activity, and immune (T and B cell) recognition of botulinum neurotoxins," *Crit. Revs. Immunol.* 19:219-260 (1999).

Atassi and Smith, "A proposal for the nomenclature of antigenic sites in peptides and proteins," *Immunochemistry* 15:609-610 (1978).

Kozaki et al., "Development of antitoxin with each of two complementary fragments of *Clostridium botulinum* type B derivative toxin," *Infection and Immunity* 18:761-766 (1977).

Kozaki et al., "Immunological characterization of Papain-induced fragments of *Clostridium botulinum* type A neurotoxin and interaction of the fragments with brain synaptosomes," *Infection and Immunity* 57:2634-2639 (1989).

Kozaki et al., "The use of monoclonal antibodies to analyze the structure of *Clostridium botulinum* type E derivative toxin," *Infection and Immunity* 52:786-791 (1986).

Krieglstein, Kerstin G. et al, Journal of protein Chemistry, vol. 13(1), pp. 49-57, 1994.

Kubota et al., "Epitope regions in the heavy chain of *Clostridium botulinum* type E neurotoxin recognized by monoclonal antibodies," *Applied & Environmental Microbiol.* 63:1214-1218 (1997).

Lacy et al., "Crystal structure of botulinum neurotoxin type A and implications for toxicity," *Nat. Struct. Biol.* 5:898-902 (1998).

Lacy, D. B. et al, "Sequence homology and structural analysis of the Clostridial neurotoxins", Journal of Molecular Biology, vol. 291, 1999, pp. 1091-1104.

LaPenotiere et al., "Expression of a large, nontoxic fragment of botulinum neurotoxin serotype A and its use as an immunogen," *Toxicon* 33:1383-1386 (1995).

Lebeda, Frank J. et al, "Predicting Differential antigen-antibody contact regions based on solvent accessibility", Journal of Protein Chemistry, vol. 16(6), 1997, pp. 607-618.

Atassi et al., "Cross-reaction of mouse antibodies against Tetanus neurotoxin with Botulinum neurotoxins A and B," *International Conference 2002, Basic and Therapeutic Aspects of Botulinum and Tetanus Toxins*,Hannover,Germany,Jun. 8-12,Abstract R12 (2002).

Atassi et al., "Localization and synthesis of the hormone-binding regions of the human thyrotropin receptor," *Proc. Natl. Acad. Sci. USA* 88:3613-3617 (1991).

Atassi et al., "Mapping of the antibody-binding regions on botulinum neurotoxin H-chain domain 855-1296 with anti-toxin antibodies from three host species," *J. Prot. Chem.* 15:691-700 (1996).

Atassi, "Immune recognition and cross-reactivity of botulinum neurotoxins," in *Scientific and Therapeutic Aspects of Botulinum Toxins* (edited by Brin et al.), pp. 385-408, Lippincott Williams and Wilkins, Philadelphia, PA (2002).

Bavari et al., "Identifying the principal protective antigenic determinants of type A botulinum neurotoxin," *Vaccine* 16:1850-1856 (1998).

Beecher, DJ et al, J. Protein Chemistry, vol. 16(7), pp. 701-712, 1997.

Byrne, MP et al, vol. 82, 2000, "Development of vaccines for prevention of botulism", pp. 955-966.

Cenci Di Bello et al., "Antagonism of the intracellular action of botulinum neurotoxin type A with monoclonal antibodies that map to light-chain epitopes," *Eur. J. Biochem.* 219:161-169 (1994).

Chen et al., "Antibody mapping to domains of botulinum neurotoxin serotype A in the complexed and uncomplexed forms," *Infect. Immun.* 65:1626-1630 (1997).

Clayton and Middlebrook, "Vaccination of mice with DNA encoding a large fragment of botulinum neurotoxin serotype A," *Vaccine* 18:1855-1862 (2000).

Clayton et al., "Protective vaccination with a recombinant fragment of *Clostridium botulinum* neurotoxin serotype A expressed from a synthetic gene in *Escherichia coli*," *Infect. Immun.* 63:2738-2742 (1995).

Dertzbaugh and West, "Mapping of protective and cross-reactive domains of the type A neurotoxin of *Clostridium botulinum*," *Vaccine* 14:1538-1544 (1996).

Dineen et al, Swiss Prot sequence Q8KHn9, Oct. 1, 2002.

Dolimbek and Atassi, "Protection against alpha-bungarotoxin poisoning by immunization with synthetic toxin peptides," *Mol. Immunol.* 33:681-689 (1996).

Dolimbek et al., "Cross reaction of tetanus and botulinum neurotoxins A and B and the boosting effect of botulinum neurotoxins A and B on a primary anti-tetanus antibody response," *Immunological Investigations* 31:247-262 (2002).

Dolimbek, BZ et al, Molecular Immunology, vol. 44, pp. 1029-1041, 2007.

Dressler et al., "Antibody-induced botulinum toxin therapy failure: Can it be overcome by increased botulinum toxin doses?" *Eur. Neurol.* 47:118-121 (2002).

Gibson et al, Swiss Prot Accession No. Q97TT9, Oct. 1, 2001.

Goschel et al., "Botulinum A toxin therapy: Neutralizing and non-neutralizing antibodies—therapeutic consequences," *Exp. Neurol.* 147:96-102 (1997).

Hambleton et al., "A possible common antigen on clostridial toxins detected by monoclonal anti-botulinum neurotoxin antibodies," 449-450 (1984).

Hanna, Philip A. MD, Neurology, vol. 50(6), pp. 1624-1629, Jun. 1998.

Jankovic, Botulinum Toxin: Clinical Implication sof Antigenicity and Immunoresistancey, in Brin et al. eds., *Scientific and Therapeutic Aspects of Botulinum Toxin*, pp. 409-415, Lippincott Williams & Wilkins, Philadelphia, PA (2002).

Jankovic, Joseph MD et al, Neurology, vol. 45(9), pp. 1743-1746, Sep. 1995.

Kikuyama eta al, Swiss Prot sequence Q9PRU1, May 1, 2000.

Klein, "Complications and adverse reactions with the use of botulinum toxin," *Dis. Mon.* 48:336-356 (2002).

Middlebrook, "Protection strategies against botulinum toxin," in Atassi and Bixler (Eds.), *Immunology of Poreteins and Peptides VIII* p. 93-98 Plunum Press New York (1995).

Mullaney et al., "Epitope mapping of neutralizing botulinum neurotoxin A antibodies by phage display," *Infect. Immun.* 69:6511-6514 (2001).

Naumann et al., "Depletion of neutralizing antibodies resensitises a secondary non-responder to botulinum A neurotoxin," *J. Neurol. Neurosurg. Psychiatry* 65:924-927 (1998).

Naumann et al (1998), Immunol. Letters.

Oblatt-Montal, M. et al, "Formation of ion channels in lipid bilayers by a peptide with the predicted transmembrane sequence of botulinum neurotoxin A", Protein Science, vol. 4, 1995, pp. 1490-1497.

Oshima et al., "Antibodies and T cells against synthetic peptides of the C-terminal domain ($H_C$) of botulinum neurotoxin type A and their cross-reaction with $H_C$," *Immunol. Letters* 60:7-12 (1998), pp. 1031-1040.

Oshima et al, "Immune recognition of botulinum neurotoxin type A: Regions recognized by T cells and antibodies against the protective $H_C$ fragment (residues 855-1296) of the toxin," *Mol. Immunol.* 34:1031-1040 (1997).

Pittman et al., "Antibody response to a delayed booster dose of anthrax vaccine and botulinum toxoid," *Vaccine* 20:2107-2115 (2002).

Pless et al., "High-affinity, protective antibodies to the binding domain of botulinum neurotoxin type A," *Infect. Immun.* 69:570-574 (2001).

Raju, R. et al, "Epitope repertoire of Human CD4+ lines propagated with Tetanus toxoid or with synthetic tetanus toxin sequences", Journal of autoimmunity, vol. 9, 1996, pp. 79-88.

Rosenberg et al., "Localization of the regions on the C-terminal domain of the heavy chain of botulinum A recognized by T lymphocytes and by antibodies after immunization of mice with pentavalent toxoid," *Immunol. Invest.* 26:491-504 (1997).

Shyu et al., "DNA vaccination using the fragment C of botulinum neurotoxin type A provided protective immunity in mice," *J. Biomed. Sci.* 7:51-57 (2000).

Simeckova-Rosenberg et al., "Protection of mice against lethal viral infection by synthetic peptides corresponding to B- and T-cell recognition sites of influenza A hemagglutinin," *Vaccine* 13:927-932 (1995).

Simpson, "The study of clostridial and related toxins. The search for unique mechanisms and common denominators," *J. Physiol. Paris* 84:143-151 (1990).

Singh et al, "Immunochemical characterization of Type A botulinum neurotoxin in its purifed and complexed forms.", Toxicon, 1996, vol. 36, No. 2, pp. 267-275.

Spanoyannis et al., "Clostridium botulinum type B neurotoxin demonstrates cross-reactivity with antibodies from patients with cervical dystonia who no longer respond to type A neurotoxin treatment," *Developmental Medicine and Child Neurology* 40:33 Scientific poster SP:8 (1998).

Tsuzuki et al., "Establishment of a monoclonal antibody recognizing an antigenic site common to *Clostridium botulinum* type B, $C_1$, D, and E toxins and tetanus toxin," *Infection and Immunity* 56:898-902 (1988).

Tugnoli, V et al, Expert. Opinion Investig. Drugs, Oct. 1997, vol. 6(10), pp. 1383-1394.

Wu et al., "Characterization of neutralizing antibodies and identification of neutralizing epitope mimics on the Clostridium botulinum neurotoxin type A," *Appl. Environ. Microbiol.* 67:3201-3207 (2001).

Office Action Date Mailed Dec. 28, 2007, U.S. Appl. No. 11/693,104, Conf. No. 8724.

Office Action Date Mailed Dec. 18, 2007, U.S. Appl. No. 11/693,111, Conf. No. 8736.

Office Action Date Mailed Jan. 23, 2008, U.S. Appl. No. 11/576,219, Conf. No. 7939.

Office Action Date Mailed Dec. 12, 2007, U.S. Appl. No. 11/693,095, Conf. No. 8710.

\* cited by examiner

Synthetic BoNT/A Peptides

| Peptide Number | Sequence Position | Amino acid sequence |
|---|---|---|
| L-Peptide | 218–231 | A V T L A H E L I H A G H R |

H$_N$-domain Peptides

| Peptide Number | Sequence Position | Amino acid sequence |
|---|---|---|
| N1 | 449–467 | A L N D L C I K V N N W D L F F S P S |
| N2 | 463–481 | F F S P S E D N F T N D L N K G E E I |
| N3 | 477–495 | K G E E I T S D T N I E A A E E N I S |
| N4 | 491–509 | E E N I S L D L I Q Q Y Y L T F N F D |
| N5 | 505–523 | T F N F D N E P E N I S I E N L S S D |
| N6 | 519–537 | N L S S D I I G Q L E L M P N I E R F |
| N7 | 533–551 | N I E R F P N G K K Y E L D K Y T M F |
| N8 | 547–565 | K Y T M F H Y L R A Q E F E H G K S R |
| N9 | 561–579 | H G K S R I A L T N S V N E A L L N P |
| N10 | 575–593 | A L L N P S R V Y T F F S S D Y V K K |
| N11 | 589–607 | D Y V K K V N K A T E A A M F L G W V |
| N12 | 603–621 | F L G W V E Q L V Y D F T D E T S E V |
| N13 | 617–635 | E T S E V S T T D K I A D I T I I I P |
| N14 | 631–649 | T I I I P Y I G P A L N I G N M L Y K |
| N15 | 645–663 | N M L Y K D D F V G A L I F S G A V I |
| N16 | 659–677 | S G A V I L L E F I P E I A I P V L G |
| N17 | 673–691 | I P V L G T F A L V S Y I A N K V L T |
| N18 | 687–705 | N K V L T V Q T I D N A L S K R N E K |
| N19 | 701–719 | K R N E K W D E V Y K Y I V T N W L A |
| N20 | 715–733 | T N W L A K V N T Q I D L I R K K M K |
| N21 | 729–747 | R K K M K E A L E N Q A E A T K A I I |
| N22 | 743–761 | T K A I I N Y Q Y N Q Y T E E E K N N |
| N23 | 757–775 | E E K N N I N F N I D D L S S K L N E |
| N24 | 771–789 | S K L N E S I N K A M I N I N K F L N |
| N25 | 785–803 | N K F L N Q C S V S Y L M N S M I P Y |
| N26 | 799–817 | S M I P Y G V K R L E D F D A S L K D |
| N27 | 813–831 | A S L K D A L L K Y I Y D N R G T L I |
| N28 | 827–845 | R G T L I G Q V D R L K D K V N N T L |
| N29 | 841–859 | V N N T L S T D I P F Q L S K Y V D N |

FIGURE 1A

H_C-domain peptides

| | | |
|---|---|---|
| C1 | 855-873 | K Y V D N Q R L L S T F T E Y I K N I |
| C2 | 869-887 | Y I K N I I N T S I L N L R Y E S N H |
| C3 | 883-901 | Y E S N H L I D L S R Y A S K I N I G |
| C4 | 897-915 | K I N I G S K V N F D P I D K N Q I Q |
| C5 | 911-929 | K N Q I Q L F N L E S S K I E V I L K |
| C6 | 925-943 | E V I L K N A I V Y N S M Y E N F S T |
| C7 | 939-957 | E N F S T S F W I R I P K Y F N S I S |
| C8 | 953-971 | F N S I S L N N E Y T I I N C M E N N |
| C9 | 967-985 | C M E N N S G W K V S L N Y G E I I W |
| C10 | 981-999 | G E I I W T L Q D T Q E I K Q R V V F |
| C11 | 995-1013 | Q R V V F K Y S Q M I N I S D Y I N R |
| C12 | 1009-1027 | D Y I N R W I F V T I T N N R L N N S |
| C13 | 1023-1041 | R L N N S K I Y I N G R L I D Q K P I |
| C14 | 1037-1055 | D Q K P I S N L G N I H A S N N I M F |
| C15 | 1051-1069 | N N I M F K L D G C R D T H R Y I W I |
| C16 | 1065-1083 | R Y I W I K Y F N L F D K E L N E K E |
| C17 | 1079-1097 | L N E K E I K D L Y D N Q S N S G I L |
| C18 | 1093-1111 | N S G I L K D F W G D Y L Q Y D K P Y |
| C19 | 1107-1125 | Y D K P Y Y M L N L Y D P N K Y V D V |
| C20 | 1121-1139 | K Y V D V N N V G I R G Y M Y L K G P |
| C21 | 1135-1153 | Y L K G P R G S V M T T N I Y L N S S |
| C22 | 1149-1167 | Y L N S S L Y R G T K F I I K K Y A S |
| C23 | 1163-1181 | K K Y A S G N K D N I V R N N D R V Y |
| C24 | 1177-1195 | N D R V Y I N V V V K N K E Y R L A T |
| C25 | 1191-1209 | Y R L A T N A S Q A G V E K I L S A L |
| C26 | 1205-1223 | I L S A L E I P D V G N L S Q V V V M |
| C27 | 1219-1237 | Q V V V M K S K N D Q G I T N K C K M |
| C28 | 1233-1251 | N K C K M N L Q D N N G N D I G F I G |
| C29 | 1247-1265 | I G F I G F H Q F N N I A K L V A S N |
| C30 | 1261-1279 | L V A S N W Y N R Q I E R S S R T L G |
| C31 | 1275-1296 | S R T L G C S W E F I P V D D G W G E R P L |

FIGURE 1B

H<sub>N</sub> domain of BoNT/A (Clostridium botulinum) (Residues 449-859 of SEQ ID NO:1)

ALNDLCIKVNNWDLFFSPSEDNFTNDLNKGEEITS
DTNIEAAEENISLDLIQQYYLTFNFDNEPENISIE
NLSSDIIGQLELMPNIERFNIERFPNGKKYELDKY
TMFHYLRAQEFEHGKSRIALTNSVNEALLNPSRVY
TFFSSDYVKKVNKATEAAMFLGWVEQLVYDFTDET
SEVSTTDKIADITIIIPYIGPALNIGNMLYKDDFV
GALIFSGAVILLEFIPEIAIPVLGTFALVSYIANK
VLTVQTIDNALSKRNEKWDEVYKYIVTNWLAKVNT
QIDLIRKKMKEALENQAEATKAIINYQYNQYTEEE
KNNINFNIDDLSSKLNESINKAMININKFLNQCSV
SYLMNSMIPYGVKRLEDFDASLKDALLKYIYDNRGT
LIGQVDRLKDKVNNTLSTDIPFQLSKYVDN

H<sub>C</sub> domain of BoNT/A (Clostridium botulinum) (Residues 855-1296 of SEQ ID NO:1)

KYVDNQRLLSTFTEYIKNIINTSILNLRYESNH
LIDLSRYASKINIGSKVNFDPIDKNQIQLFNLE
SSKIEVILKNAIVYNSMYENFSTSFWIRIPKYF
NSISLNNEYTIINCMENNSGWKVSLNYGEIIWT
LQDTQEIKQRVVFKYSQMINISDYINRWIFVTI
TNNRLNNSKIYINGRLIDQKPISNLGNIHASNN
IMFKLDGCRDTHRYIWIKYFNLFDKELNEKEIK
DLYDNQSNSGILKDFWGDYLQYDKPYYMLNLYD
PNKYVDVNNVGIRGYMYLKGPRGSVMTTNIYLN
SSLYRGTKFIIKKYASGNKDNIVRNNDRVYINV
VVKNKEYRLATNASQAGVEKILSALEIPDVGNL
SQVVVMKSKNDQGITNKCKMNLQDNNGNDIGFI
GFHQFNNIAKLVASNWYNRQIERSSRTLGCSWE
FIPVDDGWGERPL

L-Peptide (amino acids 218-231 of SEQ ID NO:1)

AVTLAHELIHAGHR

Amino acids 731 to 787 of BoNT/E (SEQ ID NO:4)

KNELTNKYDIKQIENELNQKVSIAMNNIDRFLTESSISYLMKLINEVKINKLREYDE

DETERMINING AND REDUCING IMMUNORESISTANCE TO BOTULINUM TOXIN THERAPY USING BOTULINUM TOXIN A PEPTIDES

This application is a continuation and claims priority pursuant to 35 U.S.C. §120 to U.S. patent application Ser. No. 12/028,633, filed Feb. 8, 2008 now abandoned, a continuation in part and claims priority pursuant to 35 U.S.C. §120 to U.S. patent application Ser. No. 10/821,669, filed Apr. 9, 2004, now U.S. Pat. No. 7,341,843 which claims priority benefit to U.S. Provisional Application Ser. No. 60/462,754, filed on Apr. 11, 2003 and claims priority pursuant to 35 U.S.C. §120 to U.S. patent application Ser. No. 11/576,219, filed on Mar. 28, 2007, a U.S. National Filing Application that claims priority pursuant to 35 U.S.C. §371 to International Patent Application PCT/US2005/036229, filed on Oct. 5, 2005, which claims priority benefit to U.S. Provisional Application Ser. No. 60/616,682, filed on Oct. 6, 2004 and, each of which is hereby incorporated by reference in its entirety.

All patents, patent publications and articles cited in this application are hereby incorporated by reference in their entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Linurase® (Prollenium, Inc., Ontario, Canada), Neuronox® (Medy-Tox, Inc., Ochangmyeon, South Korea) BTX-A (Lanzhou Institute Biological Products, China) and Xeomin® (Merz Pharmaceuticals, GmbH, Frankfurt, Germany); and BoNT/B preparations, such as, e.g., MyoBloc™/NeuroBloc™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

In addition, Clostridial toxin therapies are proposed for treating neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May 7, 2004); and Kei Roger Aoki, et al., Method for Treating Dystonia with Botulinum Toxin C to G, U.S. Pat. No. 6,319,505 (Nov. 20, 2001); eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004); pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, Botulinum Toxin Therapy for Fibromyalgia, U.S. Patent Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004); muscle injuries, see e.g., Gregory F. Brooks, Methods for Treating Muscle Injuries, U.S. Pat. No. 6,423,319 (Jul. 23, 2002); headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998); cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004); neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001); neuropsychiatric disorders, see e.g., Stephen Donovan, Botulinum Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003); endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000); cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005); optic disorders, see e.g., Stephen Donovan, Neurotoxin Therapy for Inner Ear Disorders, U.S. Pat. No. 6,358,926 (Mar. 19, 2002); and Stephen Donovan, Method for Treating Optic Disorders, U.S. Pat. No. 6,265,379 (Jul. 24, 2001); autonomic disorders, see, e.g., Pankai J. Pasricha and Anthony N. Kalloo, Method for Treating Gastrointestinal Muscle Disorders and Other Smooth Muscle Dysfunction, U.S. Pat. No. 5,437,291 (Aug. 1, 1995); as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R.

First, Application of Botulinum Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of Botulinum Toxin for Treatment of Downturned Mouth, U.S. Pat. No. 6,358,917 (Mar. 19, 2002); Stephen Donovan, Use of a Clostridial Toxin to Reduce Appetite, U.S. Patent Publication No. 2004/40253274 (Dec. 16, 2004); and Howard I. Katz and Andrew M. Blumenfeld, Botulinum Toxin Dental Therapies and Procedures, U.S. Patent Publication No. 2004/0115139 (Jun. 17, 2004); Kei Roger Aoki, et al., Treatment of Neuromuscular Disorders and Conditions with Different Botulinum, U.S. Patent Publication No. 2002/0010138 (Jan. 24, 2002); and Kei Roger Aoki, et al., Use of Botulinum Toxins for Treating Various Disorders and Conditions and Associated Pain, U.S. Patent Publication No. 2004/0013692 (Jan. 22, 2004). In addition, the expected use of Clostridial toxins, such as, e.g., BoNTs and TeNT, in therapeutic and cosmetic treatments of humans and other mammals is anticipated to expand to an ever widening range of diseases and ailments that can benefit from the properties of these toxins.

While a potent and effective treatment, the inhibition of neurotransmitter release and the resulting neuromuscular paralysis elicited by Clostridial toxin therapies is not permanent. The reversible nature of these paralytic effects requires periodic treatments in order to maintain the therapeutic benefits from this toxin. As a consequence of this repeated exposure, an immune response against a Clostridial toxin can occur in some patients which reduce or completely prevent the individual's responsiveness to further treatments, see, e.g., Joseph Jankovic, *Botulinum toxin: Clinical Implications of Antigenicity and Immunoresistance*, (SCIENTIFIC AND THERAPEUTIC ASPECTS OF BOTULINUM TOXIN, 409-415, Mitchell F. Brin et al., eds., Lippincott Williams & Wilkins, 2002); Dirk Dressler, *Clinical Presentation and Management of Antibody-induced Failure of Botulinum Toxin Therapy*, 19(Suppl. 8) MOV. DISORD. S92-S100 (2004); M. Zouhair Atassi, *Basic Immunological Aspects of Botulinum Toxin Therapy*, 19(Suppl. 8) MOV. DISORD. S68-S84, (2004).

Thus, there exists a need for methods of determining immunoresistance in an individual to Clostridial toxin therapy, methods of preventing or reducing immunoresistance in an individual to Clostridial toxin therapy as well as compositions to carry out these methods. The present invention satisfies this need with respect to BoNT/A therapies and provides additional related advantages as well.

BRIEF DESCRIPTION OF THE DRAWINGS

FIG. 1A shows synthetic consecutive overlapping peptides of the $H_N$ domain of BoNT/A having the indicated residues of SEQ ID NO: 1. Regions of overlap with adjacent peptides are underlined and bolded. FIG. 1B shows synthetic consecutive overlapping peptides of the $H_C$ domain of BoNT/A having the indicated residues of SEQ ID NO: 1. Regions of overlap with adjacent peptides are underlined and bolded. The L-peptide control sequence is shown as SEQ ID NO: 1.

FIG. 6 shows amino acid sequences of the $H_N$ domain of BoNT/A (SEQ ID NO: 1); the $H_C$ domain of BoNT/A (SEQ ID NO: 1); the L peptide (SEQ ID NO: 1); and amino acids 731 to 78 of BoNT/E (SEQ ID NO: 1).

FIG. 7 shows proliferative responses of LNC ($8 \times 10^5$ cells/well) from BALB/c mice primed with 1 :g of BoNT/A toxoid to BoNT/A, BoNT/B and TeNT.

FIG. 9 shows proliferative responses of BoNT/A, BoNT/B and TeNT of LNC ($7 \times 10^5$ cells/well) from SJL mice primed with 1 :g BoNT/A toxoid.

Figure 15:
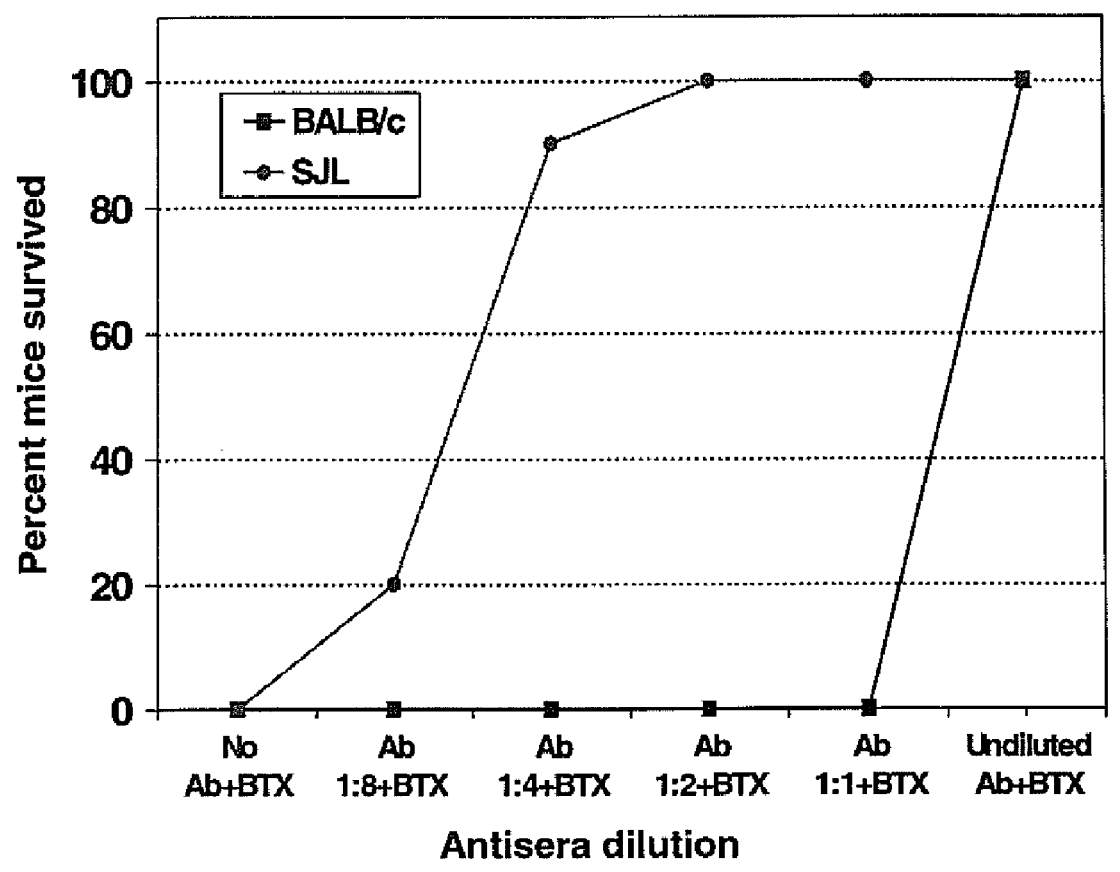

FIG. 15 shows protective activity of BALB/c and SJL anti-BoNT/A antisera obtained on day 36 after a first immunization. Antisera of each strain were tested at the indicated dilutions for their ability to protect recipient ICR mice against $1.05 \times LD_{100}$ of active BoNT/A. The results are expressed in percent survival to BoNT/A challenge versus antiserum dilution.

FIG. 21 shows binding to BoNT/A of antibodies in sera from CD patients (n=28) that are MPA-positive for anti-BoNT/A antibodies and in normal controls (n=10). Results are average of three experiments expressed in ratios of antibodies bound to BoNT/A over antibodies bound to negative controls.

FIG. 22 shows binding to BoNT/B of antibodies in MPA anti-BoNT/A positive sera from CD patients (n=28) and in normal controls (n=10). Results are in ratios of antibodies bound to BoNT/B over antibodies bound to negative controls.

DETAILED DESCRIPTION

Figure 2:
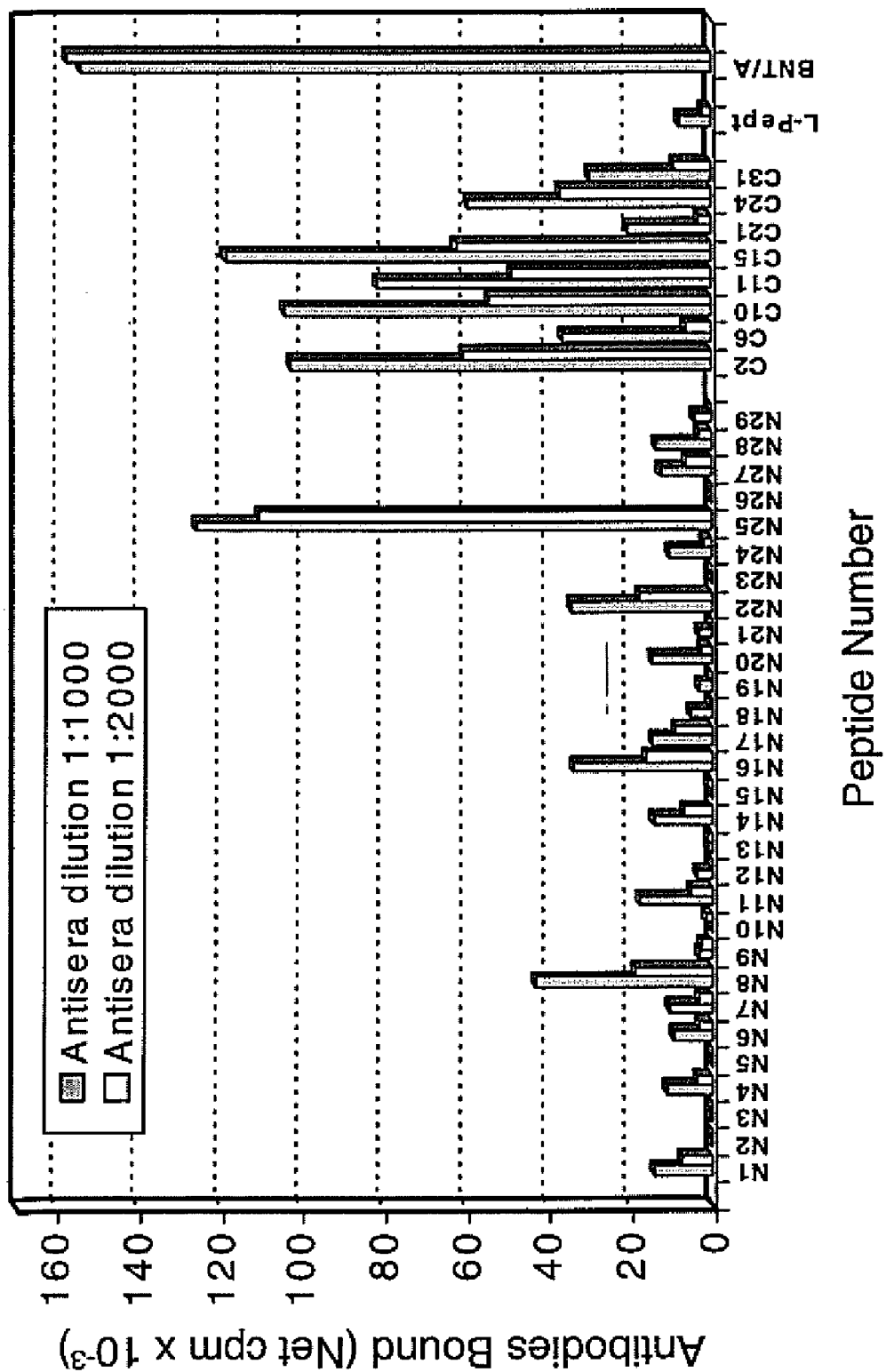
FIG. 2 shows binding of human anti-pentavalent botulinum toxoid antibodies to overlapping synthetic peptides spanning the BoNT/A $H_N$ domain and to active $H_C$ peptides. Also shown are binding to L-Peptide and full-length BoNT/A as negative and positive controls, respectively.

The present invention discloses the discovery of BoNT/A peptides which elicit antibody responses and represent the complete repertoire of epitopes found within the $H_N$ domain and $H_C$ domain of the BoNT/A heavy chain recognized by anti-BoNT/A antibodies present in three animal species, including humans. Mapping was performed using twenty-nine synthetic BoNT/A peptides, each containing nineteen residues, that overlap consecutively by five residues and correspond to the entire length of the $H_N$ domain and thirty-one synthetic BoNT/A peptides, each containing nineteen residues, that overlap consecutively by five residues and correspond to the entire length of the $H_C$ domain, with the exception of C31, which is twenty-two residues in length. BoNT/A peptides of the present invention are useful for, e.g., making peptides and peptide compositions and employing methods for determining immunoresistance to a botulinum toxin therapy in an individual, making tolerogizing compositions and employing methods for treating immunoresistance to a botulinum toxin therapy in an individual, making an immune response inducing composition and employing methods of inducing an immune response in an individual and methods of producing an anti-BoNT/A antibody.

Thus, aspects of the present invention provide isolated BoNT/A peptides having a length of at least 5 amino acids and at most 60 amino acids. It is envisioned that a BoNT/A peptide disclosed in the present specification can be derived from a naturally occurring BoNT/A, such as, e.g., a BoNT/A isoform or a BoNT/A subtype, or derived from a non-naturally occurring BoNT/A, such as, e.g., a conservative BoNT/A variant, a non-conservative BoNT/A variant, or a chimeric BoNT/A variant. It is also envisioned that a BoNT/A peptide can comprise an immunoreactive fragment of the BoNT/A peptide, the BoNT/A peptide derived from a naturally occurring BoNT/A or a non-naturally occurring BoNT/A. It is also envisioned that any and all tolerogizing compositions disclosed in the present specification can be formulated as a pharmaceutical composition. As a non-limiting example, a BoNT/A peptide or a BoNT/A peptide composition can comprise a BoNT/A peptide comprising a length of at most 60 amino acids and essentially of consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C1), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant, or a non-conservative variant, or immunoreactive fragment thereof, with the proviso that the BoNT/A peptide is not SEQ ID NO: 5.

Other aspects of the present invention further provide a tolerogizing composition comprising a tolerogizing agent and a BoNT/A peptide. It is envisioned that any and all tolerogizing agents can be useful in such a tolerogizing composition, including, without limitation, polyethylene glycol (PEG), monomethoxypolyethylene glycol (mPEG) and polyvinyl alcohol (PVA). It is also envisioned that any and all BoNT/A peptides disclosed in the present specification that produce a decreased immunological response can be useful in such a tolerogizing composition, including, without limitation, a BoNT/A derived from a naturally occurring BoNT/A, a BoNT/A derived from a non-naturally occurring BoNT/A and a BoNT/A comprising an immunoreactive fragment of the BoNT/A peptide, the BoNT/A peptide derived from a naturally occurring BoNT/A or a non-naturally occurring BoNT/A. It is also envisioned that any and all tolerogizing compositions disclosed in the present specification can be formulated as a pharmaceutical composition. As a non-limiting example, a tolerogizing composition comprising a BoNT/A peptide can have a BoNT/A peptide comprising a length of at most 60 amino acids and consisting essentially of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant or tolerogenic fragment thereof, with the proviso that the BoNT/A peptide is not SEQ ID NO: 5.

Other aspects of the present invention provide an immune response inducing composition comprising an adjuvant and a BoNT/A peptide. It is envisioned that any and all BoNT/A peptides disclosed in the present specification that produce an immunological response can be useful as a BoNT/A antigen, including, without limitation, a BoNT/A derived from a naturally occurring BoNT/A, a BoNT/A derived from a non-naturally occurring BoNT/A and a BoNT/A comprising an immunoreactive fragment of the BoNT/A peptide, the BoNT/A peptide derived from a naturally occurring BoNT/A or a non-naturally occurring BoNT/A. It is also envisioned that any and all immune response inducing compositions disclosed in the present specification can be formulated as a pharmaceutical composition. As a non-limiting example, an immune response inducing composition comprising a BoNT/A peptide can have a BoNT/A peptide comprising a length of at most 60 amino acids and consisting essentially of having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1

(C31), or a conservative variant or immunoreactive fragment thereof, with the proviso that the BoNT/A peptide is not SEQ ID NO: 5.

Other aspects of the present invention provide an antibody composition comprising an adjuvant and a BoNT/A peptide. It is envisioned that any and all BoNT/A peptides disclosed in the present specification having selectivity for an epitope contained within a BoNT/A peptide can be useful as a BoNT/A antigen, including, without limitation, a BoNT/A derived from a naturally occurring BoNT/A, a BoNT/A derived from a non-naturally occurring BoNT/A and a BoNT/A comprising an immunoreactive fragment of the BoNT/A peptide, the BoNT/A peptide derived from a naturally occurring BoNT/A or a non-naturally occurring BoNT/A. It is also envisioned that any and all antibody compositions disclosed in the present specification can be formulated as a pharmaceutical composition. As a non-limiting example, an antibody composition comprising a BoNT/A peptide can have a BoNT/A peptide comprising a length of at most 60 amino acids and consisting essentially of having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant or immunoreactive fragment thereof, with the proviso that the BoNT/A peptide is not SEQ ID NO: 5.

Still other aspects of the present invention provide methods of determining immunoresistance to botulinum toxin therapy in an individual, the methods comprising the steps of contacting a BoNT/A peptide and a test sample under conditions suitable for the selective binding of the BoNT/A peptide to an anti-botulinum toxin antibody and determining the presence of an anti-botulinum toxin antibody-BoNT/A peptide complex, the antibody-peptide complex formed by the selective binding of an anti-botulinum toxin antibody and the BoNT/A peptide, where the presence of the anti-botulinum toxin antibody-BoNT/A peptide complex indicates immunoresistance to a botulinum toxin therapy. It is envisioned that any and all BoNT/A peptides disclosed in the present specification capable of selectively binding with an anti-botulinum toxin antibody can be useful in a method for determining immunoresistance to botulinum toxin therapy in an individual, including, without limitation, a BoNT/A derived from a naturally occurring BoNT/A, a BoNT/A derived from a non-naturally occurring BoNT/A and a BoNT/A comprising an immunoreactive fragment of the BoNT/A peptide, the BoNT/A peptide derived from a naturally occurring BoNT/A or a non-naturally occurring BoNT/A.

Still other aspects of the present invention provide methods of treating immunoresistance to botulinum toxin therapy in an individual by administering to said individual a tolerogizing composition comprising a tolerogizing agent and a BoNT/A peptide wherein administration of said tolerogizing composition decreases an immunological response to a botulinum toxin antigen. It is envisioned that any and all tolerogizing compositions disclosed in the present specification can be useful in a method from preventing or reducing immunoresistance to botulinum toxin therapy in an individual.

Yet other aspects of the present invention provide methods of stimulating antibodies that neutralize botulinum toxin type A in an individual, the method comprising the step of administering to said individual an immune response inducing composition comprising an adjuvant and a BoNT/A peptide, wherein said administration stimulates the production of anti-botulinum toxin antibodies capable of preventing or ameliorating the harmful effects of botulinum toxin exposure. It is envisioned that any and all immune response inducing compositions disclosed in the present specification can be useful in a method of stimulating antibodies that neutralize botulinum toxin type A in an individual.

Yet other aspects of the present invention provide methods of stimulating the production of an anti-BoNT/A antibody in an animal, the method comprising the steps of administering to the animal an immune response inducing composition comprising an adjuvant and a BoNT/A peptide, where administration of the immune response inducing composition produces an immune response in the individual; collecting from the individual a sample containing the anti-BoNT/A antibody or anti-BoNT/A antibody-producing cell; and isolating the anti-BoNT/A antibody from the sample. It is envisioned that any and all antibody compositions disclosed in the present specification can be useful in a method of stimulating the production of an anti-BoNT/A antibody in an animal.

Still further aspects of the present invention provide immunoapheresis methods of treating immunoresistance to a botulinum toxin therapy in an individual, the method comprising the steps of removing blood from said individual, contacting the blood, or an anti-botulinum toxin antibody containing component thereof, with a BoNT/A peptide under conditions suitable for the selective binding of the BoNT/A peptide to the anti-botulinum toxin antibody, returning said anti-botulinum toxin antibody-depleted blood, or said anti-botulinum toxin antibody-depleted component thereof, to said individual. It is envisioned that any and all BoNT/A peptides disclosed in the present specification capable of selective binding with an anti-botulinum toxin antibody can be useful in an anti-botulinum toxin immunoapheresis methods of treating immunoresistance to a botulinum toxin therapy in an individual, including, without limitation, a BoNT/A derived from a naturally occurring BoNT/A, a BoNT/A derived from a non-naturally occurring BoNT/A and a BoNT/A comprising an immunoreactive fragment of the BoNT/A peptide, the BoNT/A peptide derived from a naturally occurring BoNT/A or a non-naturally occurring BoNT/A.

Botulinum neurotoxins (BoNTs) are a group of protein neurotoxins produced by *Clostridium botulinum* that are among the most toxic substances known to man. Seven immunologically distinct BoNT serotypes (A through G) are known, including two subtypes of type C(C1 and C2). Botulinum neurotoxins are synthesized from a single polypeptide chain with a molecular weight of about 150 KDa, which is activated after secretion by nicking of a single peptide bond by an endogenous or exogenous protease. In C. botulinum strains that produce BoNTs A, C, D, and some types of B and F, the proteolytic enzyme is endogenous, while in other strains such as those that produce type E and some types B and F, the proteolytic enzyme is exogenous. The nicking of the progenitor toxin generally results in generation of a di-chain molecule of two subunits, a 100 KDa heavy chain (HC) and a 50 KDa light chain (LC). With the exception of BoNT/C2, the two subunits are held together by a disulfide bond, which is important for neurotoxicity of toxin added extracellularly.

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocational domain contained within the amino-terminal half of the HC (denoted $H_N$ domain) that facilitates release of the toxin from intracellular vesicles into the cytoplasm of the target cell; and 3) a binding domain found within the carboxy-terminal half of the HC (denoted $H_C$ domain) that determines the binding activity and binding specificity of the toxin to the acceptor complex located at the surface of the target cell.

The overall cellular intoxication mechanism whereby the seven BoNT serotypes enter a neuron and inhibit neurotransmitter release is similar and can be described in four steps: 1) membrane binding, 2) complex internalization, 3) light chain translocation, and 4) exocytosis inhibition. The process is initiated when the $H_C$ domain of a BoNT binds to BoNT-specific acceptor complex located on the plasma membrane surface of a target cell. The binding specificity of an acceptor complex is thought to be achieved by specific combinations of gangliosides and protein receptors that appear to distinctly comprise each BoNT serotype-specific acceptor. Once bound, the BoNT/acceptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote enzymatic activation of the toxin. Once activated, light chain endopeptidase of the toxin is released from the intracellular vesicle into the cytosol where it specifically targets one of three known core components of the neurotransmitter release apparatus. These core proteins [vesicle-associated membrane protein (VAMP)/synaptobrevin, synaptosomal-associated protein of 25 kDa (SNAP-25) and syntaxin] are necessary for synaptic vesicle docking and fusion at the nerve terminal and constitute the synaptic members of the soluble N-ethylmaleimide-sensitive factor-attachment protein-receptor (SNARE) family. The selective proteolysis of synaptic SNAREs accounts for the total block of neurotransmitter release caused by BoNTs in vivo. For greater details see, e.g., Humeau, supra, 2000; Turton, supra, 2002; Atassi, supra, 2003; Lalli, supra, 2003, which are hereby incorporated by reference.

The complete primary structures of BoNTs A through G have been determined, see, e.g., Thomas Binz et al., *The Complete Sequence of Botulinum Neurotoxin Type A and Comparison with Other Clostridial Neurotoxins,* 265(16) J. BIOL. CHEM. 9153-9158 (1990); A. Willems et al., *Sequence of the Gene Coding for the Neurotoxin of Clostridium Botulinum Type A Associated With Infant Botulism: Comparison With Other Clostridial Neurotoxins,* 144(7) RES. MICROBIOL. 547-556 (1993); R. A. Hutson et al., *Nucleotide Sequence of the Gene Coding for Non-Proteolytic Clostridium Botulinum Type B Neurotoxin: Comparison With Other Clostridial Neurotoxins,* 28(2) CURR. MICROBIOL. 101-110 (1994); Kathryn D. Campbell et al., *Gene Probes For Identification of the Botulinal Neurotoxin Gene and Specific Identification of Neurotoxin Types B, E, And F,* 31(9) J. CLIN. MICROBIOL. 2255-2262 (1993); Daniel Hauser et al., *Nucleotide Sequence of Clostridium botulinum C1 Neurotoxin,* 18(16) NUCLEIC ACIDS RES. 4924 (1990); Daniel Hauser et al., *Comparative Analysis of C3 and Botulinal Neurotoxin Genes and Their Environment in Clostridium Botulinum Types C and D,* 175(22) J. BACTERIOL. 7260-7268 (1993); K. Kimura et al., *The Complete Nucleotide Sequence of the Gene Coding for Botulinum Type C1 Toxin in the C-ST Phage Genome,* 171(3) BIOCHEM. BIOPHYS. RES. COMMUN. 1304-1311 (1990); K. Kimura et al., *Cloning of the Structural Gene for Clostridium Botulinum Type C1 Toxin and Whole Nucleotide Sequence of its Light Chain Component,* 57(4) APPL. ENVIRON. MICROBIOL. 1168-1172 (1991); Daniel Hauser et al., *Botulinal Neurotoxin C1 Complex Genes, Clostridial Neurotoxin Homology and Genetic Transfer in Clostridium botulinum,* 33(4) TOXICON 515-526 (1995); Thomas Binz et al., *Nucleotide Sequence of the Gene Encoding Clostridium Botulinum Neurotoxin Type D,* 18(18) Nucleic Acids Res. 5556 (1990); H. Sunagawa et al., *The Complete Amino Acid Sequence of the Clostridium Botulinum Type D Neurotoxin, Deduced by Nucleotide Sequence Analysis of the Encoding Phage D-16 Phi Genome,* 54(5) J. VET. MED. SCI. 905-913 (1992); S. Poulet et al., *Sequences of the Botulinal Neurotoxin E Derived From Clostridium Botulinum Type E (Strain Beluga) and Clostridium Butyricum (Strains ATCC 43181 And ATCC 43755),* 183(1) BIOCHEM. BIOPHYS. RES. COMMUN. 107-113 (1992); Sarah M. Whelan et al., *The Complete Amino Acid Sequence of the Clostridium Botulinum Type-E Neurotoxin, Derived by Nucleotide-Sequence Analysis of the Encoding Gene,* 204(2) EUR. J. BIOCHEM. 657-667 (1992); Alison K. East et al., *Sequence of the Gene Encoding Type F Neurotoxin of Clostridium botulinum,* 75(2-3) FEMS MICROBIOL. LETT. 225-230 (1992); and Kathryn D. Campbell et al., *Nucleotide Sequence of the Gene Coding for Clostridium Botulinum (Clostridium argentinense) Type G Neurotoxin: Genealogical Comparison With Other Clostridial Neurotoxins,* 1216(3) BIOCHIM. BIOPHYS. ACTA. 487-491 (1993). In addition, the disulfide pairing in BoNT/A has been determined. Several regions of homology exist within the amino acid sequences of the different serotypes of BoNT, as described in, e.g., M. Zouhair Atassi & Minako Oshima, *Structure, Activity, and Immune (T and B Cell) Recognition of Botulinum Neurotoxins,* 19(3) CRIT. REV. IMMUNOL. 219-260 (1999).

The present invention relates to the discovery of small BoNT/A peptides which elicit antibody responses and represent the repertoire of epitopes found within both the BoNT/A $H_N$ domain and $H_C$ domain recognized by four animal species, including humans. As shown herein in Examples 2-6, antigenic regions of both domains were mapped using human, horse, mouse and chicken sera obtained following immunization with BoNT/A. Mapping was performed using twenty-nine synthetic BoNT/A peptides, each containing nineteen residues, that overlap consecutively by five residues and correspond to the entire length of the $H_N$ domain and thirty-one synthetic BoNT/A peptides, each containing nineteen residues, that overlap consecutively by five residues and correspond to the entire length of the $H_C$ domain, with the exception of C31, which is twenty-two residues in length. The amino acid sequences of the sixty peptides used for mapping are shown in FIG. 1A. Results from the mapping studies revealed 1) nineteen segments of BoNT/A that represent the complete repertoire of continuous antigenic regions on the BoNT/A H$_N$ domain; and 2) 1) nineteen segments of BoNT/A that represent the complete repertoire of continuous antigenic regions on the BoNT/A H$_C$ domain, see, e.g., Examples 2-6.

As disclosed herein in Example 8, T- and B-cell recognition profiles of the BoNT/A H$_N$ domain were mapped in two inbred mouse strains, BALB/c (H-2$^d$) and SJL (H-2$^s$), that are high responders to BoNT/A. As summarized in Table 5, the results obtained with the two high-responder mouse strains demonstrate that responses to each antibody and T cell epitope are under separate genetic control and further indicate that there is partial overlap between antibody and T cell H$_N$ recognition regions.

Figure 16:
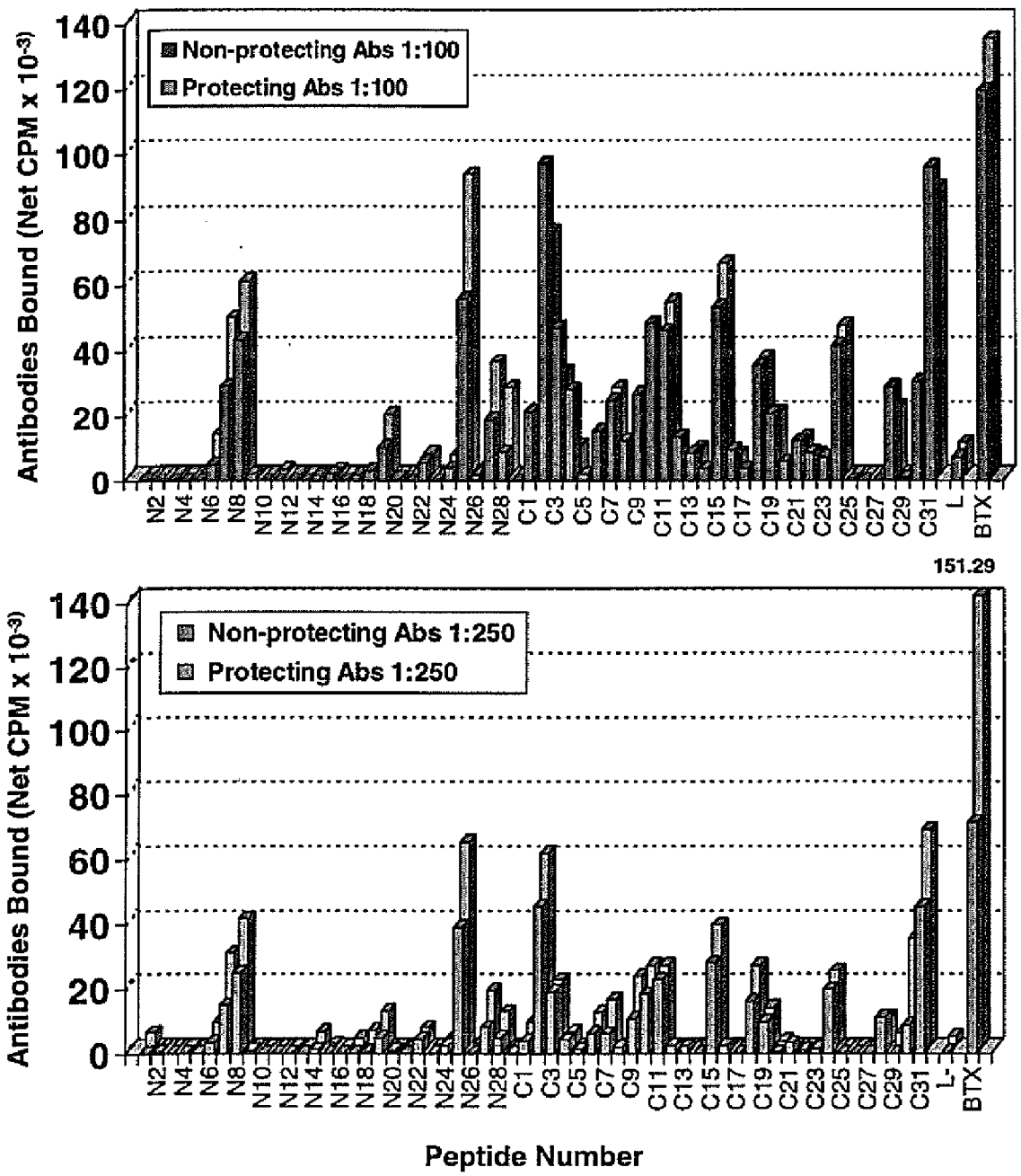
FIG. 16 shows binding of BALB/c total antibodies in non-protecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction for nonspecific binding in control wells coated with unrelated protein (BSA) or peptides and also controls of bound label to BoNT/A and to peptides in pre-immune serum of the same mice.
Figure 17:
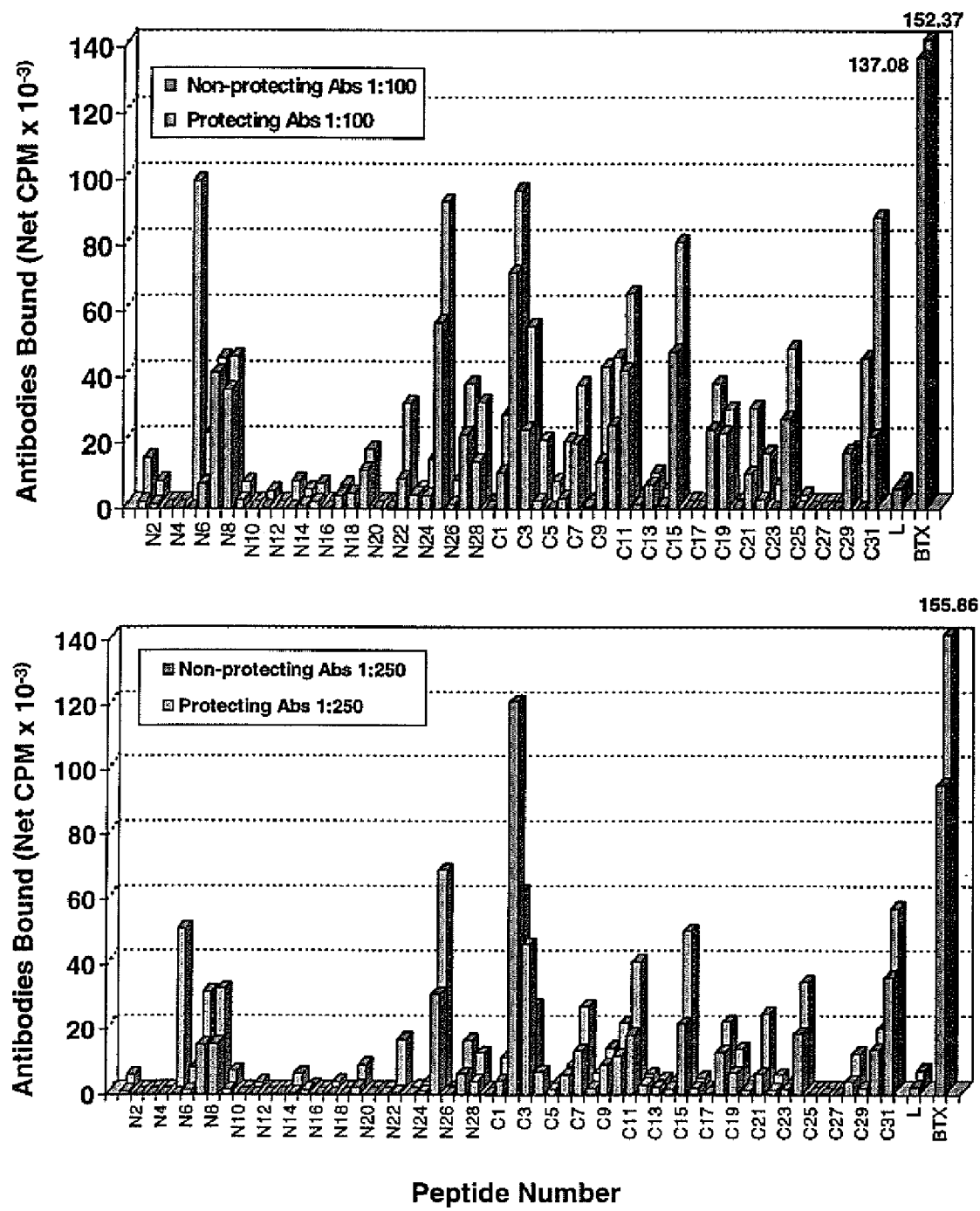
FIG. 17 shows binding of SJL total antibodies in non-protecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction as described above.
Figure 18:
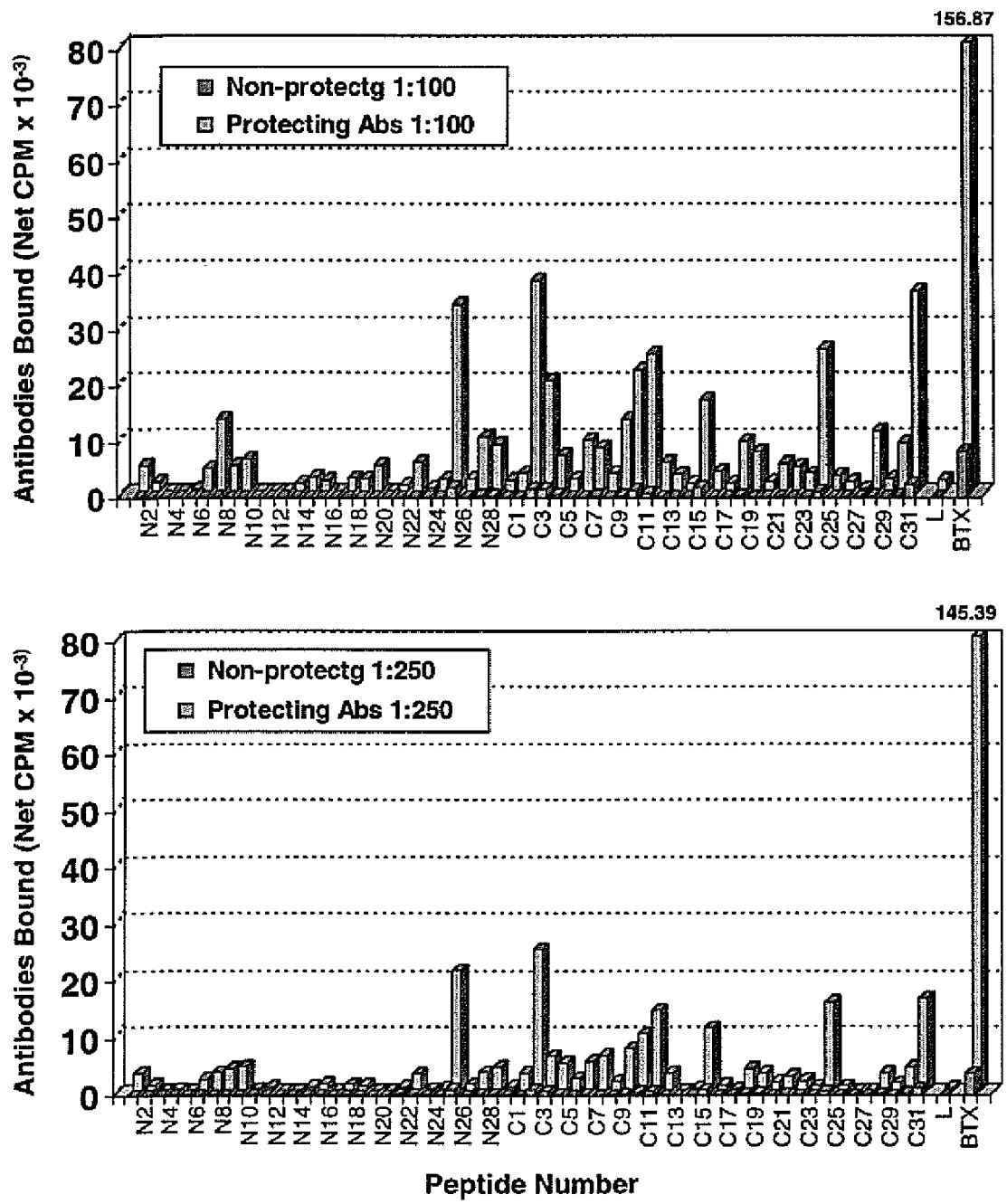
FIG. 18 shows binding of BALB/c IgG antibodies in non-protecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction as described above.
Figure 19:
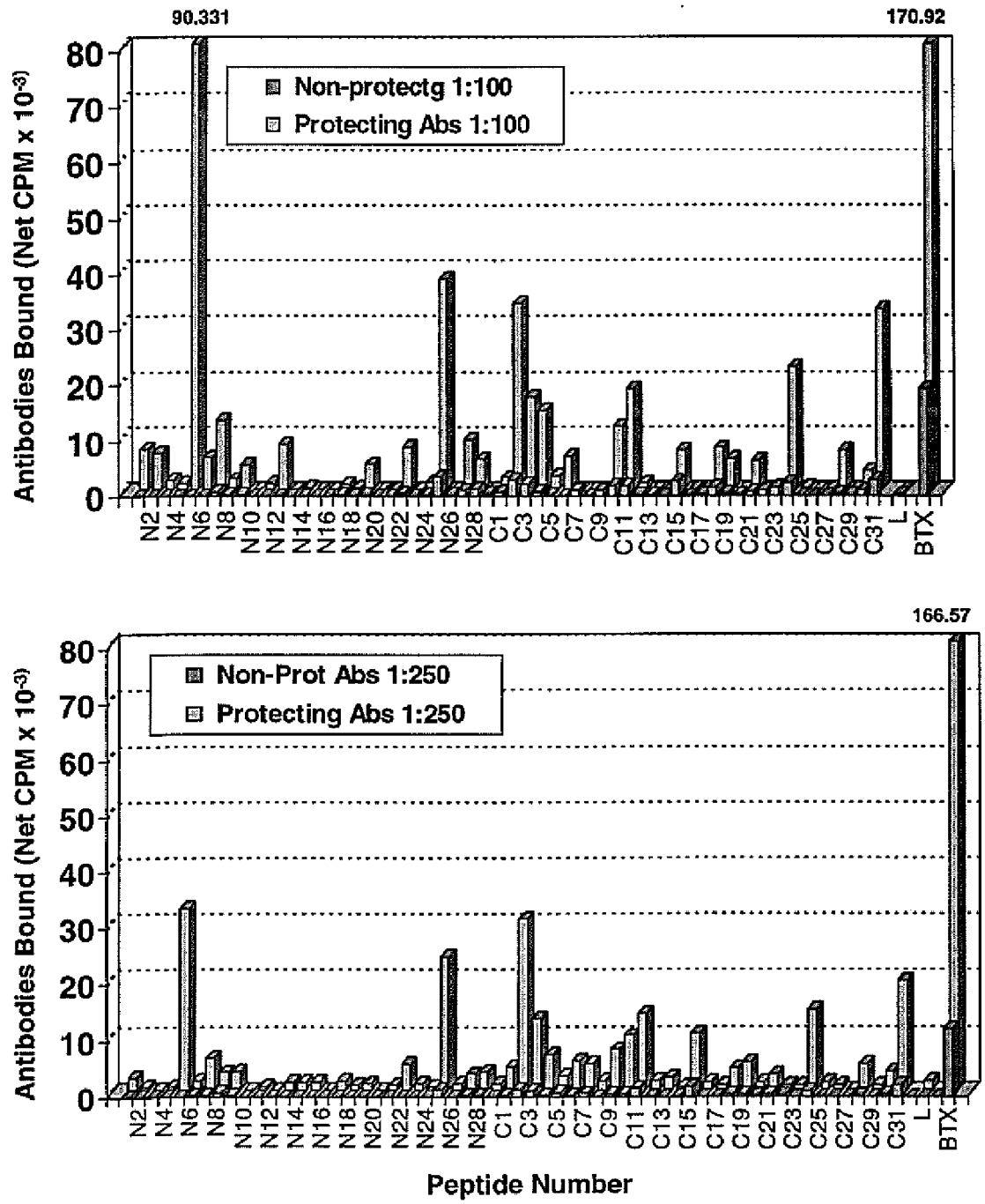
FIG. 19 shows binding of SJL IgG antibodies in non-protecting (day 26) and protecting (day 36) anti-BoNT/A antisera to the overlapping synthetic peptides spanning the entire H chain and to the L-peptide around the enzyme active site of the L chain of BoNT/A. Results are from triplicate analyses and are expressed in net cpm, after correction as described above.
Figure 20:
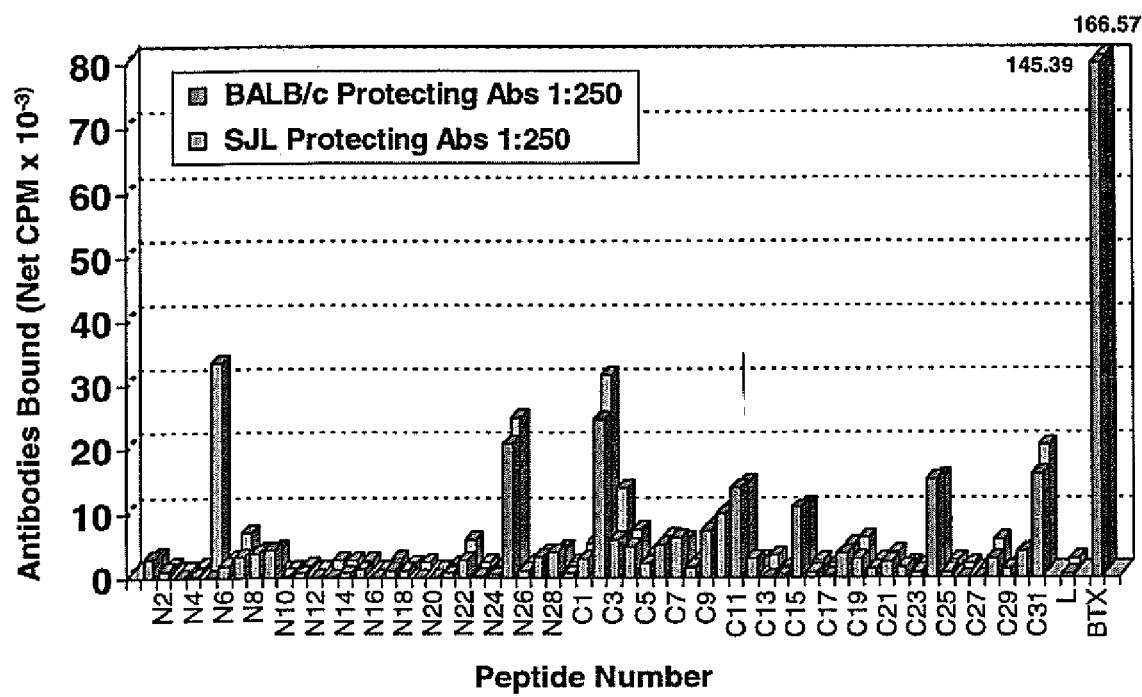
FIG. 20 shows a comparison of IgG antibody binding profiles from protective (day 36) BALB/c and SJL antisera. The data are the same as those shown in FIGS. 4 and 5. Binding studies were performed with antisera at a dilution of 1:250 (vol/vol).
Figure 23:
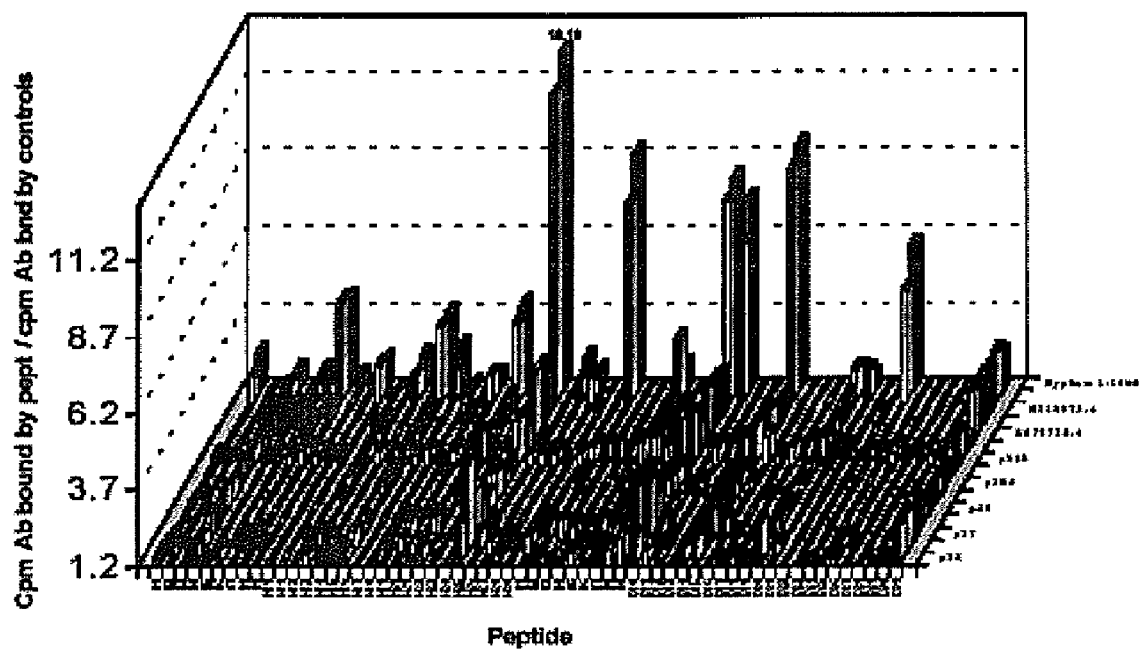
FIG. 23 shows mapping of the antibody recognition profile in serum samples from 13 CD patients. Results are expressed as a ratio of antibodies bound to peptides in the CD sera/average of antibodies bound by four negative control peptides.

Resistance in the majority of patients is associated with the appearance of blocking anti-toxin antibodies in patient serum (Hilke Göschel et al., *Botulinum A Toxin Therapy: Neutralizing and Nonneutralizing Abs—Therapeutic Consequences*, 147(1) EXP. NEUROL. 96-102, (1997); Atassi & Oshima, supra, 1999; Jankovic, supra, 2002. While all patient antibody responses against the toxin are not observed initially, additional injections of toxin appear to cause a switch of the non-blocking antibodies in the patient's serum to blocking antibodies. As further disclosed herein in Example 9, the epitope recognition profile was compared in inbred BALB/c and SJL mice before and after the switch from production of non-protective to protective antibodies. The results disclosed herein demonstrated only slight differences in the epitope recognition profiles of non-protective and protective antisera, indicating that changes in antibody binding may not always protection, or lack thereof, by serum from a given strain (FIGS. 16 and 17). Furthermore, as shown in FIGS. 18 and 19, IgG antibodies in the protective antisera of each mouse strain bound to the same peptides as did total antibodies (IgG and IgM) in the same serum, while in both mouse strains, non-protective antisera contained few, if any, IgG antibodies to these peptides. These results appear to indicate that protection can be a function of immunoglobulin class, with IgG antibodies conferring protection against botulinum toxin.

Figure 24:
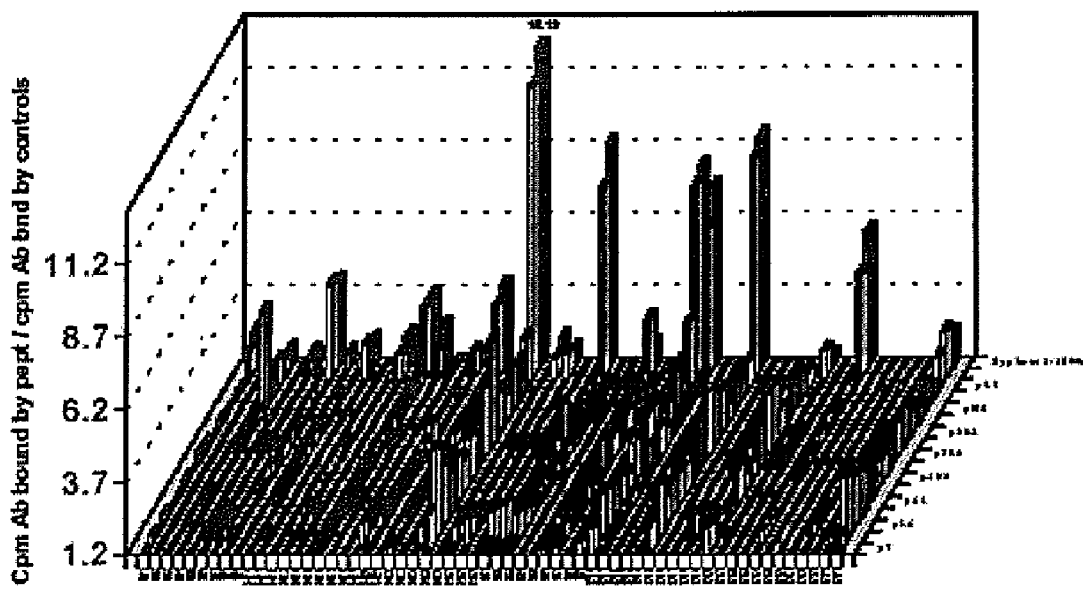
FIG. 24 shows mapping of the antibody recognition profile in serum samples from 15 CD patients. Results are expressed as a ratio of antibodies bound to peptides in the CD sera/average of antibodies bound by four negative control peptides.
Figure 25:
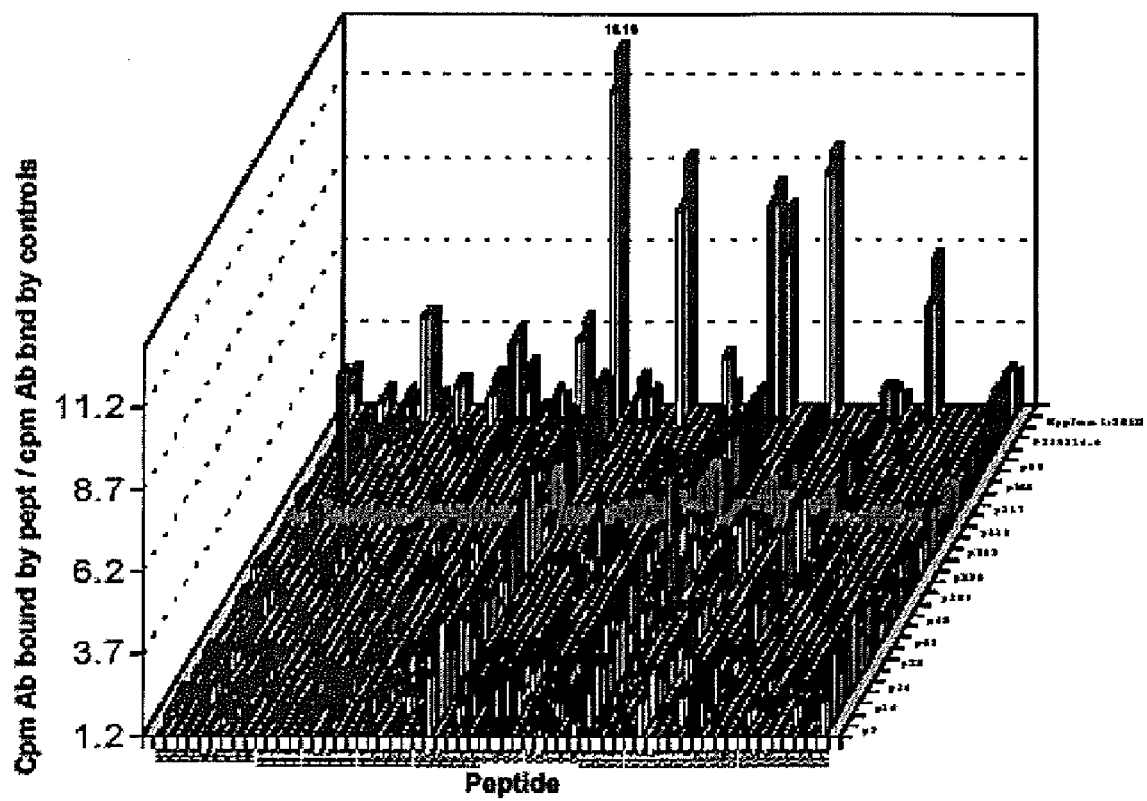
FIG. 25 shows mapping of the antibody recognition profile in serum samples from 28 CD patients. Results are expressed as a ratio of antibodies bound to peptides in the CD sera/average of antibodies bound by four negative control peptides.
Figure 26:
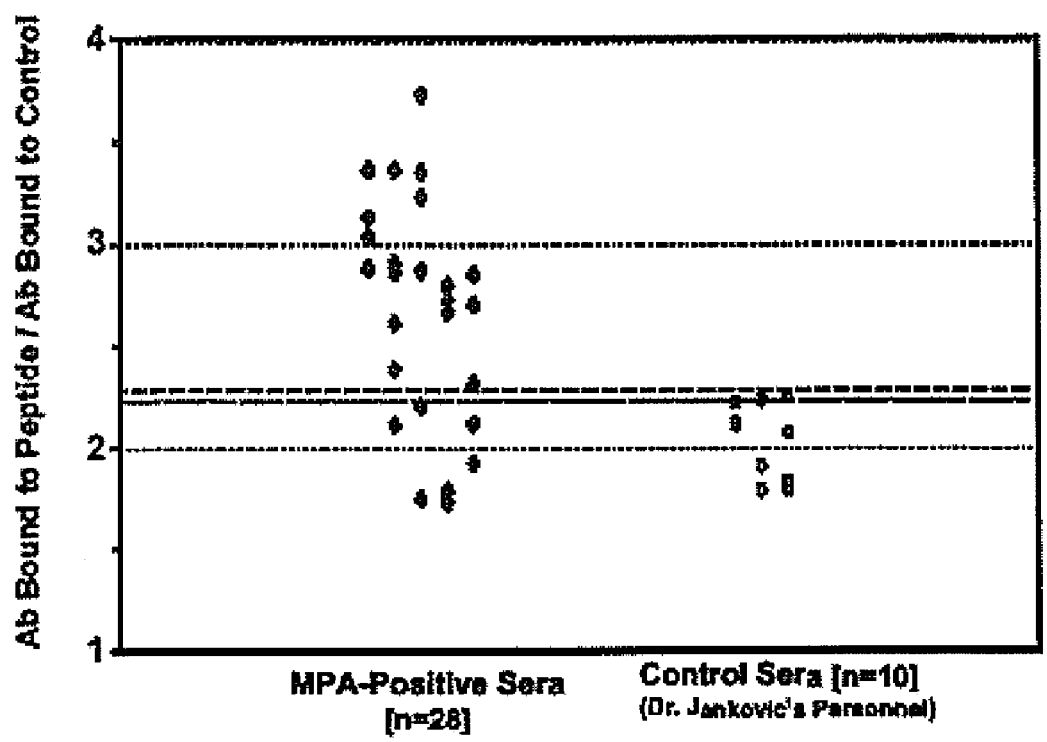
FIG. 26 shows binding to peptide N25 of antibodies in MPA-positive sera from CD patients (n=28) and in normal controls (n=10). Results are the average of four experiments and are expressed as a ratio of (antibodies bound to peptide N25)/(average of antibodies bound by negative control peptides N2, N12, C17 and C23).
Figure 27:
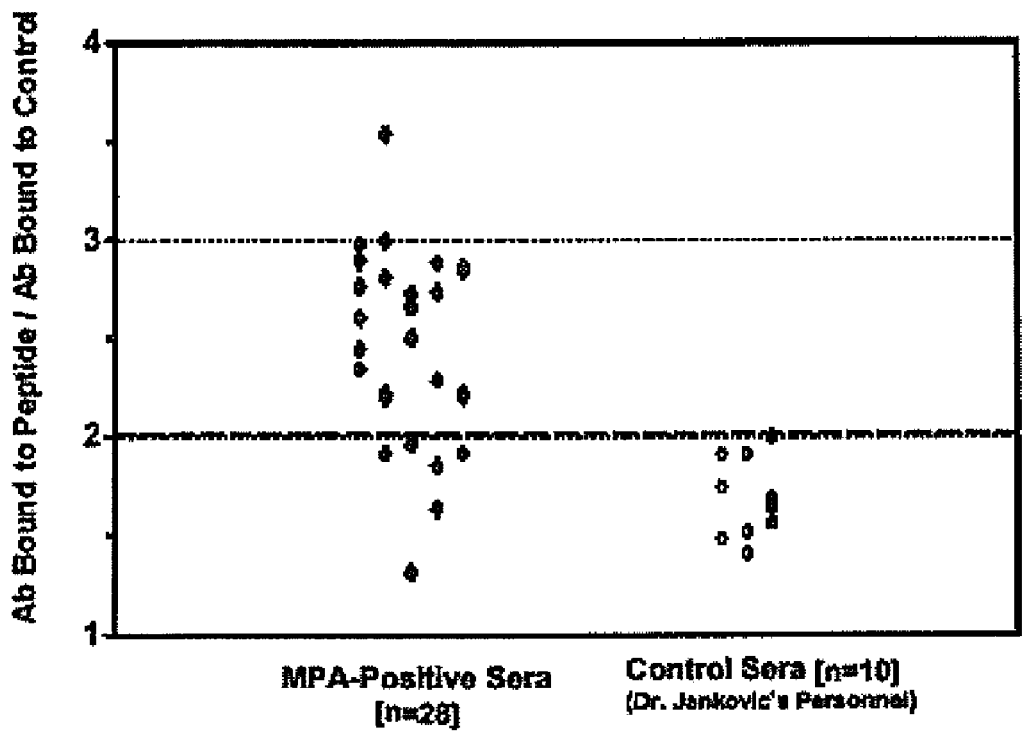
FIG. 27 shows binding to peptide C10 of antibodies in MPA-positive sera from CD patients (n=28) and in normal controls (n=10). Results are the average of four experiments and are expressed as a ratio of (antibodies bound to peptide C10)/(average of antibodies bound by negative control peptides N2, N12, C17 and C23).

Additional studies disclosed herein in Example 10 demonstrate that in vitro binding assays performed in the presence of excess tetanus toxoid can be used to determine the levels of blocking or protective anti-BoNT/A antibodies in human serum samples. In particular, sera from 28 cervical dystonia patients containing protective antibodies as indicated by the mouse protection assay (MPA) and 10 negative sera controls from unimmunized human were analyzed. As shown in FIG. 24 to 26 and summarized in Table 6, peptides which bound antibodies in MPA-positive human patient sera also bound antibodies in hyperimmune mouse sera, while the antibody-binding profile of patient sera was more restricted than the profile of the hyperimmune sera. As further disclosed herein in Example 10, several peptides bound antibodies in most patient samples, with 25 out of 28 sera containing antibodies that bound peptide N25; 24 out of 28 sera containing antibodies that bound peptide C10; and lower binding to peptides C15, C20 and C31 seen in the majority of patient samples. These results indicate that, while there is some variability among the peptide-binding profiles of MPA-positive human sera, several synthetic BoNT/A peptides bind antibodies in the large majority of human patient sera that contain protective antibodies.

Figure 30:
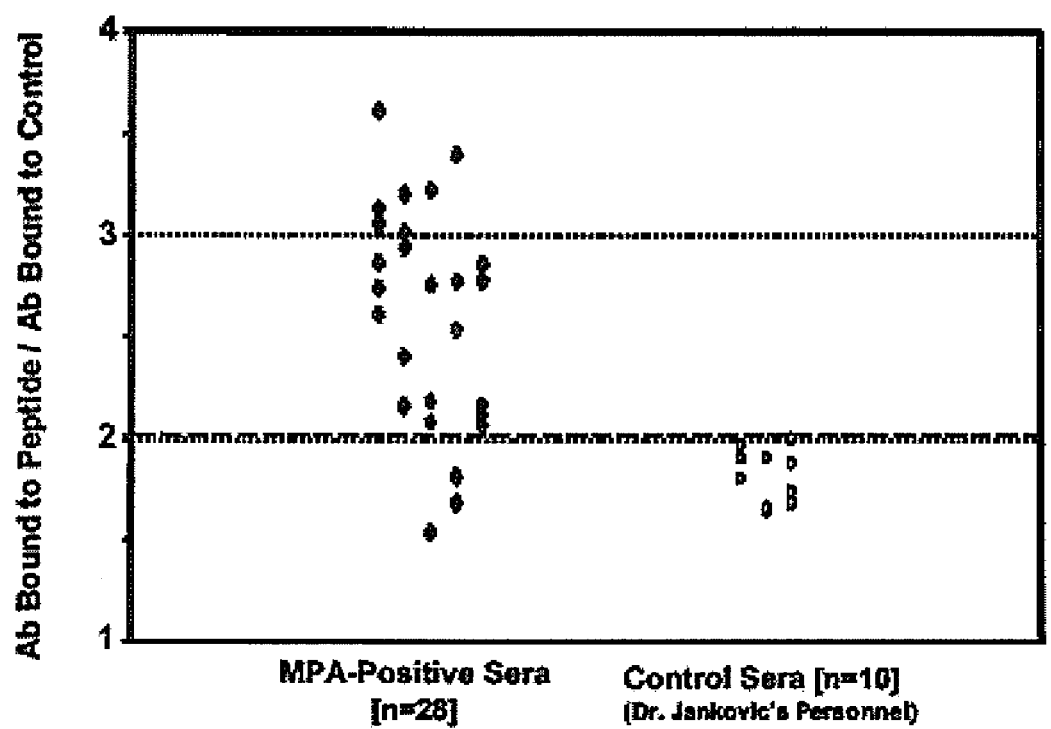
FIG. 30 shows binding to peptides (N25+C10) of antibodies in MPA-positive sera from CD patients (n=28) and in normal controls (n=10). The results, which are the average of four experiments, are expressed as a ratio of (antibodies bound to peptide N25+C10)/(average of antibodies bound by negative control peptides N2, N12, C17 and C23).
Figure 32:
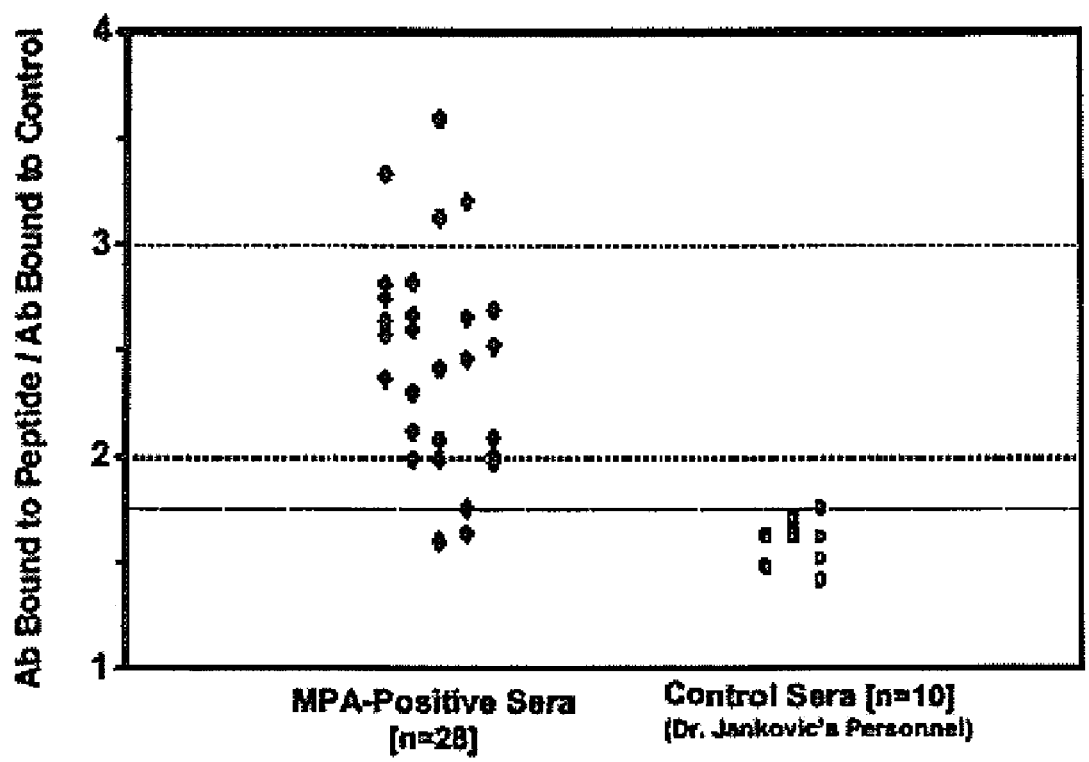
FIG. 32 shows binding to peptides (N25+C10+C15) of antibodies in MPA-positive sera from CD patients (n=28) and in normal controls (n=10). Results, which are the average of four experiments, are expressed as a ratio of (antibodies bound to peptides N25+C10+C15)/(average of antibodies bound by negative control peptides N2, N12, C17 and C23).

Further results disclosed herein demonstrate that an assay based on a combination of two or more synthetic BoNT/A peptides can be useful for detecting the presence of protective or blocking antibodies in the sera of patients treated with a BoNT/A formulation. As shown in FIG. 30, in an assay combining synthetic peptides N25 and C10, 25 out of 28 (89.3%) of the MPA-positive CD sera were discriminated from control sera. FIG. 32 shows that a combination of the synthetic peptides N25, C10 and C15 also served to distinguish 25 out of 28 (89.3%) of the MPA-positive CD sera from controls. Thus, the results disclosed herein demonstrate that a combination assay using peptides N25 and C10, or peptides N25, C10 and C15 can be useful for detecting the presence of specific anti-toxin antibodies in BOTOX® treated patients. Furthermore, one or a combination of the synthetic peptides N25, C10, N15, N20 or N31, or a conservative variant or immunoreactive fragment thereof, also can be useful in a variety of diagnostic or therapeutic applications including, without limitation, methods of predicting or determining immunoresistance to botulinum toxin therapy; methods of preventing or reducing immunoresistance to botulinum toxin therapy and related tolerogenic compositions; methods of vaccinating against botulinum toxin and related BoNT/A immune response inducing compositions; methods of removing anti-botulinum toxin antibodies from blood, plasma or serum and affinity-matrices useful therefore; and new therapeutic formulations for blocking the effect of neutralizing antibodies in situ. Such therapeutic formulations include excess synthetic protective antibody-binding peptides together with the active toxin formulation.

As mentioned above, the first step in the intoxication process is the binding of BoNT/A to a cell surface acceptor complex containing BoNT/A-specific receptor proteins and gangliosides. Using the sixty BoNT/A peptides regions necessary for the binding of the toin to the acceptor complex were identified, see, e.g., Example 11. Results from these mapping studies revealed 1) eleven segments of BoNT/A that represent the complete repertoire of continuous antigenic regions on the BoNT/A H$_N$ domain; and 2) 1) eight segments of BoNT/A that represent the complete repertoire of continuous antigenic regions on the BoNT/A H$_C$ domain, see, e.g., Examples 11.

I. BoNT/A Peptides

The present invention provides, in part, a BoNT/A peptide. As used herein, the term "BoNT/A peptide," means a peptide having an amino acid sequence length of at least five amino acids and at most 60 amino acids, the amino acid sequence derived from a naturally occurring BoNT/A or a non-naturally occurring BoNT/A. Exemplary examples of naturally-occurring BoNT/As are the BoNT/A of SEQ ID NO: 1, the BoNT/A of SEQ ID NO: 2, the BoNT/A of SEQ ID NO: 3 and the BoNT/A of SEQ ID NO: 4. Specifically excluded from the definition of a BoNT/A peptide is the 57-mer SEQ ID NO: 5 described in Toru Kubota et al., *Epitope Regions in the Heavy Chain of Clostridium Botulinum Type E Neurotoxin Recognized by Monoclonal Antibodies*, 63(4) APPL. ENVIRON. MICROBIOL. 1214-1218 (1997).

In is envisioned that a BoNT/A peptide disclosed in the present specification can have any of a variety of lengths from at least 5 amino acids to at most 60 amino acids. Therefore, aspects of this embodiment may include a BoNT/A peptide with, e.g., at least five amino acids, at least six amino acids, at least seven amino acids, at least eight amino acids, at least nine amino acids, at least ten amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 25 amino acids, at least 30 amino acids, at least 35 amino acids, at least 40 amino acids, at least 45 amino acids, at least 50 amino acids, or at least 55 amino acids. In other aspects of this embodiment may include a BoNT/A peptide with, e.g., at most six amino acids, at most seven amino acids, at most eight amino acids, at most nine amino acids, at most ten amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 25 amino acids, at most 30 amino acids, at most 35 amino acids, at most 40 amino acids, at most 45 amino acids, at most 50 amino acids, at most 55 amino acids or at most 60 amino acids.

A BoNT/A peptide disclosed in the present specification comprises at least five consecutive amino acids from the BoNT/A from which the BoNT/A peptide is derived. In aspects of this embodiment, a BoNT/A peptide comprises, e.g., at least 5 consecutive amino acids from the BoNT/A from which the BoNT/A peptide is derived, at least 6 consecutive amino acids from the BoNT/A from which the BoNT/A peptide is derived, at least 7 consecutive amino acids from the BoNT/A from which the BoNT/A peptide is derived, at least 8 consecutive amino acids from the BoNT/A from which the BoNT/A peptide is derived, at least 9 consecutive amino acids from the BoNT/A from which the BoNT/A peptide is derived, at least 10 consecutive amino acids from the BoNT/A from which the BoNT/A peptide is derived, at least 12 consecutive amino acids from the BoNT/A from which the BoNT/A peptide is derived, at least 15 consecutive amino acids from the BoNT/A from which the BoNT/A peptide is derived, at least 18 consecutive amino acids from the BoNT/A from which the BoNT/A peptide is derived, at least 20 consecutive amino acids from the BoNT/A from which the BoNT/A peptide is derived, at least 25 consecutive amino acids from the BoNT/A from which the BoNT/A peptide is derived, at least 30 consecutive amino acids from the BoNT/A from which the BoNT/A peptide is derived, at least 40 consecutive amino acids from the BoNT/A from which the BoNT/A peptide is derived or at least 50 consecutive amino acids from the BoNT/A from which the BoNT/A peptide is derived.

In other aspects of this embodiment, a BoNT/A peptide comprises, e.g., at most 5 consecutive amino acids from the BoNT/A from which the BoNT/A peptide is derived, at most 6 consecutive amino acids from the BoNT/A from which the BoNT/A peptide is derived, at most 7 consecutive amino acids from the BoNT/A from which the BoNT/A peptide is derived, at most 8 consecutive amino acids from the BoNT/A from which the BoNT/A peptide is derived, at most 9 consecutive amino acids from the BoNT/A from which the BoNT/A peptide is derived, at most 10 consecutive amino acids from the BoNT/A from which the BoNT/A peptide is derived, at most 12 consecutive amino acids from the BoNT/A from which the BoNT/A peptide is derived, at most 15 consecutive amino acids from the BoNT/A from which the BoNT/A peptide is derived, at most 18 consecutive amino acids from the BoNT/A from which the BoNT/A peptide is derived, at most 20 consecutive amino acids from the BoNT/A from which the BoNT/A peptide is derived, at most 25 consecutive amino acids from the BoNT/A from which the BoNT/A peptide is derived, at most 30 consecutive amino acids from the BoNT/A from which the BoNT/A peptide is derived, at most 40 consecutive amino acids from the BoNT/A from which the BoNT/A peptide is derived or at most 50 consecutive amino acids from the BoNT/A from which the BoNT/A peptide is derived.

In still other aspects of this embodiment, a BoNT/A peptide comprising, e.g., at least five amino acids of SEQ ID NO: 1, at least six amino acids of SEQ ID NO: 1, at least seven amino acids of SEQ ID NO: 1, at least eight amino acids of SEQ ID NO: 1, at least nine amino acids of SEQ ID NO: 1, at least ten amino acids of SEQ ID NO: 1, at least 11 amino acids of SEQ ID NO: 1, at least 12 amino acids of SEQ ID NO: 1, at least 13 amino acids of SEQ ID NO: 1, at least 14 amino acids of SEQ ID NO: 1, at least 15 amino acids of SEQ ID NO: 1, at least 16 amino acids of SEQ ID NO: 1, at least 17 amino acids of SEQ ID NO: 1, at least 18 amino acids of SEQ ID NO: 1, at least 19 amino acids of SEQ ID NO: 1, at least 20 amino acids of SEQ ID NO: 1, at least 25 amino acids of SEQ ID NO: 1, at least 30 amino acids of SEQ ID NO: 1, at least 35 amino acids of SEQ ID NO: 1, at least 40 amino acids of SEQ ID NO: 1, at least 45 amino acids of SEQ ID NO: 1, at least 50 amino acids of SEQ ID NO: 1 or at least 55 amino acids.

In still other aspects of this embodiment, a BoNT/A peptide with, e.g., at most six amino acids of SEQ ID NO: 1, at most seven amino acids of SEQ ID NO: 1, at most eight amino acids of SEQ ID NO: 1, at most nine amino acids of SEQ ID NO: 1, at most ten amino acids of SEQ ID NO: 1, at most 11 amino acids of SEQ ID NO: 1, at most 12 amino acids of SEQ ID NO: 1, at most 13 amino acids of SEQ ID NO: 1, at most 14 amino acids of SEQ ID NO: 1, at most 15 amino acids of SEQ ID NO: 1, at most 16 amino acids of SEQ ID NO: 1, at most 17 amino acids of SEQ ID NO: 1, at most 18 amino acids of SEQ ID NO: 1, at most 19 amino acids of SEQ ID NO: 1, at most 20 amino acids of SEQ ID NO: 1, at most 25 amino acids of SEQ ID NO: 1, at most 30 amino acids of SEQ ID NO: 1, at most 35 amino acids of SEQ ID NO: 1, at most 40 amino acids of SEQ ID NO: 1, at most 45 amino acids of SEQ ID NO: 1, at most 50 amino acids of SEQ ID NO: 1, at most 55 amino acids or at most 60 amino acids of SEQ ID NO: 1.

In yet other aspects of this embodiment, a BoNT/A peptide comprising, e.g., at least five consecutive amino acids of SEQ ID NO: 1, at least six consecutive amino acids of SEQ ID NO: 1, at least seven consecutive amino acids of SEQ ID NO: 1, at least eight consecutive amino acids of SEQ ID NO: 1, at least nine consecutive amino acids of SEQ ID NO: 1, at least ten amino consecutive acids of SEQ ID NO: 1, at least 11 consecutive amino acids of SEQ ID NO: 1, at least 12 consecutive amino acids of SEQ ID NO: 1, at least 13 consecutive amino acids of SEQ ID NO: 1, at least 14 consecutive amino acids of SEQ ID NO: 1, at least 15 consecutive amino acids of SEQ ID NO: 1, at least 16 consecutive amino acids of SEQ ID NO: 1, at least 17 consecutive amino acids of SEQ ID NO: 1, at least 18 consecutive amino acids of SEQ ID NO: 1, at least 19 consecutive amino acids of SEQ ID NO: 1, at least 20 consecutive amino acids of SEQ ID NO: 1, at least 25 consecutive amino acids of SEQ ID NO: 1, at least 30 consecutive amino acids of SEQ ID NO: 1, at least 35 consecutive amino acids of SEQ ID NO: 1, at least 40 consecutive amino acids of SEQ ID NO: 1, at least 45 consecutive amino acids of SEQ ID NO: 1, at least 50 consecutive amino acids of SEQ ID NO: 1 or at least 55 consecutive amino acids.

In yet other aspects of this embodiment, a BoNT/A peptide with, e.g., at most five consecutive amino acids of SEQ ID NO: 1, at most six consecutive amino acids of SEQ ID NO: 1, at most seven consecutive amino acids of SEQ ID NO: 1, at most eight consecutive amino acids of SEQ ID NO: 1, at most nine consecutive amino acids of SEQ ID NO: 1, at most ten consecutive amino acids of SEQ ID NO: 1, at most 11 consecutive amino acids of SEQ ID NO: 1, at most 12 consecutive amino acids of SEQ ID NO: 1, at most 13 consecutive amino acids of SEQ ID NO: 1, at most 14 consecutive amino acids of SEQ ID NO: 1, at most 15 consecutive amino acids of SEQ ID NO: 1, at most 16 consecutive amino acids of SEQ ID NO: 1, at most 17 consecutive amino acids of SEQ ID NO: 1, at most 18 consecutive amino acids of SEQ ID NO: 1, at most 19 consecutive amino acids of SEQ ID NO: 1, at most 20 consecutive amino acids of SEQ ID NO: 1, at most 25 consecutive amino acids of SEQ ID NO: 1, at most 30 consecutive amino acids of SEQ ID NO: 1, at most 35 consecutive amino acids of SEQ ID NO: 1, at most 40 consecutive amino acids of SEQ ID NO: 1, at most 45 consecutive amino acids of SEQ ID NO: 1, at most 50 consecutive amino acids of SEQ ID NO: 1, at most 55 consecutive amino acids or at most 60 consecutive amino acids of SEQ ID NO: 1.

A BoNT/A peptide includes, without limitation, a BoNT/A peptide comprising an amino acid sequence derived from a naturally occurring BoNT/A variant, such as, e.g., a BoNT/A isoform and a BoNT/A subtype; and a BoNT/A peptide comprising an amino acid sequence derived from a non-naturally occurring BoNT/A variant, such as, e.g., a conservative BoNT/A variant, a non-conservative BoNT/A variant or a chimeric BoNT/A peptide. As used herein, the term "BoNT/A peptide variant," whether naturally-occurring or non-naturally-occurring, means a BoNT/A peptide that has at least one amino acid change from the corresponding region of the reference BoNT/A of SEQ ID NO: 1 and can be described in percent identity to the corresponding region of that reference sequence. Unless expressly indicated, all BoNT/A peptide variants disclosed in the present specification can function in substantially the same manner as the reference BoNT/A peptide of SEQ ID NO: 1 on which the BoNT/A peptide variant is based, and can be substituted for the reference BoNT/A peptide of SEQ ID NO: 1 in any aspect of the present invention. As a non limiting example, a BoNT/A peptide comprising amino acid sequence 974-992 from a BoNT/A peptide variant will have at least one amino acid difference, such as, e.g., an amino acid substitution, deletion or addition, as compared to the amino acid sequence 974-992 of SEQ ID NO: 1. As another non limiting example, a BoNT/A peptide comprising amino acid sequence 736-754 from a BoNT/A peptide variant will have at least one amino acid difference, such as, e.g., an amino acid substitution, deletion or addition, as compared to the amino acid sequence 736-754 of SEQ ID NO: 1. As still another non limiting example, a BoNT/A peptide comprising amino acid sequence 1058-1076 from a BoNT/A peptide variant will have at least one amino acid difference, such as, e.g., an amino acid substitution, deletion or addition, as compared to the amino acid sequence 1058-1076 of SEQ ID NO: 1. As yet another non limiting example, a BoNT/A peptide comprising amino acid sequence 890-908 from a BoNT/A peptide variant will have at least one amino acid difference, such as, e.g., an amino acid substitution, deletion or addition, as compared to the amino acid sequence 890-908 of SEQ ID NO: 1.

It is recognized by those of skill in the art that there are naturally occurring BoNT/A peptide variants that differ somewhat in their amino acid sequence, and also in the nucleic acids encoding these proteins. For example, there are presently four major BoNT/A subtypes, BoNT/A1, BoNT/A2, BoNT/A bivalent and BoNT/A non-proteolytic, with specific subtypes showing approximately 95% amino acid identity when compared to another BoNT/A subtype. As used herein, the term "naturally occurring BoNT/A peptide variant" means any BoNT/A peptide derived from a naturally occurring BoNT/A produced by a naturally-occurring process, including, without limitation, BoNT/A isoforms produced from alternatively-spliced transcripts, BoNT/A isoforms produced by spontaneous mutation and BoNT/A subtypes. A naturally occurring BoNT/A peptide variant can function in substantially the same manner as the reference BoNT/A peptide of SEQ ID NO: 1 on which the naturally occurring BoNT/A peptide variant is based, and can be substituted for the reference BoNT/A peptide in any aspect of the present invention. A naturally occurring BoNT/A peptide variant may substitute one or more amino acids, two or more amino acids, three or more amino acids, four or more amino acids, five or more amino acids, ten or more amino acids, or 20 or more amino acids from the reference BoNT/A peptide on which the naturally occurring BoNT/A variant is based. A naturally occurring BoNT/A peptide variant can also substitute at least two contiguous amino acids, at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids from the reference BoNT/A peptide on which the naturally occurring BoNT/A peptide variant is based, that possess at least 50% amino acid identity, 65% amino acid identity, 75% amino acid identity, 85% amino acid identity or 95% amino acid identity to the reference BoNT/A peptide of SEQ ID NO: 1 on which the naturally occurring BoNT/A peptide variant is based. A non-limiting example of a naturally occurring BoNT/A peptide variant is a BoNT/A peptide derived from a BoNT/A isoform and a BoNT/A peptide derived from a BoNT/A subtype.

As used herein, the term "non-naturally occurring BoNT/A variant" means any BoNT/A produced with the aid of human manipulation, including, without limitation, BoNT/As produced by genetic engineering using random mutagenesis or rational design and BoNT/As produced by chemical synthesis. Non-limiting examples of non-naturally occurring BoNT/A variants include, e.g., conservative BoNT/A variants, non-conservative BoNT/A variants, BoNT/A chimeric variants and active BoNT/A fragments.

As used herein, the term "conservative BoNT/A peptide variant" means a BoNT/A peptide that has at least one amino acid substituted by another amino acid or an amino acid analog that has at least one property similar to that of the original amino acid from the reference BoNT/A peptide of SEQ ID NO: 1. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative BoNT/A peptide variant can function in substantially the same manner as the reference BoNT/A peptide on which the conservative BoNT/A peptide variant is based, and can be substituted for the reference BoNT/A peptide in any aspect of the present invention. A conservative BoNT/A peptide variant may substitute one or more amino acids, two or more amino acids, three or more amino acids, four or more amino acids, five or more amino acids, ten or more amino acids, or 20 or more amino acids from the reference BoNT/A peptide on which the conservative BoNT/A peptide variant is based. A conservative BoNT/A peptide variant can also substitute at least two contiguous amino acids, at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids from the reference BoNT/A peptide on which the conservative BoNT/A peptide variant is based, that possess at least 50% amino acid identity, 65% amino acid identity, 75% amino acid identity, 85% amino acid identity or 95% amino acid identity to the reference BoNT/A peptide on which the conservative BoNT/A peptide variant is based.

As a non-limiting example, a conservative BoNT/A peptide variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative BoNT/A peptide variant also can be, for example, a sequence in which a first basic amino acid is conservatively substituted with a second basic amino acid such as arginine, lysine, histidine, 5-hydroxylysine, N-methyllysine or an analog thereof. Similarly, a conservative BoNT/A peptide variant can be, for example, a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative BoNT/A peptide variant can be, for example, a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof.

As a non-limiting example, conservative BoNT/A peptide variants include conservative variants of a BoNT/A peptide having residues 445-471 of SEQ ID NO: 1; such conservative variants can have, for example, an arginine for lysine substitution at position 456 and an isoleucine for leucine substitution at position 462. Additional conservative variants include conservative variants of the BoNT/A peptide having residues 487-513 of SEQ ID NO: 1; such conservative variants can have, for example, a glutamic acid for aspartic acid substitution at position 497; an asparagine for glutamine substitution at position 500; and a phenylalanine for tyrosine substitution at position 502.

As used herein, the term "non-conservative BoNT/A peptide variant" means a BoNT/A peptide in which 1) at least one amino acid is deleted from the BoNT/A peptide of SEQ ID NO: 1; 2) at least one amino acid added to the BoNT/A peptide of SEQ ID NO: 1; or 3) at least one amino acid is substituted by another amino acid or an amino acid analog that does not share any property similar to that of the original amino acid from the BoNT/A peptide of SEQ ID NO: 1. A non-conservative BoNT/A peptide variant can function in substantially the same manner as the reference BoNT/A peptide on which the non-conservative BoNT/A peptide variant is based, and can be substituted for the reference BoNT/A peptide in any aspect of the present invention. A non-conservative BoNT/A peptide variant can delete substitute one or more amino acids, two or more amino acids, three or more amino acids, four or more amino acids, five or more amino acids, ten or more amino acids, or 20 or more amino acids from the reference BoNT/A peptide on which the non-conservative BoNT/A peptide variant is based. A non-conservative BoNT/A peptide variant can add substitute one or more amino acids, two or more amino acids, three or more amino acids, four or more amino acids, five or more amino acids, ten or more amino acids, or 20 or more amino acids to the reference BoNT/A peptide on which the non-conservative BoNT/A peptide variant is based. A non-conservative BoNT/A variant may substitute one or more amino acids, two or more amino acids, three or more amino acids, four or more amino acids, five or more amino acids, ten or more amino acids, or 20 or more amino acids from the reference BoNT/A peptide on which the non-conservative BoNT/A peptide variant is based. A non-conservative BoNT/A peptide variant can also substitute at least two contiguous amino acids, at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids from the reference BoNT/A peptide on which the non-conservative BoNT/A peptide variant is based, that possess at least 50% amino acid identity, 65% amino acid identity, 75% amino acid identity, 85% amino acid identity or 95% amino acid identity to the reference BoNT/A peptide on which the non-conservative BoNT/A peptide variant is based.

As used herein, the term "immunoreactive BoNT/A peptide fragment" means a BoNT/A peptide capable of selectively binding an anti-BoNT/A antibody, with the proviso that the BoNT/A peptide is not SEQ ID NO: 2. As used herein, the term "selectively" means having a unique effect or influence or reacting in only one way or with only one thing. An immunoreactive BoNT/A peptide fragment can function in substantially the same manner as the BoNT/A peptide of SEQ ID NO: 1 and can be substituted for the BoNT/A peptide of SEQ ID NO: 1 in any aspect of the present invention. An immunoreactive BoNT/A peptide fragment can be capable of selective antibody binding to anti-BoNT/A antibodies from one or more species. An immunoreactive BoNT/A peptide fragment generally has from about five amino acids to 60 amino acids. An immunoreactive BoNT/A peptide fragment can have a length of at least five amino acids, at least six amino acids, at least seven amino acids, at least eight amino acids, at least nine amino acids, at least ten amino acids, at least 12 amino acids, at least 15 amino acids, at least 18 amino acids, at least 20 amino acids, or at least 25 amino acids. An immunoreactive BoNT/A peptide fragment also can have a length of at most five amino acids, at most six amino acids, at most seven amino acids, at most eight amino acids, at most nine amino acids, at most ten amino acids, at most 12 amino acids, at most 15 amino acids, at most 18 amino acids, at most 20 amino acids, at most 25 amino acids, at most 30 amino acids, at most 35 amino acids. In particular embodiments, an immunoreactive BoNT/A peptide fragment has from five to sixty amino acids, from five to fifty amino acids, from eight to fifty amino acids, from ten to fifty amino acids, from five to twenty amino acids, from eight to twenty amino acids, from ten to twenty amino acids, from twelve to twenty amino acids or from fifteen to twenty amino acids. An immunoreactive BoNT/A peptide fragment can have any number of conservative, non-conservative, analog or mimetic substitutions, and the like, as disclosed in the present specification.

An immunoreactive fragment can be identified using any of a variety of routine assays for detecting peptide antigen-antibody complexes, the presence of which is an indicator of selective binding. Such assays include, without limitation, enzyme-linked immunosorbent assays, radioimmunoassays, western blotting, enzyme immunoassays, fluorescence immunoassays, luminescent immunoassays and the like and generally are equivalent to the radioimmunoassay disclosed herein in Example 2. Methods for detecting a complex between a peptide and an antibody, and thereby determining if the peptide is an "immunoreactive fragment" are well known to those skilled in the art and are described, for example, in ANTIBODIES: A LABORATORY MANUAL (Edward Harlow & David Lane, eds., Cold Spring Harbor Laboratory Press, 2 ed. 1998a); and USING ANTIBODIES: A LABORATORY MANUAL: PORTABLE PROTOCOL No. I (Edward Harlow & David Lane, Cold Spring Harbor Laboratory Press, 1998b), which are hereby incorporated by reference in their entirety.

As used herein, the term "amino acid" means both naturally occurring and non-naturally occurring amino acids as well as amino acid analogs and mimetics, and includes, but is not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl. As such, a BoNT/A peptide such as, e.g., a native peptide, a conservative variant, a non-conservative variant, or an immunoreactive fragment, can contain one or more non-amide linkage substitutions between amino acids, one or more naturally occurring amino acid substitutions, one or more non-naturally occurring amino acid substitutions, one or more amino acid analog substitutions, or one or more mimetic substitutions. As used herein in reference to BoNT/A, the term "naturally occurring amino acid substitution" means a BoNT/A peptide that has been altered from the BoNT/A peptide of SEQ ID NO: 1 in which a first amino acid from the BoNT/A peptide of SEQ ID NO: 1 is substituted by a naturally occurring amino acid that has at least one property similar to that of the first amino acid. Examples of naturally occurring amino acids, include, without limitation, Naturally occurring amino acids include the 20 (L)-amino acids utilized during protein biosynthesis as well as others such as, without limitation, 4-hydroxyproline, hydroxylysine, demosine, isodemosine, homocysteine, citrulline and ornithine.

As used herein in reference to BoNT/A peptide, the term "non-naturally occurring amino acid substitution" means a BoNT/A peptide that has been altered from the BoNT/A peptide of SEQ ID NO: 1 in which a first amino acid from the BoNT/A peptide of SEQ ID NO: 1 is substituted by a non-naturally occurring amino acid that has at least one property similar to that of the first amino acid. Examples of non-naturally occurring amino acids, include, without limitation, (D)-amino acids, norleucine, norvaline, p-fluorophenylalanine, ethionine and the like.

As used herein in reference to BoNT/A peptide, the term "amino acid analog substitution" means a BoNT/A peptide that has been altered from the BoNT/A peptide of SEQ ID NO: 1 in which a first amino acid from the BoNT/A peptide of SEQ ID NO: 1 is substituted by a modified natural or non-natural amino acid that has at least one property similar to that of the first amino acid. Examples of modifications to either a naturally and non-naturally occurring amino acids, include, without limitation, substitution or replacement of chemical groups or moieties on the amino acid or by derivitization of the amino acid. A BoNT/A amino acid analog can function in substantially the same manner as the BoNT/A peptide of SEQ ID NO: 1 and can be substituted for the BoNT/A peptide of SEQ ID NO: 1 in any aspect of the present invention. A BoNT/A amino acid analog may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids from the BoNT/A peptide of SEQ ID NO: 1, or a portion thereof.

As used herein in reference to BoNT/A peptide, the term "mimetic substitution" means a BoNT/A peptide that has been altered from the BoNT/A peptide of SEQ ID NO: 1 in which a first amino acid from the BoNT/A peptide of SEQ ID NO: 1 is substituted by a non-natural structure that has at least one property similar to that of the first amino acid. Examples of mimetic properties include, without limitation, topography of a peptide primary structural element, functionality of a peptide primary structural element, topology of a peptide secondary structural element, functionality of a peptide secondary structural element, of the like, or any combination thereof. A BoNT/A mimetic can function in substantially the same manner as the BoNT/A peptide of SEQ ID NO: 1 and can be substituted for the BoNT/A peptide of SEQ ID NO: 1 in any aspect of the present invention. A BoNT/A mimetic may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids from the BoNT/A peptide of SEQ ID NO: 1, or a portion thereof. As an example, an organic structure that mimics arginine can have a positive charge moiety located in similar molecular space and having the same degree of mobility as the e-amino group of the side chain of the naturally occurring arginine amino acid.

Non-limiting examples of specific protocols for making and using naturally occurring amino acids, non-naturally occurring amino acids, amino acid analogs and mimetics are described in, e.g., John Jones, AMINO ACID PEPTIDE SYNTHESIS (Oxford University Press, 2 ed., 2002); Roberts and Vellaccio, p. 341 (THE PEPTIDES: ANALYSIS, SYNTHESIS, BIOLOGY Vol. 5, Erhard Gross & Johannes Meinhofer, eds., Academic Press, Inc., 1983); Mark J. Suto et al., *Cytokine Restraining Agents*, U.S. Pat. No. 5,420,109 (May 30, 1995); Chapter 7 of Bodanzsky, PRINCIPLES OF PEPTIDE SYNTHESIS (Springer-Verlag, 2 ed. 1993); Stewart and Young SOLID PHASE PEPTIDE SYNTHESIS, Pierce Chemical Co., 2 ed. 1984); FMOC SOLID PHASE PEPTIDE SYNTHESIS: A PRACTICAL APPROACH (Weng C. Chan & Peter D. White eds., Oxford University Press, 2000); Amy S. Ripka & Daniel H. Rich, *Peptidomimetic design*, 2(4) CURR. OPIN. CHEM. BIOL. 441-452 (1998); and M. Angels Estiarte & Daniel H. Rich, *Peptidomimetics for Drug Design*, 803-861 (BURGER'S MEDICINAL CHEMISTRY AND DRUG DISCOVERY Vol. 1 PRINCIPLE AND PRACTICE, Donald J. Abraham ed., Wiley-Interscience, $6^{th}$ ed 2003), which are hereby incorporated by reference. One skilled in the art understands that these and other well known amino acid analogs and mimetics can be useful in the BoNT/A peptides of the invention.

A BoNT/A peptide disclosed in the present specification, such as, e.g., native peptide, a conservative variant, a non-conservative variant, or an immunoreactive fragment, can be fused to a heterologous protein. As used herein, the term "heterologous protein" means a protein derived from a source other than the gene encoding the BoNT/A peptide of the invention, operationally linked to a BoNT/A peptide disclosed in the present specification, to form a chimeric BoNT/A protein. Such a chimeric BoNT/A protein of the invention can have a variety of lengths including, but not limited to, a length of at most 100 residues, at most 200 residues, at most 300 residues, at most 400 residues, at most 500 residues, at most 800 residues or at most 1000 residues. Non-limiting examples of chimeric BoNT/A proteins include fusions of BoNT/A peptides with immunogenic polypeptides, such as flagellin and cholera enterotoxin; fusions of BoNT/A peptides with immunomodulatory polypeptides, such as IL-2 and B7-1; fusions of BoNT/A peptides with tolerogenic polypeptides, such as another BoNT/A peptide and an antibody selectively reactive with interleukin-12; and fusions of BoNT/A peptides with synthetic sequences.

Any of a variety of sequence alignment methods can be used to determine percent identity of a naturally-occurring BoNT/A variant or a non-naturally-occurring BoNT/A variant, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: *Improving the Sensitivity of Progressive Multiple Sequence Alignment Through Sequence Weighting, Position-Specific Gap Penalties and Weight Matrix Choice,* 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments,* 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences,* 8(5) CABIOS 501-509 (1992); Gibbs sampling, see, e.g., C. E. Lawrence et al., *Detecting Subtle Sequence Signals: A Gibbs Sampling Strategy for Multiple Alignment,* 262(5131) Science 208-214 (1993); Align-M, see, e.g., Ivo Van Walle et al., *Align-M—A New Algorithm for Multiple Alignment of Highly Divergent Sequences,* 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison,* 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment,* 302(1) J. Mol. Biol. 205-217 (2000); MUSCLE, see, e.g., Robert C. Edgar, *MUSCLE: Multiple Sequence Alignment With High Score Accuracy and High Throughput,* 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment,* 6(1) BMC Bioinformatics 66 (2005).

Thus, in one embodiment, a BoNT/A peptide can comprise a length of at most 60 amino acids and consists of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant, or a non-conservative variant, or immunoreactive fragment thereof, with the proviso that the BoNT/A peptide is not SEQ ID NO: 5.

In one embodiment of the present invention, a BoNT/A peptide has a length of at most 60 amino acids and consists of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N1), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a BoNT/A peptide has a length of at most 60 amino acids and consists of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In another embodiment of the present invention, a BoNT/A composition comprises a BoNT/A peptide that has one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a BoNT/A composition comprises a BoNT/A peptide that has one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a BoNT/A peptide has a length of at most 60 amino acids and consists of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C1), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a conservative variant thereof.

In yet another aspect of this embodiment, a BoNT/A peptide has a length of at most 60 amino acids and consists of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a conservative variant thereof.

In yet another embodiment of the present invention, a BoNT/A peptide has a length of at most 60 amino acids and consists of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a non-conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a non-conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a non-conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a non-conservative variant thereof.

In yet another aspect of this embodiment, a BoNT/A peptide has a length of at most 60 amino acids and consists of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a non-conservative variant thereof.

In yet another embodiment of the present invention, a BoNT/A peptide has a length of at most 60 amino acids and consists of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or an immunoreactive fragment thereof, with the proviso that the BoNT/A peptide is not SEQ ID NO: 5. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1

(N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or an immunoreactive fragment thereof, with the proviso that the BoNT/A peptide is not SEQ ID NO: 5.

In yet another aspect of this embodiment, a BoNT/A peptide has a length of at most 60 amino acids and consists of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or an immunoreactive fragment thereof, with the proviso that the BoNT/A peptide is not SEQ ID NO: 5.

In is envisioned that a BoNT/A peptide disclosed in the present specification can have any of a variety of lengths from at least 5 amino acids to at most 60 amino acids. Therefore, aspects of this embodiment may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids. Other aspects of this embodiment may include a BoNT/A peptide with at least, e.g., five amino acids of SEQ ID NO: 1, six amino acids of SEQ ID NO: 1, seven amino acids of SEQ ID NO: 1, eight amino acids of SEQ ID NO: 1, nine amino acids of SEQ ID NO: 1, ten amino acids of SEQ ID NO: 1, 11 amino acids of SEQ ID NO: 1, 12 amino acids of SEQ ID NO: 1, 13 amino acids of SEQ ID NO: 1, 14 amino acids of SEQ ID NO: 1, 15 amino acids of SEQ ID NO: 1, 16 amino acids of SEQ ID NO: 1, 17 amino acids of SEQ ID NO: 1, 18 amino acids of SEQ ID NO: 1, 19 amino acids of SEQ ID NO: 1, 20 amino acids of SEQ ID NO: 1, 25 amino acids of SEQ ID NO: 1, 30 amino acids of SEQ ID NO: 1, 35 amino acids of SEQ ID NO: 1, 40 amino acids of SEQ ID NO: 1, 45 amino acids of SEQ ID NO: 1, 50 amino acids of SEQ ID NO: 1, 55 amino acids or 60 amino acids of SEQ ID NO: 1. In further embodiments, such a BoNT/A peptide of the invention may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids and consist of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C1), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30) or 1275-1296 of SEQ ID NO: 1 (C31), or a conservative variant, a non-conservative variant, or immunoreactive fragment thereof, with the proviso that the BoNT/A peptide is not SEQ ID NO: 5.

In another embodiment of the present invention, a BoNT/A peptide composition can comprise one BoNT/A peptide disclosed in the present specification. In another embodiment of the present invention, a BoNT/A peptide composition can comprise a plurality of BoNT/A peptides disclosed in the present specification. Thus, aspects of this embodiment can include one or more BoNT/A peptides, two or more BoNT/A peptides, three or more BoNT/A peptides, four or more BoNT/A peptides, five or more BoNT/A peptides, six or more BoNT/A peptides, seven or more BoNT/A peptides, eight or more BoNT/A peptides, nine or more BoNT/A peptides, ten or more BoNT/A peptides, 15 or more BoNT/A peptides, 20 or more BoNT/A peptides, 25 or more BoNT/A peptides or 30 or more BoNT/A peptides. In other aspects of this embodiment can include one or more conservative BoNT/A peptide variants, two or more conservative BoNT/A peptide variants, three or more conservative BoNT/A peptide variants, four or more conservative BoNT/A peptide variants, five or more conservative BoNT/A peptide variants, six or more conservative BoNT/A peptide variants, seven or more conservative BoNT/A peptide variants, eight or more conservative BoNT/A peptide variants, nine or more conservative BoNT/A peptide variants, ten or more conservative BoNT/A peptide variants, 15 or more conservative BoNT/A peptide variants, 20 or more conservative BoNT/A peptide variants, 25 or more conservative BoNT/A peptide variants or 30 or more conservative BoNT/A peptide variants.

In further aspects of this embodiment can include one or more non-conservative BoNT/A peptide variants, two or more non-conservative BoNT/A peptide variants, three or more non-conservative BoNT/A peptide variants, four or more non-conservative BoNT/A peptide variants, five or more non-conservative BoNT/A peptide variants, six or more non-conservative BoNT/A peptide variants, seven or more non-conservative BoNT/A peptide variants, eight or more non-conservative BoNT/A peptide variants, nine or more non-conservative BoNT/A peptide variants, ten or more non-conservative BoNT/A peptide variants, 15 or more non-conservative BoNT/A peptide variants, 20 or more non-conservative BoNT/A peptide variants, 25 or more non-conservative BoNT/A peptide variants or 30 or more non-conservative BoNT/A peptide variants.

In still other aspects of this embodiment can include one or more immunoreactive BoNT/A peptide fragments, two or more immunoreactive BoNT/A peptide fragments, three or more immunoreactive BoNT/A peptide fragments, four or more immunoreactive BoNT/A peptide fragments, five or more immunoreactive BoNT/A peptide fragments, six or more immunoreactive BoNT/A peptide fragments, seven or more immunoreactive BoNT/A peptide fragments, eight or more immunoreactive BoNT/A peptide fragments, nine or more BoNT/A peptides, ten or more immunoreactive BoNT/A peptide fragments, 15 or more immunoreactive BoNT/A peptide fragments, 20 or more immunoreactive BoNT/A peptide fragments, 25 or more immunoreactive BoNT/A peptide fragments or 30 or more immunoreactive BoNT/A peptide fragments. BoNT/A peptides disclosed in the present specification can be selected, for example, depending on immunological factors, such as potency of the peptide in inducing an immune response, and technical factors, such as chemical synthesis yields. It is also understood that the two or more BoNT/A peptides can be provided separately or as part of a compound molecule such as a chimeric peptide or heterologous protein.

In an aspect of this embodiment, a BoNT/A peptide composition comprises two or more of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the selected amino acid sequence is 533-551 of SEQ ID NO: 1 (N8) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 533-551 of SEQ ID NO: 1 (N8) and 981-999 of SEQ ID NO: 1 (C10), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 533-551 of SEQ ID NO: 1 (N8), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In a further aspect of this embodiment, one of the amino acid sequences selected is 785-803 of SEQ ID NO: 1 (N25) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 785-803 of SEQ ID NO: 1 (N25) and 981-999 of SEQ ID NO: 1 (C10), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 785-803 of SEQ ID NO: 1 (N25), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 813-831 of SEQ ID NO: 1 (N27) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 813-831 of SEQ ID NO: 1 (N27) and 981-999 of SEQ ID NO: 1 (C10), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 813-831 of SEQ ID NO: 1 (N27), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5.

In an aspect of this embodiment, a BoNT/A peptide composition comprises two or more of the following amino acid sequences: 659-677 of SEQ ID NO: 1 (N16), 729-747 of SEQ ID NO: 1 (N21), 799-817 of SEQ ID NO: 1 (N26), 1065-1083 of SEQ ID NO: 1 (C16), 1163-1181 of SEQ ID NO: 1 (C23), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the amino acid sequences selected is 1065-1083 of SEQ ID NO: 1 (C16) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 1065-1083 of SEQ ID NO: 1 (C16), 1163-1181 of SEQ ID NO: 1 (C23) and 1275-1296 of SEQ ID NO: 1 (C31), or a conservative variant, a non-conservative variant or an immunoreactive fragment thereof, with the proviso that the BoNT/A peptide is not SEQ ID NO: 5. In a further aspect of this embodiment, one of the amino acid sequences selected is 799-817 of SEQ ID NO: 1 (N26) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 799-817 of SEQ ID NO: 1 (N26) and 1065-1083 of SEQ ID NO: 1 (C16), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 799-817 of SEQ ID NO: 1 (N26), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 729-747 of SEQ ID NO: 1 (N21) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 729-747 of SEQ ID NO: 1 (N21) and 1065-1083 of SEQ ID NO: 1 (C16), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 729-747 of SEQ ID NO: 1 (N21), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5.

It is also envisioned that any and all combinations of BoNT/A peptides disclosed in the specification, including, e.g., BoNT/A peptides of SEQ ID NO: 1, conservative BoNT/A peptide variants, non-conservative BoNT/A peptide variants and immunoreactive BoNT/A peptide fragments. Thus, aspects of this embodiment include one or more BoNT/A peptides comprising one or more BoNT/A peptides of SEQ ID NO: 1 and one or more conservative BoNT/A peptide variants; one or more BoNT/A peptides of SEQ ID NO: 1 and one or more non-conservative BoNT/A peptide variants; one or more BoNT/A peptides of SEQ ID NO: 1 and one or more immunoreactive BoNT/A peptide fragments; one or more conservative BoNT/A peptide variants and one or more non-conservative BoNT/A peptide variants; one or more conservative BoNT/A peptide variants and one or more immunoreactive BoNT/A peptide fragments; one or more non-conservative BoNT/A peptide variants and one or more immunoreactive BoNT/A peptide fragments; one or more BoNT/A peptides of SEQ ID NO: 1, one or more conservative BoNT/A peptide variants and one or more non-conservative BoNT/A peptide variants; one or more BoNT/A peptides of SEQ ID NO: 1, one or more conservative BoNT/A peptide variants and one or more immunoreactive BoNT/A peptide fragments; one or more BoNT/A peptides of SEQ ID NO: 1, one or more non-conservative BoNT/A peptide variants and one or more immunoreactive BoNT/A peptide fragments; one or more conservative BoNT/A peptide variants, one or more non-conservative BoNT/A peptide variants and one or more immunoreactive BoNT/A peptide fragments; or one or more BoNT/A peptides of SEQ ID NO: 1, one or more conservative BoNT/A peptide variants, one or more non-conservative BoNT/A peptide variants and one or more immunoreactive BoNT/A peptide fragments.

II. BoNT/A Tolerogenic Compositions

Tolerance is an active antigen-dependent process that occurs in an individual in response to the antigen that results from a previous exposure to the same antigen. Generally speaking, the production of antibodies by an immune response occurs by a two-step process. Initially, B lymphocytes migrating through the lymphoid tissue are exposed to an antigen whereby these cells become partial activated. Subsequently, if a partially activated B cell encounters a T cell that has also been activated by the same antigen, antibodies against that antigen are produced. If the B cell does not receive the appropriate signal from the corresponding T cell, it will become inactive or die. Immune tolerance is a natural mechanism that eliminates development of B cells that target "self," rather than foreign antigens. Therapeutic methods using tolerogizing compositions can exploit this immune tolerance system. For example, binding of a tolerogizing composition to a specific B cell is thought to stop production of pathogenic antibodies by causing the inactivation or death of these pathogenic B cells. In general, a tolerogizing composition that can be used to tolerize B cells in an antigen-specific manner lacks the ability to activate T cells, but retains the ability to bind immune B cells. Therefore, an individual suffering from an immune response to a particular antigen can be treated with a tolerogizing composition and become "tolerized" to that particular antigen.

The present invention provides, in part, a tolerogizing composition comprising a BoNT/A peptide operably linked to a tolerogizing agent. Such tolerogizing compositions are useful for inducing specific immunological non-reactivity (tolerance) to a botulinum toxin antigen. It is envisioned that any of the BoNT/A peptides disclosed in the present specification can be useful in a tolerogizing composition, with the proviso that the BoNT/A peptide induces a specific immunological non-reactivity (tolerance) to a botulinum toxin antigen. Non-limiting examples include a BoNT/A peptide derived from a naturally occurring BoNT/A, and a BoNT/A peptide derived from a non-naturally occurring BoNT/A, such as, e.g., a conservative BoNT/A variant, a non-conservative BoNT/A variant and a chimeric BoNT/A peptide. BoNT/A peptides disclosed in the present specification can be selected, e.g., depending on immunological factors, such as potency of the peptide in inducing a tolerogizing response, and technical factors, such as chemical synthesis yields. It is also understood that the two or more different BoNT/A peptides can be provided separately or as part of a compound molecule such as a chimeric BoNT/A peptide.

It is envisioned that a wide variety of tolerogizing agents can be useful in a tolerogizing composition disclosed in the present specification. As used herein, the term "tolerogizing agent" means a molecule, compound or polymer that causes, promotes or enhances tolerogenic activity when combined with a BoNT/A peptide disclosed in the present specification. As non-limiting examples, a tolerogizing agent can be a liquid, solid, or emulsion, depending, for example, on the route of administration and physical properties of the tolerogizing agent. A tolerogizing agent is operably linked to a BoNT/A peptide disclosed in the present specification. As used herein, the term "operably linked" when used in reference to a tolerogizing composition means to covalently attach a tolerogizing agent to a BoNT/A peptide in a manner that renders the peptide tolerogenic. Such tolerogizing agents can be operably linked to a BoNT/A peptide, for example, as described in M. Zouhair Atassi & Tetsuo Ashizawa, PVA or PEG Conjugates of Peptides for Epitope-Specific Immunosuppression, U.S. Pat. No. 6,048,529 (Apr. 11, 2000); Emilio Barbera-Guillem & M. Bud Nelson, Compositions and Methods for Tolerization in Immune Complex-Mediated Disease Progression, U.S. Pat. No. 6,245,752 (Jun. 12, 2001); and Edward Jess Victoria et al., APL Immunoreactive Peptides, Conjugates Thereof and Methods of Treatment for APL Antibody-Mediated Pathologies, U.S. Pat. No. 6,410,775 (Jun. 25, 2002). A variety of tolerogizing agents are useful in the invention including, without limitation, polyethylene glycol (PEG), monomethoxypolyethylene glycol (mPEG), and polyvinyl alcohol (PVA). Additional molecules are also known in the art to cause, promote or enhance tolerance, see, e.g., Paul A. Barstad, & Gilbert M. Iverson, Composition For Inducing Humoral Anergy to an Immunogen Comprising a T Cell Epitope-Deficient Analog of the Immunogen Conjugated to a Nonimmunogenic Carrier. U.S. Pat. No. 5,268,454 (Dec. 7, 1993); M. Zouhair Atassi & Tetsuo Ashizawa, PVA or PEG Conjugates of Peptides for Epitope-Specific Immunosuppression, U.S. Pat. No. 6,048,529 (Apr. 11, 2000); and Stephen M. Coutts et al., Composition for Inducing Humoral Anergy to an Immunogen Comprising a T Cell Epitope-Deficient Analog of the Immunogen Conjugated to a Nonimmunogenic Valency Platform Molecule, U.S. Pat. No. 6,060,056 (May 9, 2000).

As used herein, the term "tolerogizing response" when used in reference to a tolerogizing composition comprising a BoNT/A peptide means a BoNT/A disclosed in the present specification that has tolerogenic activity as defined by the ability either alone, or in combination with one or more other molecules, to produce a decreased immunological response to an anti-BoNT antibody. A BoNT/A peptide exhibiting a tolerogizing response can be identified using any of a variety of assays, including in vitro assays such as T-cell proliferation or cytokine secretion assays and in vivo assays such as the induction of tolerance in animal models of botulinum toxicity. T-cell proliferation assays, for example, are well recognized in the art as predictive of tolerogenic activity, see, e.g., H. Miyahara et al., *Identification and Characterization Of A Major Tolerogenic T-Cell Epitope of Type II Collagen That Suppresses Arthritis in B10.RIII Mice*, 86(1) IMMUNOLOGY 110-115 (1995); and Knut E. A. Lundin et al, *Gliadin-Specific, HLA-DQ(Alpha 1\*0501,Beta 1\*0201) Restricted T Cells Isolated From the Small Intestinal Mucosa of Celiac Disease Patients*, 178(1) J. EXP. MED. 187-196 (1993). A T-cell proliferation assay can be performed, for example, by culturing T-cells with irradiated antigen-presenting cells, such as normal spleen cells, in microtiter wells for 3 days with varying concentrations of the BoNT/A peptide to be assayed; adding $^3$H-thymidine; and measuring incorporation of $^3$H-thymidine into DNA.

A BoNT/A peptide exhibiting a tolerogizing response can also be identified using a T-cell cytokine secretion assay known in the art. In such an assay, T cells can be cultured, for example, with irradiated antigen-presenting cells in microtiter wells with varying concentrations of the fragment of interest and, after three days, the culture supernatants can be assayed for IL-2, IL-4 or IFN-γ as described in C. Czerkinsky et al., *Detection of Human Cytokine-Secreting Cells in Distinct Anatomical Compartments*, 119 IMMUNOL. REV. 5-22 (1991).

A BoNT/A peptide exhibiting a tolerogizing response can additionally be identified by its ability to induce tolerance in vivo, as indicated by a decreased immunological response, which can be a decreased T-cell response, such as a decreased proliferative response or cytokine secretion response as described above, or a decreased antibody titer to the antigen. A neonatal or adult mouse can be tolerized with a fragment of a BoNT/A peptide, and a T-cell response or anti-BoNT/A antibody titer can be assayed after challenging by immunization. As an example, a neonatal mouse can be tolerized within 48 hours of birth by intraperitoneal administration of about 100 μg of a fragment of a BoNT/A peptide emulsified with incomplete Freund's adjuvant and subsequently immunized with BoNT/A at about 8 weeks of age, see, for example, Miyahara et al., supra, 1995. An adult mouse can be tolerized intravenously with about 0.33 mg of a fragment of a BoNT/A peptide, administered daily for three days (total dose 1 mg), and immunized one week later with BoNT/A. A decreased T-cell response, such as decreased proliferation or cytokine secretion, which indicates tolerogenic activity, can be measured using T-cells harvested 10 days after immunization. In addition, a decreased anti-BoNT/A antibody titer, which also indicates tolerogenic activity, can be assayed using blood harvested 4-8 weeks after immunization. Methods for assaying a T-cell response or anti-BoNT/A antibody titer are described above and are well known in the art.

Several well-accepted models of botulinum toxicity can be useful in identifying a BoNT/A peptide exhibiting a tolerogizing response. Such models include, without limitation, rodent, rabbit and monkey models of foodborne botulism, rodent and chicken models of infant botulism and rodent models of wound botulism, which are described, for example, in Simpson (Ed.) *Botulinum Neurotoxin and Tetanus Toxin* Academic Press, Inc., San Diego, Calif. (1989). The skilled person understands that these and a variety of other well known in vitro and in vivo assays can be useful for identifying a tolerogenic fragment of a BoNT/A peptide.

In is envisioned that a tolerogizing composition can also optionally comprises one or more adjuvants. As used herein, the term "adjuvant" when used in reference to a tolerogizing composition means any substance or mixture of substances that promotes or enhances tolerogenic activity. A tolerogizing adjuvant can, for example, serve to increase the solubility of a tolerogizing composition. The use of tolerogizing adjuvants in a tolerogizing composition is well known. These tolerogizing adjuvants are diverse in nature. They may, e.g., consist of liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide ($Al(OH)_3$) is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any tolerogizing adjuvant may be used in a tolerogizing composition disclosed in the present specification as long as the adjuvant satisfies the requisite characteristics that are necessary for practicing the present invention.

Thus, in an embodiment, a tolerogizing composition comprises a BoNT/A peptide disclosed in the present specification operably linked to a tolerogizing agent. In another embodiment, a tolerogizing composition can comprise a plurality of different BoNT/A peptides disclosed in the present specification each BoNT/A peptide operably linked to a tolerogizing agent. Thus, in aspects of this embodiment, a tolerogizing composition comprises one or more different BoNT/A peptides each BoNT/A peptide operably linked to a tolerogizing agent, two or more different BoNT/A peptides each BoNT/A peptide operably linked to a tolerogizing agent, three or more different BoNT/A peptides each BoNT/A peptide operably linked to a tolerogizing agent, four or more different BoNT/A peptides each BoNT/A peptide operably linked to a tolerogizing agent, five or more different BoNT/A peptides each BoNT/A peptide operably linked to a tolerogizing agent, six or more different BoNT/A peptides each BoNT/A peptide operably linked to a tolerogizing agent, seven or more different BoNT/A peptides each BoNT/A peptide operably linked to a tolerogizing agent, eight or more different BoNT/A peptides each BoNT/A peptide operably linked to a tolerogizing agent, nine or more different BoNT/A peptides each BoNT/A peptide operably linked to a tolerogizing agent, ten or more different BoNT/A peptides each BoNT/A peptide operably linked to a tolerogizing agent, 15 or more different BoNT/A peptides each BoNT/A peptide operably linked to a tolerogizing agent or 20 or more different BoNT/A peptides each BoNT/A peptide operably linked to a tolerogizing agent.

In another embodiment of the present invention, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant or immunoreactive fragment thereof, with the proviso that the BoNT/A peptide is not SEQ ID NO: 5.

In another embodiment of the present invention, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a tolerogizing composition comprises a tolerizing agent operationally linked to a BoNT/A peptide selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C1), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a tolerogizing composition comprises a tolerizing agent operationally linked to a BoNT/A peptide selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1

(N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a conservative variant thereof.

In yet another aspect of this embodiment, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a conservative variant thereof.

In yet another embodiment of the present invention, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a non-conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C1), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a non-conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a non-conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a non-conservative variant thereof.

In yet another aspect of this embodiment, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a non-conservative variant thereof.

In yet another embodiment of the present invention, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or an immunoreactive fragment thereof, with the proviso that the BoNT/A peptide is not SEQ ID NO: 5. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or an immunoreactive fragment thereof, with the proviso that the BoNT/A peptide is not SEQ ID NO: 5.

In yet another aspect of this embodiment, a tolerogizing composition comprises a tolerizing agent operationally linked to a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or an immunoreactive fragment thereof, with the proviso that the BoNT/A peptide is not SEQ ID NO: 5.

In is envisioned that a BoNT/A peptide useful in a tolerogizing composition disclosed in the present specification can have any of a variety of lengths from at least 5 amino acids to at most 60 amino acids. Therefore, aspects of this embodiment may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids. Other aspects of this embodiment may include a BoNT/A peptide with at least, e.g., five amino acids of SEQ ID NO: 1, six amino acids of SEQ ID NO: 1, seven amino acids of SEQ ID NO: 1, eight amino acids of SEQ ID NO: 1, nine amino acids of SEQ ID NO: 1, ten amino acids of SEQ ID NO: 1, 11 amino acids of SEQ ID NO: 1, 12 amino acids of SEQ ID NO: 1, 13 amino acids of SEQ ID NO: 1, 14 amino acids of SEQ ID NO: 1, 15 amino acids of SEQ ID NO: 1, 16 amino acids of SEQ ID NO: 1, 17 amino acids of SEQ ID NO: 1, 18 amino acids of SEQ ID NO: 1, 19 amino acids of SEQ ID NO: 1, 20 amino acids of SEQ ID NO: 1, 25 amino acids of SEQ ID NO: 1, 30 amino acids of SEQ ID NO: 1, 35 amino acids of SEQ ID NO: 1, 40 amino acids of SEQ ID NO: 1, 45 amino acids of SEQ ID NO: 1, 50 amino acids of SEQ ID NO: 1, 55 amino acids or 60 amino acids of SEQ ID NO: 1. In further embodiments, such a BoNT/A peptide of the invention may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids and consist of at least 5 contiguous amino acids selected from one of the following BoNT/A amino acid sequences:

449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30) or 1275-1296 of SEQ ID NO: 1 (C31), or a conservative variant, a non-conservative variant, or immunoreactive fragment thereof, with the proviso that the BoNT/A peptide is not SEQ ID NO: 5.

In another embodiment of the present invention, a tolerogizing composition can comprise one BoNT/A peptide disclosed in the present specification. In another embodiment of the present invention, a tolerogizing composition can comprise a plurality of BoNT/A peptides disclosed in the present specification. Thus, aspects of this embodiment can include one or more BoNT/A peptides, two or more BoNT/A peptides, three or more BoNT/A peptides, four or more BoNT/A peptides, five or more BoNT/A peptides, six or more BoNT/A peptides, seven or more BoNT/A peptides, eight or more BoNT/A peptides, nine or more BoNT/A peptides, ten or more BoNT/A peptides, 15 or more BoNT/A peptides, 20 or more BoNT/A peptides, 25 or more BoNT/A peptides or 30 or more BoNT/A peptides. In other aspects of this embodiment can include one or more conservative BoNT/A peptide variants, two or more conservative BoNT/A peptide variants, three or more conservative BoNT/A peptide variants, four or more conservative BoNT/A peptide variants, five or more conservative BoNT/A peptide variants, six or more conservative BoNT/A peptide variants, seven or more conservative BoNT/A peptide variants, eight or more conservative BoNT/A peptide variants, nine or more conservative BoNT/A peptide variants, ten or more conservative BoNT/A peptide variants, 15 or more conservative BoNT/A peptide variants, 20 or more conservative BoNT/A peptide variants, 25 or more conservative BoNT/A peptide variants or 30 or more conservative BoNT/A peptide variants. In further aspects of this embodiment can include one or more non-conservative BoNT/A peptide variants, two or more non-conservative BoNT/A peptide variants, three or more non-conservative BoNT/A peptide variants, four or more non-conservative BoNT/A peptide variants, five or more non-conservative BoNT/A peptide variants, six or more non-conservative BoNT/A peptide variants, seven or more non-conservative BoNT/A peptide variants, eight or more non-conservative BoNT/A peptide variants, nine or more non-conservative BoNT/A peptide variants, ten or more non-conservative BoNT/A peptide variants, 15 or more non-conservative BoNT/A peptide variants, 20 or more non-conservative BoNT/A peptide variants, 25 or more non-conservative BoNT/A peptide variants or 30 or more non-conservative BoNT/A peptide variants. In still other aspects of this embodiment can include one or more immunoreactive BoNT/A peptide fragments, two or more immunoreactive BoNT/A peptide fragments, three or more immunoreactive BoNT/A peptide fragments, four or more immunoreactive BoNT/A peptide fragments, five or more immunoreactive BoNT/A peptide fragments, six or more immunoreactive BoNT/A peptide fragments, seven or more immunoreactive BoNT/A peptide fragments, eight or more immunoreactive BoNT/A peptide fragments, nine or more BoNT/A peptides, ten or more immunoreactive BoNT/A peptide fragments, 15 or more immunoreactive BoNT/A peptide fragments, 20 or more immunoreactive BoNT/A peptide fragments, 25 or more immunoreactive BoNT/A peptide fragments or 30 or more immunoreactive BoNT/A peptide fragments. BoNT/A peptides disclosed in the present specification useful for a tolerogizing composition can be selected, for example, depending on immunological factors, such as potency of the peptide in inducing an immune response, and technical factors, such as chemical synthesis yields. It is also understood that the two or more BoNT/A peptides can be provided separately or as part of a compound molecule such as a chimeric peptide or heterologous protein.

In an aspect of this embodiment, a tolerogizing composition comprises a tolerizing agent operationally linked to two or more of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the selected amino acid sequence is 533-551 of SEQ ID NO: 1 (N8) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 533-551 of SEQ ID NO: 1 (N8) and 981-999 of SEQ ID NO: 1 (C10), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 533-551 of SEQ ID NO: 1 (N8), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In a further aspect of this embodiment, one of the amino acid sequences selected is 785-803 of SEQ ID NO: 1 (N25) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 785-803 of SEQ ID NO: 1 (N25) and 981-999 of SEQ ID NO: 1 (C10), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 785-803 of SEQ ID NO: 1 (N25), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 813-831 of SEQ ID NO: 1 (N27) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 813-831 of SEQ ID NO: 1 (N27) and 981-999 of SEQ ID NO: 1 (C10), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 813-831 of SEQ ID NO: 1 (N27), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5.

In an aspect of this embodiment, a tolerizing composition comprises a tolerizing agent operationally linked to two or more of the following amino acid sequences: 659-677 of SEQ ID NO: 1 (N16), 729-747 of SEQ ID NO: 1 (N21), 799-817 of SEQ ID NO: 1 (N26), 1065-1083 of SEQ ID NO: 1 (C16), 1163-1181 of SEQ ID NO: 1 (C23), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the amino acid sequences selected is 1065-1083 of SEQ ID NO: 1 (C16) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 1065-1083 of SEQ ID NO: 1 (C16), 1163-1181 of SEQ ID NO: 1 (C23) and 1275-1296 of SEQ ID NO: 1 (C31), or a conservative variant, a non-conservative variant or an immunoreactive fragment thereof, with the proviso that the BoNT/A peptide is not SEQ ID NO: 5. In a further aspect of this embodiment, one of the amino acid sequences selected is 799-817 of SEQ ID NO: 1 (N26) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 799-817 of SEQ ID NO: 1 (N26) and 1065-1083 of SEQ ID NO: 1 (C16), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 799-817 of SEQ ID NO: 1 (N26), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 729-747 of SEQ ID NO: 1 (N21) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 729-747 of SEQ ID NO: 1 (N21) and 1065-1083 of SEQ ID NO: 1 (C16), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 729-747 of SEQ ID NO: 1 (N21), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5.

It is also envisioned that any and all combinations of BoNT/A peptides disclosed in the specification, including, e.g., BoNT/A peptides of SEQ ID NO: 1, conservative BoNT/A peptide variants, non-conservative BoNT/A peptide variants and immunoreactive BoNT/A peptide fragments, can be used in a tolerogizing composition. Thus, aspects of this embodiment include one or more BoNT/A peptides comprising one or more BoNT/A peptides of SEQ ID NO: 1 and one or more conservative BoNT/A peptide variants; one or more BoNT/A peptides of SEQ ID NO: 1 and one or more non-conservative BoNT/A peptide variants; one or more BoNT/A peptides of SEQ ID NO: 1 and one or more immunoreactive BoNT/A peptide fragments; one or more conservative BoNT/A peptide variants and one or more non-conservative BoNT/A peptide variants; one or more conservative BoNT/A peptide variants and one or more immunoreactive BoNT/A peptide fragments; one or more non-conservative BoNT/A peptide variants and one or more immunoreactive BoNT/A peptide fragments; one or more BoNT/A peptides of SEQ ID NO: 1, one or more conservative BoNT/A peptide variants and one or more non-conservative BoNT/A peptide variants; one or more BoNT/A peptides of SEQ ID NO: 1, one or more conservative BoNT/A peptide variants and one or more immunoreactive BoNT/A peptide fragments; one or more BoNT/A peptides of SEQ ID NO: 1, one or more non-conservative BoNT/A peptide variants and one or more immunoreactive BoNT/A peptide fragments; one or more conservative BoNT/A peptide variants, one or more non-conservative BoNT/A peptide variants and one or more immunoreactive BoNT/A peptide fragments; or one or more BoNT/A peptides of SEQ ID NO: 1, one or more conservative BoNT/A peptide variants, one or more non-conservative BoNT/A peptide variants and one or more immunoreactive BoNT/A peptide fragments.

In another embodiment, a tolerogizing composition comprises a tolerogizing agent. In an aspect of this embodiment, a BoNT/A peptide is operably linked to polyethylene glycol (PEG). In another aspect of this embodiment, a BoNT/A peptide is operably linked to monomethoxypolyethylene glycol (mPEG). In another aspect of this embodiment, a BoNT/A peptide is operably linked to polyvinyl alcohol (PVA).

III. BoNT/A Immune Response Inducing Compositions

The present invention provides, in part, an immune response inducing composition comprising an adjuvant and a BoNT/A peptide. Such immune response inducing compositions are useful for inducing specific immunity against one or more botulinum toxins such as, e.g., BoNT/A. Such specific immunity can protect an individual from intoxication produced by exposure to botulinum toxin. As used herein, the term "immune response inducing composition" means a composition which, when administered to an individual, stimulates an immune response against an antigen. With reference to an immune response inducing composition comprising an adjuvant and a BoNT/A peptide, the antigen is a BoNT/A peptide disclosed in the present specification. The term "immune response" refers to any response by the immune system of an individual to an immune response inducing composition or other immunogenic compound. Exemplary immune responses include, but not limited to cellular as well as local and systemic humoral immunity, such as CTL responses, including antigen-specific induction of CD8+ CTLs, helper T-cell responses, including T-cell proliferative responses and cytokine release, and B-cell responses including, e.g., an antibody producing response. The term "inducing an immune response" refers to administration of an immune response inducing composition or other immunogenic compound or a nucleic acid encoding the immune response inducing composition or other immunogenic compound, wherein an immune response is affected, i.e., stimulated, initiated or induced. An immune response inducing composition can be useful, for example, for preventing or ameliorating intoxication produced by unwanted exposure to botulinum toxin. Administration of an immune response inducing composition has been shown to effectively block the effect of protein toxins, see, e.g., Behzod Z. Dolimbek & M. Zouhair Atassi, 13(5) J. PROT. CHEM. 490-493 (1994); M. Zouhair Atassi et al., *Antibody and T-Cell Recognition of Alpha-Bungarotoxin and its Synthetic Loop-Peptides,* 32(12) MOL. IMMUNOL. 919-929 (1995); and Behzod Z. Dolimbek et al., *Protection Against Alpha-Bungarotoxin Poisoning by Immunization with Synthetic Toxin Peptides,* 33(7-8) MOL. IMMUNOL. 681-689 (1996).

Thus, the present invention further provides a BoNT/A immune response inducing composition comprising a BoNT/A peptide disclosed in the present specification. In one embodiment of the present invention, a BoNT/A immune response inducing composition comprises a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a BoNT/A immune response inducing composition comprises a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a BoNT/A immune response inducing composition comprises a BoNT/A peptide selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a BoNT/A immune response inducing composition comprises a BoNT/A peptide selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1

(C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a BoNT/A immune response inducing composition comprises a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a conservative variant thereof.

In yet another aspect of this embodiment, a BoNT/A immune response inducing composition comprises a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a conservative variant thereof.

In yet another embodiment of the present invention, a BoNT/A immune response inducing composition comprises a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a non-conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a non-conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a non-conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a non-conservative variant thereof.

In yet another aspect of this embodiment, a BoNT/A immune response inducing composition comprises a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a non-conservative variant thereof.

In yet another embodiment of the present invention, a BoNT/A immune response inducing composition comprises a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or an immunoreactive fragment thereof, with the proviso that the BoNT/A peptide is not SEQ ID NO: 5. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1

(N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or an immunoreactive fragment thereof, with the proviso that the BoNT/A peptide is not SEQ ID NO: 5.

In yet another aspect of this embodiment, a BoNT/A immune response inducing composition comprises a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or an immunoreactive fragment thereof, with the proviso that the BoNT/A peptide is not SEQ ID NO: 5.

In is envisioned that a BoNT/A peptide useful in a BoNT/A immune response inducing composition disclosed in the present specification can have any of a variety of lengths from at least 5 amino acids to at most 60 amino acids. Therefore, aspects of this embodiment may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids. Other aspects of this embodiment may include a BoNT/A peptide with at least, e.g., five amino acids of SEQ ID NO: 1, six amino acids of SEQ ID NO: 1, seven amino acids of SEQ ID NO: 1, eight amino acids of SEQ ID NO: 1, nine amino acids of SEQ ID NO: 1, ten amino acids of SEQ ID NO: 1, 11 amino acids of SEQ ID NO: 1, 12 amino acids of SEQ ID NO: 1, 13 amino acids of SEQ ID NO: 1, 14 amino acids of SEQ ID NO: 1, 15 amino acids of SEQ ID NO: 1, 16 amino acids of SEQ ID NO: 1, 17 amino acids of SEQ ID NO: 1, 18 amino acids of SEQ ID NO: 1, 19 amino acids of SEQ ID NO: 1, 20 amino acids of SEQ ID NO: 1, 25 amino acids of SEQ ID NO: 1, 30 amino acids of SEQ ID NO: 1, 35 amino acids of SEQ ID NO: 1, 40 amino acids of SEQ ID NO: 1, 45 amino acids of SEQ ID NO: 1, 50 amino acids of SEQ ID NO: 1, 55 amino acids or 60 amino acids of SEQ ID NO: 1. In further embodiments, such a BoNT/A peptide of the invention may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids and consist of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30) or 1275-1296 of SEQ ID NO: 1 (C31), or a conservative variant, a non-conservative variant, or immunoreactive fragment thereof, with the proviso that the BoNT/A peptide is not SEQ ID NO: 5.

In another embodiment of the present invention, a BoNT/A immune response inducing composition can comprise one BoNT/A peptide disclosed in the present specification. In another embodiment of the present invention, a BoNT/A immune response inducing composition can comprise a plurality of BoNT/A peptides disclosed in the present specification. Thus, aspects of this embodiment can include one or more BoNT/A peptides, two or more BoNT/A peptides, three or more BoNT/A peptides, four or more BoNT/A peptides, five or more BoNT/A peptides, six or more BoNT/A peptides, seven or more BoNT/A peptides, eight or more BoNT/A peptides, nine or more BoNT/A peptides, ten or more BoNT/A peptides, 15 or more BoNT/A peptides, 20 or more BoNT/A peptides, 25 or more BoNT/A peptides or 30 or more BoNT/A peptides. In other aspects of this embodiment can include one or more conservative BoNT/A peptide variants, two or more conservative BoNT/A peptide variants, three or more conservative BoNT/A peptide variants, four or more conservative BoNT/A peptide variants, five or more conservative BoNT/A peptide variants, six or more conservative BoNT/A peptide variants, seven or more conservative BoNT/A peptide variants, eight or more conservative BoNT/A peptide variants, nine or more conservative BoNT/A peptide variants, ten or more conservative BoNT/A peptide variants, 15 or more conservative BoNT/A peptide variants, 20 or more conservative BoNT/A peptide variants, 25 or more conservative BoNT/A peptide variants or 30 or more conservative BoNT/A peptide variants. In further aspects of this embodiment can include one or more non-conservative BoNT/A peptide variants, two or more non-conservative BoNT/A peptide variants, three or more non-conservative BoNT/A peptide variants, four or more non-conservative BoNT/A peptide variants, five or more non-conservative BoNT/A peptide variants, six or more non-conservative BoNT/A peptide variants, seven or more non-conservative BoNT/A peptide variants, eight or more non-conservative BoNT/A peptide variants, nine or more non-conservative BoNT/A peptide variants, ten or more non-conservative BoNT/A peptide variants, 15 or more non-conservative BoNT/A peptide variants, 20 or more non-conservative BoNT/A peptide variants, 25 or more non-conservative BoNT/A peptide variants or 30 or more non-conservative BoNT/A peptide variants. In still other aspects of this embodiment can include one or more immunoreactive BoNT/A peptide fragments, two or more immunoreactive BoNT/A peptide fragments, three or more immunoreactive BoNT/A peptide fragments, four or more immunoreactive BoNT/A peptide fragments, five or more immunoreactive BoNT/A peptide fragments, six or more immunoreactive BoNT/A peptide fragments, seven or more immunoreactive BoNT/A peptide fragments, eight or more immunoreactive BoNT/A peptide fragments, nine or more BoNT/A peptides, ten or more immunoreactive BoNT/A peptide fragments, 15 or more immunoreactive BoNT/A peptide fragments, 20 or more immunoreactive BoNT/A peptide fragments, 25 or more immunoreactive BoNT/A peptide fragments or 30 or more immunoreactive BoNT/A peptide fragments. BoNT/A peptides disclosed in the present specification useful for a BoNT/A immune response inducing composition can be selected, for example, depending on immunological factors, such as potency of the peptide in inducing an immune response, and technical factors, such as chemical synthesis yields. It is also understood that the two or more BoNT/A peptides can be provided separately or as part of a compound molecule such as a chimeric peptide or heterologous protein.

In an aspect of this embodiment, a BoNT/A immune response inducing composition comprises two or more of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the selected amino acid sequence is 533-551 of SEQ ID NO: 1 (N8) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 533-551 of SEQ ID NO: 1 (N8) and 981-999 of SEQ ID NO: 1 (C10), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 533-551 of SEQ ID NO: 1 (N8), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In a further aspect of this embodiment, one of the amino acid sequences selected is 785-803 of SEQ ID NO: 1 (N25) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 785-803 of SEQ ID NO: 1 (N25) and 981-999 of SEQ ID NO: 1 (C10), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 785-803 of SEQ ID NO: 1 (N25), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 813-831 of SEQ ID NO: 1 (N27) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 813-831 of SEQ ID NO: 1 (N27) and 981-999 of SEQ ID NO: 1 (C10), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 813-

831 of SEQ ID NO: 1 (N27), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5.

In an aspect of this embodiment, a BoNT/A immune response inducing composition comprises two or more of the following amino acid sequences: 659-677 of SEQ ID NO: 1 (N16), 729-747 of SEQ ID NO: 1 (N21), 799-817 of SEQ ID NO: 1 (N26), 1065-1083 of SEQ ID NO: 1 (C16), 1163-1181 of SEQ ID NO: 1 (C23), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the amino acid sequences selected is 1065-1083 of SEQ ID NO: 1 (C16) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 1065-1083 of SEQ ID NO: 1 (C16), 1163-1181 of SEQ ID NO: 1 (C23) and 1275-1296 of SEQ ID NO: 1 (C31), or a conservative variant, a non-conservative variant or an immunoreactive fragment thereof, with the proviso that the BoNT/A peptide is not SEQ ID NO: 5. In a further aspect of this embodiment, one of the amino acid sequences selected is 799-817 of SEQ ID NO: 1 (N26) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 799-817 of SEQ ID NO: 1 (N26) and 1065-1083 of SEQ ID NO: 1 (C16), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 799-817 of SEQ ID NO: 1 (N26), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 729-747 of SEQ ID NO: 1 (N21) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 729-747 of SEQ ID NO: 1 (N21) and 1065-1083 of SEQ ID NO: 1 (C16), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 729-747 of SEQ ID NO: 1 (N21), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5.

It is also envisioned that any and all combinations of BoNT/A peptides disclosed in the specification, including, e.g., BoNT/A peptides of SEQ ID NO: 1, conservative BoNT/A peptide variants, non-conservative BoNT/A peptide variants and immunoreactive BoNT/A peptide fragments, can be used in a BoNT/A immune response inducing composition. Thus, aspects of this embodiment include one or more BoNT/A peptides comprising one or more BoNT/A peptides of SEQ ID NO: 1 and one or more conservative BoNT/A peptide variants; one or more BoNT/A peptides of SEQ ID NO: 1 and one or more non-conservative BoNT/A peptide variants; one or more BoNT/A peptides of SEQ ID NO: 1 and one or more immunoreactive BoNT/A peptide fragments; one or more conservative BoNT/A peptide variants and one or more non-conservative BoNT/A peptide variants; one or more conservative BoNT/A peptide variants and one or more immunoreactive BoNT/A peptide fragments; one or more non-conservative BoNT/A peptide variants and one or more immunoreactive BoNT/A peptide fragments; one or more BoNT/A peptides of SEQ ID NO: 1, one or more conservative BoNT/A peptide variants and one or more non-conservative BoNT/A peptide variants; one or more BoNT/A peptides of SEQ ID NO: 1, one or more conservative BoNT/A peptide variants and one or more immunoreactive BoNT/A peptide fragments; one or more BoNT/A peptides of SEQ ID NO: 1, one or more non-conservative BoNT/A peptide variants and one or more immunoreactive BoNT/A peptide fragments; one or more conservative BoNT/A peptide variants, one or more non-conservative BoNT/A peptide variants and one or more immunoreactive BoNT/A peptide fragments; or one or more BoNT/A peptides of SEQ ID NO: 1, one or more conservative BoNT/A peptide variants, one or more non-conservative BoNT/A peptide variants and one or more immunoreactive BoNT/A peptide fragments.

In yet another embodiment of the present invention, a BoNT/A immune response inducing composition can optionally comprises one or more carriers. The main objective of these carriers is to enhance the immunogenicity of an antigen, a hapten, or any other antigenic compound that is immunogenic, non-immunogenic, or weakly immunogenic when not associated with the carrier. The use of carriers in therapeutic compositions of the BoNT/A immune response inducing type is well known, see, e.g., David W. Waggoner, Jr. et al., Immunogenicity-enhancing carriers and compositions thereof and methods of using the same, U.S. Patent Publication No. 20040057958 (Mar. 25, 2004), which is hereby incorporated by reference in its entirety.

In yet another embodiment of the present invention, a BoNT/A immune response inducing composition also optionally comprises one or more adjuvants. The term "adjuvant", as used herein, means any substance or mixture of substances that increases or diversifies the immune response to an antigenic compound. An adjuvant can, for example, serve to reduce the number of immunizations or the amount of antigen required for protective immunization. In certain embodiments, an BoNT/A immune response inducing composition optionally comprises one or more adjuvants. The use of adjuvants in therapeutic compositions of the BoNT/A immune response inducing type is well known. The main objective of these adjuvants is to allow an increase in the immune response. These adjuvants are diverse in nature. They may, for example, consist of liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide (Al(OH).sub.3) is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any adjuvant may be used in the immunogenic composition of the present invention as long as the adjuvant satisfies the requisite characteristics that are necessary for practicing the present invention. As indicated above, the carrier of the compositions of the present invention itself may act as an adjuvant. Specific adjuvants and methods of making and using are are described in, e.g., Gupta et al. BoNT/A immune response inducing, 11: 993-306, 1993; Arnon, R. (Ed.) Synthetic BoNT/A immune response inducings 1:83-92, CRC Press, Inc., Boca Raton, Fla., 1987; and David W. Waggoner, Jr. et al., *Immunogenicity-Enhancing Carriers and Compositions Thereof and Methods of Using the Same*, U.S. Patent Publication No. 20040057958 (Mar. 25, 2004), which are hereby incorporated by reference in their entirety. Additional adjuvants include any compound described in Chapter 7 (pp 141-227) of "BoNT/A immune response inducing Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptomycin or a mixture thereof.

In yet another embodiment of the present invention, a BoNT/A immune response inducing composition can includes a BoNT/A peptide which is, for example, conjugated to, or expressed as, a fusion protein with another molecule. The molecule selected for fusion to a BoNT/A peptide will depend on the particular design of the BoNT/A immune response inducing. Non-limiting examples of BoNT/A fusion proteins useful in the invention include fusions with molecules that increase immune response against the BoNT/A peptide, such as cholera enterotoxin A2 and other peptides against which an immune response is desired, such as another BoNT peptide. In one embodiment, a BoNT/A immune response inducing of the invention contains a BoNT/A peptide fused to a peptide or protein adjuvant.

IV. BoNT/A Antibody Compositions

The present invention provides, in part, an antibody composition comprising an adjuvant and a BoNT/A peptide. Such antibody compositions are useful for stimulating an anti-BoNT/A antibody having selectivity for an epitope contained within a BoNT/A peptide disclosed in the present specification.

In one embodiment of the present invention, an antibody composition selectively binds to an eptiope contained within a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant or immunoreactive fragment thereof, with the proviso that the BoNT/A peptide is not SEQ ID NO: 5.

In another embodiment of the present invention, an antibody composition selectively binds to an eptiope contained within a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, an antibody composition selectively binds to an eptiope contained within a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, an antibody composition selectively binds to an eptiope contained within a BoNT/A peptide selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, an antibody composition selectively binds to an eptiope contained within a BoNT/A peptide selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1

(N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, an antibody composition selectively binds to an epitope contained within a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a conservative variant thereof.

In yet another aspect of this embodiment, an antibody composition selectively binds to an epitope contained within a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28)

or 1275-1296 of SEQ ID NO: 1 (C31), or a conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a conservative variant thereof.

In yet another embodiment of the present invention, an antibody composition selectively binds to an epitope contained within a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a non-conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a non-conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a non-conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a non-conservative variant thereof.

In yet another aspect of this embodiment, an antibody composition selectively binds to an epitope contained within a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a non-conservative variant thereof.

In yet another embodiment of the present invention, an antibody composition selectively binds to an epitope contained within a BoNT/A peptide having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or an immunoreactive fragment thereof, with the proviso that the BoNT/A peptide is not SEQ ID NO: 5. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or an immunoreactive fragment thereof, with the proviso that the BoNT/A peptide is not SEQ ID NO: 5.

In yet another aspect of this embodiment, an antibody composition selectively binds to an epitope contained within a BoNT/A peptide having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or an immunoreactive fragment thereof, with the proviso that the BoNT/A peptide is not SEQ ID NO: 5.

In is envisioned that a BoNT/A peptide useful as an epitope for an antibody composition disclosed in the present specification can have any of a variety of lengths from at least 5 amino acids to at most 60 amino acids. Therefore, aspects of this embodiment may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids. Other aspects of this embodiment may include a BoNT/A peptide with at least, e.g., five amino acids of SEQ ID NO: 1, six amino acids of SEQ ID NO: 1, seven amino acids of SEQ ID NO: 1, eight amino acids of SEQ ID NO: 1, nine amino acids of SEQ ID NO: 1, ten amino acids of SEQ ID NO: 1, 11 amino acids of SEQ ID NO: 1, 12 amino acids of SEQ ID NO: 1, 13 amino acids of SEQ ID NO: 1, 14 amino acids of SEQ ID NO: 1, 15 amino acids of SEQ ID NO: 1, 16 amino acids of SEQ ID NO: 1, 17 amino acids of SEQ ID NO: 1, 18 amino acids of SEQ ID NO: 1, 19 amino acids of SEQ ID NO: 1, 20 amino acids of SEQ ID NO: 1, amino acids of SEQ ID NO: 1, 30 amino acids of SEQ ID NO: 1, 35 amino acids of SEQ ID NO: 1, 40 amino acids of SEQ ID NO: 1, 45 amino acids of SEQ ID NO: 1, 50 amino acids of SEQ ID NO: 1, 55 amino acids or 60 amino acids of SEQ ID NO: 1. In further embodiments, such a BoNT/A peptide of the invention may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids and consist of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30) or 1275-1296 of SEQ ID NO: 1 (C31), or a conservative variant, a non-conservative variant, or immunoreactive fragment thereof, with the proviso that the BoNT/A peptide is not SEQ ID NO: 5.

In another embodiment of the present invention, a BoNT/A peptide useful as an epitope for an antibody composition can comprise one BoNT/A peptide disclosed in the present specification. In another embodiment of the present invention, a BoNT/A peptide useful as an epitope for an antibody composition can comprise a plurality of BoNT/A peptides disclosed in the present specification. Thus, aspects of this embodiment can include one or more BoNT/A peptides, two or more BoNT/A peptides, three or more BoNT/A peptides, four or more BoNT/A peptides, five or more BoNT/A peptides, six or more BoNT/A peptides, seven or more BoNT/A peptides, eight or more BoNT/A peptides, nine or more BoNT/A peptides, ten or more BoNT/A peptides, 15 or more BoNT/A peptides, 20 or more BoNT/A peptides, 25 or more BoNT/A peptides or 30 or more BoNT/A peptides. In other aspects of this embodiment can include one or more conservative BoNT/A peptide variants, two or more conservative BoNT/A peptide variants, three or more conservative BoNT/A peptide variants, four or more conservative BoNT/A peptide variants, five or more conservative BoNT/A peptide variants, six or more conservative BoNT/A peptide variants, seven or more conservative BoNT/A peptide variants, eight or more conservative BoNT/A peptide variants, nine or more conservative BoNT/A peptide variants, ten or more conservative BoNT/A peptide variants, 15 or more conservative BoNT/A peptide variants, 20 or more conservative BoNT/A peptide variants, 25 or more conservative BoNT/A peptide variants or 30 or more conservative BoNT/A peptide variants. In further aspects of this embodiment can include one or more non-conservative BoNT/A peptide variants, two or more non-conservative BoNT/A peptide variants, three or more non-conservative BoNT/A peptide variants, four or more non-conservative BoNT/A peptide variants, five or more non-conservative BoNT/A peptide variants, six or more non-conservative BoNT/A peptide variants, seven or more non-conservative BoNT/A peptide variants, eight or more non-conservative BoNT/A peptide variants, nine or more non-conservative BoNT/A peptide variants, ten or more non-conservative BoNT/A peptide variants, 15 or more non-conservative BoNT/A peptide variants, 20 or more non-conservative BoNT/A peptide variants, 25 or more non-conservative BoNT/A peptide variants or 30 or more non-conservative BoNT/A peptide variants. In still other aspects of this embodiment can include one or more immunoreactive BoNT/A peptide fragments, two or more immunoreactive BoNT/A peptide fragments, three or more immunoreactive BoNT/A peptide fragments, four or more immunoreactive BoNT/A peptide fragments, five or more immunoreactive BoNT/A peptide fragments, six or more immunoreactive BoNT/A peptide fragments, seven or more immunoreactive BoNT/A peptide fragments, eight or more immunoreactive BoNT/A peptide fragments, nine or more BoNT/A peptides, ten or more immunoreactive BoNT/A peptide fragments, 15 or more immunoreactive BoNT/A peptide fragments, 20 or more immunoreactive BoNT/A peptide fragments, 25 or more immunoreactive BoNT/A peptide fragments or 30 or more immunoreactive BoNT/A peptide fragments. BoNT/A peptides disclosed in the present specification useful as an epitope for an antibody composition can be selected, for example, depending on immunological factors, such as potency of the peptide in inducing an immune response, and technical factors, such as chemical synthesis yields. It is also understood that the two or more BoNT/A peptides can be provided separately or as part of a compound molecule such as a chimeric peptide or heterologous protein.

It is also envisioned that any and all combinations of BoNT/A peptides disclosed in the specification, including, e.g., BoNT/A peptides of SEQ ID NO: 1, conservative BoNT/A peptide variants, non-conservative BoNT/A peptide variants and immunoreactive BoNT/A peptide fragments, can be useful as an epitope for an antibody composition. Thus, aspects of this embodiment include one or more BoNT/A peptides comprising one or more BoNT/A peptides of SEQ ID NO: 1 and one or more conservative BoNT/A peptide variants; one or more BoNT/A peptides of SEQ ID NO: 1 and one or more non-conservative BoNT/A peptide variants; one or more BoNT/A peptides of SEQ ID NO: 1 and one or more immunoreactive BoNT/A peptide fragments; one or more conservative BoNT/A peptide variants and one or more non-conservative BoNT/A peptide variants; one or more conservative BoNT/A peptide variants and one or more immunoreactive BoNT/A peptide fragments; one or more non-conservative BoNT/A peptide variants and one or more immunoreactive BoNT/A peptide fragments; one or more BoNT/A peptides of SEQ ID NO: 1, one or more conservative BoNT/A peptide variants and one or more non-conservative BoNT/A peptide variants; one or more BoNT/A peptides of SEQ ID NO: 1, one or more conservative BoNT/A peptide variants and one or more immunoreactive BoNT/A peptide fragments; one or more BoNT/A peptides of SEQ ID NO: 1, one or more non-conservative BoNT/A peptide variants and one or more immunoreactive BoNT/A peptide fragments; one or more conservative BoNT/A peptide variants, one or more non-conservative BoNT/A peptide variants and one or more immunoreactive BoNT/A peptide fragments; or one or more BoNT/A peptides of SEQ ID NO: 1, one or more conservative BoNT/A peptide variants, one or more non-conservative BoNT/A peptide variants and one or more immunoreactive BoNT/A peptide fragments.

The term "antibody", as used herein, includes polyclonal and monoclonal antibodies, as well as antigenic compound-binding fragments of such antibodies including, without limitation, Fab, F(ab').sub.2, Fd, Fv fragments, and single chain derivatives of the same. "Antibody" also includes cell-associated antibodies, such as Ig receptors, for example. In addition, the term "antibody" includes naturally occurring antibodies, as well as non-naturally occurring antibodies, including, for example, chimeric, bifunctional, and humanized antibodies, and related synthetic isoforms. As used herein, an "epitope" means the site on an antigen that is recognized and bound by a particular antibody or T-cell receptor. The minimal size of a protein epitope, as defined herein, is about five amino acids, and a protein epitope typically comprises at least eight amino acids. It is to be noted, however, that an epitope might comprise a portion of an antigen other than the amino acid sequence, e.g., a carbohydrate moiety or a lipid moiety. Furthermore, an epitope may be discontinuous, i.e., it comprises amino acid residues that are not adjacent in the polypeptide but are brought together into an epitope by way of the secondary, tertiary, or quaternary structure of the protein. As used herein, the term "selectively binds" means the discriminatory binding of the antibody to the indicated target peptide or polypeptide such that the antibody does not substantially cross react with unrelated peptides or polypeptides. Specific reactivity can include binding properties such as binding specificity, binding affinity and binding avidity. For example, an antibody can bind a target peptide or polypeptide with a binding affinity (Kd) of about $10^{-4}$ M or more, $10^{-6}$ M or more, $10^{-7}$ M or more, $10^{-8}$ M or more, $10^{-9}$ M or more, or $10^{-10}$ M or more. Specific protocols for making and using antibodies as well as detecting, and measuring antibody binding are known in the art and disclosed herein, see, e.g., Harlow & Lane, supra, 1998a; Harlow & Lane, supra, 1998b; MOLECULAR CLONING, A LABORATORY MANUAL, supra, 2001; and CURRENT PROTOCOLS IN MOLECULAR BIOLOGY, supra, 2004. BoNT/A peptides disclosed in the present specification used to selectively bind an antibody composition disclosed in the present specification can be selected, for example, depending on immunological factors, such as potency of the peptide in inducing a tolerogizing response, and technical factors, such as chemical synthesis yields.

V. Methods of Determining BoNT/A Immunoresistance

Patients treated with a BoNT therapy can develop immunoresistance to the treatment, thereby reducing or eliminating the beneficial effect of the BoNT therapy. Therefore, methods that determine whether a patient is mounting an immune response against a BoNT therapy are of major importance. These assays would allow the immunoresponsive state of the patient to be evaluated periodically during the course of a BoNT therapy. By knowing the predisposition of an individual 1) the potential value of a specific BoNT treatment can be determined prior to its administration to a patient; and 2) the possible benefit from continued BoNT therapy can be assessed and any possible adjustments to a treatment determined. Therefore, these assays present a major benefit in terms of providing better patient care and reducing health care costs. The BoNT/A peptides disclosed in the present specification are useful in methods of determining immunoresistance to BoNT therapy in an individual. For example, these peptides each contain one or more epitopes recognized by anti-BoNT/A antibodies contained in antisera from animals immunized with BoNT/A, and thus can serve as binding substrates for anti-BoNT antibodies.

Thus, the present invention provides, in part, a method of determining immunoresistance to botulinum toxin therapy in an individual by detecting the presence or absence in the individual of anti-botulinum toxin antibodies immunoreactive with a BoNT/A peptide disclosed in the present specification, where the presence of anti-BoNT antibodies immunoreactive with the a BoNT/A peptide indicates immunoresistance to botulinum toxin therapy.

The present invention also provides, in part, a method of determining immunoresistance to botulinum toxin therapy in an individual, the method comprising the steps of contacting a BoNT/A peptide and test sample and detecting the amount of complexes formed by the BoNT/A peptide and an anti-botulinum toxin antibody, where the presence of the antibody-peptide complex indicates immunoresistance to a botulinum toxin therapy.

The present invention also provides, in part, a method of determining immunoresistance to BoNT therapy in an individual, the method comprising the steps of contacting a BoNT/A peptide and a test sample, detecting the amount of complexes formed by the BoNT/A peptide and anti-BoNT antibody and correlating the amount of the antibody-peptide complexes formed from the test sample relative to the amount of complexes formed by the BoNT/A peptide and the anti-BoNT antibody from a control sample.

The present invention also provides, in part, a method of determining immunoresistance to botulinum toxin therapy in an individual, the method comprising the steps of contacting a test sample from said individual with a BoNT/A peptide immunoreactive to an anti-botulinum toxin antibody under conditions suitable for forming an immunoreactive complex of said immunoreactive BoNT/A peptide and said anti-botulinum toxin antibody and detecting the presence or absence of said immunoreactive complex; wherein the presence of said immunoreactive complex indicates immunoresistance to a botulinum toxin therapy.

The present invention also provides, in part, a method of determining immunoresistance to botulinum toxin therapy in an individual, the methods comprising the steps of contacting a BoNT/A peptide and a test sample under conditions suitable for the selective binding of the BoNT/A peptide to an anti-botulinum toxin antibody and detecting the presence of an anti-botulinum toxin antibody-BoNT/A peptide complex, the antibody-peptide complex formed by the selective binding of an anti-botulinum toxin antibody and the BoNT/A peptide, where the presence of the anti-botulinum toxin antibody-BoNT/A peptide complex indicates immunoresistance to a botulinum toxin therapy.

It is further understood that a methods of determining immunoresistance to BoNT therapy in an individual can be used to predict the likelihood of the individual developing immunoresistance or to confirm that the presence of anti-BoNT antibodies are a cause underlying immunoresistance to botulinum toxin therapy.

Aspects of the present invention provide, in part, determining immunoresistance to botulinum toxin therapy in an individual. As used herein, the term "immunoresistance," when used in reference to botulinum toxin therapy, means an individual that does not fully respond to a botulinum toxin therapy, or shows a reduced beneficial effect of botulinum toxin therapy resulting from the presence in the individual of anti-botulinum toxin antibodies that bind to a botulinum toxin. Non-limiting examples of a botulinum toxin immunoresistance include, e.g., a BoNT/A immunoresistance, a BoNT/B immunoresistance, a BoNT/C1 immunoresistance, a BoNT/D immunoresistance, a BoNT/E immunoresistance, a BoNT/F immunoresistance and a BoNT/G immunoresistance. A non-limiting example of reduced efficacy would be the presence in an individual of at least one neutralizing anti-BoNT/A antibody that binds to a BoNT/A toxin in a manner that reduces or prevents the specificity or activity of the toxin. Another non-limiting example of reduced efficacy would be the presence in an individual of at least one neutralizing anti-BoNT/B antibody that binds to a BoNT/B toxin in a manner that reduces or prevents the specificity or activity of the toxin. As used herein, the term "botulinum toxin therapy" is synonymous with "BoNT therapy" and means a treatment, remedy, cure, healing, rehabilitation or any other means of counteracting something undesirable in a mammal requiring neuromodulation using a botulinum toxin or administering to a mammal one or more controlled doses of a medication, preparation or mixture of a botulinum toxin that has medicinal, therapeutic, curative, cosmetic, remedial or any other beneficial effect. Non-limiting examples of a botulinum toxin therapy include, e.g., a BoNT/A therapy, a BoNT/B therapy, a BoNT/C1 therapy, a BoNT/D therapy, a BoNT/E therapy, a BoNT/F therapy and a BoNT/G therapy. The term botulinum toxin therapy encompasses, without limitation, the use of any naturally occurring or modified or engineered form of a botulinum toxin or a domain or fragment thereof, in any formulation, combined with any carrier or active ingredient and administered by any route of administration. Well-known botulinum toxin therapies include, without limitation, a BoNT/A therapy, such as, e.g., a BOTOX® therapy, a Dysport®/Reloxin® therapy, a Linurase® therapy, a Neuronox® therapy, a BTX-A therapy, and a Xeomin® therapy; and a BoNT/B therapy, such as, e.g., a MyoBloc™/NeuroBloc™ therapy. Appropriate therapeutic and cosmetic uses of a botulinum toxin therapy are known in the art. As used herein, the term "individual," when used in reference to botulinum toxin therapy, means any organism capable of raising anti-BoNT antibodies against a BoNT toxin, including, but not limited to, birds and mammals, including mice, rats, goats, sheep, horses, donkeys, cows, primates and humans.

Thus, the present invention provides a method of determining immunoresistance to botulinum toxin therapy in an individual by determining the presence or absence in the individual of antibodies immunoreactive with a BoNT/A peptide composition disclosed in the present specification, where the presence of antibodies immunoreactive with the a BoNT/A peptide indicates immunoresistance to BoNT/A therapy. In one embodiment of the present invention, a method of determining the presence or absence of an anti-BoNT/A antibody in an individual comprises the steps of combining a BoNT/A peptide and test sample and detecting the amount of complexes formed by said BoNT/A peptide and anti-BoNT/A antibody. In a preferred embodiment of the present invention, a method of determining the presence or absence of an anti-BoNT/A antibody in an individual comprises the steps of combining a BoNT/A peptide and a test sample, detecting the amount of complexes formed by said BoNT/A peptide and BoNT/A antibody and correlating the amount of said complexes formed from said test sample relative to the amount of complexes formed by said BoNT/A peptide and said antibody from a control sample.

In one aspect of the present invention, all steps of a method for determining the presence or absence of a BoNT/A antibody are performed in solution. In other aspects of the method disclosed in the present specification, it is also envisioned that a method can optionally attach an assay component to a solid or insoluble material. Such a solid support can be, without limitation, e.g., a tube; plate; pins or "dipsticks"; column; particle, bead or other spherical or fibrous chromatographic media, such as, e.g., agarose beads, sepharose beads, silica beads and plastic beads; sheets or membranes, such as, e.g., nitrocellulose and polyvinylidene fluoride (PVDF). The solid support selected can have a physical property that renders it readily separable from soluble or unbound material and generally allows unbound materials, such as, e.g., excess reagents, reaction by-products, or solvents, to be separated or otherwise removed (by, e.g., washing, filtration, centrifugation, etc.) from solid support-bound assay component. Non-limiting examples of how to make and use a solid support-bound assay component are described in, e.g., MOLECULAR CLONING, A LABORATORY MANUAL, supra, 2001; and CURRENT PROTOCOLS IN MOLECULAR BIOLOGY, supra, 2004.

It is envisioned that any and all BoNT/A peptides disclosed in the present specification capable of selectively binding with an anti-botulinum toxin antibody can be useful in a method for determining immunoresistance to botulinum toxin therapy in an individual, including, without limitation, a BoNT/A derived from a naturally occurring BoNT/A, a BoNT/A derived from a non-naturally occurring BoNT/A and a BoNT/A comprising an immunoreactive fragment of the BoNT/A peptide, the BoNT/A peptide derived from a naturally occurring BoNT/A or a non-naturally occurring BoNT/A.

Thus, in an embodiment of the present invention, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant or immunoreactive fragment thereof, with the proviso that the BoNT/A peptide is not SEQ ID NO: 5.

In another embodiment of the present invention, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a BoNT/A peptide useful in a method disclosed in the present specification for determining the presence or absence of an anti-BoNT/A antibody is selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, a BoNT/A peptide useful in a method disclosed in the present specification for determining the presence or absence of an anti-BoNT/A antibody is selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a conservative variant thereof.

In yet another aspect of this embodiment, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a conservative variant thereof.

In yet another embodiment of the present invention, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a non-conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a non-conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a non-conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a non-conservative variant thereof.

In yet another aspect of this embodiment, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a non-conservative variant thereof.

In yet another embodiment of the present invention, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or an immunoreactive fragment thereof, with the proviso that the BoNT/A peptide is not SEQ ID NO: 5. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or an immunoreactive fragment thereof, with the proviso that the BoNT/A peptide is not SEQ ID NO: 5.

In yet another aspect of this embodiment, a BoNT/A peptide useful in a method disclosed in the present specification for determining the presence or absence of an anti-BoNT/A antibody has a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or an immunoreactive fragment thereof, with the proviso that the BoNT/A peptide is not SEQ ID NO: 5.

In is envisioned that a BoNT/A peptide useful in a method disclosed in the present specification for determining the presence or absence of an anti-BoNT/A antibody can have any of a variety of lengths from at least 5 amino acids to at most 60 amino acids. Therefore, aspects of this embodiment may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids. Other aspects of this embodiment may include a BoNT/A peptide with at least, e.g., five amino acids of SEQ ID NO: 1, six amino acids of SEQ ID NO: 1, seven amino acids of SEQ ID NO: 1, eight amino acids of SEQ ID NO: 1, nine amino acids of SEQ ID NO: 1, ten amino acids of SEQ ID NO: 1, 11 amino acids of SEQ ID NO: 1, 12 amino acids of SEQ ID NO: 1, 13 amino acids of SEQ ID NO: 1, 14 amino acids of SEQ ID NO: 1, 15 amino acids of SEQ ID NO: 1, 16 amino acids of SEQ ID NO: 1, 17 amino acids of SEQ ID NO: 1, 18 amino acids of SEQ ID NO: 1, 19 amino acids of SEQ ID NO: 1, 20 amino acids of SEQ ID NO: 1, 25 amino acids of SEQ ID NO: 1, 30 amino acids of SEQ ID NO: 1, 35 amino acids of SEQ ID NO: 1, 40 amino acids of SEQ ID NO: 1, 45 amino acids of SEQ ID NO: 1, 50 amino acids of SEQ ID NO: 1, 55 amino acids or 60 amino acids of SEQ ID NO: 1. In further embodiments, such a BoNT/A peptide of the invention may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids and consist of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30) or 1275-1296 of SEQ ID NO: 1 (C31), or a conservative variant, a non-conservative variant, or immunoreactive fragment thereof, with the proviso that the BoNT/A peptide is not SEQ ID NO: 5.

In another embodiment of the present invention, a BoNT/A peptide useful in a method disclosed in the present specification for determining the presence or absence of an anti-BoNT/A antibody can comprise one BoNT/A peptide disclosed in the present specification. In another embodiment of the present invention, a BoNT/A peptide useful in a method disclosed in the present specification for determining the presence or absence of an anti-BoNT/A antibody can comprise a plurality of BoNT/A peptides disclosed in the present specification. Thus, aspects of this embodiment can include one or more BoNT/A peptides, two or more BoNT/A peptides, three or more BoNT/A peptides, four or more BoNT/A peptides, five or more BoNT/A peptides, six or more BoNT/A peptides, seven or more BoNT/A peptides, eight or more BoNT/A peptides, nine or more BoNT/A peptides, ten or more BoNT/A peptides, 15 or more BoNT/A peptides, 20 or more BoNT/A peptides, 25 or more BoNT/A peptides or 30 or more BoNT/A peptides. In other aspects of this embodiment can include one or more conservative BoNT/A peptide variants, two or more conservative BoNT/A peptide variants, three or more conservative BoNT/A peptide variants, four or more conservative BoNT/A peptide variants, five or more conservative BoNT/A peptide variants, six or more conservative BoNT/A peptide variants, seven or more conservative BoNT/A peptide variants, eight or more conservative BoNT/A peptide variants, nine or more conservative BoNT/A peptide variants, ten or more conservative BoNT/A peptide variants, 15 or more conservative BoNT/A peptide variants, 20 or more conservative BoNT/A peptide variants, 25 or more conservative BoNT/A peptide variants or 30 or more conservative BoNT/A peptide variants. In further aspects of this embodiment can include one or more non-conservative BoNT/A peptide variants, two or more non-conservative BoNT/A peptide variants, three or more non-conservative BoNT/A peptide variants, four or more non-conservative BoNT/A peptide variants, five or more non-conservative BoNT/A peptide variants, six or more non-conservative BoNT/A peptide variants, seven or more non-conservative BoNT/A peptide variants, eight or more non-conservative BoNT/A peptide variants, nine or more non-conservative BoNT/A peptide variants, ten or more non-conservative BoNT/A peptide variants, 15 or more non-conservative BoNT/A peptide variants, 20 or more non-conservative BoNT/A peptide variants, 25 or more non-conservative BoNT/A peptide variants or 30 or more non-conservative BoNT/A peptide variants. In still other aspects of this embodiment can include one or more immunoreactive BoNT/A peptide fragments, two or more immunoreactive BoNT/A peptide fragments, three or more immunoreactive BoNT/A peptide fragments, four or more immunoreactive BoNT/A peptide fragments, five or more immunoreactive BoNT/A peptide fragments, six or more immunoreactive BoNT/A peptide fragments, seven or more immunoreactive BoNT/A peptide fragments, eight or more immunoreactive BoNT/A peptide fragments, nine or more BoNT/A peptides, ten or more immunoreactive BoNT/A peptide fragments, 15 or more immunoreactive BoNT/A peptide fragments, 20 or more immunoreactive BoNT/A peptide fragments, 25 or more immunoreactive BoNT/A peptide fragments or 30 or more immunoreactive BoNT/A peptide fragments. BoNT/A peptides disclosed in the present specification useful for determining the presence or absence of an anti-BoNT/A antibody can be selected, for example, depending on immunological factors, such as potency of the peptide in inducing an immune response, and technical factors, such as chemical synthesis yields. It is also understood that the two or more BoNT/A peptides can be provided separately or as part of a compound molecule such as a chimeric peptide or heterologous protein.

In an aspect of this embodiment, a method of determining the presence or absence of a BoNT/A antibody uses two or more immunoreactive BoNT/A peptides selected from the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the selected amino acid sequence is 533-551 of SEQ ID NO: 1 (N8) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 533-551 of SEQ ID NO: 1 (N8) and 981-999 of SEQ ID NO: 1 (C10), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 533-551 of SEQ ID NO: 1 (N8), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In a further aspect of this embodiment, one of the amino acid sequences selected is 785-803 of SEQ ID NO: 1 (N25) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 785-803 of SEQ ID NO: 1 (N25) and 981-999 of SEQ ID NO: 1 (C10), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 785-803 of SEQ ID NO: 1 (N25), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 813-831 of SEQ ID NO: 1 (N27) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 813-831 of SEQ ID NO: 1 (N27) and 981-999 of SEQ ID NO: 1 (C10), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 813-831 of SEQ ID NO: 1 (N27), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5.

In an aspect of this embodiment, a method of determining the presence or absence of a BoNT/A antibody uses two or more immunoreactive BoNT/A peptides selected from the following amino acid sequences: 659-677 of SEQ ID NO: 1 (N16), 729-747 of SEQ ID NO: 1 (N21), 799-817 of SEQ ID NO: 1 (N26), 1065-1083 of SEQ ID NO: 1 (C16), 1163-1181 of SEQ ID NO: 1 (C23), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the amino acid sequences selected is 1065-1083 of SEQ ID NO: 1 (C16) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 1065-1083 of SEQ ID NO: 1 (C16), 1163-1181 of SEQ ID NO: 1 (C23) and 1275-1296 of SEQ ID NO: 1 (C31), or a conservative variant, a non-conservative variant or an immunoreactive fragment thereof, with the proviso that the BoNT/A peptide is not SEQ ID NO: 5. In a further aspect of this embodiment, one of the amino acid sequences selected is 799-817 of SEQ ID NO: 1 (N26) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 799-817 of SEQ ID NO: 1 (N26) and 1065-1083 of SEQ ID NO: 1 (C16), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 799-817 of SEQ ID NO: 1 (N26), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 729-747 of SEQ ID NO: 1 (N21) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 729-747 of SEQ ID NO: 1 (N21) and 1065-1083 of SEQ ID NO: 1 (C16), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 729-747 of SEQ ID NO: 1 (N21), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5.

It is also envisioned that any and all combinations of BoNT/A peptides disclosed in the specification can be useful for determining the presence or absence of a BoNT/A antibody, including, e.g., BoNT/A peptides of SEQ ID NO: 1, conservative BoNT/A peptide variants, non-conservative BoNT/A peptide variants and immunoreactive BoNT/A peptide fragments. Thus, aspects of this embodiment include one or more BoNT/A peptides comprising one or more BoNT/A peptides of SEQ ID NO: 1 and one or more conservative BoNT/A peptide variants; one or more BoNT/A peptides of SEQ ID NO: 1 and one or more non-conservative BoNT/A peptide variants; one or more BoNT/A peptides of SEQ ID NO: 1 and one or more immunoreactive BoNT/A peptide fragments; one or more conservative BoNT/A peptide variants and one or more non-conservative BoNT/A peptide variants; one or more conservative BoNT/A peptide variants and one or more immunoreactive BoNT/A peptide fragments; one or more non-conservative BoNT/A peptide variants and one or more immunoreactive BoNT/A peptide fragments; one or more BoNT/A peptides of SEQ ID NO: 1, one or more conservative BoNT/A peptide variants and one or more non-conservative BoNT/A peptide variants; one or more BoNT/A peptides of SEQ ID NO: 1, one or more conservative BoNT/A peptide variants and one or more immunoreactive BoNT/A peptide fragments; one or more BoNT/A peptides of SEQ ID NO: 1, one or more non-conservative BoNT/A peptide variants and one or more immunoreactive BoNT/A peptide fragments; one or more conservative BoNT/A peptide variants, one or more non-conservative BoNT/A peptide variants and one or more immunoreactive BoNT/A peptide fragments; or one or more BoNT/A peptides of SEQ ID NO: 1, one or more conservative BoNT/A peptide variants, one or more non-conservative BoNT/A peptide variants and one or more immunoreactive BoNT/A peptide fragments.

Aspects of the present invention provide, in part, a sample. As used herein, the term "sample" means any biological matter that contains or potentially contains at least one anti-BoNT antibody. An anti-BoNT antibody can be a neutralizing anti-BoNT antibody or a non-neutralizing anti-BoNT antibody. As used herein, the term "neutralizing anti-BoNT antibodies" means any anti-BoNT antibody that will, under physiological conditions, bind to a region of a BoNT toxin in such a manner as to reduce or prevent the toxin from exerting its effect in a BoNT therapy. Non-limiting examples of a neutralizing anti-BoNT antibody include, e.g., a neutralizing anti-BoNT/A antibody, a neutralizing anti-BoNT/B antibody, a neutralizing anti-BoNT/C1 antibody, a neutralizing anti-BoNT/D antibody, a neutralizing anti-BoNT/E antibody, a neutralizing anti-BoNT/F antibody and a neutralizing anti-BoNT/G antibody. As used herein, the term "non-neutralizing anti-BoNT antibodies" means any anti-BoNT antibody that will, under physiological conditions, bind to a region of a BoNT toxin, but not prevent the toxin from exerting its effect in a BoNT therapy. Non-limiting examples of a non-neutralizing anti-BoNT antibody include, e.g., a non-neutralizing anti-BoNT/A antibody, a non-neutralizing anti-BoNT/B antibody, a non-neutralizing anti-BoNT/C1 antibody, a non-neutralizing anti-BoNT/D antibody, a non-neutralizing anti-BoNT/E antibody, a non-neutralizing anti-BoNT/F antibody and a non-neutralizing anti-BoNT/G antibody. It is envisioned that any and all samples that can contain anti-BoNT antibodies can be used in this method, including, without limitation, blood, plasma, serum and lymph fluid. As used herein, the term "blood" means a bodily fluid including a cellular component and plasma and encompasses both whole blood and a blood component thereof, such as, e.g., sera. In addition, any and all individuals capable of raising anti-BoNT antibodies against a BoNT toxin can serve as a source for a sample including, but not limited to, birds and mammals, including mice, rats, goats, sheep, horses, donkeys, cows, primates and humans. Non-limiting examples of specific protocols for blood collection and serum preparation are described in, e.g., Marjorie Schaub Di Lorenzo & Susan King Strasinger, BLOOD COLLECTION IN HEALTHCARE (F.A. Davis Company, 2001); and Diana Garza & Kathleen Becan-McBride, PHLEBOTOMY HANDBOOK: BLOOD COLLECTION ESSENTIALS (Prentice Hall, $6^{th}$ ed., 2002). These protocols are routine procedures well within the scope of one skilled in the art and from the teaching herein.

A sample can be a test sample, or a sample can be a control sample. As used herein, the term "test sample" means any sample in which the presence or absence of an anti-BoNT antibody is sought to be determined. A test sample can be obtained from an individual prior to exposure to a BoNT toxin, after a single BoNT treatment, after multiple BoNT toxin treatments, before onset of resistance to a BoNT therapy, or after onset of resistance to a BoNT therapy. As used herein, the term "control sample" means any sample in which the presence or absence of an anti-BoNT antibody is known, and includes both negative and positive control samples. A negative control sample can be obtained from an individual who was never exposed to BoNT toxin and may include, without limitation, a sample from the same individual supplying the test sample, but taken before undergoing a BoNT therapy; a sample taken from a different individual; a pooled sample taken from a plurality of different individuals. A positive control sample can be obtained from an individual manifesting BoNT immunoresistance and includes, without limitation, samples testing positive in a patient-based testing assays; samples testing positive in an in vivo bioassay; and samples showing hyperimmunity against an anti-BoNT antiserum.

Any of the above methods of the invention can be practiced, if desired, by selectively detecting the presence or absence in the individual of IgG antibodies immunoreactive with each BoNT/A peptide. Thus, it is foreseen that anti-BoNT antibodies can be purified from a sample. Anti-BoNT antibodies can be purified from a sample, using a variety of procedures including, without limitation, Protein A/G chromatography and affinity chromatography. Non-limiting examples of specific protocols for purifying antibodies from a sample are described in, e.g., ANTIBODIES: A LABORATORY MANUAL (Edward Harlow & David Lane, eds., Cold Spring Harbor Laboratory Press, $2^{nd}$ ed. 1998); USING ANTIBODIES: A LABORATORY MANUAL: PORTABLE PROTOCOL No. I (Edward Harlow & David Lane, Cold Spring Harbor Laboratory Press, 1998); and MOLECULAR CLONING, A LABORATORY MANUAL, supra, (2001). In addition, non-limiting examples of antibody purification methods as well as well-characterized reagents, conditions and protocols are readily available from commercial vendors that include, without limitation, Pierce Biotechnology, Inc., Rockford, Ill.; and Zymed Laboratories, Inc., South San Francisco, Calif. These protocols are routine procedures well within the scope of one skilled in the art.

Techniques for determining a level of IgG antibodies immunoreactive with a BoNT/A peptide are well known in the art. For example, a solid-phase radioimmunoassay for IgG anti-BoNT antibodies can be performed using an anti-mouse IgG secondary antibody. A variety of additional anti-IgG antibodies, including anti-human IgG antibodies, are well known in the art and are commercially available, including, but not limited to, rabbit anti-human IgG from Bethyl Laboratories, Inc. (Montgomery, Tex.) and goat anti-human IgG from Zymed Laboratories, Inc (San Francisco, Calif.). Thus, the methods of the invention can be practiced using any of the immunoassays described hereinabove or well known in the art which are specific for detection of IgG antibodies, for example, through use of an anti-IgG secondary antibody.

The present invention additionally provides a method of determining immunoresistance to botulinum toxin therapy in an individual by determining the level of IgG antibodies immunoreactive with the botulinum toxin in the individual; and comparing the level of IgG antibodies to a control level of IgG antibodies, where an increase in the level of IgG antibodies in the individual as compared to the control level indicates immunoresistance to the botulinum toxin therapy. Such an increase can be, for example, at least a 5-fold increase or at least a 10-fold increase. In one embodiment, the control level of IgG antibodies is determined in a individual that has not been treated with botulinum toxin therapy. In another embodiment, the control level of IgG antibodies is determined in an individual that is responsive to the botulinum toxin therapy. The methods of the invention can be used to determine immunoresistance to any of several botulinum toxin therapies including, without limitation, a BoNT/A therapy, a BoNT/B therapy, a BoNT/C1 therapy, a BoNT/D therapy, a BoNT/E therapy, a BoNT/F therapy and a BoNT/G therapy.

Thus, an embodiment, the sample comprises blood. In aspect of this embodiment, the sample comprises mouse blood, rat blood, goat blood, sheep blood, horse blood, donkey blood, cow blood, primate blood and human blood. In another embodiment, the sample comprises plasma. In aspect of this embodiment, the sample comprises mouse plasma, rat plasma, goat plasma, sheep plasma, horse plasma, donkey plasma, cow plasma, primate plasma and human plasma. In another embodiment, the sample comprises serum. In aspect of this embodiment, the sample comprises mouse serum, rat serum, goat serum, sheep serum, horse serum, donkey serum, cow serum, primate serum and human serum. In another embodiment, the sample comprises lymph fluid. In aspect of this embodiment, the sample comprises mouse lymph fluid, rat lymph fluid, goat lymph fluid, sheep lymph fluid, horse lymph fluid, donkey lymph fluid, cow lymph fluid, primate lymph fluid and human lymph fluid. In yet another embodiment, the sample is a test sample. In yet another embodiment, the sample is a control sample.

Any of the above methods of the invention can be practiced, if desired, by selectively detecting the presence or absence in the individual of IgG antibodies immunoreactive with each of the amino acid sequences. Any of a variety of means can be used to determine the presence or absence of antibodies immunoreactive with each of the specified amino acid sequences including, yet not limited to, enzyme-linked immunosorbent assays and radioimmunoassays, see e.g., MOLECULAR CLONING, A LABORATORY MANUAL, supra, 2001; and CURRENT PROTOCOLS IN MOLECULAR BIOLOGY, supra, 2004. In one embodiment, the botulinum toxin therapy is BoNT/A therapy.

A variety of assays are useful in a method of the invention for determining the presence or absence of antibodies immunoreactive with a BoNT/A peptide including, without limitation, enzyme-linked immunosorbent assays and radioimmunoassays, see e.g., MOLECULAR CLONING, A LABORATORY MANUAL, supra, 2001; and CURRENT PROTOCOLS IN MOLECULAR BIOLOGY, supra, 2004. The methods of the invention can be useful for predicting or determining immunoresistance to any of a variety of botulinum toxin therapies including, but not limited to, BOTOX® therapy.

The term "immunoresistance," as used herein in reference to botulinum toxin therapy, means a reduction in beneficial effect of botulinum toxin therapy in an individual resulting from the presence in the individual of antibodies that bind to botulinum toxin. As used herein, the term "botulinum toxin therapy" means administration to an individual one or more controlled doses of botulinum toxin to obtain a beneficial therapeutic or cosmetic effect. The term botulinum toxin therapy encompasses, without limitation, the use of any naturally occurring or modified or engineered form of a botulinum toxin or a domain or fragment thereof, in any formulation, combined with any carrier or active ingredient and administered by any route of administration. An exemplary well-known botulinum toxin therapy is BOTOX® therapy. Appropriate therapeutic and cosmetic uses of botulinum toxin therapy are known in the art as discussed above.

A variety of assay formats employing one or more BoNT/A peptides of the invention can be used to determine the presence or absence of antibodies immunoreactive with a BoNT/A and, therefore, to predict or determine immunoresistance to botulinum toxin therapy according to a method of the invention. Such assay formats generally involve detecting an antigen-antibody interaction. Non-limiting examples include radioimmunoassays, enzyme immunoassays, fluorescence immunoassays, luminescent immunoassays and other nonradioisotopic assay formats. Non-competitive assays can be performed, for example, by attaching one or more selected BoNT/A peptides to a solid support; adding a test specimen; adding a secondary antibody, which is an antibody selective for the test antibody; and detecting the secondary antibody, typically by a physical property or enzymatic activity of the secondary antibody. In such an assay, the amount of signal that is detected can be proportional to the amount of antibodies which are immunoreactive with the one or more BoNT/A peptides and are present in the test specimen.

Aspects of the present invention provide, in part, determining the presence or absence of anti-BoNT antibodies immunoreactive with a BoNT/A peptide. In is envisioned that any and all assay formats suitable for indicating the presence or absence of anti-BoNT antibody-BoNT/A peptide complexes and, therefore, to determine immunoresistance to botulinum toxin therapy according to a method of the present invention. Such assay formats generally involve detecting an antigen-antibody interaction. Non-limiting examples include radioimmunoassays, enzyme-linked immunosorbent assays, enzyme immunoassays, fluorescence immunoassays, luminescent immunoassays and other nonradioisotopic assay formats, see e.g., MOLECULAR CLONING, A LABORATORY MANUAL, supra, 2001; and CURRENT PROTOCOLS IN MOLECULAR BIOLOGY, supra, 2004. Non-competitive assays can be performed, for example, by attaching one or more selected BoNT/A peptides to a solid support; adding a test specimen; adding a secondary antibody, which is an antibody selective for the test antibody; and detecting the secondary antibody, typically by a physical property or enzymatic activity of the secondary antibody. In such an assay, the amount of signal that is detected can be proportional to the amount of antibodies which are immunoreactive with the one or more BoNT/A peptides and are present in the test specimen.

It is further foreseen that an assay format can either qualitatively or quantitatively determine the presence of an anti- BoNT antibody-BoNT/A peptide complex. Qualitative measurements can be determined by a wide variety of methods, such as, e.g., audioradiography, immunoblotting techniques, and the like. Quantitative measurements can be determined by a wide variety of methods, such as, e.g., scintillation counters, spectrophotometers, densitometers, fluorometers, spectroluminometers, luminometers, high pressure liquid chromatography, and the like. In addition, control samples can also be assayed with a test sample using this method in order to provide baseline values useful for comparisons with a test sample. Thus, a negative control comprises a sample known not to contain any anti-BoNT antibodies. A negative control can establish a parameter for background noise levels and provide a means to distinguish false positive results from an actual BoNT immune resistance response. A sample known to contain high levels of neutralizing anti-BoNT antibodies from an individual diagnosed with BoNT immunoresistance could serve as a positive control. A positive control can provide a parameter from which a test sample can be evaluated to determine the relative severity of immunoresistance occurring in a test patient. One skilled in the art understands that, if desired, a quantitative method can be used for qualitative measurements. In addition, one skilled in the art understands that the selection of a method of measurement is determined by the detection means employed.

In one aspect of the present invention, all steps of a method for determining the presence or absence of an anti-BoNT antibody are performed in solution. In other aspects of the method disclosed in the present specification, it is also envisioned that a method can optionally attach an assay component to a solid or insoluble material. Such a solid support can be, without limitation, e.g., a tube; plate; pins or "dipsticks", column; particle, bead or other spherical or fibrous chromatographic media, such as, e.g., agarose beads, sepharose beads, silica beads and plastic beads; sheets or membranes, such as, e.g., nitrocellulose and polyvinylidene fluoride (PVDF). The solid support selected can have a physical property that renders it readily separable from soluble or unbound material and generally allows unbound materials, such as, e.g., unbound antibodies, excess reagents, reaction by-products, or solvents, to be separated or otherwise removed (by, e.g., washing, filtration, centrifugation, etc.) from solid support-bound assay components. Non-limiting examples of how to make and use a solid support-bound assay component are described in, e.g., MOLECULAR CLONING, A LABORATORY MANUAL, supra, 2001; and CURRENT PROTOCOLS IN MOLECULAR BIOLOGY, supra, 2004.

As a general procedure, because the exact amount of a BoNT/A peptide can be readily determined by one skilled in the art, the assay amounts of a sample and an anti-BoNT antibody can be determined based on a fixed assay amount of a BoNT/A peptide.

In an embodiment, it is envisioned that detecting the presence of any and all binding levels of a BoNT/A peptide to an anti-BoNT antibody capable of being detected by an assay format disclosed in the present specification are useful in aspects of the present invention. Thus, aspects of this embodiment may include detecting the presence of, e.g., at least 10% complex formation of a BoNT/A peptide with an anti-BoNT antibody, at least 20% complex formation of a BoNT/A peptide with an anti-BoNT antibody, at least 30% complex formation of a BoNT/A peptide with an anti-BoNT antibody, at least 40% complex formation of a BoNT/A peptide with an anti-BoNT antibody, at least 50% complex formation of a BoNT/A peptide with an anti-BoNT antibody, at least 60% complex formation of a BoNT/A peptide with an anti-BoNT antibody, at least 70% complex formation of a BoNT/A peptide with an anti-BoNT antibody, at least 80% complex formation of a BoNT/A peptide with an anti-BoNT antibody, or at least 90% complex formation of a BoNT/A peptide with an anti-BoNT antibody. In other aspects of this embodiment may include detecting the presence of, e.g., at most 10% complex formation of a BoNT/A peptide with an anti-BoNT antibody, at most 20% complex formation of a BoNT/A peptide with an anti-BoNT antibody, at most 30% complex formation of a BoNT/A peptide with an anti-BoNT antibody, at most 40% complex formation of a BoNT/A peptide with an anti-BoNT antibody, at most 50% complex formation of a BoNT/A peptide with an anti-BoNT antibody, at most 60% complex formation of a BoNT/A peptide with an anti-BoNT antibody, at most 70% complex formation of a BoNT/A peptide with an anti-BoNT antibody, at most 80% complex formation of a BoNT/A peptide with an anti-BoNT antibody, or at most 90% complex formation of a BoNT/A peptide with an anti-BoNT antibody. To ascertain an appropriate assay amount of a BoNT/A peptide in this embodiment, the binding capacity of a BoNT/A peptide preparation towards an anti-BoNT antibody is determined using a fixed amount of an anti-BoNT antibody and a range of BoNT/A peptide amounts in order to generate an saturation curve for anti-BoNT antibody-BoNT/A peptide complex formation. This protocol is routine procedure well within the scope of one skilled in the art and from the teaching herein.

In yet another embodiment, a wide range of BoNT/A peptide amounts can be used in methods disclosed in the present specification. The assay amount of a BoNT/A peptide can be varied as appropriate by one skilled in the art and generally depends, in part, on the amount of anti-BoNT antibodies used, the volume of sample used and the assay format employed. Therefore, aspects of this embodiment may include a BoNT/A peptide amount of, e.g., at least 1 ng, at least 10 ng, at least 100 ng, at least 1 μg, at least 2.5 μg, at least 5.0 μg or at least 10 μg. In other aspects of this embodiment may include a BoNT/A peptide amount of, e.g., at most 1 ng, at most 10 ng, at most 100 ng, at most 1 μg, at most 2.5 μg, at most 5.0 μg or at most 10 μg. In an aspect of this embodiment, the assay amount of a BoNT/A peptide is 100 ng. In another aspect of this embodiment, the assay amount of a BoNT/A peptide is 1 μg. In another aspect of this embodiment, the assay amount of a BoNT/A peptide is 2.5 μg.

In yet another embodiment of the present invention, a wide range of sample volumes can be used in methods disclosed in the present specification. The assay amount of a sample can be varied as appropriate by one skilled in the art and generally depends, in part, on the amount of sample available, the BoNT/A peptide amount being used, the anti-BoNT antibody amount present in a sample and the assay format employed. Thus, aspects of this embodiment a sample volume can include, e.g., at least 1 μL, at least 2.5 μL, at least 5 μL, at least 10 μL, at least 20 μL, at least 30 μL, at least 40 μL, at least 50 μL, or at least 100 μL. In other aspects of this embodiment a sample volume can include, e.g., at most 1 μL, at most 2.5 μL, at most 5 μL, at most 10 μL, at most 20 μL, at most 30 μL, at most 40 μL, at most 50 μL, or at most 100 μL. In an aspect of this embodiment, the assay amount of a sample is 50 μL.

In still another embodiment, it is envisioned that a wide range of assay volumes can be used in methods disclosed in the present specification. Thus aspects of this embodiment an assay volume can include, e.g. at least, 1 μL, at least 2 μL, at least 3 μL, at least 4 μL, at least 5 μL, at least 10 μL, at least 20 μL, at least 30 μL, at least 40 μL, at least 50 μL, at least 100 μL, at least 200 μL, at least 300 μL, at least 400 μL, at least 500 μL, or at least 1000 μL. In other aspects of this embodiment assay volume can include, e.g. at most 1 μL, at most 2 μL, at most 3

μL, at most 4 μL, at most 5 μL, at most 10 μL, at most 20 μL, at most 30 μL, at most 40 μL, at most 50 μL, at most 100 μL, at most 200 μL, at most 300 μL, at most 400 μL, at most 500 μL, or at most 1000 μL.

In still another embodiment, it is envisioned that any and all temperatures that allow the formation of an anti-BoNT antibody-BoNT/A peptide complex can be used in methods disclosed in the present specification. Assay temperatures can be varied as appropriate by one skilled in the art and generally depend, in part, on the BoNT/A peptide amount, the anti-BoNT antibody amount present in a sample, the sample volume used, the assay volume used, the assay format employed and assay time. Thus, an assay temperature should not be as low as to cause the solution to freeze and should not be as high as to denature the BoNT/A peptides, anti-BoNT antibodies or other proteins disclosed in the present specification. In an aspect of this embodiment, the assay is performed within a temperature range above 0° C., but below 40° C. In another aspect of this embodiment, the assay is performed within a temperature range of about 4° C. to about 37° C. In yet another aspect of this embodiment, the assay is performed within a temperature range of about 2° C. to 10° C. In yet another aspect of this embodiment, the assay is performed at about 4° C. In still another aspect of this embodiment, the assay is performed within a temperature range of about 10° C. to about 18° C. In still another aspect of this embodiment, the assay is performed at about 16° C. In yet another aspect of this embodiment, the assay is performed within a temperature range of about 18° C. to about 32° C. In yet another aspect of this embodiment, the assay is performed at about 20° C. In another aspect of this embodiment, the assay is performed within a temperature range of about 32° C. to about 40° C. In another aspect of this embodiment, the assay is performed at about 37° C.

In still another embodiment, it is foreseen that any and all times sufficient for the formation of an anti-BoNT antibody-BoNT/A peptide complex can be used in methods disclosed in the present specification. Assay times can be varied as appropriate by one skilled in the art and generally depend, in part, on the BoNT/A peptide amount, the anti-BoNT antibody amount present in a sample, the sample volume used, the assay volume used, the assay format employed and the incubation temperature. Therefore, aspects of this embodiment include assay times of, e.g., at least 1 minute, at least 2 minutes, at least 3 minutes, at least 4 minutes, at least 5 minutes, at least 10 minutes, at least 15 minutes, at least 20 minutes, at least 25 minutes, at least 30 minutes, at least 45 minutes, at least 60 minutes, or at least 120 minutes. It is understood by one skilled in the art that an assay temperature can affect the formation of an anti-BoNT antibody-BoNT/A peptide complex disclosed in the present invention, and thereby can influence the length of time required to achieve sufficient complex formation. Thus, in an aspect of this embodiment, assay times of at least 45 minutes are used in an assay temperature range of about 2° C. to about 10° C. In another aspect of this embodiment, assay times of at least 30 minutes are used in an assay temperature range of about 10° C. to about 18° C. In yet another aspect of this embodiment, assay times of at least 15 minutes are used in an assay temperature range of about 18° C. to about 32° C. In another aspect of this embodiment, assay times of at least 5 minutes are used in an assay temperature range of about 32° C. to about 40° C. In another aspect of this embodiment, an assay time of 15 minutes is used at an assay temperature of about 37° C.

In a further embodiment, it is also envisioned that any and all buffers that allow the formation of an anti-BoNT antibody-BoNT/A peptide complex can optionally be used in methods disclosed in the present specification. Assay buffers can be varied as appropriate by one skilled in the art and generally depend, in part, on the pH value desired for the assay format employed, the BoNT/A peptide, the anti-BoNT antibody and the assay format employed. Therefore, aspects of this embodiment may optionally include, e.g., 2-amino-2-hydroxymethyl-1,3-propanediol (Tris) buffers; Phosphate buffers, such as, e.g., potassium phosphate buffers and sodium phosphate buffers; Good buffers, such as, e.g., 2-(N-morpholino) ethanesulfonic acid (MES), piperazine-N,N'-bis(2-ethanesulfonic acid) (PIPES), N,N'-bis(2-hydroxyethyl)-2-aminoethanesulfonic acid (BES), 3-(N-morpholino) propanesulfonic acid (MOPS), N-(2-hydroxyethyl) piperazine-N'-(2-ethanesulfonic acid) (HEPES), piperazine-N,N'-bis(2-hydroxypropanesulfonic acid) (POPSO), N-tris(hydroxymethyl) methylglycine (Tricine), N-tris (hydroxymethyl)methyl-3-aminopropanesulfonic acid (TAPS), 3-[(1,1-dimethyl-2-hydroxyethyl)amino]-2-hydroxypropanesulfonic acid (AMPSO), 3-(cyclohexylamino)-2-hydroxy-1-propanesulfonic acid (CAPSO), and 3-(cyclohexylamino)-1-propanesulfonic acid (CAPS); saline buffers, such as, e.g., Phosphate-buffered saline (PBS), HEPES-buffered saline, and Tris-buffered saline (TBS); Acetate buffers, such as, e.g., magnesium acetate, potassium acetate, and Tris acetate; and the like, or any combination thereof. In addition, the buffer concentration in a method disclosed in the present specification can be varied as appropriate by one skilled in the art and generally depend, in part, on the buffering capacity of a particular buffer being used and the detection means employed. Thus, aspects of this embodiment may include a buffer concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific buffers are described in, e.g., MOLECULAR CLONING, A LABORATORY MANUAL, supra, (2001); and CURRENT PROTOCOLS IN MOLECULAR BIOLOGY, supra, (2004).

In a further embodiment, it is also envisioned that any and all salts that allow the formation of an anti-BoNT antibody-BoNT/A peptide complex can optionally be used in methods disclosed in the present specification. Assay salts can be varied as appropriate by one skilled in the art and generally depend, in part, on the physiological conditions desired for the assay format employed, the BoNT/A peptide, the anti-BoNT antibody and the assay format employed. Therefore, aspects of this embodiment may optionally include, e.g., sodium chloride, potassium chloride, calcium chloride, magnesium chloride, manganese chloride, zinc chloride, magnesium sulfate, zinc sulfate, and the like, or any combination thereof. In addition, the salt concentration in a method disclosed in the present specification can be varied as appropriate by one skilled in the art and generally depend, in part, on the buffering capacity of a particular buffer being used and the detection means employed. Thus, aspects of this embodiment may include a salt concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific salts are described in, e.g., MOLECULAR CLONING, A LABORATORY MANUAL, supra, (2001); and CURRENT PROTOCOLS IN MOLECULAR BIOLOGY, supra, (2004).

In a further embodiment, it is also envisioned that any and all enhancing agents that allow the formation of an anti-BoNT antibody-BoNT/A peptide complex can optionally be used in methods disclosed in the present specification. Assay enhancing agents can be varied as appropriate by one skilled in the art and generally depend, in part, on the assay conditions desired for the assay format employed, the BoNT/A peptide, the anti-BoNT antibody and the assay format employed. Therefore, aspects of this embodiment may optionally include, e.g., stabilizing agents including proteins, such as, e.g., bovine serum albumin and milk proteins, such as, e.g., casein, thyroglobulin, fetuin, asialofetuin, cytochrome c and bovine submaxillary mucin and polyamines, such as, e.g., spermidine and spermine; chelating agents including, e.g., ethylenediamine tetraacetic acid (EDTA) and ethylene glycol bis(β-aminoethyl ether) N,N,N',N'-tetraacetic acid (EGTA); reducing agents, including, e.g., β-mercaptoethanol and dithiothreitol (DTT); dimethylsulfoxide (DMSO); and the like, or any combination thereof. In addition, the enhancing agent concentration in a method disclosed in the present specification can be varied as appropriate by one skilled in the art and generally depend, in part, on the assay conditions desired for the assay and the detection means employed. In an aspect of this embodiment, concentrations for a stabilizing agent may include, e.g., at least 10 µg/mL, at least 50 µg/mL, at least 100 µg/mL, at least 200 µg/mL or at least 500 µg/mL. In another aspect of this embodiment, concentrations for a chelating agent may include, e.g., at least 10 nM, at least 50 nM, at least 100 nM, at least 500 nM, at least 1 mM or at least 10 mM. In yet another aspect of this embodiment, concentrations for a reducing agent may include, e.g., at least 10 nM, at least 50 nM, at least 100 nM, at least 500 nM, at least 1 mM, at least 10 mM or at least 100 mM. Non-limiting examples of how to make and use specific enhancing agents are described in, e.g., MOLECULAR CLONING, A LABORATORY MANUAL, supra, (2001); and CURRENT PROTOCOLS IN MOLECULAR BIOLOGY, supra, (2004).

In an additional embodiment of the invention, it is also foreseen that a wide variety of processing formats can be used in conjunction with the methods of the present invention, including, without limitation, manual processing, partial automated-processing, semi-automated-processing, full automated-processing, high throughput processing, high content processing, and the like or any combination thereof.

It is understood by one skilled in the art that a wide variety of factors can influence assay conditions, including, without limitation, solution variations, buffer variations, reagent variations, equipment variations and facility variations. Thus, any particular assay condition selected by one skilled in the art will require routine experimentation in order to optimize the method to account for such factors. These optimization protocols are routine procedures well within the scope of one skilled in the art and the teaching herein.

As a non-limiting example, a competitive assay can be performed by attaching one or more selected BoNT/A peptides to a solid support; adding simultaneously a test specimen and an enzyme-labeled secondary antibody; and adding a substrate that produces a detectable compound when acted upon by the enzyme. In this type of assay format, the amount of signal that is detected is inversely proportional to the amount of anti-BoNT antibody present in the test specimen.

In one embodiment, the presence or absence of anti-BoNT antibodies immunoreactive with a BoNT/A peptide is determined using an enzyme-linked immunosorbent assay (ELISA). In another embodiment, the presence or absence of anti-BoNT antibodies immunoreactive with a BoNT/A peptide is determined using a radioimmunoassay.

Various detection methods can be employed in any of the assay formats disclosed in the present specification, including without limitation, a radiation detection method, a fluorescence detection method, a fluorescence resonance energy transfer (FRET) detection method, a phosphorescence detection method, a chemiluminescence detection method, a bioluminescence detection method, an electrochemiluminescence detection method, a chromagenic detection method and an enzyme-activity detection method. In addition, any of a variety of marker compounds suitable for the detection system selected, can be operably-linked to a BoNT/A peptide as a labeled molecule including, without limitation, a radioisotope, fluorescent compound, a phosphorescent compound, a chemiluminescent compound, a bioluminescent compound, and the like. Thus, in one aspect of the present invention, a marker compound suitable for the selected detection system is operably-linked to a BoNT/A peptide as the labeled molecule suitable for any method. As used herein, the term "operably linked" when used in reference to a labeled molecule, means any of a variety of chemical reactions that can join a marker compound disclosed in the present specification to a BoNT/A peptide disclosed in the present specification such that a single peptide, comprising a peptide and marker compound, suitable to perform a method disclosed in the present specification is produced.

Non-limiting examples of radioisotopes that may be operably-linked to a BoNT/A peptide disclosed in the specification include, e.g., $^{3}$Hydrogen, $^{14}$Carbon, $^{22}$Sodium, $^{32}$Phosphorus, $^{33}$Phosphorus, $^{35}$Sulfur, $^{36}$Chlorine, $^{45}$Calcium, $^{51}$Chromium, $^{57}$Cobalt, $^{58}$Cobalt, $^{59}$Iron, $^{63}$Nickel, $^{65}$Zinc, $^{75}$Selenium, $^{86}$Rubidium, $^{103}$Ruthenium, $^{109}$Cadmium, $^{125}$Iodine, $^{131}$Iodine, and the like. Non-limiting examples of fluorescent compounds that may be operably-linked to a BoNT/A peptide disclosed in the specification include, e.g., fluorescein, fluorescamine, isocyanate, isothiocyanate, rhodamine, phycoerythrin, phycocyanin, allophycocyanin, o-phthaldehyde, Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Cy-2, Cy-3, Cy-5, Cy-7 and the like. Non-limiting examples of chemiluminescent compounds that may be operably-linked to a BoNT/A peptide disclosed in the specification include, e.g., imidazoles, such as, e.g., lophine; acylhydrazines, such as, e.g., luminal and isoluminol; acridinium salts and esters, such as, e.g., lucigenin; oxalate salts and esters, such as, e.g., bis(2,4,6-trichlorophenyl) oxalate (TCPO) and bis(2,4-dinitrophenyl) oxalate (DNPO); Tris (2,2N-bipyridine) ruthenium compounds, such as, e.g., ruthenium(bipyridine)$_3$, and the like. Non-limiting examples of bioluminescent compounds that may be operably-linked to a BoNT/A peptide disclosed in the specification include, e.g., bacterial luciferins, dinoflagellate luciferins, vargulins, porichthys luciferins, coelenterazines, beetle luciferins, 4-methylumbelliferone esters, and the like.

Likewise, any of a variety of peptides suitable for the detection method selected, can be operably-linked to a BoNT/A peptide as a fusion protein including, without limitation, a peptide necessary for producing florescence, a peptide necessary for producing phosphorescence, a peptide necessary for producing chemiluminescence, a peptide necessary for producing bioluminescence, and the like. As used herein, the term "operably linked" when used in reference to a fusion protein, means any of a variety of cloning methods that can join a first nucleic acid sequence composition encoding a first peptide disclosed in the present specification in-frame with a second nucleic acid sequence composition encoding a second peptide disclosed in the present specification such that a single peptide, comprising both the first and second peptides, suitable to perform a method disclosed in the present specification is produced when expressed. In one embodiment, a peptide suitable for the detection method selected, is operably-linked to a BoNT/A peptide.

Non-limiting examples of a peptide necessary for producing florescence that may be operably-linked to a BoNT/A peptide disclosed in the specification include, e.g., photoproteins, such as, e.g., aequorin; obelin; Aequorea fluorescent proteins, such, e.g., green fluorescent protein (GFP), cyan fluorescent protein (CFP), blue fluorescent protein (BFP), red fluorescent protein (RFP), yellow fluorescent protein (YFP), ultraviolet fluorescent protein (GFPuv), their fluorescence-enhancement variants, including EGFP, ECFP, EBFP and EYFP, their peptide destabilization variants, and the like; and Red coral reef fluorescent proteins (RCFPs), such, e.g., Discosoma red fluorescent protein (DsRed), Anemonia red fluorescent protein (AsRed), Heteractis far-red fluorescent protein (HcRed), Anemonia cyan fluorescent protein (AmCyan), Zoanthus green fluorescent protein (ZsGreen), Zoanthus yellow fluorescent protein (ZsYellow), their fluorescence-enhancement variants, including DsRed2, AsRed2, their peptide destabilization variants, and the like. Non-limiting examples of a peptide necessary for producing chemiluminescence that may be operably-linked to a BoNT/A peptide disclosed in the specification include, e.g., alkaline phosphatases, horseradish peroxidases, xanthine oxidases, glucose oxidases and β-galactosidases. Non-limiting examples of a peptide necessary for producing bioluminescence that may be operably-linked to a BoNT/A peptide disclosed in the specification include, e.g., bacterial luciferases, dinoflagellate luciferases, virgule luciferases, coelenterate luciferases, beetle luciferases, and the like. Non-limiting examples of a peptide necessary for producing chromogenic compound that may be operably-linked to a BoNT/A peptide disclosed in the specification include, e.g., alkaline phosphatases, horseradish peroxidases, ureases, β-glucourimidases, glucose oxidases and β-galactosidases.

Non-limiting examples of specific protocols for selecting, making and using detection systems, making and using peptides labeled with a marker compound and making and using fusion proteins are described in, e.g., MOLECULAR CLONING A LABORATORY MANUAL, supra, (2001); METHODS IN ENZYMOLOGY, VOL. 305, BIOLUMINESCENCE AND CHEMILUMINESCENCE, PART C (Miriam M. Ziegler & Thomas O. Baldwin eds., Academic Press, 2000); Y. Fuster Mestre et al., *Flow-chemiluminescence: A Growing Modality of Pharmaceutocal Analysis*, 16 LUMINESCENCE 213-235, (2001); Lee F. Greer III & Aladar A. Szalay, *Imaging of Light Emission From the Expression of Luciferases in Living Cells and Organisms: A Review*, 17 LUMINESCENCE 43-74, (2002); Richard W. Horobin & John A. Kiernan, CONN'S BIOLOGICAL STAINS: A HANDBOOK OF DYES, STAINS AND FLUOROCHROMES FOR USE IN BIOLOGY AND MEDICINE (BIOS Scientific Publishers, 10$^{th}$ ed. 2002); HANDBOOK OF FLUORESCENT PROBES AND RESEARCH CHEMICALS, (Molecular Probes, Inc., 9$^{th}$ ed, 2004), and CURRENT PROTOCOLS IN MOLECULAR BIOLOGY, supra, (2004). In addition, non-limiting examples of how to make and use detection systems, labeled peptides and fusion protein disclosed in the present specification, as well as well-characterized reagents, conditions and protocols are readily available from commercial vendors that include, without limitation, Amersham Biosciences, Piscataway, N.J.; BD Biosciences-Clontech, Palo Alto, Calif.; Bio-Rad Laboratories, Hercules, Calif.; Cayman Chemical Co., Ann Arbor, Mich.; Molecular Probes, Inc., Eugene, Oreg.; PerkinElmer Life and Analytical Sciences, Inc., Boston, Mass.; Pierce Biotechnology, Inc., Rockford, Ill.; Princeton Separations, Adelphia, N.J.; and Vector Laboratories, Burlingame, Calif. These protocols are routine procedures within the scope of one skilled in the art and from the teaching herein.

Thus, in an embodiment, a BoNT/A peptide is operably-linked to a radioisotope. In an aspect of this embodiment, a BoNT/A peptide is operably-linked to $^3$Hydrogen, $^{14}$Carbon, $^{22}$Sodium, $^{32}$Phosphorus, $^{33}$Phosphorus, $^{35}$Sulfur, $^{36}$Chlorine, $^{45}$Calcium, $^{51}$Chromium, $^{57}$Cobalt, $^{58}$Cobalt, $^{59}$Iron, $^{63}$Nickel, $^{65}$Zinc, $^{75}$Selenium, $^{86}$Rubidium, $^{103}$Ruthenium, $^{109}$Cadmium, $^{125}$Iodine or $^{131}$Iodine. In another aspect of this embodiment, the presence of anti-BoNT antibody-BoNT/A peptide complexes is quantitatively determined using a scintillation counter. In another aspect of this embodiment, the absence of anti-BoNT antibody-BoNT/A peptide complexes is quantitatively determined using a scintillation counter.

In yet another embodiment, a BoNT/A peptide is operably-linked to a fluorescent compound. In an aspect of this embodiment, a BoNT/A peptide is operably-linked to a fluorescein, a fluorescamine, an isocyanate, an isothiocyanate, a rhodamine, a phycoerythrin, a phycocyanin, an allophycocyanin, an o-phthaldehyde, an Alexa Fluor® 350, an Alexa Fluor® 430, an Alexa Fluor® 488, an Alexa Fluor® 532, an Alexa Fluor® 546, an Alexa Fluor® 555, an Alexa Fluor® 568, an Alexa Fluor® 594, an Alexa Fluor® 633, an Alexa Fluor® 647, an Alexa Fluor® 660, an Alexa Fluor® 680, an Alexa Fluor® 700, an Alexa Fluor® 750, a Cy-2, a Cy-3, a Cy-5 or a Cy-7. In another aspect of this embodiment, the presence of anti-BoNT antibody-BoNT/A peptide complexes is quantitatively determined using a spectrofluorimeter (see, e.g., Example 8). In another aspect of this embodiment, the absence of anti-BoNT antibody-BoNT/A peptide complexes is quantitatively determined using a spectrofluorimeter.

In another embodiment, a BoNT/A peptide is operably-linked to a photoprotein. In an aspect of this embodiment, a BoNT/A peptide is operably linked to an aequorin, an obelin, a GFP, an EGFP, a CFP, an ECFP, a BFP, an EBFP, a YFP, an EYFP, a GFPuv, a DsRed, a DsRed2, a AsRed, a AsRed2, a HcRed, an AmCyan, a ZsGreen or a ZsYellow. In another aspect of this embodiment, the presence of anti-BoNT antibody-BoNT/A peptide complexes is quantitatively determined using a spectrofluorimeter. In another aspect of this embodiment, the absence of anti-BoNT antibody-BoNT/A peptide complexes is quantitatively determined using a spectrofluorimeter.

In yet another embodiment, a BoNT/A peptide is operably-linked to a chemiluminescent compound. In an aspect of this embodiment, a BoNT/A peptide is operably linked to an imidazole, an acridinium salt, an acridinium ester, an oxalate salt, an oxalate ester, or a Tris (2,2N-bipyridine) ruthenium compound. In another aspect of this embodiment, the presence of anti-BoNT antibody-BoNT/A peptide complexes is quantitatively determined using a luminometer. In another aspect of this embodiment, the absence of anti-BoNT antibody-BoNT/A peptide complexes is quantitatively determined using a luminometer.

In yet another embodiment, a BoNT/A peptide is operably-linked to a peptide necessary for producing chemiluminescence. In an aspect of this embodiment, a BoNT/A peptide is operably linked to an alkaline phosphatase, a horseradish peroxidase, a xanthine oxidase, a glucose oxidase or a β-galactosidase. In another aspect of this embodiment, the presence of anti-BoNT antibody-BoNT/A peptide complexes is quantitatively determined using a luminometer. In another aspect of this embodiment, the absence of anti-BoNT antibody-BoNT/A peptide complexes is quantitatively determined using a luminometer.

In yet another embodiment, a BoNT/A peptide is operably-linked to a peptide necessary for producing bioluminescence. In an aspect of this embodiment, a BoNT/A peptide is operably linked to a bacterial luciferase, a dinoflagellate luciferase, a vargula luciferase, a coelenterate luciferase or a beetle luciferase. In another aspect of this embodiment, the presence of anti-BoNT antibody-BoNT/A peptide complexes is quantitatively determined using a luminometer. In another aspect of this embodiment, the absence of anti-BoNT antibody-BoNT/A peptide complexes is quantitatively determined using a luminometer.

In yet another embodiment, a BoNT/A peptide is operably-linked to a peptide necessary for producing a chromogenic product. In an aspect of this embodiment, a BoNT/A peptide is operably linked to an alkaline phosphatase, a horseradish peroxidase, an urease, a β-glucourimidase, a glucose oxidase or a β-galactosidase. In another aspect of this embodiment, the presence of anti-BoNT antibody-BoNT/A peptide complexes is quantitatively determined using a spectrophotometer. In another aspect of this embodiment, the absence of anti-BoNT antibody-BoNT/A peptide complexes is quantitatively determined using a spectrophotometer.

Aspects of the present invention provide, in part, comparing the amount of anti-BoNT antibody-BoNT/A peptide complexes formed in the test sample to the amount of anti-BoNT antibody-BoNT/A peptide complexes formed in the control sample. In an embodiment, the amount of anti-BoNT antibody-BoNT/A peptide complexes in the test sample is increased as compared to the amount of anti-BoNT antibody-BoNT/A peptide complexes formed in the control sample. In an aspect of this embodiment, an increase in the amount of anti-BoNT antibody-BoNT/A peptide complexes formed in the test sample as compared to a positive control sample indicates an increase of immunoresistance to a BoNT therapy in the individual. In another aspect of this embodiment, an increase in the amount of anti-BoNT antibody-BoNT/A peptide complexes formed in the test sample as compared to a negative control sample indicates an increase of immunoresistance to a BoNT therapy in the individual. In another embodiment, the amount of anti-BoNT antibody-BoNT/A peptide complexes formed in the test sample is decreased as compared to the amount of anti-BoNT antibody-BoNT/A peptide complexes formed in the control sample. In an aspect of this embodiment, a decrease in the amount of anti-BoNT antibody-BoNT/A peptide complexes formed in the test sample as compared to a positive control sample indicates a decrease of immunoresistance to a BoNT therapy in the individual. In another aspect of this embodiment, a decrease in the amount of anti-BoNT antibody-BoNT/A peptide complexes formed in the test sample as compared to a negative control sample indicates a decrease of immunoresistance to a BoNT therapy in the individual.

In an embodiment, the presence of anti-BoNT antibody-BoNT/A peptide complexes in the test sample indicates the presence of immunoresistance to a BoNT therapy in the individual. In an aspect of this embodiment, the presence of anti-BoNT antibody-BoNT/A peptide complexes in the test sample is compared to the presence of anti-BoNT antibody-BoNT/A peptide complexes in the control sample. In an aspect of this embodiment, the presence of anti-BoNT antibody-BoNT/A peptide complexes in the test sample as compared to a negative control sample indicates the presence of immunoresistance to a BoNT therapy in the individual.

In another embodiment, the absence of anti-BoNT antibody-BoNT/A peptide complexes in the test sample indicates the absence of immunoresistance to a BoNT therapy in the individual. In another aspect of this embodiment, the absence of anti-BoNT antibody-BoNT/A peptide complexes in the test sample is compared to the absence of anti-BoNT antibody-BoNT/A peptide complexes in the control sample. In another aspect of this embodiment, the absence of anti-BoNT antibody-BoNT/A peptide complexes in the test sample as compared to a positive control sample indicates the absence of immunoresistance to a BoNT therapy in the individual.

Aspects of the present invention provide, in part, comparing the amount of free or unbound BoNT/A peptides in the test sample to the amount of free or unbound BoNT/A peptides in the control sample. In an embodiment, the amount of free or unbound BoNT/A peptides in the test sample increases as compared to the amount of free or unbound BoNT/A peptides in the control sample. In an aspect of this embodiment, an increase in the amount of free or unbound BoNT/A peptides in the test sample as compared to a positive control sample indicates a decrease of immunoresistance to a BoNT therapy in the individual. In another aspect of this embodiment, an increase in the amount of free or unbound BoNT/A peptides in the test sample as compared to a negative control sample indicates a decrease of immunoresistance to a BoNT therapy in the individual. In another embodiment, the amount of free or unbound BoNT/A peptides in the test sample decreases as compared to the amount of free or unbound BoNT/A peptides in the control sample. In an aspect of this embodiment, a decrease in the amount of free or unbound BoNT/A peptides in the test sample as compared to a positive control sample indicates an increase of immunoresistance to a BoNT therapy in the individual. In another aspect of this embodiment, a decrease in the amount of free or unbound BoNT/A peptides in the test sample as compared to a negative control sample indicates an increase of immunoresistance to a BoNT therapy in the individual.

Aspects of the present invention provide, in part, comparing the amount of free or unbound anti-BoNT antibodies in the test sample to the amount of free or unbound anti-BoNT antibodies in the control sample. In an embodiment, the amount of free or unbound anti-BoNT antibodies in the test sample increases as compared to the amount of free or unbound anti-BoNT antibodies in the control sample. In an aspect of this embodiment, an increase in the amount of free or unbound anti-BoNT antibodies in the test sample as compared to a positive control sample indicates an increase of immunoresistance to a BoNT therapy in the individual. In another aspect of this embodiment, an increase in the amount of free or unbound anti-BoNT antibodies in the test sample as compared to a negative control sample indicates an increase of immunoresistance to a BoNT therapy in the individual. In another embodiment, the amount of free or unbound anti-BoNT antibodies in the test sample decreases as compared to the amount of free or unbound anti-BoNT antibodies in the control sample. In an aspect of this embodiment, a decrease in the amount of free or unbound anti-BoNT antibodies in the test sample as compared to a positive control sample indicates a decrease of immunoresistance to a BoNT therapy in the individual. In another aspect of this embodiment, a decrease in the amount of free or unbound anti-BoNT antibodies in the test sample as compared to a negative control sample indicates a decrease of immunoresistance to a BoNT therapy in the individual.

Thus, in one embodiment, a method of determining immunoresistance to botulinum toxin therapy in an individual comprising the step of determining the presence or absence in the individual of anti-BoNT antibodies immunoreactive with a BoNT/A peptide, where the presence of the anti-BoNT antibody-BoNT/A peptide complex is indicative of immunoresistance to a BoNT therapy.

In another embodiment, a method of determining immunoresistance to BoNT therapy in an individual, the method comprising the steps of combining a BoNT/A peptide and a test sample under conditions suitable for the selective binding of the BoNT/A peptide to an anti-BoNT antibody and determining the presence of an anti-BoNT antibody-BoNT/A peptide complex, the antibody-peptide complex formed by the selective binding of an anti-BoNT antibody and the BoNT/A peptide, where the presence of the anti-BoNT antibody-BoNT/A peptide complex is indicative of immunoresistance to a BoNT therapy.

In another embodiment, a method of determining immunoresistance to BoNT therapy in an individual, the method comprising the steps of combining a BoNT/A peptide and a test sample under conditions suitable for the selective binding of the BoNT/A peptide to an anti-BoNT antibody and determining the presence of an anti-BoNT antibody-BoNT/A peptide complex, the antibody-peptide complex formed by the selective binding of an anti-BoNT antibody and the BoNT/A peptide and correlating the amount of an antibody-peptide complex formed from the test sample relative to the amount of an antibody-peptide complex formed by the BoNT/A peptide combined to a control sample where the presence of the anti-BoNT antibody-BoNT/A peptide complex is indicative of immunoresistance to a BoNT therapy.

VI. Methods of Treating BoNT/A Immunoresistance

Patients treated with a botulinum toxin therapy can develop immunoresistance to the therapeutic treatment, reducing or eliminating the beneficial effect of botulinum toxin therapy. Methods that prevent or reduce the development of a BoNT-specific immune response in an individual, which in turn can prevent or reduce immunoresistance to a botulinum toxin therapy, are of major importance. These treatments would allow for 1) the suppression of a potential deleterious immune response in a patient undergoing BoNT therapy thereby affording a more prolonged treatment course relative to current therapies; 2) the suppression of a BoNT immunoresponsive state in a patient thereby offering additional treatments that would otherwise have been ineffective. Therefore, these assays present a major benefit in terms of providing better patient care and reducing health care costs. The BoNT/A peptides disclosed in the present specification are useful in methods of determining immunoresistance to botulinum toxin therapy in an individual. These peptides each contain one or more epitopes recognized by antibodies contained in antisera from animals immunized with BoNT/A, and thus can serve as binding substrates for anti-BoNT/A antibodies. The methods disclosed in the present specification can be useful for preventing or reducing immunoresistance to any of a variety of botulinum toxin therapies including, but not limited to, a BoNT/A therapy, a BoNT/B therapy, a BoNT/C1 therapy, a BoNT/D therapy, a BoNT/E therapy, a BoNT/F therapy and a BoNT/G therapy.

Thus, the present invention provides, in part, a method of treating immunoresistance to botulinum toxin therapy in an individual by administering to the individual a tolerogizing composition comprising a tolerogizing agent operably linked to a BoNT/A peptide the administration preventing or reducing immunoresistance to botulinum toxin therapy. In addition, the present invention provides, in part, a method of preventing or reducing immunoresistance to botulinum toxin therapy in an individual by administering to said individual a tolerogizing composition comprising a tolerogizing agent and a BoNT/A peptide wherein administration of said tolerogizing composition decreases an immunological response to a botulinum toxin antigen. It is envisioned that any and all tolerogizing compositions disclosed in the present specification can be useful in a method of treating immunoresistance to botulinum toxin therapy in an individual. Those skilled in the art can readily determine for a particular tolerogizing composition, a suitable pharmacological composition, an appropriate antigen payload; route of administration; volume of dose; and tolerogizing regimen useful in a particular individual, for example, humans.

Aspects of the present invention provide, in part, a method of treating immunoresistance to botulinum toxin therapy, such as, e.g., a BoNT/A immunoresistance condition, a BoNT/B immunoresistance condition, a BoNT/C1 immunoresistance condition, a BoNT/D immunoresistance condition, a BoNT/E immunoresistance condition, a BoNT/F immunoresistance condition or a BoNT/G immunoresistance condition. As used herein, the term "treating," when used in reference to administering to an individual a tolerogizing composition, means reducing a symptom of a condition characterized by resistance to a BoNT therapy, or delaying or preventing onset of a symptom of a condition characterized by a BoNT immunoresistance in the individual. For example, the term "treating" means reducing a symptom of a condition characterized by a BoNT immunoresistance by, e.g., at least 30%, at least 40%, at least 50%, at least 60%, at least 70%, at least 80%, at least 90% or at least 100%. The effectiveness of a tolerogizing composition in treating a condition characterized by BoNT immunoresistance can be determined by observing one or more clinical symptoms or physiological indicators associated with the condition. An improvement in a condition characterized by BoNT immunoresistance also can be indicated by a reduced need for a concurrent therapy. Those of skill in the art will know the appropriate symptoms or indicators associated with specific conditions and will know how to determine if an individual is a candidate for treatment with a tolerogizing composition disclosed in the present specification. In particular, it is understood that those skilled in the art will be able to determine if a condition is characterized by BoNT immunoresistance, e.g., by comparison of levels of BoNT immunoresistance from an individual suspected to have an immunoresistance to a BoNT therapy with an individual not suspected to have an immunoresistance to a BoNT therapy.

Aspects of the present invention provide, in part, administration of a tolerogizing composition. As used herein, the term "administration" means any delivery mechanism that provides a tolerogizing composition to an individual that potentially results in a clinically, therapeutically, cosmetically or experimentally beneficial result. A tolerogizing composition useful in the methods of the invention can be administered to an individual by any of a variety of routes depending, for example, on the type and location of BoNT immunoresistance to be treated, the tolerogizing composition, or other compound to be included in the composition, and the history, risk factors and symptoms of the subject. Routes of administration suitable for the methods of the invention include both local and systemic administration. Local administration results in significantly more tolerogizing composition being delivered to a specific location as compared to the entire body of the subject, whereas, systemic administration results in delivery of a tolerogizing composition to essentially the entire body of the subject. A tolerogizing composition can also be administered peripherally. As used herein, the term "peripheral administration" or "administered peripherally" means introducing an agent into an individual outside of the central nervous system. Peripheral administration encompasses any route of administration other than direct administration to the spine or brain. As such, it is clear that intrathecal and epidural administration as well as cranial injection or implantation is not within the scope of the term "peripheral administration" or "administered peripherally."

Administration of a tolerogizing composition can be by a variety of routes including, without limitation, orally in any acceptable form, such as, e.g., tablet, liquid, capsule, powder, or the like; topically in any acceptable form, such as, e.g., patch, drops, creams, gels or ointments; by injection, in any acceptable form, such as, e.g., intravenous, intraperitoneal, intramuscular, subcutaneous, parenteral or epidural; and by implant, such as, e.g., subcutaneous pump, intrathecal pump, suppository, bioerodible delivery system, non-bioerodible delivery system or other implanted extended or slow release device or formulation. As a non-limiting example, oral tolerance is well-recognized in the art (see, for example, Weiner, *Hospital Practice*, pp. 53-58 (Sep. 15, 1995). Additionally, an exemplary list of biodegradable polymers and methods of use are described in, e.g., Handbook of Biodegradable Polymers (Abraham J. Domb et al., eds., Overseas Publishers Association, 1997); Controlled Drug Delivery: Designing Technologies for the Future (Kinam Park & Randy J. Mrsny eds., American Chemical Association, 2000); Vernon G. Wong, Method for Reducing or Preventing Transplant Rejection in the Eye and Intraocular Implants for Use Therefor, U.S. Pat. No. 6,699,493 (Mar. 2, 2004); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/0137059 (Jul. 15, 2004). In general administration of a tolerogizing composition to an individual can depend on, e.g., the type immunoresistance, the BoNT/A peptide included in the composition, the tolerogizing agent included in the composition, and the history, risk factors and symptoms of the individual.

A tolerogizing composition can be administered to an individual prior to administering botulinum toxin therapy to prevent the development of immunoresistance, during a course of botulinum toxin therapy, or after onset of immunoresistance, such as, e.g., when symptoms of resistance are first apparent. In addition, a tolerogizing composition can be administered to an individual who is at increased risk for immunoresistance to botulinum toxin therapy. Those skilled in the art will be able to determine an appropriate candidate for receiving a tolerogizing composition of the invention based on, e.g., the particular condition to be treated and the presence or likelihood of symptoms of immunoresistance.

Thus, in one embodiment, a method of the present invention is practiced by administering a tolerogizing composition prior to an individual receiving a BoNT therapy, such as, e.g., a BoNT/A therapy, a BoNT/B therapy, a BoNT/C1 therapy, a BoNT/D therapy, a BoNT/E therapy, a BoNT/F therapy or a BoNT/G therapy. Such an individual can be, for, e.g., an individual at increased risk for developing immunoresistance to botulinum toxin therapy. In another embodiment, a method of the present invention is practiced by administering a tolerogizing composition after an individual has received a BoNT therapy, such as, e.g., a BoNT/A therapy, a BoNT/B therapy, a BoNT/C1 therapy, a BoNT/D therapy, a BoNT/E therapy, a BoNT/F therapy or a BoNT/G therapy. In yet another embodiment, a method of the present invention is practiced by administering a tolerogizing composition to an individual who has not been diagnosed with a BoNT immunoresistance condition, such as, e.g., a BoNT/A immunoresistance condition, a BoNT/B immunoresistance condition, a BoNT/C1 immunoresistance condition, a BoNT/D immunoresistance condition, a BoNT/E immunoresistance condition, a BoNT/F immunoresistance condition or a BoNT/G immunoresistance condition. In yet another embodiment, a method of the present invention is practiced by administering a tolerogizing composition to an individual that has been diagnosed with a BoNT/A immunoresistance condition.

In another embodiment, a tolerogizing composition is administered to an individual. In aspects of this embodiment, a tolerogizing composition is administered orally to an individual, a tolerogizing composition is administered topically to an individual, a tolerogizing composition is injected to an individual or a tolerogizing composition is implanted in an individual.

A tolerogizing composition useful in a method of the invention is administered to an individual in an effective amount. As used herein, the term "effective amount" when used in reference to treating BoNT immunoresistance means the minimum dose necessary to achieve the desired therapeutic effect and includes a dose sufficient to reduce a symptom associated with a BoNT immunoresistance response. In aspects of this embodiment, an effect amount of a tolerogizing composition reduces a symptom associated with a BoNT immunoresistance response by, e.g., at least 30%, at least 40%, at least 50%, at least 60%, at least 70%, at least 80%, at least 90% or at least 100%. In other aspects of this embodiment, an effect amount of a tolerogizing composition reduces a symptom associated with a BoNT immunoresistance response by, e.g., at most 30%, at most 40%, at most 50%, at most 60%, at most 70%, at most 80%, at most 90% or at most 100%.

The appropriate effective amount to be administered for a particular application of the methods can be determined by those skilled in the art, using the guidance provided herein. For example, an effective amount can be extrapolated from in vitro assays and in vivo administration studies using animal models prior to administration to humans. Such a effect amount generally is in the range of 0.1-1000 mg/day and can be, e.g., in the range of 0.1-500 mg/day, 0.5-500 mg/day, 0.5-100 mg/day, 0.5-50 mg/day, 0.5-20 mg/day, 0.5-10 mg/day or 0.5-5 mg/day. An effective dose of a tolerogizing composition useful for inducing tolerance in an individual will depend upon the particular BoNT/A peptide used, the tolerogizing agent used, and the route administration. In addition, the actual amount of the effective dose of a tolerogizing composition to be administered to an individual will be determined by a physician taking into account the cause of the BoNT immunoresistance, the severity of the BoNT immunoresistance and the particular characteristics of the individual, such as age, weight, general health and the like. Where repeated administration is used, the frequency of administration depends, in part, on the half-life of the tolerogizing composition. One skilled in the art will recognize that the condition of the individual can be monitored throughout the course of therapy and that the effective amount of a tolerogizing composition that is administered can be adjusted accordingly. It is also understood that the frequency and duration of dosing will be dependent, in part, on the relief desired and the half-life of the tolerogizing composition.

Aspects of the present invention provide, in part, a tolerogizing composition. It is envisioned that any of the tolerogizing composition disclosed in the present specification can be useful in a method of treating immunoresistance to botulinum toxin therapy in an individual, with the proviso that the tolerogizing composition prevents or reduces the immunoresistance to a botulinum toxin therapy. Non-limiting examples include tolerogizing compositions comprising BoNT/A peptide derived from a naturally occurring BoNT/A operably linked to a tolerogizing agent, such as, e.g., BoNT/A peptide derived from the BoNT/A of SEQ ID NO: 1 operably linked to a tolerogizing agent, a BoNT/A peptide derived from a BoNT/A isoform operably linked to a tolerogizing agent or a BoNT/A peptide derived from a BoNT/A subtype operably linked to a tolerogizing agent; and a BoNT/A peptide derived from a non-naturally occurring BoNT/A operably linked to a tolerogizing agent, such as, e.g., a BoNT/A peptide derived from a conservative BoNT/A variant operably linked to a tolerogizing agent, a BoNT/A peptide derived from a non-conservative BoNT/A variant operably linked to a tolerogizing agent and a BoNT/A peptide derived from a chimeric BoNT/A peptide operably linked to a tolerogizing agent. BoNT/A peptides within a tolerogizing composition disclosed in the present specification can be selected on, e.g., immunological factors, such as the selectivity of the BoNT/A peptide for an anti-BoNT antibody, and technical factors, such as chemical synthesis yields. It is also understood that the two or more different BoNT/A peptides can be provided separately or as part of a compound molecule such as a chimeric BoNT/A peptide.

A tolerogizing composition useful in the invention generally is administered in a pharmaceutical acceptable composition. As used herein, the term "pharmaceutically acceptable" means any molecular entity or composition that does not produce an adverse, allergic or other untoward or unwanted reaction when administered to an individual. As used herein, the term "pharmaceutically acceptable composition" means a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilize, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" means any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7$^{th}$ ed. 1999); REMINGTON: THE SCIENCE AND PRACTICE OF PHARMACY (Alfonso R. Gennaro ed., Lippincott, Williams & Wilkins, 20 ed. 2000); GOODMAN & GILMAN'S THE PHARMACOLOGICAL BASIS OF THERAPEUTICS (Joel G. Hardman et al., eds., McGraw-Hill Professional, 10$^{th}$ ed. 2001); and HANDBOOK OF PHARMACEUTICAL EXCIPIENTS (Raymond C. Rowe et al., APhA Publications, 4$^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

In an embodiment, a method of treating immunoresistance to a botulinum toxin therapy in an individual comprises the step of administering to the individual a tolerogizing composition comprising a tolerogizing agent operably linked to a BoNT/A peptide, where the administration prevents or reduces immunoresistance to botulinum toxin therapy.

VII. Method for Stimulating an Immune Response in an Individual Against BoNT

A BoNT/A immune response inducing of the invention can stimulate an immune response against botulinum toxin in an individual, resulting in the production of antibodies that bind to and neutralize botulinum toxin. Such an immune response increases the ability of an individual's immune system to destroy botulinum toxin and thereby prevent harmful effects of botulinum toxin exposure. Thus, the present invention provides, in part, a method of stimulating antibodies that neutralize botulinum toxin type A in an individual, the method comprising the step of administering to said individual an immune response inducing composition comprising an adjuvant and a BoNT/A peptide, wherein said administration stimulates the production of anti-botulinum toxin antibodies capable of preventing or ameliorating the harmful effects of botulinum toxin exposure.

Aspects of the present invention provide, in part, a immune response inducing composition. It is envisioned that any of the immune response inducing composition disclosed in the present specification can be useful in a method of treating immunoresistance to botulinum toxin therapy in an individual, with the proviso that the immune response inducing composition stimulates the production of antibodies that neutralize botulinum toxin type A. Non-limiting examples include immune response inducing compositions comprising BoNT/A peptide derived from a naturally occurring BoNT/A, such as, e.g., BoNT/A peptide derived from the BoNT/A of SEQ ID NO: 1, a BoNT/A peptide derived from a BoNT/A isoform or a BoNT/A peptide derived from a BoNT/A subtype; and a BoNT/A peptide derived from a non-naturally occurring BoNT/A, such as, e.g., a BoNT/A peptide derived from a conservative BoNT/A variant, a BoNT/A peptide derived from a non-conservative BoNT/A variant and a BoNT/A peptide derived from a chimeric BoNT/A peptide. BoNT/A peptides within a immune response inducing composition disclosed in the present specification can be selected on, e.g., immunological factors, such as the immunoreactivity of the BoNT/A peptide, and technical factors, such as chemical synthesis yields. It is also understood that the two or more different BoNT/A peptides can be provided separately or as part of a compound molecule such as a chimeric BoNT/A peptide.

It is envisioned that any and all adjuvants can be useful in such an immune response inducing composition. As used herein, the term "adjuvant" when used in reference to an immune response inducing composition means any substance or mixture of substances that increases or diversifies the immune response to an antigenic compound. An adjuvant can, for example, serve to reduce the number of immunizations or the amount of antigen required for protective immunization. The use of adjuvants in an immune response inducing composition is well known. The main objective of these adjuvants is to allow an increase in the immune response. These adjuvants are diverse in nature. Various adjuvants used to increase the immunological response include, but are not limited to, e.g., the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); lipopolysaccharide (LPS), surface active substances, such as, e.g., lysolecithin, pluronic polyols, polyanions, peptides and dinitrophenol; adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide (Al(OH)$_3$) is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any adjuvant may be used in the immunogenic composition of the present invention as long as the adjuvant satisfies the requisite characteristics that are necessary for practicing the present invention. As indicated above, the carrier of the compositions of the present invention itself may act as an adjuvant. Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptomycin or a mixture thereof.

Thus, the present invention provides a method of preventing or reducing BoNT/A toxicity in an individual by administering to an individual a BoNT/A immune response inducing composition disclosed in the present specification. A BoNT/A immune response inducing composition can be administered to an individual prior to Botulinum toxin exposure to reduce or prevent BoNT/A toxicity, or after exposure to a Botulinum toxin, for example, when symptoms of toxicity are first apparent. In addition, a BoNT/A immune response inducing composition can be administered to an individual who is at increased risk for BoNT/A toxicity. Those skilled in the art will be able to determine an appropriate candidate for receiving a BoNT/A immune response inducing composition of the invention based on, for example, the particular condition to be treated and the presence or likelihood Botulinum toxin exposure. In one embodiment, a method of the present invention is practiced by administering a BoNT/A immune response inducing composition to an individual prior to exposure to a Botulinum toxin. Such an individual can be, for example, an individual at increased risk for exposure to a Botulinum toxin. In another embodiment, a method of the present invention is practiced by administering a BoNT/A immune response inducing composition after the individual has been exposed to a Botulinum toxin. In yet another embodiment, a method of the present invention is practiced by administering a BoNT/A immune response inducing composition to an individual who has not been diagnosed with Botulinum toxicity. In yet another embodiment, a method of the present invention is practiced by administering a BoNT/A immune response inducing composition to an individual who has been diagnosed with Botulinum toxicity.

One skilled in the art can determine if a BoNT/A immune response inducing induces an immune response, as methods for detecting immune responses are well known in the art. Non-limiting examples involve measuring the titer of BoNT/A-selective antibodies in an animal primed with the BoNT/A immune response inducing and boosted with the antigen, or determining the presence of antibodies in the blood of an immunized animal that are cross-reactive with the antigen by ELISA, Western blotting or other well-known methods. Cell-mediated immune responses can be determined, for example, by measuring cytotoxic T cell response to antigen using a variety of methods described hereinabove or well known in the art.

A BoNT/A immune response inducing composition useful in a method of the invention can be administered by any of a variety of routes, as described below. Those skilled in the art can readily determine for a particular BoNT/A BoNT/A immune response inducing, the appropriate antigen payload;

route of immunization; volume of dose; and vaccination regimen useful in a particular animal, for example, humans.

As disclosed herein a BoNT/A immune response inducing composition is administered to an individual to treat a condition characterized by BoNT/A immunoresistance. As used herein, the term "treating," when used in reference to administering to a human or other mammal an effective amount of a BoNT/A immune response inducing composition, means reducing a symptom of a condition characterized by BoNT/A toxicity, or delaying or preventing onset of a symptom of a condition characterized by BoNT/A toxicity in the individual. For example, the term "treating" can mean reducing a symptom of a condition characterized by BoNT/A toxicity by at least 30%, 40%, 60%, 70%, 80%, 90% or 100%. The effectiveness of a BoNT/A immune response inducing composition in treating a condition characterized by BoNT/A toxicity can be determined by observing one or more clinical symptoms or physiological indicators associated with the condition. An improvement in a condition characterized by BoNT/A toxicity also can be indicated by a reduced need for a concurrent therapy. Those of skill in the art will know the appropriate symptoms or indicators associated with specific conditions and will know how to determine if an individual is a candidate for treatment with a BoNT/A immune response inducing composition disclosed in the present specification. In particular, it is understood that those skilled in the art will be able to determine if a condition if characterized by BoNT/A toxicity, for example, by comparison of levels of BoNT/A toxicity from a normal control individual.

The appropriate effective amount to be administered for a particular application of the methods can be determined by those skilled in the art, using the guidance provided herein. For example, an effective amount can be extrapolated from in vitro and in vivo assays as described herein above. One skilled in the art will recognize that the condition of the patient can be monitored throughout the course of therapy and that the effective amount of a BoNT/A immune response inducing composition that is administered can be adjusted accordingly.

A BoNT/A immune response inducing composition useful in the invention generally is administered in a pharmaceutical acceptable composition. As used herein, the term "pharmaceutically acceptable" refer to any molecular entity or composition that does not produce an adverse, allergic or other untoward or unwanted reaction when administered to an individual. As used herein, the term "pharmaceutically acceptable composition" refers to a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient."

Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, $7^{th}$ ed. 1999); REMINGTON: THE SCIENCE AND PRACTICE OF PHARMACY (Alfonso R. Gennaro ed., Lippincott, Williams & Wilkins, $20^{th}$ ed. 2000); GOODMAN & GILMAN'S THE PHARMACOLOGICAL BASIS OF THERAPEUTICS (Joel G. Hardman et al., eds., McGraw-Hill Professional, $10^{th}$ ed. 2001); and HANDBOOK OF PHARMACEUTICAL EXCIPIENTS (Raymond C. Rowe et al., APhA Publications, $4^{th}$ edition 2003) which are hereby incorporated by reference in their entirety. These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

A BoNT/A immune response inducing composition useful in a method of the invention is administered to an individual in an effective amount. Such an effective amount generally is the minimum dose necessary to achieve the desired therapeutic effect, which can be, for example, that amount roughly necessary to reduce the symptoms associated with BoNT/A toxicity. For example, the term "effective amount" when used with respect to treating BoNT/A toxicity can be a dose sufficient to the symptoms, for example, by at least 30%, 40%, 50%, 60%, 70%, 80%, 90% or 100%. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the BoNT/A toxicity, the age and weight of the patient, the patient's general physical condition, the BoNT/A immune response inducing composition, the cause of the BoNT/A toxicity and the route of administration. Where repeated administration is used, the frequency of administration depends, in part, on the half-life of the BoNT/A immune response inducing composition. Suppositories and extended release formulations can be useful in the invention and include, for example, dermal patches, formulations for deposit on or under the skin and formulations for intramuscular injection. It is understood that slow-release formulations also can be useful in the methods of the invention. The subject receiving the BoNT/A immune response inducing composition can be any mammal or other vertebrate capable of experiencing BoNT/A toxicity, for example, a human, primate, horse, cow, dog, cat or bird.

Various routes of administration can be useful for treating BoNT/A toxicity, according to a method of the invention. A pharmaceutical composition useful in the methods of the invention can be administered to a mammal by any of a variety of means depending, for example, on the type and location of BoNT/A toxicity to be treated, the BoNT/A immune response inducing composition or other compound to be included in the composition, and the history, risk factors and symptoms of the subject. Routes of administration suitable for the methods of the invention include both systemic and local administration. As non-limiting examples, a pharmaceutical composition useful for treating BoNT/A toxicity can be administered orally or by subcutaneous pump; by dermal patch; by intravenous, subcutaneous or intramuscular injection; by topical drops, creams, gels or ointments; as an implanted or injected extended release formulation; as a bioerodible or non-bioerodible delivery system; by subcutaneous minipump or other implanted device; by intrathecal pump or injection; or by epidural injection. An exemplary list of biodegradable polymers and methods of use are described in, e.g., HANDBOOK OF BIODEGRADABLE POLYMERS (Abraham J. Domb et al., eds., Overseas Publishers Association, 1997); CONTROLLED DRUG DELIVERY: DESIGNING TECHNOLOGIES FOR THE FUTURE (Kinam Park & Randy J. Mrsny eds., American Chemical Association, 2000); Vernon G. Wong, Method for Reducing or Preventing Transplant Rejection in the Eye and Intraocular Implants for Use Therefor, U.S. Pat. No. 6,699,493 (Mar. 2, 2004); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/0137059 (Jul. 15, 2004), which are hereby incorporated by reference in their entirety. It is understood that the frequency and duration of dosing will be dependent, in part, on the relief desired and the half-life of the BoNT/A toxicity.

In particular embodiments, a method of the invention is practiced by peripheral administration of a BoNT/A immune response inducing composition. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation are not within the scope of the term "peripheral administration" or "administered peripherally."

Peripheral administration can be local or systemic. Local administration results in significantly more of a pharmaceutical composition being delivered to and about the site of local administration than to regions distal to the site of administration. Systemic administration results in delivery of a pharmaceutical composition to essentially the entire peripheral nervous system of the subject and may also result in delivery to the central nervous system depending on the properties of the composition.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

VIII. Method of Preparing Anti-BoNT/A Antibody Compositions

A BoNT/A peptide composition disclosed in the present specification can be used in a process for preparing an anti-BoNT antibody composition. Thus, the present invention provides a method of preparing an anti-BoNT/A antibody by administering to an animal a BoNT/A peptide disclosed in the present specification; collecting from the animal a sample containing an antibody or antibody-producing cell; and processing the sample to isolate the anti-BoNT/A antibody, with the proviso that the BoNT/A peptide is not SEQ ID NO: 5. Antibodies to be prepared according to a method of the invention include polyclonal and monoclonal antibodies. An anti-BoNT/A antibody prepared according to a method of the invention, or a monoclonal anti-BoNT/A antibody of the invention as described further below, can be used in a variety of applications. Such applications include, for example, detection of botulinum toxin in a sample, such as a substance suspected to be contaminated with BoNT/A.

The present invention provides, in part, a method of stimulating an anti-BoNT/A antibody in an animal, the method comprising the steps of administering to the individual an immune response inducing composition comprising an adjuvant and a BoNT/A peptide, where administration of the immune response inducing composition produces an immune response in the individual, collecting from the individual a sample containing the anti-BoNT/A antibody or anti-BoNT/A antibody-producing cell; and isolating the anti-BoNT/A antibody from the sample.

Aspects of the present invention provide, in part, an anti-BoNT antibody composition. It is envisioned that any of the anti-BoNT antibody composition disclosed in the present specification can be useful in a method of stimulating the production of an anti-BoNT/A antibody in an animal, with the proviso that the anti-BoNT antibody composition stimulates the production of antibodies against botulinum toxin type A. Non-limiting examples include anti-BoNT antibody compositions comprising BoNT/A peptide derived from a naturally occurring BoNT/A, such as, e.g., BoNT/A peptide derived from the BoNT/A of SEQ ID NO: 1, a BoNT/A peptide derived from a BoNT/A isoform or a BoNT/A peptide derived from a BoNT/A subtype; and a BoNT/A peptide derived from a non-naturally occurring BoNT/A, such as, e.g., a BoNT/A peptide derived from a conservative BoNT/A variant, a BoNT/A peptide derived from a non-conservative BoNT/A variant and a BoNT/A peptide derived from a chimeric BoNT/A peptide. BoNT/A peptides within an anti-BoNT antibody composition disclosed in the present specification can be selected on, e.g., immunological factors, such as the immunoreactivity of the BoNT/A peptide, and technical factors, such as chemical synthesis yields. It is also understood that the two or more different BoNT/A peptides can be provided separately or as part of a compound molecule such as a chimeric BoNT/A peptide.

Aspects of the present invention provide, in part, an anti-BoNT/A antibody. As used herein, the term "antibody" means a molecule made in response to a particular antigen response and includes, without limitation, polyclonal antibodies, monoclonal antibodies and antigenic compound-binding fragments of such antibodies, such as, e.g., Fab, F(ab')$_2$, Fc, Fd, Fv fragments, and single chain derivatives of the same. Polyclonal antibodies refer to a heterogeneous population of antibody molecules that contain at least two species of antibody capable of binding to a particular antigen. By definition, a polyclonal antibody binds to at least two different epitopes. Monoclonal antibodies refer to a homogeneous population of antibody molecules that contain only one species of antibody capable of binding a particular antigen. By definition, a monoclonal antibody binds to a single epitope. Antibody also includes cell-associated antibodies, such as Ig receptors, for example. In addition, the term "antibody" includes naturally occurring antibodies, as well as non-naturally occurring antibodies, including, for example, chimeric, bifunctional, and humanized antibodies, and related synthetic isoforms.

As used herein, the term "anti-BoNT/A antibody" means an anti-BoNT/A antibody that selectively binds to a BoNT/A. As used herein, the term "selectively" means having a unique effect or influence or reacting in only one way or with only one thing. As used herein, the term "selectively binds" means the discriminatory binding of the antibody to the indicated target epitope such that the antibody does not substantially cross react with unrelated epitopes. Selective binding includes binding properties such as, e.g., binding specificity, binding affinity and binding avidity. Binding specificity is the ability of an antibody to discriminate between a molecule containing its epitope and a molecule that does not contain that epitope. An anti-BoNT/A antibody disclosed in the present specification is characterized by having a binding specificity for its epitope of at least 10-fold greater relative to a BoNT/A not comprising that epitope. In aspects of this embodiment, an anti-BoNT/A antibody binding specificity for its epitope relative to a BoNT/A not comprising that epitope is, e.g., at least 10-fold greater, at least 100-fold greater, at least 1.000-fold greater or at least 10.000-fold greater. Binding affinity is the strength with which an antibody binds its epitope. In an embodiment, an anti-BoNT/A antibody disclosed in the present specification is characterized by having a binding affinity of at least $1\times10^{-5}$ $M^{-1}$. For example, an anti-BoNT/A antibody disclosed in the present specification can bind a target peptide with a binding affinity of at least $1\times10^{-5}$ $M^{-1}$, at least $1\times10^{-6}$ $M^{-1}$, at least $1\times10^{-7}$ $M^1$, at least $1\times10^{-8}$ $M^{-1}$, at least $1\times10^{-9}$ $M^{-1}$, or at least $1\times10^{-1}$ $M^{-1}$. Several methods for detecting or measuring antibody binding are known in the art and disclosed herein.

Binding avidity refers to an antibody that can bind more than one epitope of a target molecule and the binding affinities of these epitopes. It is envisioned that an anti-BoNT/A antibody disclosed in the present specification can selectively bind to any and all epitopes for that antibody. As used herein, an "epitope" is synonymous with "antigenic determinant" and means the site on a target molecule, such as, e.g., a peptide, polysaccharide or lipid-containing molecule, that is bound by a particular antibody or T-cell receptor. The minimal size of a peptide epitope, as defined herein, is about five amino acids, and a peptide epitope typically comprises at least eight amino acids. A peptide epitope may be discontinuous, i.e., it comprises amino acid residues that are not adjacent in the peptide but are brought together into an epitope by way of the secondary, tertiary, or quaternary structure of the peptide. Furthermore, it is also noted that an epitope might comprise a portion of a molecule other than an amino acid sequence, such as, e.g., a carbohydrate moiety, a lipid moiety like lipoproteins or glycolipids, or a chemically-modified amino acid moiety like a phosphorylated amino acid. In aspects of this embodiment, an anti-BoNT/A antibody can selectively bind a BoNT/A epitope comprising at least five amino acids, at least six amino acids, at least seven amino acids, at least eight amino acids, at least nine amino acids, at least ten amino acids or at least 20 amino acids. In other aspects of this embodiment, an anti-BoNT/A antibody can selectively bind a BoNT/A epitope comprising at most five amino acids, at most six amino acids, at most seven amino acids, at most eight amino acids, at most nine amino acids, at most ten amino acids or at most 20 amino acids.

An anti-BoNT/A antibody disclosed in the present specification can be produced by a wide variety of methods that are well known in the art. Specific protocols for making and using antibodies as well as detecting, and measuring antibody binding specificity, binding affinity and binding avidity are known in the art, see, e.g., Harlow & Lane, supra, 1998a; Harlow & Lane, supra, 1998b; Molecular Cloning, A Laboratory Manual, supra, 2001; and Current Protocols in Molecular Biology, supra, 2004; David Anderson et al., Therapeutic Polypeptides, Nucleic Acids Encoding Same, and Methods of Use, U.S. Pat. No. 7,034,132 (Apr. 25, 2005); and Beatriz M. Carreno et al., Antibodies Against CTLA4, U.S. Pat. No. 7,034,121 (Apr. 25, 2006).

As a non-limiting example, anti-BoNT/A polyclonal antibodies can be produced by injecting an individual, such as, e.g., a rabbit, a goat, a mouse or another mammal, with one or more injections of an immune inducing composition disclosed in the present specification. The resulting anti-BoNT/A polyclonal antibodies produced can be screened from serum of the immunized individual with a BoNT/A peptide disclosed in the present specification using a radioimmunoassay or enzyme-linked immunosorbent assay.

As another non-limiting example, an anti-BoNT/A monoclonal antibody can be produced using a hybridoma method. In this method, an individual, such as, e.g., a mouse, a hamster, or another appropriate host individual, is typically exposed to one or more injections of an immune inducing composition disclosed in the present specification to elicit lymphocytes that produce or are capable of producing anti-BoNT/A antibodies that will specifically bind to the BoNT/A antigen. Alternatively, the lymphocytes can be immunized in vitro using a suitable cell culture line. Generally, either peripheral blood lymphocytes are used, if cells of human origin are desired, or spleen cells or lymph node cells are used, if non-human mammalian sources are desired. The lymphocytes are then fused with an immortalized cell line using a suitable fusing agent, such as polyethylene glycol, to form a hybridoma cell, see, e.g., Goding, Monoclonal Antibodies: Principles and Practice, Academic Press, (1986) pp. 59-103. Immortalized cell lines are usually transformed mammalian cells, particularly myeloma cells of rodent, bovine and human origin. Usually, rat or mouse myeloma cell lines are employed. The culture medium in which the hybridoma cells are grown can then be assayed for the presence of anti-BoNT/A monoclonal antibodies directed against the BoNT/A antigen disclosed in the present specification, see, e.g., Harlow & Lane, supra, 1998a; and Harlow & Lane, supra, 1998b. For example, hybridoma supernatants can be screened using anti-BoNT/A-positive sera in an immunoprecipitation assay or by an in vitro binding assay, such as, e.g., a radioimmunoassay (RIA) or an enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). After the desired hybridoma cells are identified, the clones can be subcloned by limiting dilution procedures until isolate cell line is produced.

As an alternative to preparing monoclonal antibody-secreting hybridomas, an anti-BoNT/A monoclonal antibody can be identified and isolated by screening a recombinant combinatorial immunoglobulin library, such as, e.g., an antibody phage display library, with a BoNT/A peptide and isolate immunoglobulin library members that bind a BoNT/A peptide. Kits for generating and screening phage display libraries are commercially available, such as, e.g., the Recombinant Phage Antibody System (Pharmacia); and the SurfZAP™ Phage Display Kit (Stratagene). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; McCafferty et al. U.S. Pat. No. 6,172,197; Johnson et al. U.S. Pat. No. 6,140,471; Jespers et al. U.S. Pat. No. 6,017,732; Griffiths et al. U.S. Pat. No. 6,010,884; McCafferty et al. U.S. Pat. No. 5,969,108; Griffiths et al. U.S. Pat. No. 5,962,255; Griffiths et al. U.S. Pat. No. 5,885,793; Borrebaeck et al. U.S. Pat. No. 6,027,930; Borrebaeck et al. U.S. Pat. No. 5,712,089.

Non-naturally occurring anti-BoNT/A antibodies can be constructed using solid phase peptide synthesis, produced recombinantly or obtained, e.g., by screening combinatorial libraries consisting of variable heavy chains and variable light chains as described in, e.g., Huse et al., 246 Science 1275-1281 (1989). These and other methods of making, for example, chimeric, humanized, CDR-grafted, single chain, and bifunctional antibodies are well known to those skilled in the art, see, e.g., Winter and Harris, 14 Immunol. Today 243-246 (1993); Ward et al., 341 Nature 544-546 (1989); Harlow and Lane, supra, 1988a; Hilyard et al., *Protein Engineering: A Practical Approach* (IRL Press 1992); and Borrabeck, *Antibody Engineering,* 2d ed. (Oxford University Press 1995).

Aspects of the present invention provide, in part, collecting a sample containing the anti-BoNT/A antibody or anti-BoNT/A antibody-producing cell. As used herein, the term "sample containing the anti-BoNT/A antibody or anti-BoNT/A antibody-producing cell" means any biological matter that contains or potentially contains at least one anti-BoNT/A antibody. It is envisioned that any and all samples that can contain an anti-BoNT/A antibody can be used in this method, including, without limitation, blood, plasma, serum and lymph fluid. It is also envisioned that any cell capable of producing an anti-BoNT/A antibody can be used in this method, including, without limitation, a CD8 cells, a CTL cell, a helper T-cell and a B-cell. A variety of well known methods can be used for collecting from an individual a sample containing the anti-BoNT/A antibody or anti-BoNT/A antibody-producing cell, see, e.g., Harlow & Lane, supra, 1998a; and Harlow & Lane, supra, 1998b. Similarly, a variety of well known methods can be used for processing a sample to isolate an anti-BoNT/A antibody. A procedure for collecting a sample can be selected based on the type of antibody to be isolated. As a non-limiting example, when isolating anti-BoNT/A polyclonal antibodies, an appropriate sample can be a blood sample containing anti-BoNT/A antibodies, whereas when isolating monoclonal anti-BoNT/A antibodies, an appropriate sample can be an anti-BoNT/A antibody-producing cell such as a spleen cell.

Aspects of the present invention provide, in part, isolating the anti-BoNT/A antibody from the sample. Methods of isolating an anti-BoNT/A antibody, such as, e.g., anti-BoNT/A polyclonal antibodies or a anti-BoNT/A monoclonal antibody are well known to those skilled in the art, see, e.g., Harlow and Lane, supra, 1998a; and Harlow and Lane, supra, 1998b. For example, BoNT/A polyclonal antibodies can be isolated from the sample by well known techniques, such as, e.g., affinity chromatography using protein A or protein G, which provide primarily the IgG fraction of immune serum. Subsequently, or alternatively, the specific BoNT/A polyclonal antibody sought may be immobilized on a column to purify the immune specific antibody by immunoaffinity chromatography. An anti-BoNT/A monoclonal antibody can be isolated from the culture medium or ascites fluid by conventional immunoglobulin purification procedures such as, e.g., protein A-Sepharose, hydroxylapatite chromatography, gel electrophoresis, dialysis, or affinity chromatography.

Thus, in an embodiment, a method of producing an anti-BoNT/A antibody comprises the steps of administering to an animal a BoNT/A antigen, collecting from the animal a sample containing the anti-BoNT/A antibody or anti-BoNT/A antibody-producing cell, and isolating the anti-BoNT/A antibody from the sample. In an aspect of this embodiment, the anti-BoNT/A antibody is a polyclonal anti-BoNT/A antibody. In another aspect of this embodiment, the anti-BoNT/A antibody is a monoclonal anti-BoNT/A antibody. In a further aspect of this embodiment, a a monoclonal anti-BoNT/A antibody produced in an IgG subtype.

IX. Method of Reducing Anti-BoNT/A Antibodies

Patients treated with a BoNT therapy can develop immunoresistance to the treatment, thereby reducing or eliminating the beneficial effect of the BoNT therapy. Therefore, blood purifying methods that reduce or eliminate anti-BoNT antibodies from a patient mounting an immune response against a BoNT therapy are of major importance. Immunoapheretic methods would provide a remedy for BoNT immunoresistance, thereby allowing a patient to continue undergoing a BoNT therapy. Therefore, these methods present a major benefit in terms of providing better patient care and reducing health care costs. The BoNT/A peptides disclosed in the present specification are useful in methods of reducing or eliminating anti-BoNT antibodies from an individual. In general, blood from an individual exhibiting signs of immunoresistance to a BoNT therapy can be treated extracorporeally to remove anti-BoNT antibodies using an immunosorbent composition comprising at least one BoNT/A peptide disclosed in the present specification and the treated blood returned back into the individual. Therapeutic immunopheresis has been successfully applied, see, e.g., A. du Moulin et al., *Antibody-based immunoadsorption as a Therapeutic Means,* 11(3) Blood Purif. 145-149 (1993); W. O. Richter et al., *Efficacy and Safety of Immunoglobulin Apheresis,* 43(1) ASAIO J. 53-59 (1997); Watts A. Foley et al., *Plasma Perfusion by Apheresis Through a Gal Immunoaffinity Column Successfully Depletes anti-Gal Antibody: Experience with 320 Aphereses in Baboons,* 7 Xenotransplant. 181-185 (2000); Monika Graninger et al, *Immunoadsorption Therapy (Therasorb) in Patients with Severe Lupus Erythematosus,* 29 Acta. Med. Austriaca 26-29 (2002); Daniel R. Henderson et al., Methods of Enhancing Effectiveness of Therapeutic Viral Immunogenic Agent Administration, U.S. Pat. No. 6,406,861 (Jun. 18, 2002); and Robert Koll et al., Treatment of Cardiomyopathy by Removal of Autoantibodies, U.S. Pat. No. 7,022,322 (Apr. 4, 2006).

Thus, the present invention provides, in part, an anti-BoNT immunoapheresis method of treating immunoresistance to a BoNT therapy in an individual, the method comprising the steps of contacting an anti-BoNT antibody containing component from the individual extracorporeally with a BoNT/A peptide immunosorbent under conditions suitable for the selective binding of the BoNT/A peptide to the anti-BoNT antibody, the BoNT/A peptide having a length of at least 5 amino acids and at most 60 amino acids and returning the anti-BoNT antibody depleted component back into the individual. It is understood that any of the above methods of removing botulinum toxin blocking antibodies from a patient can be practiced by selectively removing IgG anti-botulinum toxin antibodies.

Aspects of the present invention provide, in part, an anti-BoNT immunoapheresis method. As used herein, the term "anti-BoNT immunoapheresis" is synonymous with "anti-BoNT immunoadsorption" and means the separation and removal of anti-BoNT antibodies from an anti-BoNT antibody containing component withdrawn from an individual and the remainder of the treated anti-BoNT antibody containing component returned back into the individual. By definition, anti-BoNT antibody adsorption by anti-BoNT immunoapheresis is an extracorporeal procedure.

Thus, in an embodiment, an anti-BoNT immunoapheresis method of treating immunoresistance to a BoNT therapy in an individual reduces the amount of anti-BoNT antibodies from an anti-BoNT antibody containing component. In aspects of this embodiment, the amount of anti-BoNT antibodies removed from an anti-BoNT antibody containing component is, e.g., at least 10% of the anti-BoNT antibodies from the anti-BoNT antibody containing component, at least 20% of the anti-BoNT antibodies from the anti-BoNT antibody containing component, at least 30% of the anti-BoNT antibodies from the anti-BoNT antibody containing component, at least 40% of the anti-BoNT antibodies from the anti-BoNT antibody containing component, at least 50% of the anti-BoNT antibodies from the anti-BoNT antibody containing component, at least 60% of the anti-BoNT antibodies from the anti-BoNT antibody containing component, at least 70% of the anti-BoNT antibodies from the anti-BoNT antibody containing component, at least 80% of the anti-BoNT antibodies from the anti-BoNT antibody containing component and at least 90% of the anti-BoNT antibodies from the anti-BoNT antibody containing component.

In other aspects of this embodiment, the amount of anti-BoNT antibodies removed from an anti-BoNT antibody containing component is, e.g., at most 10% of the anti-BoNT antibodies from the anti-BoNT antibody containing component, at most 20% of the anti-BoNT antibodies from the anti-BoNT antibody containing component, at most 30% of the anti-BoNT antibodies from the anti-BoNT antibody containing component, at most 40% of the anti-BoNT antibodies from the anti-BoNT antibody containing component, at most 50% of the anti-BoNT antibodies from the anti-BoNT antibody containing component, at most 60% of the anti-BoNT antibodies from the anti-BoNT antibody containing component, at most 70% of the anti-BoNT antibodies from the anti-BoNT antibody containing component, at most 80% of the anti-BoNT antibodies from the anti-BoNT antibody containing component and at most 90% of the anti-BoNT antibodies from the anti-BoNT antibody containing component.

Aspects of the present invention provide, in part, an anti-BoNT antibody containing component from the individual. Non-limiting examples of an anti-BoNT antibody containing component from the individual include, blood, serum, an isolated IgG antibody component and lymph fluid. Typically, blood removal and serum separation are achieved using an automated blood cell separator machine, see, e.g., Alessandro Zuccato and Rigaste S. Zeno, Method for the Specific Immunoadsorption of Selected Pathogenic Factors, PCT Publication WO 96/16666 (Jun. 6, 1996); and Robert Koll et al., Treatment of Cardiomyopathy by Removal of Autoantibodies, U.S. Pat. No. 7,022,322 (Apr. 4, 2006). Non-limiting examples of such a machine include, e.g., an autopheresis-Ctm Therapeutic Plasma System (TPS) is employed (Baxter Healthcare Corp, Deerfield, Ill.) and a COBE-Spectra pheresis unit (Blood Component Technology, Inc., Lakewood, Colo.).

Aspects of the present invention provide, in part, a BoNT/A peptide immunosorbent. As used herein, the term "BoNT/A peptide immunosorbent" means a molecule comprising a BoNT/A peptide that selectively binds to an anti-BoNT antibody. It is envisioned that any of the BoNT/A peptides disclosed in the present specification can be useful for anti-BoNT immunoapheresis for extracorporeal removal of anti-BoNT antibodies. Non-limiting examples include a BoNT/A peptide derived from a naturally occurring BoNT/A, such as, e.g., the BoNT/A of SEQ ID NO: 1, SEQ ID NO: 3, SEQ ID NO: 5, SEQ ID NO: 7, SEQ ID NO: 9, SEQ ID NO: 11 or SEQ ID NO: 13, a BoNT/A isoform or a BoNT/A subtype; and a BoNT/A peptide derived from a non-naturally occurring BoNT/A, such as, e.g., a conservative BoNT/A variant, a non-conservative BoNT/A variant and a chimeric BoNT/A peptide. BoNT/A peptides disclosed in the present specification can be selected, e.g., depending on immunological factors, such as potency of the peptide in eliciting an immunogenic response, and technical factors, such as chemical synthesis yields. It is also understood that the two or more different BoNT/A peptides can be provided separately or as part of a compound molecule such as a chimeric BoNT/A peptide.

Thus, in an embodiment, an immunoapheresis method of treating immunoresistance to a botulinum toxin therapy in an individual comprising the steps of removing blood from said individual, contacting the blood, or an anti-botulinum toxin antibody containing component thereof, with a BoNT/A peptide under conditions suitable for the selective binding of the BoNT/A peptide to the anti-botulinum toxin antibody, returning said anti-botulinum toxin antibody-depleted blood, or said anti-botulinum toxin antibody-depleted component thereof, to said individual.

In an embodiment of the present invention, blood, or an antibody-containing component thereof, is contacted with a BoNT/A peptide composition having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant or immunoreactive fragment thereof, with the proviso that the BoNT/A peptide is not SEQ ID NO: 5.

In another embodiment of the present invention, blood, or an antibody-containing component thereof, is contacted with a BoNT/A peptide composition having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, blood, or an antibody-containing component thereof, is contacted with a BoNT/A peptide composition having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28)

or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, blood, or an antibody-containing component thereof, is contacted with a BoNT/A peptide composition selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31). In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31). In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31). In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31).

In yet another aspect of this embodiment, blood, or an antibody-containing component thereof, is contacted with a BoNT/A peptide composition selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31). In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31).

In yet another embodiment of the present invention, blood, or an antibody-containing component thereof, is contacted with a BoNT/A peptide composition having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a conservative variant thereof.

In yet another aspect of this embodiment, blood, or an antibody-containing component thereof, is contacted with a BoNT/A peptide composition having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a conservative variant thereof.

In yet another embodiment of the present invention, blood, or an antibody-containing component thereof, is contacted with a BoNT/A peptide composition having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or a non-conservative variant thereof. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or a non-conservative variant thereof. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or a non-conservative variant thereof. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or a non-conservative variant thereof.

In yet another aspect of this embodiment, blood, or an antibody-containing component thereof, is contacted with a BoNT/A peptide composition having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or a non-conservative variant thereof. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or a non-conservative variant thereof.

In yet another embodiment of the present invention, blood, or an antibody-containing component thereof, is contacted with a BoNT/A peptide composition having a length of at most 60 amino acids and consisting of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30), or 1275-1296 of SEQ ID NO: 1 (C31), or an immunoreactive fragment thereof, with the proviso that the BoNT/A peptide is not SEQ ID NO: 5. In an aspect of this embodiment, such a BoNT/A peptide is selected from one of the following amino acid sequences: 463-481 of SEQ ID NO: 1 (N2), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 589-607 of SEQ ID NO: 1 (N11), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20), 1135-1153 of SEQ ID NO: 1 (C21), 1177-1195 of SEQ ID NO: 1 (C24), 1261-1279 of SEQ ID NO: 1 (C30) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 463-481 of SEQ ID NO: 1 (N2), 533-551 of SEQ ID NO: 1 (N7), 547-565 of SEQ ID NO: 1 (N8), 561-579 of SEQ ID NO: 1 (N9), 659-677 of SEQ ID NO: 1 (N16), 743-761 of SEQ ID NO: 1 (N22), 785-803 of SEQ ID NO: 1 (N25), 813-831 of SEQ ID NO: 1 (N27), 883-901 of SEQ ID NO: 1 (C3), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1121-1139 of SEQ ID NO: 1 (C20) or 1177-1195 of SEQ ID NO: 1 (C24) or 1275-1296 of SEQ ID NO: 1 (C31), or an immunoreactive fragment thereof, with the proviso that the BoNT/A peptide is not SEQ ID NO: 5. In another aspect of this embodiment, such a BoNT/A peptide is selected from one of the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), or 1275-1296 of SEQ ID NO: 1 (C31), or an immunoreactive fragment thereof, with the proviso that the BoNT/A peptide is not SEQ ID NO: 5.

In yet another aspect of this embodiment, blood, or an antibody-containing component thereof, is contacted with a BoNT/A peptide composition having a length of at most 60 amino acids and consisting of at least 5 contiguous amino acids selected from one of the following BoNT/A amino acid sequences: 463-481 of SEQ ID NO: 1 (N2), 505-523 of SEQ ID NO: 1 (N5), 519-537 of SEQ ID NO: 1 (N6), 533-551 of SEQ ID NO: 1 (N7), 603-621 of SEQ ID NO: 1 (N12), 645-663 of SEQ ID NO: 1 (N15), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 533-551 of SEQ ID NO: 1 (N7), 659-677 of SEQ ID NO: 1 (N16), 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1107-1125 of SEQ ID NO: 1 (C19), 1163-1181 of SEQ ID NO: 1 (C23), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 701-719 of SEQ ID NO: 1 (N19), 729-747 of SEQ ID NO: 1 (N21), 757-775 of SEQ ID NO: 1 (N23), 799-817 of SEQ ID NO: 1 (N26), 1065-1083 of SEQ ID NO: 1 (C16), 1079-1097 of SEQ ID NO: 1 (C17), 1107-1125 of SEQ ID NO: 1 (C19), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28) or 1275-1296 of SEQ ID NO: 1 (C31), or an immunoreactive fragment thereof, with the proviso that the BoNT/A peptide is not SEQ ID NO: 5. In yet another aspect of this embodiment, such a BoNT/A peptide is selected from one of the following amino acid sequences: 729-747 of SEQ ID NO: 1 (N21) 799-817 of SEQ ID NO: 1 (N26), 1065-1083 of SEQ ID NO: 1 (C16), 1163-1181 of SEQ ID NO: 1 (C23) or 1275-1296 of SEQ ID NO: 1 (C31), or an immunoreactive fragment thereof, with the proviso that the BoNT/A peptide is not SEQ ID NO: 5.

In is envisioned that a BoNT/A peptide useful in a method disclosed in the present specification for contacting blood, or an antibody-containing component thereof, can have any of a variety of lengths from at least 5 amino acids to at most 60 amino acids. Therefore, aspects of this embodiment may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids. Other aspects of this embodiment may include a BoNT/A peptide with at least, e.g., five amino acids of SEQ ID NO: 1, six amino acids of SEQ ID NO: 1, seven amino acids of SEQ ID NO: 1, eight amino acids of SEQ ID NO: 1, nine amino acids of SEQ ID NO: 1, ten amino acids of SEQ ID NO: 1, 11 amino acids of SEQ ID NO: 1, 12 amino acids of SEQ ID NO: 1, 13 amino acids of SEQ ID NO: 1, 14 amino acids of SEQ ID NO: 1, 15 amino acids of SEQ ID NO: 1, 16 amino acids of SEQ ID NO: 1, 17 amino acids of SEQ ID NO: 1, 18 amino acids of SEQ ID NO: 1, 19 amino acids of SEQ ID NO: 1, 20 amino acids of SEQ ID NO: 1, 25 amino acids of SEQ ID NO: 1, 30 amino acids of SEQ ID NO: 1, 35 amino acids of SEQ ID NO: 1, 40 amino acids of SEQ ID NO: 1, 45 amino acids of SEQ ID NO: 1, 50 amino acids of SEQ ID NO: 1, 55 amino acids or 60 amino acids of SEQ ID NO: 1. In further embodiments, such a BoNT/A peptide of the invention may include a BoNT/A peptide with at least, e.g., five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, 55 amino acids or 60 amino acids and consist of at least 5 contiguous amino acids selected from one of the following BoNT/A amino acid sequences: 449-467 of SEQ ID NO: 1(N1), 463-481 of SEQ ID NO: 1 (N2), 491-509 of SEQ ID NO: 1 (N4), 505-523 of SEQ ID NO: 1 (N5), 519-537 of SEQ ID NO: 1 (N6), 533-551 of SEQ ID NO: 1 (N7), 547-565 of SEQ ID NO: 1 (N8), 561-579 of SEQ ID NO: 1 (N9), 575-593 of SEQ ID NO: 1 (N10), 589-607 of SEQ ID NO: 1 (N11), 631-649 of SEQ ID NO: 1 (N14), 645-663 of SEQ ID NO: 1 (N15), 659-677 of SEQ ID NO: 1 (N16), 673-691 of SEQ ID NO: 1 (N17), 701-719 of SEQ ID NO: 1 (N19), 715-733 of SEQ ID NO: 1 (N20), 729-747 of SEQ ID NO: 1 (N21), 743-761 of SEQ ID NO: 1 (N22), 757-775 of SEQ ID NO: 1 (N23), 771-789 of SEQ ID NO: 1 (N24), 785-803 of SEQ ID NO: 1 (N25), 799-817 of SEQ ID NO: 1 (N26), 813-831 of SEQ ID NO: 1 (N27), 827-845 of SEQ ID NO: 1 (N28), 869-887 of SEQ ID NO: 1 (C2), 883-901 of SEQ ID NO: 1 (C3), 911-929 of SEQ ID NO: 1 (C5), 925-943 of SEQ ID NO: 1 (C6), 939-957 of SEQ ID NO: 1 (C7), 967-985 of SEQ ID NO: 1 (C9), 981-999 of SEQ ID NO: 1 (C10), 995-1013 of SEQ ID NO: 1 (C11), 1051-1069 of SEQ ID NO: 1 (C15), 1065-1083 of SEQ ID NO: 1 (C16), 1079-1097 of SEQ ID NO: 1 (C17), 1107-1125 of SEQ ID NO: 1 (C19), 1121-1139 of SEQ ID NO: 1 (C20), 1135-1153 of SEQ ID NO: 1 (C21), 1149-1167 of SEQ ID NO: 1 (C22), 1163-1181 of SEQ ID NO: 1 (C23), 1177-1195 of SEQ ID NO: 1 (C24), 1191-1209 of SEQ ID NO: 1 (C25), 1233-1251 of SEQ ID NO: 1 (C28), 1247-1265 of SEQ ID NO: 1 (C29), 1261-1279 of SEQ ID NO: 1 (C30) or 1275-1296 of SEQ ID NO: 1 (C31), or a conservative variant, a non-conservative variant, or immunoreactive fragment thereof, with the proviso that the BoNT/A peptide is not SEQ ID NO: 5.

In another embodiment of the present invention, a BoNT/A peptide composition useful for contacting blood, or an antibody-containing component thereof, in a method disclosed in the present specification can comprise one BoNT/A peptide disclosed in the present specification. In another embodiment of the present invention, a BoNT/A peptide composition useful for contacting blood, or an antibody-containing component thereof, in a method disclosed in the present specification can comprise a plurality of BoNT/A peptides disclosed in the present specification. Thus, aspects of this embodiment can include one or more BoNT/A peptides, two or more BoNT/A peptides, three or more BoNT/A peptides, four or more BoNT/A peptides, five or more BoNT/A peptides, six or more BoNT/A peptides, seven or more BoNT/A peptides, eight or more BoNT/A peptides, nine or more BoNT/A peptides, ten or more BoNT/A peptides, 15 or more BoNT/A peptides, 20 or more BoNT/A peptides, 25 or more BoNT/A peptides or 30 or more BoNT/A peptides. In other aspects of this embodiment can include one or more conservative BoNT/A peptide variants, two or more conservative BoNT/A peptide variants, three or more conservative BoNT/A peptide variants, four or more conservative BoNT/A peptide variants, five or more conservative BoNT/A peptide variants, six or more conservative BoNT/A peptide variants, seven or more conservative BoNT/A peptide variants, eight or more conservative BoNT/A peptide variants, nine or more conservative BoNT/A peptide variants, ten or more conservative BoNT/A peptide variants, 15 or more conservative BoNT/A peptide variants, 20 or more conservative BoNT/A peptide variants, 25 or more conservative BoNT/A peptide variants or 30 or more conservative BoNT/A peptide variants. In further aspects of this embodiment can include one or more non-conservative BoNT/A peptide variants, two or more non-conservative BoNT/A peptide variants, three or more non-conservative BoNT/A peptide variants, four or more non-conservative BoNT/A peptide variants, five or more non-conservative BoNT/A peptide variants, six or more non-conservative BoNT/A peptide variants, seven or more non-conservative BoNT/A peptide variants, eight or more non-conservative BoNT/A peptide variants, nine or more non-conservative BoNT/A peptide variants, ten or more non-conservative BoNT/A peptide variants, 15 or more non-conservative BoNT/A peptide variants, 20 or more non-conservative BoNT/A peptide variants, 25 or more non-conservative BoNT/A peptide variants or 30 or more non-conservative BoNT/A peptide variants. In still other aspects of this embodiment can include one or more immunoreactive BoNT/A peptide fragments, two or more immunoreactive BoNT/A peptide fragments, three or more immunoreactive BoNT/A peptide fragments, four or more immunoreactive BoNT/A peptide fragments, five or more immunoreactive BoNT/A peptide fragments, six or more immunoreactive BoNT/A peptide fragments, seven or more immunoreactive BoNT/A peptide fragments, eight or more immunoreactive BoNT/A peptide fragments, nine or more BoNT/A peptides, ten or more immunoreactive BoNT/A peptide fragments, 15 or more immunoreactive BoNT/A peptide fragments, 20 or more immunoreactive BoNT/A peptide fragments, 25 or more immunoreactive BoNT/A peptide fragments or 30 or more immunoreactive BoNT/A peptide fragments. BoNT/A peptides disclosed in the present specification useful for contacting blood, or an antibody-containing component thereof, can be selected, for example, depending on immunological factors, such as potency of the peptide in inducing an immune response, and technical factors, such as chemical synthesis yields. It is also understood that the two or more BoNT/A peptides can be provided separately or as part of a compound molecule such as a chimeric peptide or heterologous protein.

In an aspect of this embodiment, a method disclosed in the present specification of contacting blood, or an antibody-containing component thereof, uses two or more immunoreactive BoNT/A peptides selected from the following amino acid sequences: 533-551 of SEQ ID NO: 1 (N7), 547-565 of SEQ ID NO: 1 (N8), 743-761 of SEQ ID NO: 1 (N22), 785-803 of SEQ ID NO: 1 (N25), 813-831 of SEQ ID NO: 1 (N27), 995-1013 of SEQ ID NO: 1 (C11); 1051-1069 of SEQ ID NO: 1 (C15), 1177-1195 of SEQ ID NO: 1 (C24), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the selected amino acid sequence is 533-551 of SEQ ID NO: 1 (N8) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 533-551 of SEQ ID NO: 1 (N8) and 981-999 of SEQ ID NO: 1 (C10), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 533-551 of SEQ ID NO: 1 (N8), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In a further aspect of this embodiment, one of the amino acid sequences selected is 785-803 of SEQ ID NO: 1 (N25) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 785-803 of SEQ ID NO: 1 (N25) and 981-999 of SEQ ID NO: 1 (C10), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 785-803 of SEQ ID NO: 1 (N25), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 813-831 of SEQ ID NO: 1 (N27) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 813-831 of SEQ ID NO: 1 (N27) and 981-999 of SEQ ID NO: 1 (C10), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 813-831 of SEQ ID NO: 1 (N27), 981-999 of SEQ ID NO: 1 (C10) and 1051-1069 of SEQ ID NO: 1 (C15), or a conservative variant, a non-conservative variant or an immunoreactive fragment thereof, with the proviso that the BoNT/A peptide is not SEQ ID NO: 5.

In an aspect of this embodiment, a method disclosed in the present specification of contacting blood, or an antibody-containing component thereof, uses two or more immunoreactive BoNT/A peptides selected from the following amino acid sequences: 659-677 of SEQ ID NO: 1 (N16), 729-747 of SEQ ID NO: 1 (N21), 799-817 of SEQ ID NO: 1 (N26), 1065-1083 of SEQ ID NO: 1 (C16), 1163-1181 of SEQ ID NO: 1 (C23), and 1275-1296 of SEQ ID NO: 1 (C31), or a conservative variant, a non-conservative variant or an immunoreactive fragment thereof, with the proviso that the BoNT/A peptide is not SEQ ID NO: 5. In another aspect of this embodiment, one of the amino acid sequences selected is 1065-1083 of SEQ ID NO: 1 (C16) or a conservative variant, a non-conservative variant or an immunoreactive fragment thereof, with the proviso that the BoNT/A peptide is not SEQ ID NO: 5. In yet another aspect of this embodiment, the following two amino acid sequences are selected: 1065-1083 of SEQ ID NO: 1 (C16) and 1163-1181 of SEQ ID NO: 1

(C23), or a conservative variant, a non-conservative variant or an immunoreactive fragment thereof, with the proviso that the BoNT/A peptide is not SEQ ID NO: 5. In yet another aspect of this embodiment, the following three amino acid sequences are selected: 1065-1083 of SEQ ID NO: 1 (C16), 1163-1181 of SEQ ID NO: 1 (C23) and 1275-1296 of SEQ ID NO: 1 (C31), or a conservative variant, a non-conservative variant or an immunoreactive fragment thereof, with the proviso that the BoNT/A peptide is not SEQ ID NO: 5. In a further aspect of this embodiment, one of the amino acid sequences selected is 799-817 of SEQ ID NO: 1 (N26) or a conservative variant, a non-conservative variant or an immunoreactive fragment thereof, with the proviso that the BoNT/A peptide is not SEQ ID NO: 5. In a still further aspect of this embodiment, the following two amino acid sequences are selected: 799-817 of SEQ ID NO: 1 (N26) and 1065-1083 of SEQ ID NO: 1 (C16), or a conservative variant, a non-conservative variant or an immunoreactive fragment thereof, with the proviso that the BoNT/A peptide is not SEQ ID NO: 5. In a still further aspect of this embodiment, the following three amino acid sequences are selected: 799-817 of SEQ ID NO: 1 (N26), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5. In an additional aspect of this embodiment, one of the amino acid sequences selected is 729-747 of SEQ ID NO: 1 (N21) or a conservative variant, a non-conservative variant or an immunoreactive fragment thereof, with the proviso that the BoNT/A peptide is not SEQ ID NO: 5. In another additional aspect of this embodiment, the following two amino acid sequences are selected: 729-747 of SEQ ID NO: 1 (N21) and 1065-1083 of SEQ ID NO: 1 (C16), or a conservative variant, a non-conservative variant or an immunoreactive fragment thereof, with the proviso that the BoNT/A peptide is not SEQ ID NO: 5. In another additional aspect of this embodiment, the following three amino acid sequences are selected: 729-747 of SEQ ID NO: 1 (N21), 1065-1083 of SEQ ID NO: 1 (C16) and 1163-1181 of SEQ ID NO: 1 (C23), or a conservative variant, a non-conservative variant or an immunoreactive fragment thereof, with the proviso that the BoNT/A peptide is not SEQ ID NO: 5.

It is also envisioned that any and all combinations of BoNT/A peptides disclosed in the specification can be useful for contacting blood, or an antibody-containing component thereof, including, e.g., BoNT/A peptides of SEQ ID NO: 1, conservative BoNT/A peptide variants, non-conservative BoNT/A peptide variants and immunoreactive BoNT/A peptide fragments. Thus, aspects of this embodiment include one or more BoNT/A peptides comprising one or more BoNT/A peptides of SEQ ID NO: 1 and one or more conservative BoNT/A peptide variants; one or more BoNT/A peptides of SEQ ID NO: 1 and one or more non-conservative BoNT/A peptide variants; one or more BoNT/A peptides of SEQ ID NO: 1 and one or more immunoreactive BoNT/A peptide fragments; one or more conservative BoNT/A peptide variants and one or more non-conservative BoNT/A peptide variants; one or more conservative BoNT/A peptide variants and one or more immunoreactive BoNT/A peptide fragments; one or more non-conservative BoNT/A peptide variants and one or more immunoreactive BoNT/A peptide fragments; one or more BoNT/A peptides of SEQ ID NO: 1, one or more conservative BoNT/A peptide variants and one or more non-conservative BoNT/A peptide variants; one or more BoNT/A peptides of SEQ ID NO: 1, one or more conservative BoNT/A peptide variants and one or more immunoreactive BoNT/A peptide fragments; one or more BoNT/A peptides of SEQ ID NO: 1, one or more non-conservative BoNT/A peptide variants and one or more immunoreactive BoNT/A peptide fragments; one or more conservative BoNT/A peptide variants, one or more non-conservative BoNT/A peptide variants and one or more immunoreactive BoNT/A peptide fragments; or one or more BoNT/A peptides of SEQ ID NO: 1, one or more conservative BoNT/A peptide variants, one or more non-conservative BoNT/A peptide variants and one or more immunoreactive BoNT/A peptide fragments.

The ability of an anti-BoNT/A antibody prepared according to a method of the invention to neutralize the effects of botulinum toxicity on an individual, and, thus, "protect against" botulinum toxicity, can be determined in an animal model using a variety of methods well known to those skilled in the art. Exemplary animal models of botulism include rodent, rabbit and monkey models of foodborne botulism, rodent and chicken models of infant botulism and rodent models of wound botulism, all of which are described, for example, in Simpson, supra, 1989. It is understood that any of the above methods of removing botulinum toxin blocking antibodies from a patient can be practiced by selectively removing IgG anti-botulinum toxin antibodies. It is further understood that the two or more amino acid sequences can be provided separately or as part of a compound molecule such as a chimeric peptide or heterologous protein.

The BoNT/A peptides disclosed herein also can be useful for therapeutic immunoadsorption for extracorporeal removal of anti-BoNT/A antibodies. Such therapeutic immunoadsorption is well known in the art. In general, blood can be removed from a patient to be treated or having been treated with a botulinum toxin therapeutic such as BOTOX®; and anti-botulinum toxin antibodies subsequently removed from the blood, serum or plasma using affinity chromatography with one or more BoNT/A peptides of the invention are attached to a biocompatible support. In one embodiment, an N25 BoNT/A peptide is used for therapeutic immunoadsorption such that anti-N25 antibodies are removed from blood, serum or plasma. In another embodiment, one or a combination of N25, C10, C15, C20 or C31 BoNT/A peptides are used for therapeutic immunoadsorption such that antibodies to epitopes in the peptides used for the immunoadsorption are removed from blood, serum or plasma.

Biocompatible solid supports having combinations of two or more BoNT/A peptides can be useful in plasma or other pheresis, or pheresis can be performed using a series of affinity columns or other solid supports each having a different BoNT/A peptide. It is understood that the blood, serum, plasma or lymph are contacted with the one or more BoNT/A peptides attached to a biocompatible solid support under conditions that promote binding between the one or more BoNT/A peptides and anti-botulinum toxin antibodies in the patient fluid. As an example, extracorporeal hemoperfusion can be performed as described in M. Abdul Mazid, Affinity Supports for Hemoperfusion, U.S. Pat. No. 5,149,425 (Sep. 22, 1992). Such conditions can include, without limitation, contact temperatures in the range of 35° C. and 40° C., and contact times of about one to six hours. It is understood that the unbound portion of the blood, plasma, or serum, which is significantly antibody-depleted, is reintegrated with cellular components of whole blood as necessary and reintroduced into the patient on a continuous basis or following collection. One skilled in the art further understands that, if desired, the antibody-depleted blood, plasma or serum can be assayed prior to reintroduction in the patient, for example, using one of the BoNT/A peptide binding assays or protection assays disclosed herein.

Several techniques can be useful for removing anti-BoNT/A antibodies complexed with a BoNT/A peptide. As an example, a solid phase system can utilize a solid phase matrix which is a solid phrase support to which the one or more BoNT/A peptides are bound. The blood, plasma or serum containing the blocking antibodies is passed over the solid support, exiting the solid support and leaving behind the blocking antibody/peptide complexes. A variety of biocompatible solid supports can be useful in the methods of the invention. Such supports are chemically inert with respect to human antibody-containing fluids, have sufficient binding capacity, and generally are in the form of a continuous large surface such as a sheet or column, or in the form of particles or vesicles. Exemplary solid supports useful in the invention, including those useful for affinity chromatography, encompass, without limitation, silica; synthetic silicates such as porous glass, for example, glass fiber filters; biogenic silicates such as diatomaceous earth; silicate-containing materials such as kaolinite and borosilicate; and synthetic polymers such as polystyrene, polypropylene and polysaccharides, see, e.g., A. Heather Good, et al., Methods and Compositions for Attenuating Antibody-mediated Xenograft Rejection in Human Recipients, U.S. Pat. No. 6,607,723 (Aug. 19, 2003); and Mazid, supra, 1992. Biocompatible solid supports useful in the invention further include, yet are not limited to, agarose, which is a neutral linear polysaccharide generally composed of D-galactose and altered 3,6-anhydrogalactose residues, for example, Sepharose (Pharmacia); activated gels, cellulose, nitrocellulose, polyvinylchloride, and diazotized paper. The skilled person understands that these and a variety of other well known biocompatible solid supports can be useful in the methods of the invention.

The one or more BoNT/A peptides can be covalently or noncovalently bound to the solid support using well known methods. Supports which can be non-covalently bound by incubation with the immunosorbent include, without limitation, nitrocellulose, borosilicate, filters, polyvinylchloride, polystyrene and diazotized paper. Activated solid supports such as activated matrices also are well known in the art and commercially available and useful in the invention. Such activated solid supports encompass, without limitation, epoxy-activated agarose; CNBr-activated agarose; 6-aminohexanoic acid and 1,6-diaminohexane-agarose, thiopropyl agarose; carbonyldiimidazole-activated agarose; and aminoethyl and hydrazide-activated polyacrylamide, see, e.g., Daniel R. Henderson et al., Methods of Enhancing Effectiveness of Therapeutic Viral Immunogenic Agent Administration, U.S. Pat. No. 6,406,861 (Jun. 18, 2001; and Joseph P. Balint, Anti-human IGM Immunoadsorbent and Process for Producing Said Immunoadsorbent, U.S. Pat. No. 4,762,787 (Aug. 9, 1988).

In one embodiment, the methods of the invention for selectively removing blocking anti-botulinum toxin antibodies are performed using an affinity column. An affinity column is a cylindrical container with filters on both ends which contains a solid support to which the one or more BoNT/A peptides are bound. One skilled in the art understands that plasma or serum generally is passed through a column since whole blood contains cells and particulate matter such as platelets which can impede column flow. In another embodiment, a sheet such as a nitrocellulose sheet is pre-bound with one or more BoNT/A peptides, and blood, plasma or serum is incubated with the immunosorbent-linked nitrocellulose. In a further embodiment, one or more BoNT/A peptides are bound to large polystyrene petri dishes. Blood, plasma or serum from an individual is incubated with the BoNT/A peptide-linked polystyrene and is decanted, leaving behind the blocking antibodies complexed to the one or more BoNT/A peptides.

It is further understood that pre-clearance of antibodies, or a class of antibody such as the IgG class, can be performed prior to selective removal of anti-botulinum toxin antibodies. From the pre-cleared antibody pool, BoNT/A peptide-reactive antibodies can be selected, and the remaining antibodies reconstituted into the blood to be reperfused into the individual, thus reducing the volume to be passed over the blocking antibody selective support and also reducing non-specific binding. As a non-limiting example, non-specific Protein G Sepharose columns such as PROSORBA® (IMRE; Munich, Germany) or Ig-THERASORB® (Plasmaselect; Teterow, Germany) can be used to remove a significant portion of IgG antibody. A variety of additional techniques suitable for general pre-clearance of antibodies are well known in the art and include, yet are not limited to, ammonium sulfate precipitation with ion exchange chromatography; caprylic acid; DEAE-matrices (ion-exchange chromatography); hydroxyapatite chromatography, and gel filtration (Sepharose), see, e.g., Harlow & Lane, supra, 1998a; and Harlow & Lane, supra, 1998b.

In still a further embodiment, one or more BoNT/A peptides are bound to lipid vesicles, and the lipid vesicle-immunosorbent is mixed with a patient's plasma or serum to allow binding to the blocking antibodies. The plasma or serum is subsequently filtered to remove the lipid vesicle-immunosorbent-antibody complex, see, e.g., James F. Marten, Therapeutic Apheresis, U.S. Pat. No. 4,643,718 (Feb. 17, 1987).

One skilled in the art further understands that one or more BoNT/A peptides of the invention can be used for liquid phase separation of blocking antibodies from blood, plasma or serum. Liquid phase separation can be performed, for example, by conjugating one or more BoNT/A peptides to a hapten such as, without limitation, dinitrophenol or fluorescein. After mixing the hapten/BoNT/A peptide conjugate with a patient's blood, plasma or serum, the conjugate forms complexes with anti-botulinum toxin blocking antibodies. As a non-limiting example, such antibody complexes can be precipitated using polyethylene glycol (PEG), and the precipitated complexes separated from the blood, plasma or serum using centrifugation, see, e.g., Paul A. Liberti & Paul Pollara, Selective Removal of Immunospecifically Recognizable Substances from Solution, U.S. Pat. No. 4,551,435 (Nov. 5, 1985). One skilled in the art appreciates that these and other solid-phase and liquid-phase systems can be use 5,149 d to separate BoNT/A peptide/blocking antibody complexes from blood, plasma or serum.

As disclosed herein in Example 10 and discussed above, one or more of the synthetic peptides N25, C10, N15, N20 or N31 binds protective antibodies in the large majority of protective patient sera in a sample of 28 cervical dystonia patients treated with BOTOX® and having MPA-protective sera. Based on this finding, one or more of the BoNT/A peptides N25, C10, N15, N20 or N31, or a conservative variant or immunoreactive fragment thereof, can be useful for decreasing patient non-responsiveness when administered in excess together with a therapeutic botulinum toxin preparation.

The present invention additionally provides a method of predicting or determining immunoresistance to botulinum toxin therapy in an individual by determining the level of IgG antibodies immunoreactive with the botulinum toxin in the individual; and comparing the level of IgG antibodies to a control level of IgG antibodies, where an increase in the level of IgG antibodies in the individual as compared to the control level indicates immunoresistance to the botulinum toxin therapy. Such an increase can be, for example, at least a 5-fold increase or at least a 10-fold increase. In one embodiment, the control level of IgG antibodies is determined in an individual who has not been treated with botulinum toxin therapy. In another embodiment, the control level of IgG antibodies is determined in an individual who is responsive to the botulinum toxin therapy. The methods of the invention can be used to predict or determine immunoresistance to any of several botulinum toxin therapies including, without limitation, BoNT/A therapy.

Techniques for determining a level of IgG antibodies immunoreactive with a botulinum toxin such as BoNT/A are well known in the art and are described herein. For example, Example 9 describes a solid-phase radioimmunoassay for IgG anti-BoNT/A antibodies using an anti-mouse IgG secondary antibody. A variety of additional anti-IgG antibodies, including anti-human IgG antibodies, are well known in the art and are commercially available, including, but not limited to, rabbit anti-human IgG from Bethyl Laboratories, Inc. (Montgomery, Tex.) and goat anti-human IgG from Zymed Laboratories, Inc (San Francisco, Calif.). Thus, the methods of the invention can be practiced using any of the immunoassays described hereinabove or well known in the art which are specific for detection of IgG antibodies, for example, through use of an anti-IgG secondary antibody.

It is understood that modifications that do not substantially affect the activity of the various embodiments of this invention are also included within the definition of the invention provided herein. Accordingly, the following examples are intended to illustrate but not limit the present invention.

EXAMPLES

Example 1

Synthesis of BoNT/A Peptides

BoNT/A peptides were prepared by solid-phase peptide synthesis on a benzyloxybenzyl alcohol resin to which 9-fluorenylmethylcar-bonyl (Fmoc)-glycine had been coupled. The $N^\alpha$-Fmoc amino acid derivatives were obtained from Vega or from Peninsula Laboratories. The side-chain protecting groups were as follows: for aspartic acid, β-tert-butyl ester; for glutamic acid, γ-tert-butyl ester; for cysteine, S-tert-butyl; for histidine, im-trityl; for lysine, E-tert-butoxy-carbonyl; for serine, threonine, or tyrosine, O-tert-butyl; for arginine, $N^\omega$-methoxy-2,3,6-trimethylphenyl-sulfonyl. Removal of the $N^\alpha$-Fmoc group before each coupling was done by treatment of the peptide resin with 20% piperidine in dimethylformamide (DMF) for 10 min. This was followed by washing (3 times each, 30 sec) with DMF, methanol, and then DMF. Coupling of consecutive amino acids was done for 2 hr by using 3-molar excess of each of the Fmoc amino acid derivatives, diisopropylcarbodiimide in $DMF/CH_2Cl_2$, 1:1 (vol/vol) and 1-hydroxybenzotriazole. The resin was then washed with DMF and methanol (three times each, 30 sec), followed by two 30-sec washes of $CH_2Cl_2$. The completion of coupling after each residue was monitored by ninhydrin, and recoupling was repeated when necessary. After the last cycle and deprotection of the Fmoc-group, the peptide was cleaved from the resin by treatment (2.5 hr) with 55% trifluoroacetic acid in $CH_2Cl_2$, and the solvent was removed on a rotary evaporator. The peptide was washed three times with cold ether, dissolved in water, and freeze-dried. The products were purified by chromatography on CM-Sephadex C50 or DEAE-Sephadex A50. The peptides thus obtained were homogeneous by high-voltage paper electrophoresis and by analytical HPLC on a C18 column using a gradient of 0.1% trifluoracetic acid in water/0.1% trifluoracetic acid in acetonitrile. The amino acid sequence for each peptide was determined and found to have an amino acid composition consistent with that expected from BoNT/A (see FIG. 1).

Example 2

Mapping of Human Anti-Pentavalent Botulinum Toxoid Antibodies Using BoNT/A Synthetic Peptides This example shows antigenic mapping of botulinum toxin A with human anti-BoNT antisera using 29 BoNT/A synthetic peptides that encompass the $H_N$ domain of BoNT/A.

Human antisera against BoNT/A were prepared by immunizing human volunteers with a toxoid preparation made from BoNTs A, B, C, D and E as described in Atassi et al. supra, 1996. The binding assays described below were performed using IgG fractions of these antisera. For use as a control, an IgG fraction was prepared using pre-immune human serum.

For use in antigenic mapping, BoNT/A peptides were synthesized, purified and subjected to amino acid analysis by the procedure previously reported, see, e.g., M. Zouhair Atassi et al., *Localization and Synthesis of the Hormone-Binding Regions of the Human Thyrotropin Receptor*, 88(9) PROC. NATL. ACAD. SCI. USA 3613-3617 (1991). Each peptide was found to have an amino acid composition consistent with that expected from its covalent structure shown in FIG. 1. BoNTs A and B were purchased from Metabiologics, Inc. (Madison, Wis.).

BoNT/A peptides (2.5 μg in 50 μl of PBS) or active BoNT/A (1 μg in 50 μl PBS) were added to the wells of flexible polyvinyl chloride 96-well plates (Becton Dickinson; San Jose, Calif.) and allowed to bind for 18 hours at 4° C. After washing five times with PBS, the plates were blocked for 1 hour at 37° C. with 1% bovine serum albumin (BSA) in PBS. Aliquots (50 μl) of anti-toxin antisera that had been prediluted with 0.1% BSA in PBS (dilutions were human IgG fraction, 1:1000 and 1:2000 (vol/vol)) were pipetted into the appropriate wells and kept at 4° C. for 20 hours. The wells were washed five times with PBS before adding 50 μl of affinity-purified rabbit Ig against human IgG and IgM (Dako Corporation; Carpinteria, Calif.) diluted 1:1000 with 0.1% BSA in PBS to the wells of the plate, and incubating for 2 hours at 37° C.

The wells were then washed five times with PBS, and 50 μl of $^{125}$I-labeled Protein A ($2\times10^5$ cpm in 0.1% BSA in PBS) was distributed to the wells and allowed to incubate for 2 hours at room temperature. Finally, the plates were washed thoroughly to remove unbound radioactivity, the individual wells were cut out and transferred into separate tubes, and bound radioactivity was counted in a gamma-counter (1277 Gamma Master; LKB, Finland). Controls included binding of preimmune or normal sera to BoNT/A and its peptides, as well as binding of immune sera to BSA and unrelated peptides.

Assays were performed in triplicate. Results of the triplicate analyses were expressed as mean of net cpm A SD, after correction for nonspecific binding in control wells that were coated with BSA and unrelated peptides.

As shown in FIG. 2, human anti-BoNT antisera were observed to bind to several BoNT/A peptides. Peptide N25 (785-803) was observed to be immunodominant followed, in decreasing order, by regions N8 (residues 547-565 of SEQ ID NO: 1), N22 (residues 743-761 of SEQ ID NO: 1), and N16

(residues 659-677 of SEQ ID NO: 1). Lower, but reproducible, amounts of antibodies were bound, in decreasing order, by peptides N11 (residues 589-607 of SEQ ID NO: 1), N17 (residues 673-691 of SEQ ID NO: 1), N20 (residues 715-733 of SEQ ID NO: 1), N14 (residues 631-649 of SEQ ID NO: 1), N28 (residues 827-845 of SEQ ID NO: 1), N27 (residues 813-831 of SEQ ID NO: 1), N4 (residues 491-509 of SEQ ID NO: 1), N24 (residues 771-789 of SEQ ID NO: 1) and N7 (residues 533-551 of SEQ ID NO: 1). The remaining $H_N$ peptides bound little or no antibodies. As shown in FIG. 2, human antibodies bound to the $H_C$ peptides C2, C6, C10, C11, C15, C21, C24, C31 (FIG. 2) in agreement with previous studies, see, e.g., Atassi et al., supra, 1996. Human anti-BoNT antisera exhibited no binding to a control peptide corresponding to amino acids 218-231 of BoNT light chain ("L peptide). Nonimmune human IgG did not bind to any peptides, and human anti-BoNT antisera showed no antibody binding to unrelated proteins and peptides. The results define antigenic portions of the $H_N$ domain of BoNT/A.

The three-dimensional structure of BoNT/A reveals the solvent-exposed portions of the primary BoNT/A sequence, D. Borden Lacy et al. *Crystal Structure of Botulinum Neurotoxin Type A and Implications for Toxicity,* 5(10) NAT. STRUCT. BIOL. 898-902 (1996). Comparison with the results obtained in the present study revealed that the immunodominant antibody-binding regions reside on surface locations on the H subunit of BoNT/A.

In sum, these results demonstrate that BoNT/A peptides N25, N8, N22, N16, N11, N17, N20, N14, N28, N27, N4, N24, N7, C2, C6, C10, C11, C15, C21, C24, and C31 were recognized by human anti-BoNT antisera.

Example 3

Mapping of Horse BoNT/A Toxoid Antibodies Using BoNT/A Synthetic Peptides

This example describes antigenic mapping of BoNT/A with horse anti-BoNT antisera using 29 BoNT/A synthetic peptides that encompass the $H_N$ domain of BoNT/A.

Horse antisera were prepared by subcutaneous immunization, in multiple sites every two weeks for over a year, with a formaldehyde-inactivated BoNT/A in Ribi adjuvant. The antisera tested in the binding studies were obtained after four injections according to procedures described in Atassi et al., supra, 1996. For use as controls, non-immune horse sera were obtained from the animals before immunization.

Peptide binding assays were performed as described in Example 2, except that the dilution for horse antisera was 1:300 (vol/vol). The secondary antibodies were affinity purified rabbit anti-horse IgG obtained from Accurate Chemical & Scientific Corporation (Weston, N.Y.) and were diluted 1:500 (vol/vol).

Figure 4:
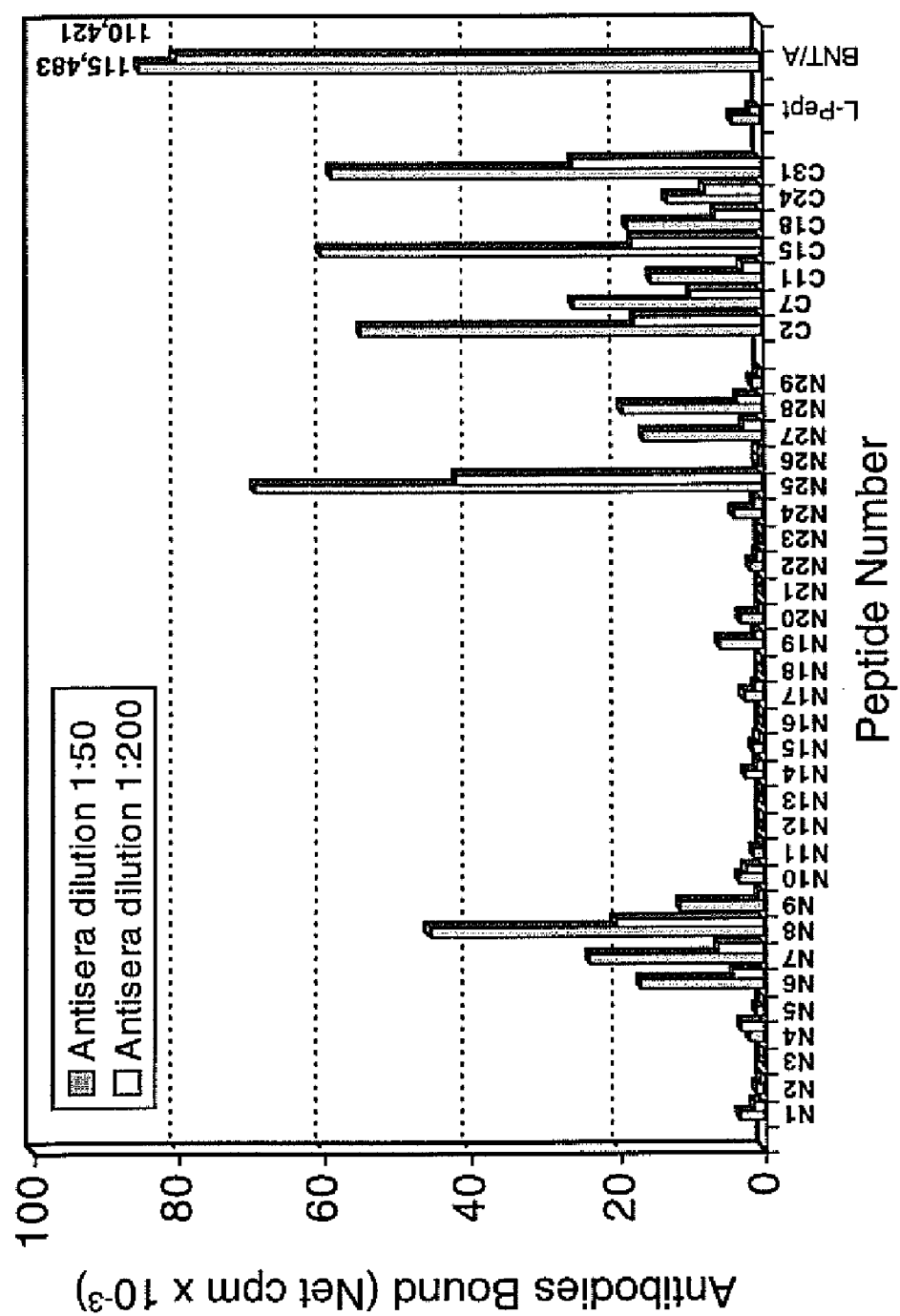
FIG. 4 shows binding of chicken anti-BoNT/A antibodies to 60 synthetic overlapping peptides spanning the entire H-subunit of BoNT/A. Also shown are binding to L-Peptide and full-length BoNT/A as negative and positive controls, respectively.
Figure 5:
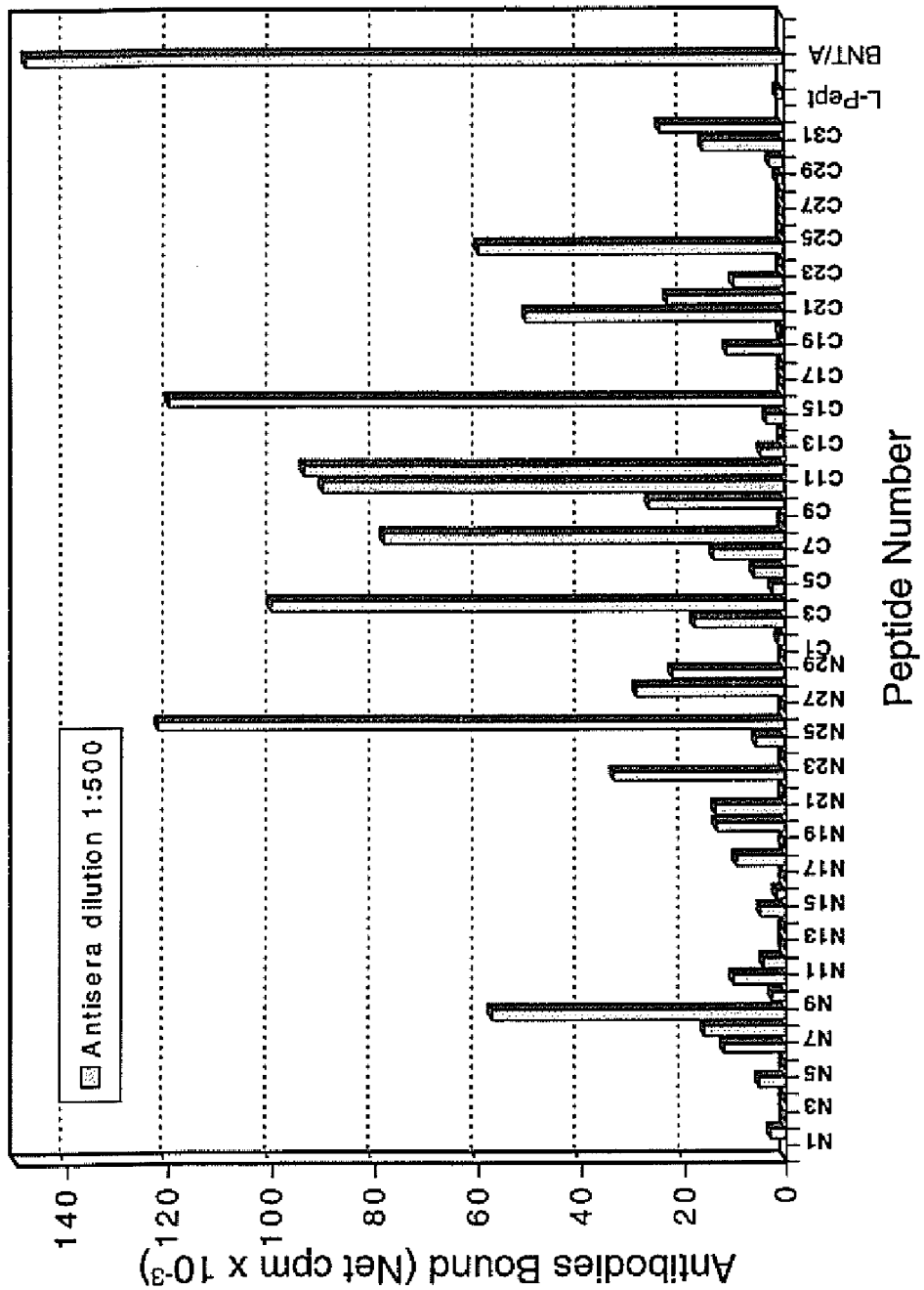
FIG. 5 shows binding of horse anti-BoNT/A antibodies to active BoNT/A overlapping synthetic peptides spanning the BoNT/A $H_N$ domain and to active $H_C$ peptides. Also shown are binding to L-Peptide and full-length BoNT/A as negative and positive controls, respectively.

As with the antisera of human, mouse and chicken as described in Examples 2-4, one or more regions within the overlapping peptides N7/N8/N9 (residues 533-551/547-565/561-579 of SEQ ID NO: 1) were observed to be immunodominant, and peptides N27 (residues 813-831 of SEQ ID NO: 1), N25 (residues 785-803 of SEQ ID NO: 1), N22 (residues 743-761 of SEQ ID NO: 1) and N20 (residues 715-733 of SEQ ID NO: 1) possessed binding activity (see FIG. 4). However, horse antibodies exhibited a high level of binding to peptide N2 (residues 463-481 of SEQ ID NO: 1), whereas other sera had low levels of binding to peptide N1 (residues 449-467 of SEQ ID NO: 1). Therefore, the horse immune response to the BoNT/A region in the vicinity of peptide N2 is shifted to the right by a few residues. The N2 region is also more immunogenic in horse than in human, mouse and chicken. As shown in FIG. 5, horse anti-BoNT antisera were also observed to bind to $H_C$ peptides C1, C5, C7, C18, C22, C25, C30 and C31, in agreement with previous studies, see, e.g., Atassi et al., supra, 1996. Using the horse anti-BoNT antisera, no binding to a control peptide corresponding to amino acids 218-231 of BoNT light chain was observed. The antisera had no binding to unrelated proteins, and preimmune horse sera bound none of the $H_N$ or $H_C$ peptides.

In sum, these results demonstrate that peptides N7, N8, N9, N27, N25, N22, N20, N2, N1, C1, C5, C7, C18, C22, C25, C30 and C31 were recognized by horse anti-BoNT antisera.

Example 4

Mapping of Mouse Anti-Pentavalent Botulinum Toxoid Antibodies Using BoNT/A Synthetic Peptides This example describes antigenic mapping of BoNT/A with mouse anti-BoNT antisera using 29 BoNT/A synthetic peptides that encompass the $H_N$ domain of BoNT/A.

Mouse anti-BoNT antisera were prepared in outbred ICR mice by subcutaneous immunization with BoNT pentavalent toxoid. Antisera used in these studies were obtained 91 days after the first injection, see, e.g., Atassi et al., supra, 1996. Mice were purchased from the National Cancer Institute, and Jackson Laboratory (Bar Harbor, Me.). For use as controls, non-immune mouse sera were obtained from the animals before immunization.

Peptide binding assays were performed as described in Example 2, except that the dilution for antisera of outbred mice was 1:50 and 1:200 (vol/vol). The secondary antibodies (mouse IgG (H+ L)+IgM (Mu chain) were obtained from Accurate Chemical & Scientific Corporation (Westbury, N.Y.) and were diluted 1:2000 (vol/vol).

Figure 3:
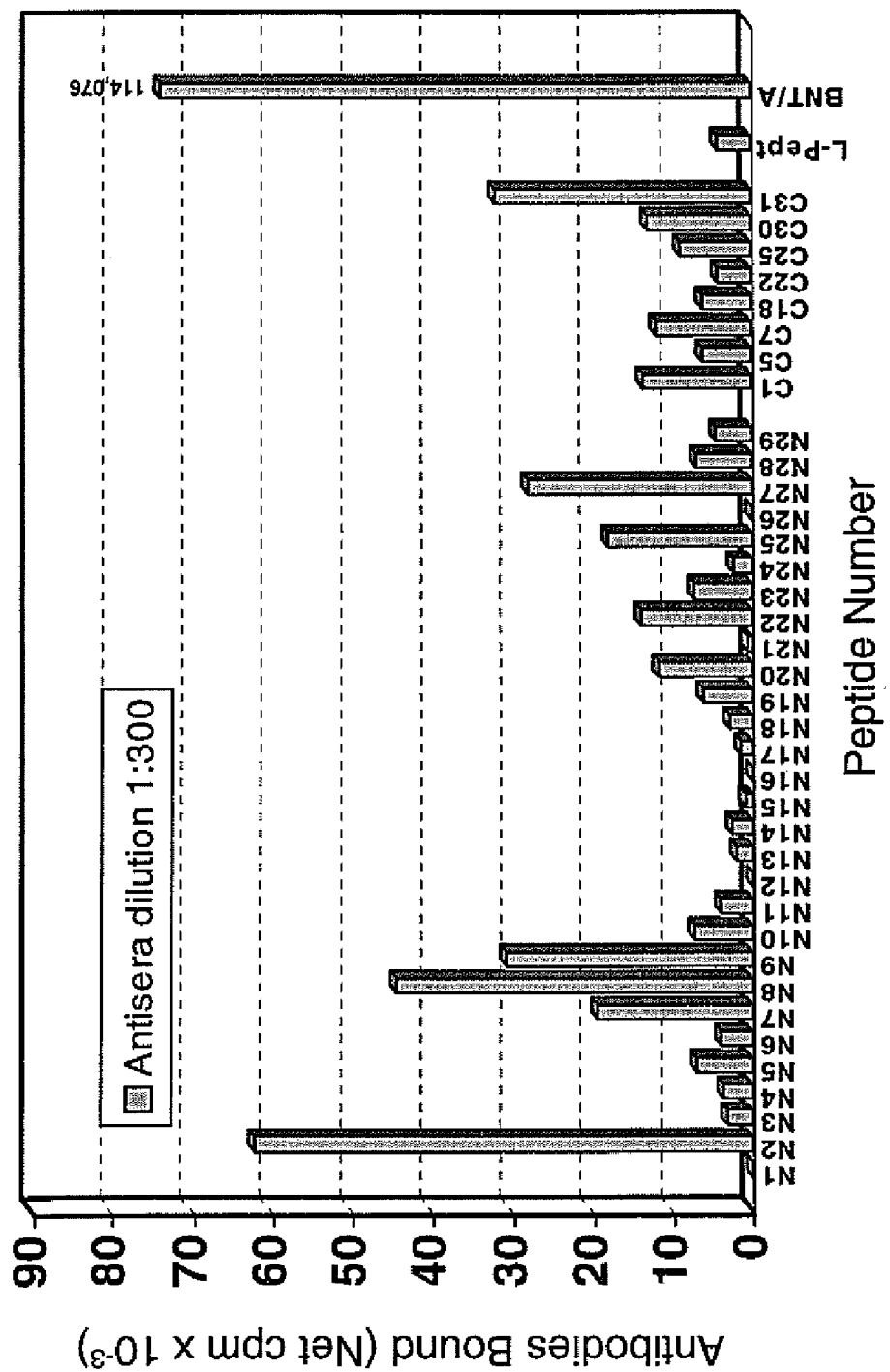
FIG. 3 shows binding of anti-pentavalent botulinum toxoid antibodies of ICR outbred mice to synthetic overlapping peptides spanning the BoNT/A $H_N$ domain. Also shown are binding to L-Peptide and full-length BoNT/A as negative and positive controls, respectively.

As shown in FIG. 3, mouse anti-BoNT antisera were observed to bind to several BoNT/A peptides. At a dilution of 1:50 (vol/vol), peptide N25 (785-803) was immunodominant, followed by one or more regions within the overlap N6/N7/N8/N9 (residues 519-537/533-551/547-565/561-579 of SEQ ID NO: 1) and one or more weaker regions within the overlap N27/N28 (residues 813-831/827-845 of SEQ ID NO: 1). At a dilution of 1:200 (vol/vol), peptide N25 (residues 785-803 of SEQ ID NO: 1) remained immunodominant; in addition, high amounts of antibodies were bound by the overlap N6/N7/N8 (residues 519-537/533-551/547-565 of SEQ ID NO: 1), low amounts of antibodies were bound by the overlap N27/N28 (residues 813-831/827-845 of SEQ ID NO: 1), indicating that at least one weak epitope resides within this region (See FIG. 3). As shown in FIG. 3, the $H_C$ peptides that possessed antibody binding were C2, C7, C11, C15, C16, C24 and C31, in agreement with previously reported results, see, e.g., Atassi et al., supra, 1996. Mouse anti-BoNT antisera exhibited no binding to a control peptide corresponding to amino acids 218-231 of BoNT light chain ("L peptide"). The mouse anti-BoNT antisera exhibited no antibody binding to unrelated proteins and peptides. Preimmune sera from the same mice did not bind to any of the $H_N$ or $H_C$ peptides.

In sum, these results demonstrate that peptides N25, N6, N7, N8, N9, N27, N28, C2, C7, C11, C15, C16, C24 and C31 were recognized by mouse anti-BoNT antisera.

Example 5

Mapping of Chicken BoNT/A Toxoid Antibodies Using BoNT/A Synthetic Peptides

This example describes antigenic mapping of BoNT/A with chicken anti-BoNT antisera using 29 BoNT/A synthetic peptides that encompass the $H_N$ domain of BoNT/A.

Chicken antisera were prepared by monthly subcutaneous injection of formaldehyde-inactivated BoNT/A in Ribi adjuvant. Sera used in this study were obtained after four injections. For use as controls, non-immune chicken sera were obtained from the animals before immunization.

Peptide binding assays were performed as described in Example 2, except that the dilution for chicken antisera was 1:500 (vol/vol). The secondary antibodies (rabbit antiserum against chicken IgG) were diluted 1:500 (vol/vol).

As shown in FIG. 4, chicken anti-BoNT antisera were observed to bind to several BoNT/A peptides. In particular, peptide N25 (residues 785-803 of SEQ ID NO: 1) was the most immunodominant region, followed by N8 (residues 547-565 of SEQ ID NO: 1) (FIG. 4). In addition, lower levels of antibodies were directed, in the following decreasing order of antibody level, against peptides N22 (residues 743-761 of SEQ ID NO: 1), N27 (residues 813-831 of SEQ ID NO: 1), N28 (residues 827-845 of SEQ ID NO: 1), N7 (residues 533-551 of SEQ ID NO: 1), N6 (residues 519-537 of SEQ ID NO: 1), N19 (residues 701-719 of SEQ ID NO: 1) and N20 (residues 715-733 of SEQ ID NO: 1). The antibody-binding profile of the peptides corresponding to the entire H chain, including the $H_C$ domain is shown in FIG. 4. In the $H_C$ domain, chicken antibodies recognized essentially seven major regions, each of which can contain one or more antigenic sites or epitopes. The regions were located within the peptides C15 (residues 1051-1069 of SEQ ID NO: 1) and C24 (1177-1195 of SEQ ID NO: 1) and the overlaps C2/C3 (residues 869-887/883-901 of SEQ ID NO: 1), C6/C7 (residues 925-943/939-957 of SEQ ID NO: 1), C9/C10/C11 (residues 967-985/981-999/995-1013 of SEQ ID NO: 1), C20/C21/C22 (residues 1121-1139/1135-1153/1149-1167 of SEQ ID NO: 1) and C30/C31 (residues 1261-1279/1275-1296 of SEQ ID NO: 1). The chicken antisera showed no antibody binding to unrelated proteins and peptides, and chicken anti-BoNT antisera exhibited no binding to a control peptide corresponding to amino acids 218-231 of BoNT light chain. Preimmune chicken sera bound none of the $H_N$ or $H_C$ peptides.

The binding profile of the chicken anti-BoNT/A antibodies to the panel of $H_C$ peptides was similar to that of human antibodies as shown in Table 1. In sum, these results demonstrate that peptides N25, N8 N22, N27, N28, N7, N6, N19, N20, C15, C24, C2, C3, C6, C7, C9, C10, C11, C20, C21, C22, C30, and C31 were recognized by chicken anti-BoNT antisera.

Example 6

Comparison of BoNT/A Antigenicity Between Human, Mouse, Chicken and Horse

This example defines several common immunogenic regions of BoNT/A by antigen mapping obtained with antisera from four different species.

The results shown in Examples 2-5 indicate that antisera against BoNT/A raised in human, horse, mouse and chicken recognize similar immunodominant regions on the $H_N$ domain of BoNT/A. These regions resided, with slight shifts to the left or to the right, within the peptides N6/N7/N8/N9 (residues 519-537/533-551/547-565/561-579 of SEQ ID NO: 1) overlap (human, horse and mouse), peptide N22 (residues 743-761 of SEQ ID NO: 1) (human, horse and chicken), peptide N25 (residues 785-803 of SEQ ID NO: 1) and peptides N27/N28 (residues 813-831/827-845 of SEQ ID NO: 1). These results are summarized in Table 2, below.

Whereas peptide N2 was strongly immunodominant with horse antisera, it was unreactive with human, mouse and chicken antisera. However with human, mouse and chicken antisera, peptide N1 reacted weakly and therefore, the reaction of horse antibodies with peptide N2 can represent a shift to the right of the epitope recognized by the horse antibodies. The overlap N16/N17 was highly reactive with human antibodies, whereas with mouse and chicken antisera peptide 17 showed a low level of reactivity. With horse antisera, antibodies against N16/N17 were not detected.

In sum, this example shows that anti-BoNT antibodies from human, mouse, horse and chicken recognize several common immunogenic regions of the BoNT/A $H_N$ domain.

TABLE 1

| Peptide No. | Sequence Position (residues of SEQ ID NO: 1) | Human | Horse | Mouse | Chicken |
|---|---|---|---|---|---|
| N1 | 449-467 | ++ | − | + | ± |
| N2 | 463-481 | − | +++++ | − | − |
| N3 | 477-495 | − | ± | − | − |
| N4 | 491-509 | ++ | + | ± | + |
| N5 | 505-523 | − | + | − | − |
| N6 | 519-537 | ++ | + | +++ | ++ |
| N7 | 533-551 | ++ | +++ | +++ | +++ |
| N8 | 547-565 | +++++ | +++++ | +++++ | +++++ |
| N9 | 561-579 | + | ++++ | ++++ | ± |
| N10 | 575-593 | ± | ++ | + | ++ |
| N11 | 589-607 | +++ | + | − | + |
| N12 | 603-621 | + | − | − | − |
| N13 | 617-635 | − | ± | − | − |
| N14 | 631-649 | ++ | ± | ± | + |
| N15 | 645-663 | − | − | − | ± |
| N16 | 659-677 | ++++ | − | − | − |
| N17 | 673-691 | ++ | − | ± | ++ |
| N18 | 687-705 | + | ± | − | − |
| N19 | 701-719 | ± | + | + | ++ |
| N20 | 715-733 | ++ | ++ | ± | ++ |
| N21 | 729-747 | ± | − | − | − |
| N22 | 743-761 | ++++ | ++ | + | ++++ |
| N23 | 757-775 | − | + | − | − |
| N24 | 771-789 | ++ | ± | + | + |
| N25 | 785-803 | +++++ | +++ | +++++ | +++++ |
| N26 | 799-817 | − | − | − | − |
| N27 | 813-831 | ++ | ++++ | +++ | ++++ |
| N28 | 827-845 | ++ | + | +++ | +++ |
| N29 | 841-859 | + | + | − | − |
| L-Peptide | 218-231 | − | − | − | − |
| Active BoNT/A | — | +++++ | +++++ | +++++ | +++++ |

(+) or (−) signs are based on net cpm values and denote the following: (−), less than 1,500 cpm; (±), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm.

TABLE 2

| Peptide No. | Sequence Position (Residues of SEQ ID NO: 1) | Human | Horse | Mouse | Chicken |
|---|---|---|---|---|---|
| C1 | 855-873 | − | +++ | ± | − |
| C2 | 869-887 | +++ | − | +++ | +++ |
| C3 | 883-901 | − | + | + | +++++ |
| C4 | 897-915 | − | ± | − | ± |
| C5 | 911-929 | ++ | + | − | + |
| C6 | 925-943 | +++ | − | − | ++ |
| C7 | 939-957 | + | ++ | + | +++++ |

TABLE 2-continued

| Peptide No. | Sequence Position (Residues of SEQ ID NO: 1) | Human | Horse | Mouse | Chicken |
|---|---|---|---|---|---|
| C8 | 953-971 | − | − | − | − |
| C9 | 967-985 | + | − | ± | ++++ |
| C10 | 981-999 | +++ | ± | − | +++++ |
| C11 | 995-1013 | +++++ | + | + | +++++ |
| C12 | 1009-1027 | − | − | − | + |
| C13 | 1023-1041 | − | + | − | − |
| C14 | 1037-1055 | − | + | − | + |
| C15 | 1051-1069 | +++++ | ± | ++ | +++++ |
| C16 | 1065-1083 | − | − | − | − |
| C17 | 1079-1097 | − | + | − | − |
| C18 | 1093-1111 | − | + | + | ++ |
| C19 | 1107-1125 | ± | − | − | − |
| C20 | 1121-1139 | + | + | ± | +++++ |
| C21 | 1135-1153 | ++ | ± | ± | +++ |
| C22 | 1149-1167 | ± | + | − | ++ |
| C23 | 1163-1181 | ± | − | − | − |
| C24 | 1177-1195 | +++ | − | ++ | +++++ |
| C25 | 1191-1209 | ± | ++ | − | − |
| C26 | 1205-1223 | − | + | − | − |
| C27 | 1219-1237 | + | − | − | − |
| C28 | 1233-1251 | + | − | − | − |
| C29 | 1247-1265 | ++ | ± | − | ± |
| C30 | 1261-1279 | + | ++ | − | +++ |
| C31 | 1275-1296 | ++ | +++ | ++ | +++ |
| L-Peptide | 218-231 | − | − | − | − |
| Active BoNT/A | — | +++++ | +++++ | +++++ | +++++ |

(+) or (−) signs are based on net cpm values and denote the following: (−), less than 1,500 cpm; (±), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm.

Example 7

Identification of Immunodominant Regions of BoNT/A

This example shows the identification of several immunodominant regions of human anti-BoNT antibodies within the H chain of BoNT/A.

The antigenic regions of BoNT were determined using anti-BoNT antisera obtained from human, mouse, horse and chicken, as shown in Examples 2-5. The location of antigenic regions can be narrowed to shorter domains by the following analysis.

In this analysis, the size of an antigenic site was assigned to be 10-11 residues. The H-chain of BoNT/A was therefore broken down into 13 antigenic sites. The 13 antigenic sites are defined in Table 3, below. The table gives the approximate locations of only the antigenic regions that bind 15,000 cpm of antibody or greater. Although only the immunodominant regions are shown in Table 3, regions binding lower amounts of antibodies can be of equivalent immunological significance.

TABLE 3

| $H_N$ Domain Regions | | $H_C$ Domain Regions | |
|---|---|---|---|
| Antigenic Regions | Amino Acid Residue of SEQ ID NO: 1 | Antigenic Regions | Amino Acid Residue of SEQ ID NO: 1 |
| NR1 | 554-564 | CR1 | 854-887 |
| NR2 | 593-602 | CR2 | 933-943 |
| NR3 | 666-676 | CR3 | 986-995 |
| NR4 | 748-757 | CR4 | 1000-1009 |

TABLE 3-continued

| $H_N$ Domain Regions | | $H_C$ Domain Regions | |
|---|---|---|---|
| Antigenic Regions | Amino Acid Residue of SEQ ID NO: 1 | Antigenic Regions | Amino Acid Residue of SEQ ID NO: 1 |
| NR5 | 785-794 | CR5 | 1056-1065 |
| | | CR6 | 1137-1147 |
| | | CR7 | 1183-1192 |
| | | CR8 | 1276-1289 |

In sum, this example shows that BoNT/A immunodominant regions having 10-11 residues can be determined based on reactivity of anti-BoNT antisera obtained from human, mouse, horse and chicken with BoNT/A peptides.

Example 8

Mapping of T- and B-Cell Recognition Profiles of the BoNT/A $H_N$ Domain in Two High-Responder Mouse Strains This example demonstrates that responses to each antibody or T cell epitope are under separate genetic control and that there is partial, but not complete, coincidence between antibody and T cell $H_N$ recognition regions.

A. T Cell Recognition of $H_N$ Peptides after One Injection with Toxoid

Figure 7:
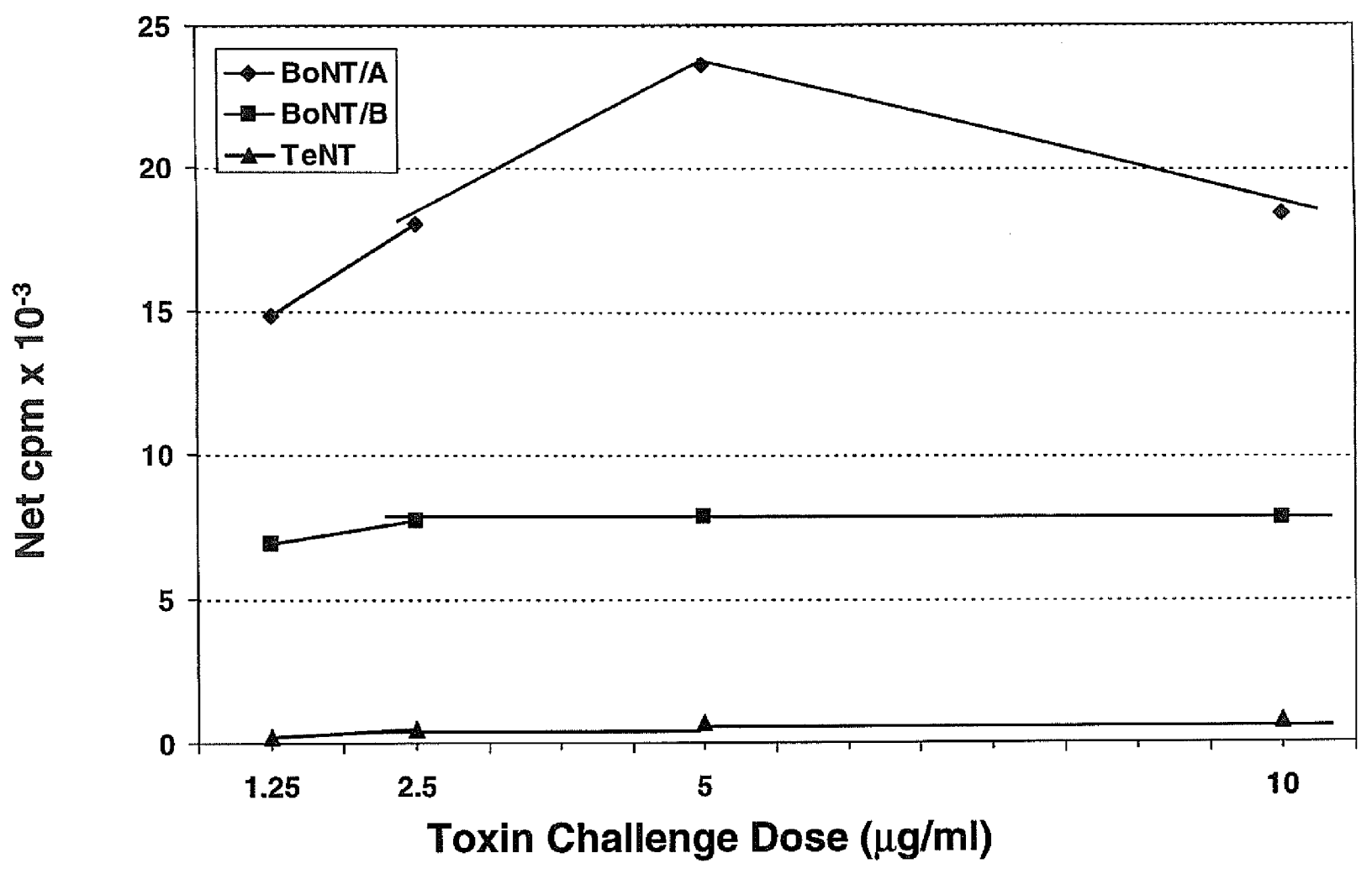
Figure 8:
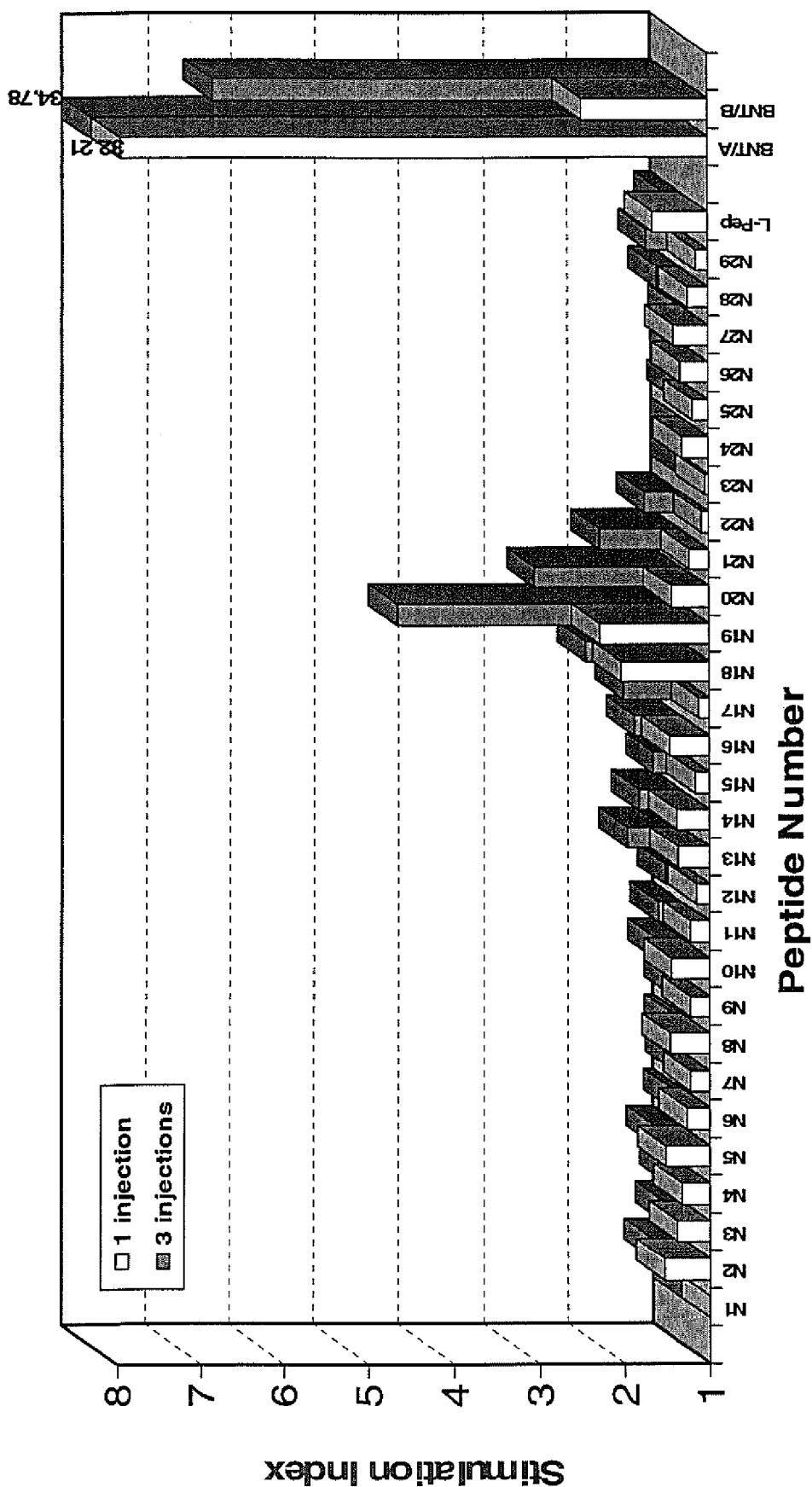
FIG. 8 shows proliferative responses of LNC ($5 \times 10^5$ cells/well) of Balb/c mice after 1 injection or after 3 injections with BoNT/A toxoid (1 :g/mouse/injection).

Exemplary proliferative responses of BALB/c lymph node cells (LNCs) were determined at various doses of toxoid as shown in FIG. 7. The response profile to the full panel of $H_N$ peptides spanning the entire N-terminal domain of the BoNT/A heavy chain was subsequently determined. As shown in FIG. 8, BALB/c T cells primed with one injection of BoNT/A toxoid recognized one major region localized within overlap N18/N19 (residues 687-705/701-719 of SEQ ID NO: 1) while the remaining peptides had no detectable stimulating activity in vitro. BoNT/A-primed BALB/c T cells showed substantial cross-reaction with BoNT/B (SI values: BoNT/A 23.62, BoNT/B 7.89) but had no cross-reactivity with TeNT (FIG. 7).

Figure 9:
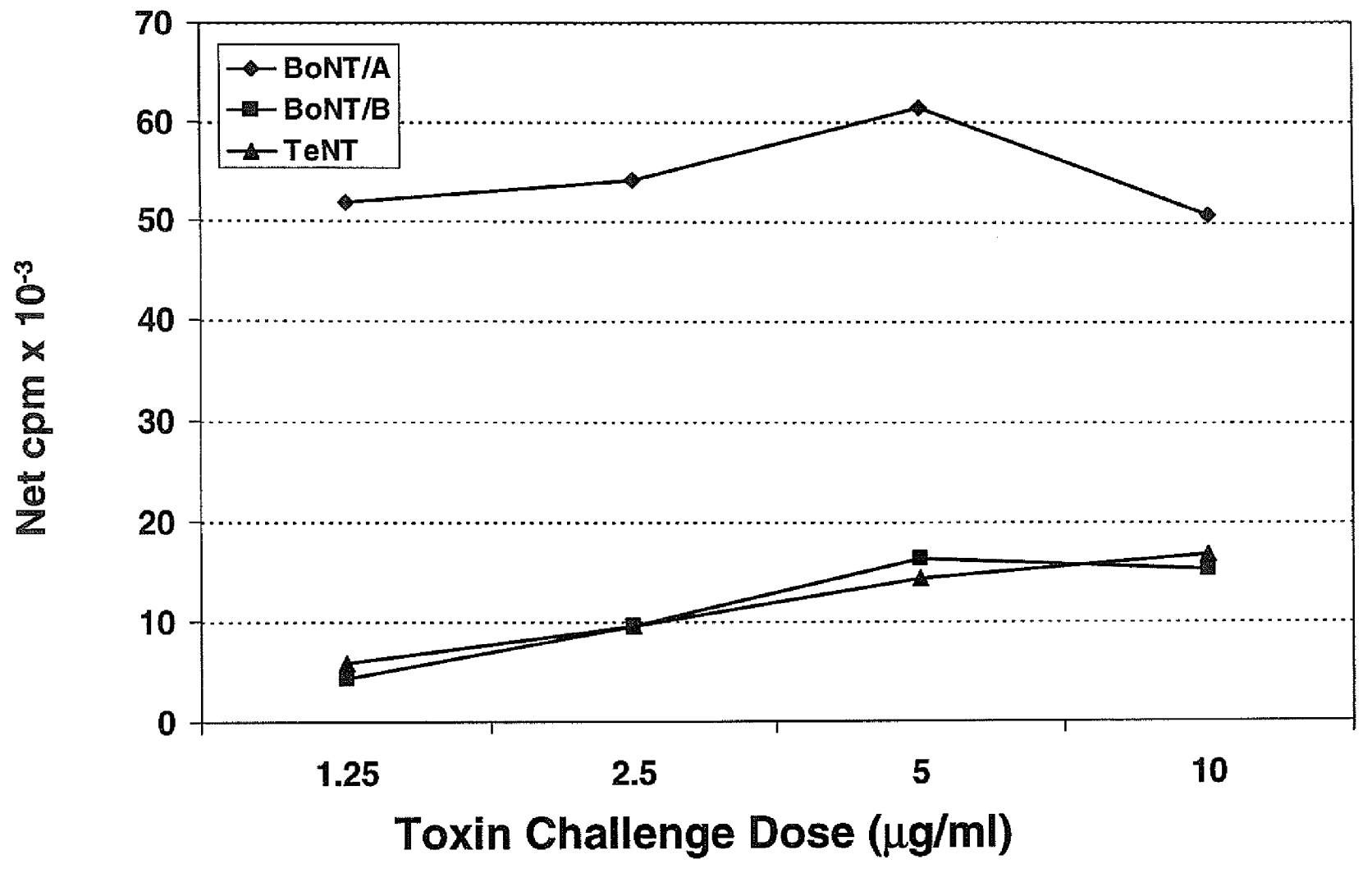

Unlike BALB/c T cells, the T cells from a BoNT/A-primed second inbred strain of mice, SJL/JCr, cross-reacted with both BoNT/B and TeNT (FIG. 9). As summarized in FIG. 10, BoNT/A-primed SJL T cells responded to challenge with a number of the overlapping peptides of $H_N$. In particular, peptides N9 (residues 561-579 of SEQ ID NO: 1), N11 (residues 589-607 of SEQ ID NO: 1), N13 (residues 617-635 of SEQ ID NO: 1), N29 (residues 841-859 of SEQ ID NO: 1) and the L-chain peptide (218-231) stimulated strong-to-medium in vitro T cell responses (SI>5). In addition, peptides N2 (residues 463-481 of SEQ ID NO: 1), N16 (residues 659-677 of SEQ ID NO: 1) and N21 (residues 729-747 of SEQ ID NO: 1) and N28 (residues 827-845 of SEQ ID NO: 1) demonstrated weak (SI>3) stimulating activities. Toxoid-primed T cells of BALB/c and SJL did not respond to the unrelated hen lysozyme or ovalbumin proteins, demonstrating the specificity of the response.

Female BALB/c (H-$2^d$; National Cancer Institute; Frederick, Md.) and SJL/JCr (H-$2^s$; (Jackson Laboratory; Bar Harbor, Me.) mice, 7 to 9 weeks old, were used in all experiments. Synthetic peptides were synthesized, purified and characterized as described above. The twenty-nine consecutive overlapping peptides correspond to the complete $H_N$ domain (residues 449-859 of SEQ ID NO: 1) and a peptide around the enzymatic active site of the light chain (L-peptide, residues 218-231) of BoNT/A (FIG. 1A). The peptides were 19 residues in length and overlapped consecutively by five residues.

Immunization of mice with BoNT/A toxoid for T cell studies was performed as follows. The optimum priming dose of BoNT/A toxoid was determined in the BALB/c and SJL mouse strains. Mice were immunized subcutaneously at the base of tail with various doses of toxoid (0.125-5 µg/mouse) in a 50-µl emulsion of equal volumes of the toxoid solution in 0.15 M NaCl in 0.01 M sodium phosphate buffer, pH 7.2 (PBS), and complete Freund's adjuvant (CFA) containing *Mycobacterium tuberculosis*, strain H37Ra (Difco Laboratories; Detroit, Mich.). For both mouse strains, the highest T cell response was obtained at a priming dose of 1 µg/mouse, and subsequent experiments were performed with this dose. The peptides were used in vitro at five doses (5, 10, 20, 40, 80 µg/ml), and the toxin was used in vitro at doses of 1.25, 2.5, 5 and 10 µg/ml.

Lymphocyte proliferation assays were performed as follows. Single-cell suspensions of LNC from toxoid-primed mice were prepared in Hank's balanced salt solution. The cells were washed and resuspended in RPMI 1640 with 1% normal mouse serum and supplemented as described in J. S. Rosenberg et al., *Localization of the Regions on the C-Terminal Domain of the Heavy Chain of Botulinum A Recognized by T Lymphocytes and by Antibodies After Immunization of Mice With Pentavalent Toxoid*, 26(4) IMMUNOL. INVEST. 491-504 (1997). The number of viable cells was determined by vital staining with fluorescein diacetate. A fixed number of viable LNC ($5\times10^5$ to $8\times10^5$ cells/well) was cocultured in triplicate with various concentrations of mitogen, BoNT/A or synthetic peptides of BoNT/A, BoNT/B or TeNT and control proteins and peptides. The viability of the cells was confirmed in each assay by their responses to ConA and LPS. Negative controls included proteins unrelated to BoNT/A (ovalbumin, myoglobin and hen lysozyme) as well as unrelated control synthetic peptides. After three days of incubation at 37° C. in a humidified, 5% $CO_2$ atmosphere, lymphocytes were pulsed for 18 hours with [$^3$H]-thymidine (2 µCi/well; Research Products International; Mount Prospect, Ill.) and subsequently harvested onto glass microfiber filters (Whatman; Clinton, N.J.) before counting by liquid scintillation.

Figure 10:
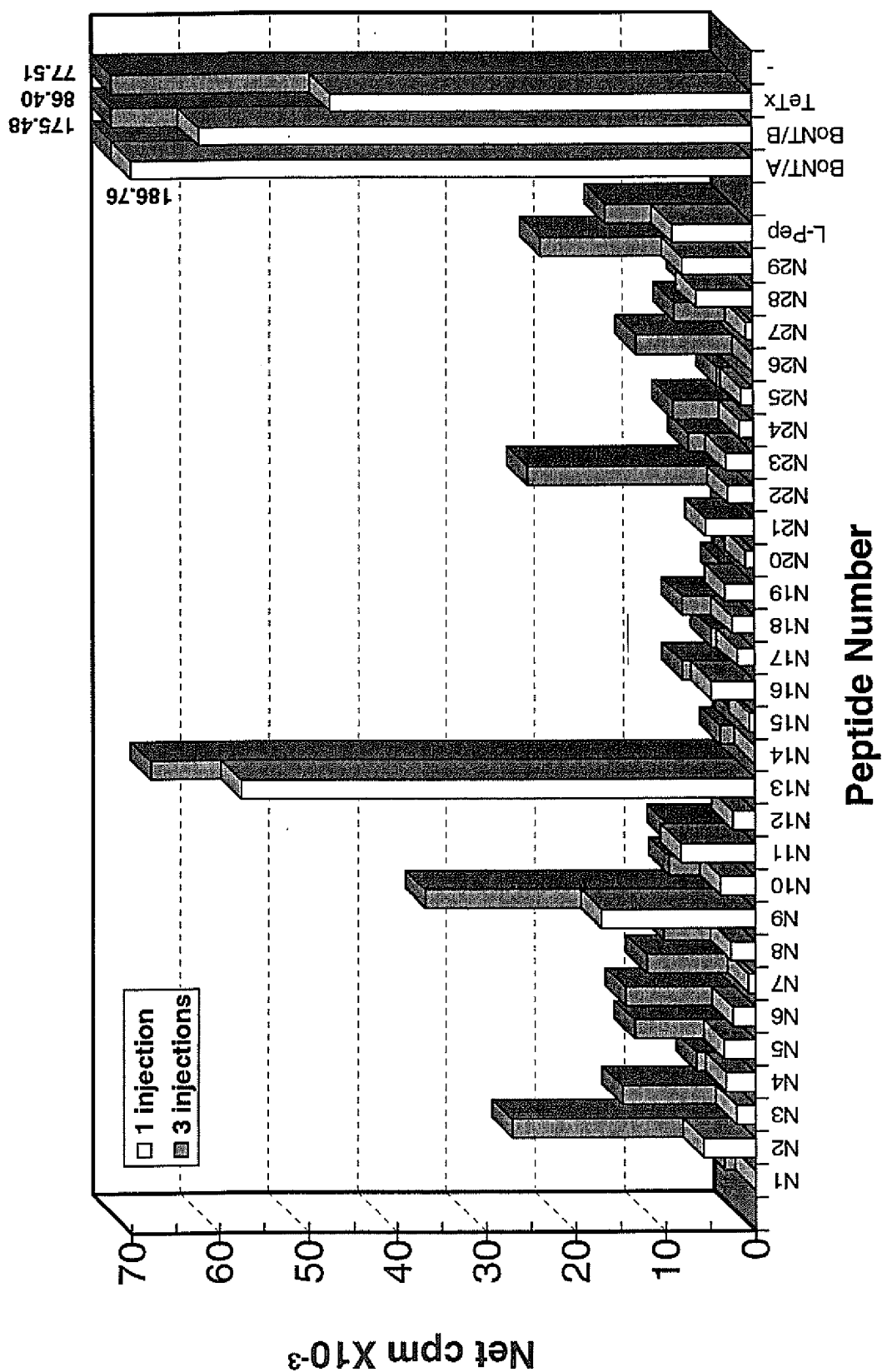
FIG. 10 shows proliferative responses of LNC ($5 \times 10^5$ cells/well) of SJL mice to various synthetic BoNT/A peptides after 1 injection or after 3 injections with BoNT/A toxoid (1 :g/mouse/injection).
Figure 11:
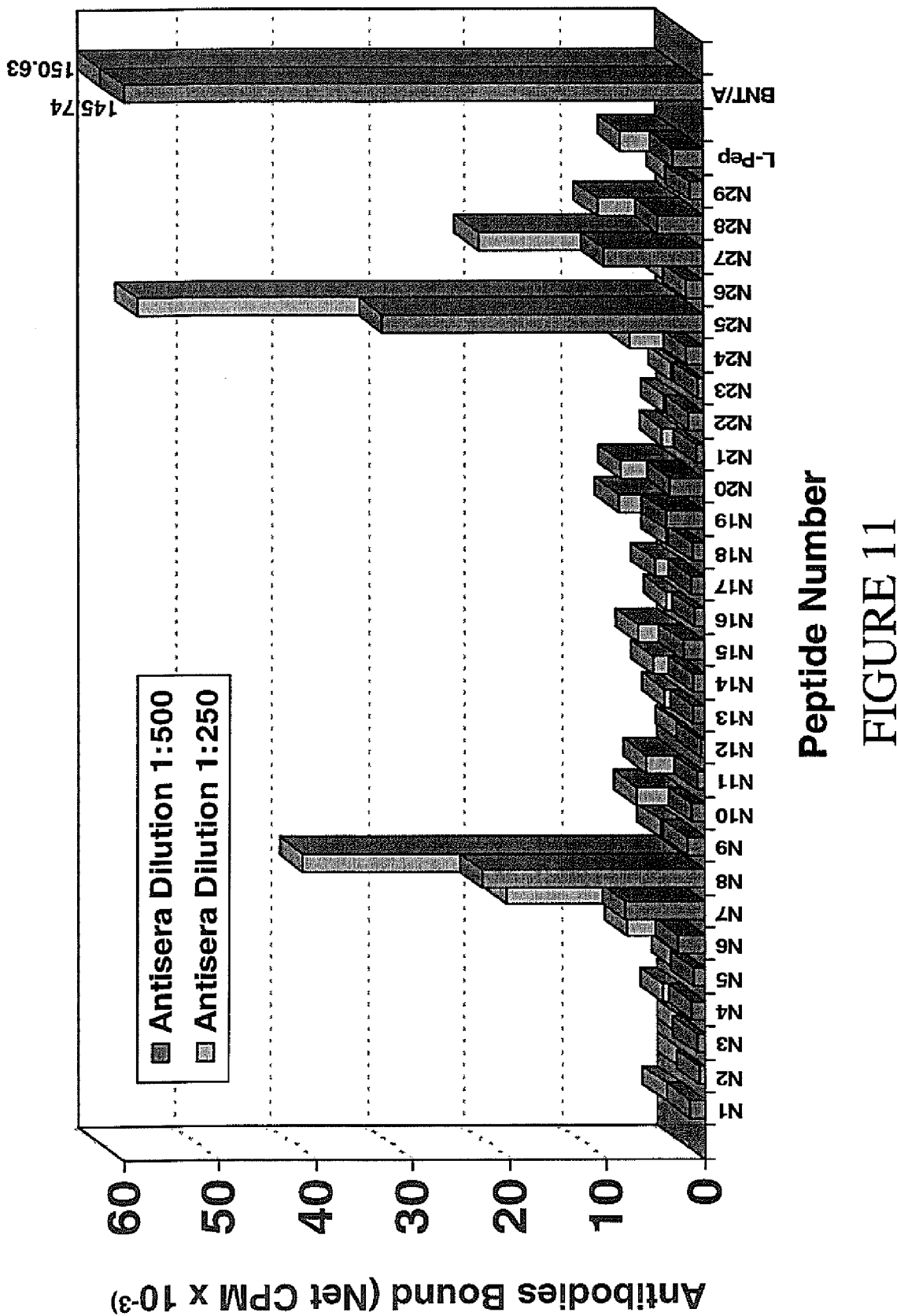
FIG. 11 shows binding of Balb/c anti-BoNT/A antibodies to BoNT/A and to overlapping synthetic peptides spanning the $H_N$-domain. Antisera were assayed at two dilutions (1:500 and 1:250, vol/vol).
Figure 12:
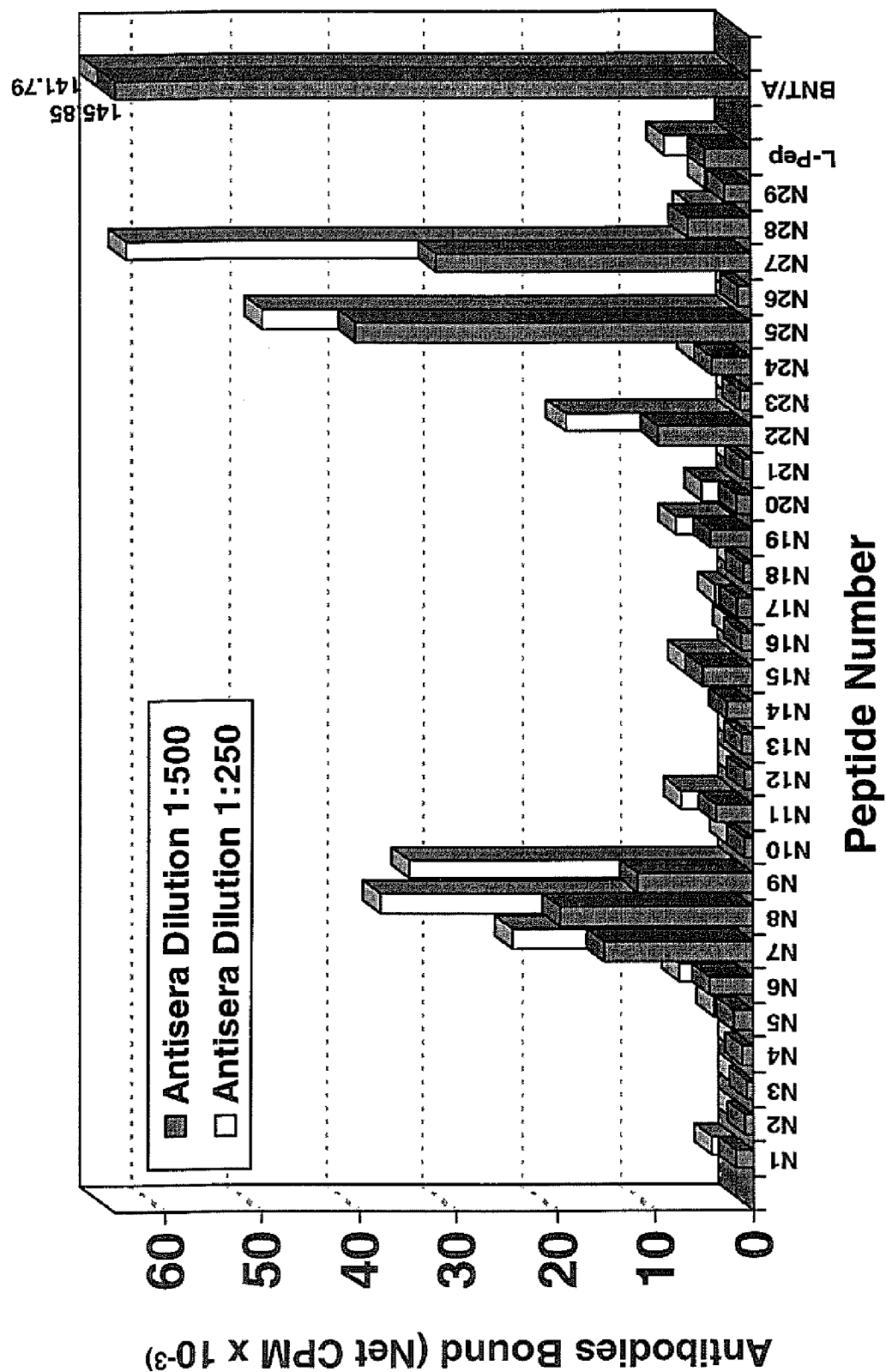
FIG. 12 shows binding of SJL anti-BoNT/A antibodies to BoNT/A and to overlapping synthetic peptides of the $H_N$-chain. Antisera were assayed at dilutions of 1:500 and 1:250.

B. Mapping of the T Cell Recognition Profiles after Three Injections with Toxoid To determine T cell recognition profiles at the time antisera were obtained, proliferative responses were determined for LNC obtained from BALB/c and SJL mice that were used to prepare hyperimmune anti-toxoid antisera for the antibody-binding studies. LNC were harvested at the time of the final bleed on week 10 (i.e. 2 weeks after the last of three injections of toxoid). The proliferative responses to the peptides and toxins of LNC from once-primed and from three-times immunized BALB/c and SJL are shown in FIGS. 8 and 10; the results for both BALB/c and SJL are summarized in Table 4. As shown in FIG. 8, the two recognition profiles for T cells from BALB/c mice were only slightly different (FIG. 8). Hyperimmune T cells responded to challenge in vitro with peptides N18 (residues 687-705 of SEQ ID NO: 1), N19 (residues 701-719 of SEQ ID NO: 1) and N20 (residues 715-733 of SEQ ID NO: 1), with the response to peptide N19 (residues 701-719 of SEQ ID NO: 1) stronger after multiple injections. The recognition profile of the other peptides remained essentially unchanged, and BALB/c hyperimmune T cells did not cross-react with BoNT/B and TeNT.

TABLE 4

T cell recognition regions on BoNT/A $H_N$ domain

| Peptide No. | Sequence Position (residues of SEQ ID NO: 1) | BALB/c (H-2$^d$) | | SJL (H-2$^S$) | |
|---|---|---|---|---|---|
| | | One Injection | Three Injections | One Injection | Three Injections |
| $H_N$ Domain | | | | | |
| N1 | 449-467 | − | − | − | − |
| N2 | 463-481 | − | − | + | ++++ |
| N3 | 477-495 | − | − | − | ++ |
| N4 | 491-509 | − | − | − | − |
| N5 | 505-523 | − | − | ± | ++ |
| N6 | 519-537 | − | − | − | ++ |
| N7 | 533-551 | − | − | − | ++ |
| N8 | 547-565 | − | − | − | + |
| N9 | 561-579 | − | − | +++ | ++++ |
| N10 | 575-593 | − | − | ± | + |
| N11 | 589-607 | − | − | ++ | + |
| N12 | 603-621 | − | − | − | − |
| N13 | 617-635 | − | − | +++++ | +++++ |
| N14 | 631-649 | − | − | − | − |
| N15 | 645-663 | − | − | − | − |
| N16 | 659-677 | − | − | + | + |
| N17 | 673-691 | − | − | − | − |
| N18 | 687-705 | ± | ± | − | ± |
| N19 | 701-719 | + | ++ | − | − |
| N20 | 715-733 | − | + | − | − |
| N21 | 729-747 | − | − | + | − |
| N22 | 743-761 | − | − | − | ++++ |
| N23 | 757-775 | − | − | − | ± |
| N24 | 771-789 | − | − | − | + |
| N25 | 785-803 | − | − | − | − |
| N26 | 799-817 | − | − | − | ++ |
| N27 | 813-831 | − | − | − | + |
| N28 | 827-845 | − | − | + | ± |
| N29 | 841-859 | − | − | ++ | +++ |
| Controls | | | | | |
| L-Peptide | 218-231 | − | − | ++ | ++ |
| BoNT/A | — | +++++ | +++++ | +++++ | +++++ |
| BoNT/B | — | + | +++ | +++++ | +++++ |
| TeNT | — | − | − | +++++ | +++++ |

The recognition profiles of once-primed and of hyperimmune LNC from SJL mice showed greater differences (FIG. 10 and Table 4). As shown in FIG. 10, hyperimmune T cells showed higher cross-reactivity with BoNT/B and TeNT than once-primed cells. In addition, the responses of hyperimmune SJL T cells to peptides N2 (residues 463-481 of SEQ ID NO: 1), N9 (residues 561-579 of SEQ ID NO: 1), N13 (residues 617-635 of SEQ ID NO: 1), N22 (residues 743-761 of SEQ ID NO: 1) and N29 (residues 841-859 of SEQ ID NO: 1) increased markedly. Hyperimmune SJL T cells also responded well to peptides N3 (residues 477-495 of SEQ ID NO: 1), N5 (residues 505-523 of SEQ ID NO: 1), N6 (residues 519-537 of SEQ ID NO: 1), N7 (residues 533-551 of SEQ ID NO: 1), N8 (residues 547-565 of SEQ ID NO: 1), N10 (residues 575-593 of SEQ ID NO: 1), N11 (residues 589-607 of SEQ ID NO: 1), N24 (residues 771-789 of SEQ ID NO: 1), N26 (residues 799-817 of SEQ ID NO: 1), N27 (residues 813-831 of SEQ ID NO: 1) and the L-peptide (218-231).

Immunization of mice with BoNT/A toxoid for late T cell responses and antibody binding studies was performed as follows. Mouse antisera were prepared by injection of BALB/c and SJL mice subcutaneously in the hind footpads with 5 µg of toxoid emulsified in complete Freund's adjuvant (CFA). Mice were injected with boosters at 4 and 8 weeks with a similar dose of toxoid, using incomplete Freund's adjuvant (Difco Laboratories; Detroit, Mich.) instead of CFA.

Sera were collected prior to the first immunization (pre-immune sera) and two weeks after each injection. For each mouse strain, sera of the respective bleeds from ten mice were pooled and kept at −20° C. until use. Antisera collected on week 10, i.e. 2 weeks after the last injection with toxoid, were employed for peptide binding studies. At the time of the last bleed, lymph nodes were removed, and single cell suspensions prepared for lymphocyte proliferation assays.

Figure 13:
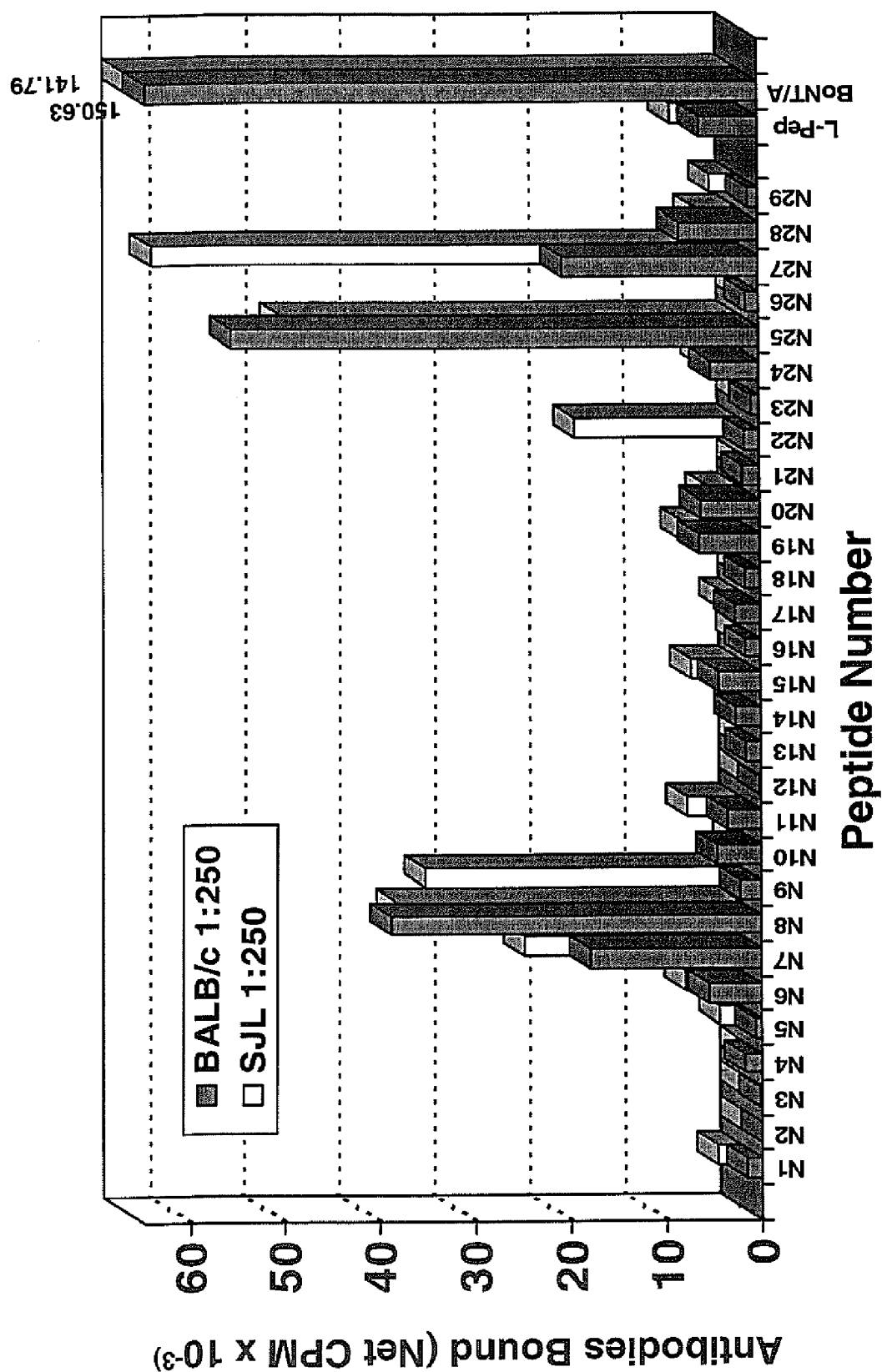
FIG. 13 shows a comparison of the binding profiles of BALB/c and SJL anti-BoNT/A toxoid antibodies at an antisera dilution of 1:250 (vol/vol), to BoNT/A and to overlapping synthetic peptides of the $H_N$-domain.

C. Binding of Anti-BoNT/A Antibodies to Overlapping Synthetic Peptides and Toxins Mapping of antibody binding profiles to peptides in the BALB/c and SLJ inbred mouse strains was performed by assaying antisera at two dilutions (1:250 and 1:500 (vol/vol)). As shown in FIGS. 5 and 6, respectively, the binding profiles of anti-toxoid antibodies from BALB/c and SJL mice were substantially similar. FIG. 13 shows a direct comparison of BALB/c and SJL antisera binding, and Table 5 summarizes the binding profiles for BALB/c and SJL Abs to the $H_N$ peptides at a dilution of 1:250 (vol/vol). Antibodies from both mouse strains showed high binding to $H_N$ peptides N7, N8, N25 and N27 and low binding to peptides N6, N11, N15 and N19.

Some differences in the binding profiles of antibodies from the two mouse strains were also apparent. In particular, BALB/c antisera showed medium antibody binding to peptide N28 and low antibody binding to peptides N10, N20 and N24, which represented epitopes either unrecognized or poorly recognized by SJL antibodies. On the other hand, SJL antibodies showed high binding to peptides N9 and N22, which were poorly recognized by BALB/c antibodies. In addition, SJL antisera contained much higher amounts of antisera that bound to peptide N27 than did antisera from the other mouse strain. In order to complete the profiles of the H chain recognition by BALB/c and SJL antibodies, Table 5 shows binding profiles to $H_C$ peptides previously reported, see, e.g., Rosenberg et al., supra, 1997.

Solid phase radioimmunoassays were performed using Staphylococcal protein A (Pharmacia Biotech; Piscataway, N.J.) radiolabeled with $^{125}I$ (Amersham Corp.; Arlington Heights, Ill.) using the chloramine-T method. Unbound $^{125}I$ was separated from the radiolabeled protein A by gel filtration on a Sephadex G-25 column (0.8×20 cm) equilibrated with PBS containing 0.1% bovine serum albumin (BSA; Sigma Chemicals; St. Louis, Mo.).

Binding of mouse anti-toxoid antibodies to active BoNT/A and synthetic peptides was determined using polyvinylchloride 96-well plates (Becton Dickinson Labware; Oxnard, Calif.), which were coated with each of the 31 overlapping peptides (2.5 µg in 50 µl of PBS/well) or with BoNT/A (1 µg in 50 µl of PBS/well). Wells coated with proteins and synthetic peptides unrelated to BoNTs were used as negative controls. Following overnight incubation at 4° C., plates were washed extensively with PBS and incubated for one hour at 37° C. with 1% BSA in PBS (100 µl/well) to block nonspecific binding in subsequent steps. After washing with PBS, plates were incubated at 37° C. for three hours with mouse antisera (50 µl/well) appropriately prediluted in 0.1% BSA in PBS. For mapping studies, antisera were prediluted 1:250 and 1:500 (vol/vol). Wells were washed with PBS and incubated at 37° C. for two hours with 50 µl of affinity purified rabbit anti-mouse (IgG+IgM) antisera (Accurate Chem. Sci. Corp.; Westbury, N.Y.) pre-diluted 1:1000 (v/v) with 0.1% BSA in PBS. After washing with PBS, $^{125}I$-labeled protein A was added to the wells (2×10⁵ cpm in 50 µl 0.1% BSA-PBS/well). Plates were subsequently incubated for two hours at room temperature, washed, dried and the wells cut out and counted in a gamma counter (1227 Gammamaster; LKB; Turku, Finland). All determinations were performed in triplicate, and the results expressed as net cpm±SD, after corrections for nonspecific binding in controls wells that were coated with BSA and of the correlate pre-immune mouse sera to each tested antigen.

TABLE 5

T cells and Abs recognition regions on BoNT/A $H_N$ domain[a]

| Peptide No. | Sequence Position (residues of SEQ ID NO: 1) | BALB/c (H-2$^d$) Abs | BALB/c (H-2$^d$) T Cell | SJL (H-2$^S$) Abs | SJL (H-2$^S$) T Cell |
|---|---|---|---|---|---|
| N1 | 449-467 | ± | − | − | − |
| N2 | 463-481 | − | − | − | ++++ |
| N3 | 477-495 | − | − | − | ++ |
| N4 | 491-509 | ± | − | − | − |
| N5 | 505-523 | − | − | − | ++ |
| N6 | 519-537 | + | − | + | ++ |
| N7 | 533-551 | +++ | − | +++ | ++ |
| N8 | 547-565 | ++++ | − | ++++ | + |
| N9 | 561-579 | ± | − | +++ | ++++ |
| N10 | 575-593 | + | − | − | + |
| N11 | 589-607 | + | − | − | + |
| N12 | 603-621 | − | − | − | − |
| N13 | 617-635 | − | − | − | +++++ |
| N14 | 631-649 | − | − | − | − |
| N15 | 645-663 | + | − | + | − |
| N16 | 659-677 | − | − | − | + |
| N17 | 673-691 | − | − | − | − |
| N18 | 687-705 | − | ± | − | ± |
| N19 | 701-719 | + | ++ | + | − |
| N20 | 715-733 | + | + | − | − |
| N21 | 729-747 | − | − | − | − |
| N22 | 743-761 | ± | − | +++ | ++++ |
| N23 | 757-775 | − | − | − | ± |
| N24 | 771-789 | + | − | − | + |
| N25 | 785-803 | ++++ | − | ++++ | − |
| N26 | 799-817 | − | − | − | ++ |
| N27 | 813-831 | +++ | − | ++++ | + |
| N28 | 827-845 | ++ | − | ± | ± |
| N29 | 841-859 | − | − | − | +++ |
| Controls | | | | | |
| L-Peptide | 218-231 | + | − | + | ++ |
| BoNT/A | — | | +++++ | | +++++ |
| BoNT/B | — | | ++ | | +++++ |
| TeNT | — | | − | | +++++ |

[a]For the purpose of this table, (+) and (−) assignments were based on net cpm values for Ab binding and SI values for T cell proliferation. For Ab binding, the symbols denote the following values: (−), less than 1,500 cpm; (±), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm. For T cell proliferation, the symbols indicate the following: (−), SI value less then 2.0; (±) 2.0-2.5; (+), SI 2.6-3.5; (++), SI 3.6-6.0; (+++), SI 6.1-10.0; (++++), 10.1-25 (+++++) SI >25.0.

TABLE 6

T cells and Abs recognition regions on BoNT/A $H_C$ domain[a,b]

| Peptide No. | Sequence Position (residues of SEQ ID NO: 1) | BALB/c (H-2$^d$) Abs | BALB/c (H-2$^d$) T Cell | SJL (H-2$^S$) Abs | SJL (H-2$^S$) T Cell |
|---|---|---|---|---|---|
| C1 | 855-873 | − | − | + | − |
| C2 | 869-887 | ++ | − | +++ | − |
| C3 | 883-901 | ++ | − | ++ | − |
| C4 | 897-915 | − | ++ | − | ++++ |
| C5 | 911-929 | − | − | + | + |
| C6 | 925-943 | + | − | + | + |
| C7 | 939-957 | + | ++ | + | +++ |
| C8 | 953-971 | − | − | − | ++ |
| C9 | 967-985 | + | − | + | − |
| C10 | 981-999 | + | − | + | − |
| C11 | 995-1013 | + | − | +++ | − |
| C12 | 1009-1027 | − | + | − | + |
| C13 | 1023-1041 | + | − | − | ++ |

TABLE 6-continued

T cells and Abs recognition regions on BoNT/A H$_C$ domain[a,b]

| Peptide No. | Sequence Position (residues of SEQ ID NO: 1) | BALB/c (H-2$^d$) Abs | BALB/c (H-2$^d$) T Cell | SJL (H-2$^s$) Abs | SJL (H-2$^s$) T Cell |
|---|---|---|---|---|---|
| C14 | 1037-1055 | − | − | − | + |
| C15 | 1051-1069 | + | − | ++ | +++ |
| C16 | 1065-1083 | − | − | − | + |
| C17 | 1079-1097 | − | − | − | ++ |
| C18 | 1093-1111 | − | ± | + | + |
| C19 | 1107-1125 | + | ++ | + | + |
| C20 | 1121-1139 | − | + | + | ++ |
| C21 | 1135-1153 | ++ | − | + | + |
| C22 | 1149-1167 | − | − | + | + |
| C23 | 1163-1181 | − | − | − | ++ |
| C24 | 1177-1195 | − | − | +++ | + |
| C25 | 1191-1209 | − | − | + | + |
| C26 | 1205-1223 | − | − | + | − |
| C27 | 1219-1237 | − | − | − | − |
| C28 | 1233-1251 | − | − | + | + |
| C29 | 1247-1265 | − | − | − | + |
| C30 | 1261-1279 | − | − | + | − |
| C31 | 1275-1296 | ++ | − | ++ | ++ |
| Controls | | | | | |
| L-Peptide | 218-231 | + | − | + | ++ |
| BoNT/A | — | | +++++ | | +++++ |
| BoNT/B | — | | ++ | | +++++ |
| TeNT | — | | − | | +++++ |

[a] Results of The Hc domain peptide recognition by anti-toxoid Abs and T cells of BALB/c and SJL mice are from Rosenberg et al., supra, 1997.
[b] For the purpose of this table, (+) and (−) assignments were based on net cpm values for Ab binding and SI values for T cell proliferation. For Ab binding, the symbols denote the following values: (−), less than 1,500 cpm; (±), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm. For T cell proliferation, the symbols indicate the following: (−), SI value less then 2.0; (±) 2.0-2.5; (+), SI 2.6-3.5; (++), SI 3.6-6.0; (+++), SI 6.1-10.0; (++++), 10.1-25 (+++++) SI >25.0.

D. Protective Activity of Anti-BoNT/A Antibodies In Vivo

Figure 14:
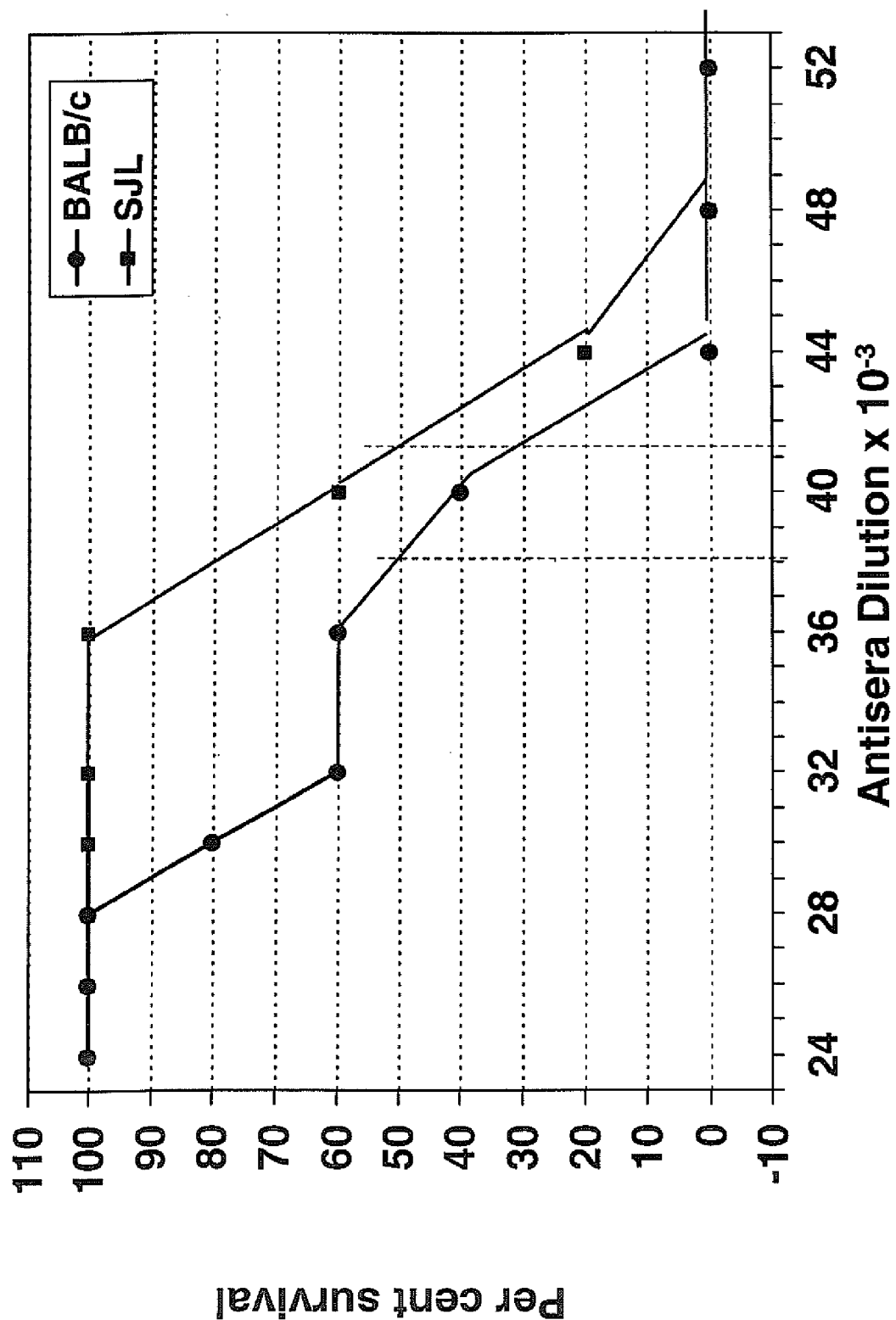
FIG. 14 shows protective activity of different dilutions of BALB/c and SJL anti-BoNT/A antisera. The results are expressed in percent survival to BoNT/A challenge versus antiserum dilution.

Anti-BoNT/A antisera from BALB/c and SJL mice were assayed for the ability to protect against a lethal dose of active BoNT/A as described further below. Serial dilutions of BALB/c and SJL antisera were assayed for the ability to protect ICR mice against 1.05×LD$_{100}$ (i.e., 6.5 μg) of BoNT/A. As shown in FIG. 14, antisera of both BALB/c and SJL contained high titers of blocking antibodies that protected mice at very high dilutions. Anti-toxin antisera of BALB/c mice were fully protective in recipient ICR mice at dilutions up to 1:28000 (vol/vol), and 50% protection was obtained at 1:38000 (vol/vol). SJL antisera were even more protective, fully protecting recipient ICR mice against a lethal dose of active BoNT/A at 1:36000 dilution (vol/vol), while 50% protection was achieved at 1:41000 dilution (vol/vol). As expected, non-immune sera were not protective at any dilution. These results indicate that anti-toxoid antibodies can be useful for conferring protection against botulinum toxin.

The presence of blocking antibodies in mouse antisera against BoNT/A was determined by a mouse protection assay essentially as follows. The survival of outbred (ICR) mice against various doses of BoNT/A administered intravenously was determined using five mice at each dose. The dose at which no mice survived (i.e., LD$_{100}$) was 5.0 μg/mouse when a fresh preparation of BoNT/A was tested. At the time the mouse protection assays were performed, after storage of toxoid for about 6 months at −20° C. in PBS containing 20% glycerin, the LD$_{100}$ was 6.2 μg/mouse. To determine the protective activity of BALB/c and SJL anti-BoNT/A antisera, ICR mice were injected intravenously in the tail with a mixture of 1.05×LD$_{100}$ of active BoNT/A (i.e., 6.5 μg/mouse) and 100 μl of serial dilutions of the indicated mouse antiserum. Each dilution was injected into five mice, and the mice were observed three times a day for six days. Where test antisera contained blocking antibodies, all mice recovered and survived the challenge. When protecting antibodies were either absent or their amounts too low at high dilution, then none or only some of the mice survived the BoNT/A challenge. The results were plotted as percent survival versus antisera dilutions.

Example 9

Submolecular Recognition Profiles in Two Mouse Strains of Non-Protective and Protective Anti-Bont/A Antibodies This example demonstrates that the switch in BALB/c and SJL mice from non-protective to protective antibodies is not associated with major changes in epitope recognition profiles but is rather associated with the immunoglobulin class of the antibodies.

A. Protective Activity of Anti-BoNT/A Antibodies In Vivo

As described above, female BALB/c (H-2$^d$) and SJL/JCr (H-2$^s$) mice, 7 to 9 weeks old, were used in all experiments. The mouse protection assay was performed as described in Example 8 above. Formaldehyde-inactivated, and active BoNT/A were purchased from Metabiologics (Madison, Wis.).

Anti-toxin antisera of BALB/c and SJL remained unprotective in recipient ICR mice on 26 day after the first BoNT/A injection. Mice were boosted on day 27, and nine days after the second injection (i.e., day 36 after the first injection), antisera were tested for protection. BALB/c antisera were protective against a challenge dose of 1.05×LD$_{100}$, when administered undiluted. SJL antisera were protective on day 36; these antisera were protective at dilutions up to 1:4 and were not protective at dilutions of 1:8. Non-immune sera were not protective even when undiluted. These results serve to define the timing of the switch between production of unprotective and protective anti-BoNT/A antibodies.

B. Binding Profile of Non-Protective and Protective Total Antibodies

For mapping of peptide binding profiles, antisera were assayed at dilutions of 1:100 and 1:250 (vol/vol). Binding profiles of total (IgG and IgM) anti-toxin antibodies from BALB/c and SJL mice were determined for two bleeds: The bleed on day 26 containing non-protective antibodies and the bleed following it on day 36 in which the antibodies demonstrated protective activity.

As shown in FIG. 16, upper panel, non-protective and protective BALB/c antisera showed very similar peptide-binding profiles at a dilution of 1:100. At a dilution of 1:250, the protective BALB/c antisera displayed higher binding to essentially every peptide (FIG. 16, lower panel). The BALB/c antibody-binding peptides were: N6, N7, N25, C2, C3, C9, C10, C11, C15, C18, C24, C30 and C31. Antibodies in the non-protective and protective antisera bound to peptide C30 at similar levels at a dilution of 1:100. However, at a dilution of 1:250, antibody binding to C30 in the non-protective antisera was greatly diminished while binding in the protective antisera remained unaffected, indicating a lower affinity of the antibodies directed against region C30 in the non-protective antisera. Low, but reproducible amounts of antibodies were bound by peptides N19, C6, C7 and C28.

The binding profiles for SJL total antibodies are shown in FIG. 17 at dilutions of 1:100 and 1:250 (vol/vol), upper and lower panels, respectively. In the case of the SJL mice, some differences were apparent between non-protective and protective antisera when total antibodies were analyzed. Peptides N5, N22 and C21, which were recognized by protective antisera, were only slightly recognized (N22 and C21) or not recognized (N5) by non-protective sera. Additionally, in the protective antisera, peptides N7, N8, N25, C1, C15 and less so N27, N28 bound two-fold or higher amounts of antibodies as compared with non-protective antisera. Additional peptides, C4 and C29, bound higher amounts of antibodies in protective sera as compared to non-protective sera at a dilution of 1:100. However these differences disappeared at 1:250, indicating that these antibodies were of relatively low affinity. Peptides C2, C3, C7, C18, C19, C24, C30 and C31 also bound higher amounts of antibodies in protective sera as compared with non-protective antisera, but the differences were less than double. As expected, anti-toxin antibodies did not bind to unrelated proteins or peptides, and pre-immune sera displayed no binding to BoNT/A or its peptides, indicative of specific binding.

In sum, these results demonstrate only very small differences between the peptide recognition profiles of protective and non-protective antisera. These results further indicate that differences in antibody binding levels likely do not account for the difference in protective activity of the non-protective and protective antisera.

Assays were performed as follows. A total of 60 consecutive overlapping peptides corresponding to the complete H subunit (residues 449-1296 of SEQ ID NO: 1), and a peptide around the enzymatic active site of the light chain (L-peptide, residues 218-231), of BoNT/A (FIG. 1) were synthesized, purified and characterized as described above. The peptides were 19 residues long and overlapped consecutively by five residues except for the last peptide in the sequence (C31, residues 1275-1296 of SEQ ID NO: 1). Mice were immunized as described above, with two boosters given at days 27 and 60 with a similar dose of toxoid, using incomplete Freund's adjuvant. Sera were collected prior to the first immunization (preimmune sera) and on days 20, 26, 36, 46, 57, 68 and 70. For each mouse strain, sera of the respective bleeds from 10 mice were pooled and kept at −20° C. The non-protective sera from day 26 and protective sera from day 36 were employed for peptide binding studies. Binding was determined by solid-phase radioimmunoassay as described in Example 8 above, except that affinity-purified rabbit anti-mouse (IgG and IgM) or anti-mouse IgG antisera (Accurate Chem. Sci. Corp.; Westbury, N.Y.) was used as appropriate.

C. Binding of Non-Protective and Protective IgG Antibodies to Synthetic BoNT/A Peptides and to BoNT/A As described above, differences in total antibody reactivity between protective and non-protective antisera, particularly in the case of BALB/c antisera, appeared insufficient to explain the protective properties of the antisera. The peptide-binding profiles of IgG antibodies alone showed different results. In their binding to active BoNT/A, BALB/c and SJL protective antisera had 13-36 fold higher levels of IgG antibodies relative to non-protective antisera. The profiles for BALB/c and SJL protective and non-protective antibodies are shown in FIGS. 18 and 19, respectively. IgG antibodies in the protective antisera of each mouse strain bound to the same peptides as did total antibodies (IgG and IgM) in the correlate antiserum. However, in both mouse strains, the non-protective antisera contained few, if any, IgG antibodies that bound to these peptides, even at a dilution of 1:100. Again, specific binding was demonstrated by the absence of binding to unrelated proteins and peptides, and by the absence of BoNT/A binding by non-immune sera.

These results demonstrate that protective antibodies had much higher IgG levels that bound to BoNT/A and to synthetic BoNT/A peptides (FIG. 18). In their binding to active BoNT/A, BALB/c protective antisera had up to 36-fold higher amounts of IgG antibodies relative to non-protective antisera (FIG. 18). Similarly, for SJL, the protective antibodies had up to 16-fold higher levels of IgG that bound to active BoNT/A than did the non-protective antibodies (FIG. 19). Furthermore, non-protective SJL and BALB/c antibodies each exhibited little or no binding to the peptides. These results demonstrate that the major difference between the protective and non-protective antibodies was the fact that non-protective antibodies, obtained after only one immunization with BoNT/A, were primarily of the IgM class. In contrast, protective antibodies obtained 10 days after the first booster displayed an IgM-to-IgG switch. In sum, these results indicate that protection is associated with antibodies of the IgG class.

Example 10

Mapping of the H Chain Recognition Profile in Antisera from a Cohort of Cervical Dystonia (CD) Patients This example demonstrates that an in vitro assay can be used to determine amounts of blocking or protective antibodies against BoNT/A in human serum samples. This example further demonstrates that a combination assay using, for example, two or three synthetic BoNT/A peptides can be used for sensitive detection of the presence of specific anti-toxin antibodies in, for example, BOTOX® treated patients.

A. Methods for Data Analysis

MPA-positive cervical dystonia (CD) serum samples were obtained from Allergan, Parkinson's Disease Center and Movement Disorders Clinic of Baylor College of Medicine, and the Arizona Dystonia Institute. CD patient sera protected against a lethal dose of BoNT/A in a mouse protection bioassay were screened with 60 synthetic toxin peptides corresponding to the entire H chain of BoNT/A (FIG. 1). The IgG fraction of hyperimmune sera of human volunteers (obtained from the Department of the Army) against pentavalent toxin (BoNT/A, B, C, D and E) was used as a positive control. An aliquot (50 µl) of each of the 60 synthetic overlapping peptides, dissolved in 0.01 M phosphate buffer, pH 7.2 containing 0.15 M NaCl (1.0 µg/50 µl of PBS), was added to three wells of a flexible polyvinyl chloride 96-well plate. Peptides were allowed to bind for two hours at 37° C. followed by overnight incubation at 4° C. Plates were washed five times with PBS to remove unbound peptide and then blocked for one hour at 37° C. with 0.5% bovine serum albumin in PBS (BSA/PBS). An appropriate volume of each of the mouse protection assay (MPA)-positive CD sera was preincubated with an equal volume of TeNT toxoid (1 mg/ml) for three hours at 37° C. after which it was diluted to 1:500 (vol/vol) with 0.1% BSA/PBS, pipetted (50 µl) into peptide-coated wells and allowed to react for three hours at 37° C. followed by further incubation overnight at 4° C. After washing the wells five times with PBS, 50 µl of prediluted (1:500 vol/vol, in 0.1% BSA/PBS) immunoglobulin fraction of rabbit anti-human IgG (DAKO Corporation; Carpinteria, Calif. A0424)+IgM (Mu chain; DAKO, A0426) was added and allowed to react at 37° C. for two hours. The wells were washed five times with PBS followed by addition of 50 µl of $^{125}$I-Protein A ($2 \times 10^5$ CPM in 0.1% BSA/PBS) to each well and incubation for two hours at room temperature. Finally, plates were washed thoroughly to eliminate unbound radioactivity; individual wells were cut out and transferred into separate tubes; and the incorporated radioactivity was counted in a gamma-counter (1277 Gamma Master; LKB, Finland). The results, which were obtained from triplicate analyses, were expressed as the ratios of mean CPM bound by peptides over CPM bound by control peptides or bovine serum albumin (BSA).

For determining antibody binding to BoNT/A or BoNT/B, triplicate wells were coated with the appropriate inactive BoNT/A or BoNT/B toxin (0.5 μg/50 μl of PBS). A similar procedure was then used to determine the amount of antibody bound by BoNT/A or BoNT/B using human MPA-positive CD sera pre-absorbed with TeNT.

B. Assay of Total Antibodies Bound to BoNT/A and BoNT/B

Due to varying amounts of anti-TeNT antibodies in human sera and the cross-reactivity of these antibodies with both BoNT/A as well as BoNT/B, see, e.g., Behzod Z. Dolimbek et al., *Cross Reaction of Tetanus and Botulinum Neurotoxins A and B and the Boosting Effect of Botulinum Neurotoxins A and B on a Primary Anti-Tetanus Antibody Response*, 31(3-4) IMMUNOL. INVEST. 247-262 (2002), the binding assay described above was modified. Essentially, the reaction with BoNT/A or synthetic BoNT/A peptides was carried out either after absorption of the sera with TeNT or, more conveniently, in the presence of a large excess of TeNT as described further below. The pool of positive control antisera was obtained from human volunteers, and was tested at two dilutions (1:1000 and 1:2000, vol/vol).

Binding studies of the antisera from CD patients as well as sera from unimmunized controls showed that the sera had different levels of non-specific binding to unrelated protein (BSA) and peptides. This high non-specific binding affected both the net cpm values as well as the ratio of the signal (specific binding) to background (non-specific binding). Sera from the same cervical dystonia patients prior to toxin treatment (pre-immune sera) were not available to correct for the non-specific binding. However, the amount of radiolabel bound by certain synthetic H peptides was observed to be essentially the same as the amount of radiolabel bound to unrelated proteins and peptides. These non-antibody-binding H chain peptides (for example, N2, N3, N5, N6, N7, N9, N10, N11, N12, etc.; see FIG. 1) were utilized as an internal control for each serum. In particular, binding was expressed for each serum as a ratio of the amount of antibody bound by a test peptide over the average of the amounts of antibody bound by four of the non-antibody binding H-chain peptides (N2, N12, C17 and C23). The value for such a ratio of antibodies bound to a given peptide from a given serum was essentially constant.

Figures 21, 22:
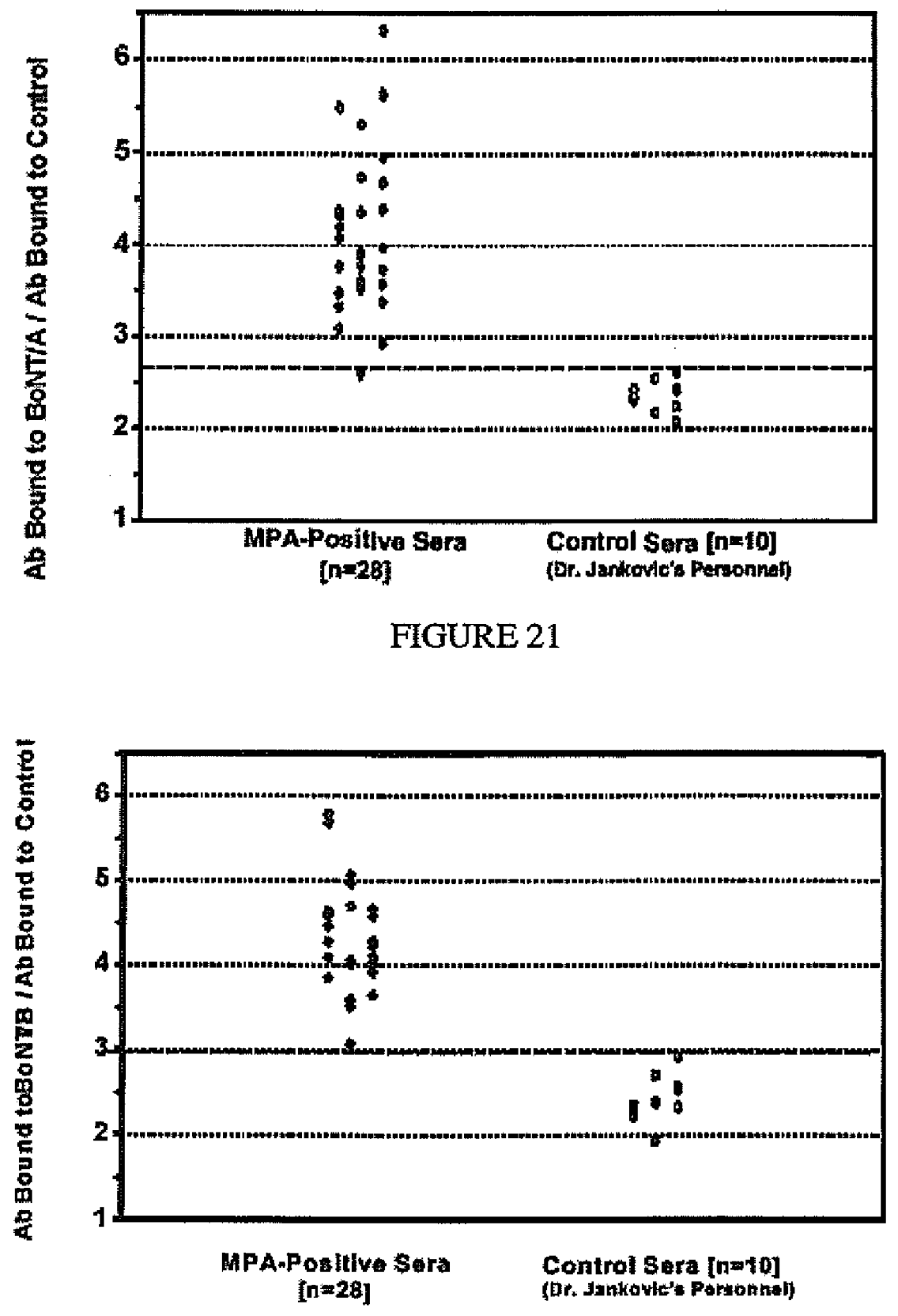

In assays to determine the total amounts of antibody present in CD patient sera, BSA and the four non-binding peptides N2, N12, C17 and C23 were used as negative controls. The results of antibody binding to BoNT/A toxoid in 28 MPA-positive CD sera and 10 human sera from unimmunized controls are summarized in FIG. 21. The results show that 27 out of 28 (96.4%) MPA-positive sera bound antibody levels that were clearly higher than those bound by the controls. These results validate the use of assays performed with human sera in a large excess of TeNT to determine the total amounts of antibodies to BoNT/A present in the serum of a patient in the course of treatment with BOTOX®.

In determining the total amount of anti-BoNT/B antibodies present in CD patient sera, BSA was used as the negative control. The results of binding to the BoNT/B toxoid of antibodies in 28 MPA-positive CD sera and 10 human sera from unimmunized controls are summarized in FIG. 22. The results show that 27 out of 28 (96.4%) of MPA-positive sera bound antibody levels that were clearly higher than those bound by the controls, while one was close to the borderline. These results validate the use of this assay for determining total amounts of antibodies to BoNT/B present in patient serum in the course of treatment with a BoNT/B formulation.

C. Mapping of Epitopes Recognized by Antibodies in of MPA-Positive Sera of Cervical Dystonia Patients The results of mapping by the synthetic H-chain peptides of antibodies from 28 CD patients that were MPA positive are shown in FIG. 24 to 26 and summarized in Table 6. These data, which represent four replicate experiments, are compared to binding profiles obtained with hyperimmune human sera at 1:1000 and 1:2000 (vol/vol). As described above, the results in FIG. 24 to 26 and in Table 6 are based on the ratio of cpm bound by a given peptide/cpm bound by BSA and/or average of cpm bound by peptides N2, N12, C17 and C23. In Table 6, (−) denotes no detectable binding; (±) indicates very low but reproducible binding (ratio of specific over non-specific binding of 1.61-2.0); and different numbers of (+) signs indicate different levels of binding. As can be seen by comparison with the data reported above, peptides which bound antibodies in the sera of the CD patients also bound antibodies within hyperimmune sera. However, not every peptide that bound antibodies in hyperimmune serum was able to bind antibodies in patient sera, indicating that the antibody-binding profile of the patients' sera was more restricted than the profile of the hyperimmune sera.

Furthermore, variability was seen among the binding profiles for different patients. As an example, the antisera of some patients bound peptide N4, whereas other sera had no such binding-activity. This inter-patient variability is consistent with the fact that immune responses to protein antigens are known to be under genetic control and that the response to each epitope within a protein is under separate genetic control, see, e.g., K. Okuda et al., *Genetic Control of Immune Response to Sperm Whale Myoglobin in Mice. I. T Lymphocyte Proliferative Response Under H-2-Linked Ir Gene Control*, 121(3) J. IMMUNOL. 866-868 (1978).

Significantly, however, some peptides bound antibodies in most of the patients. For example, 25 out of 28 sera contained antibodies that bound to peptide N25, although the amounts bound varied from patient to patient with three sera (patients 45, 304 and 310) having marginal levels of antibodies to this peptide. Peptide C10 bound antibodies in sera of 24 out of 28 patients, with the sera of patients 43, 45, 53 and SD displaying very low (±) or no (−) antibody binding to peptide C10. Peptide C15 displayed low (+) to medium (++) binding to antibodies in 17 patient sera; very low (±) binding with nine patient sera; and no binding with two sera. The antibody-binding activity of peptide C20 was generally lower than peptides N25 or C10 but was low (+) to high (+++) in nine of the patient sera, while eight sera showed no antibody binding, and 11 sera showed very low (O), but reproducible, levels of binding. In addition, peptide C31 bound antibodies in 17 sera, showed very low binding in eight patient sera, and displayed no detectable antibody binding with three patient sera. These results indicate that, while there is some peptide-binding variability among MPA-positive CD patient sera, several synthetic BoNT/A peptides bind antibodies in the large majority of patient sera.

Figure 28:
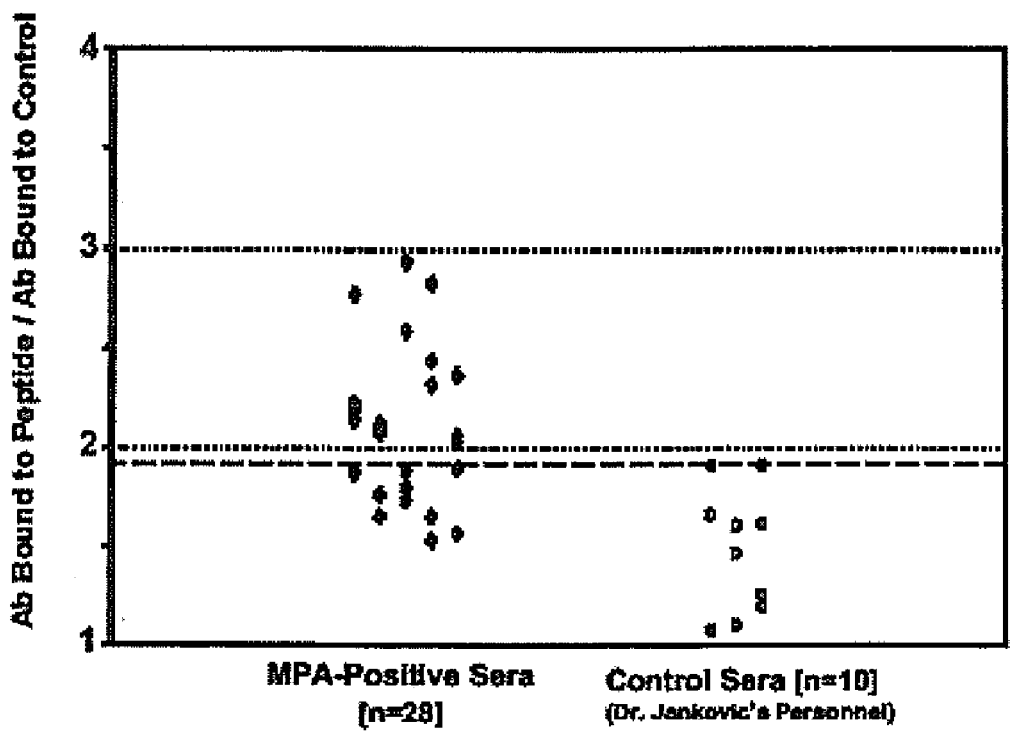
FIG. 28 shows binding to peptide C15 of antibodies in MPA-positive sera from CD patients (n=28) and in normal controls (n=10). Results are the average of four experiments and are expressed as a ratio of (antibodies bound to peptide C10)/(average of antibodies bound by negative control peptides N2, N12, C17 and C23).
Figure 29:
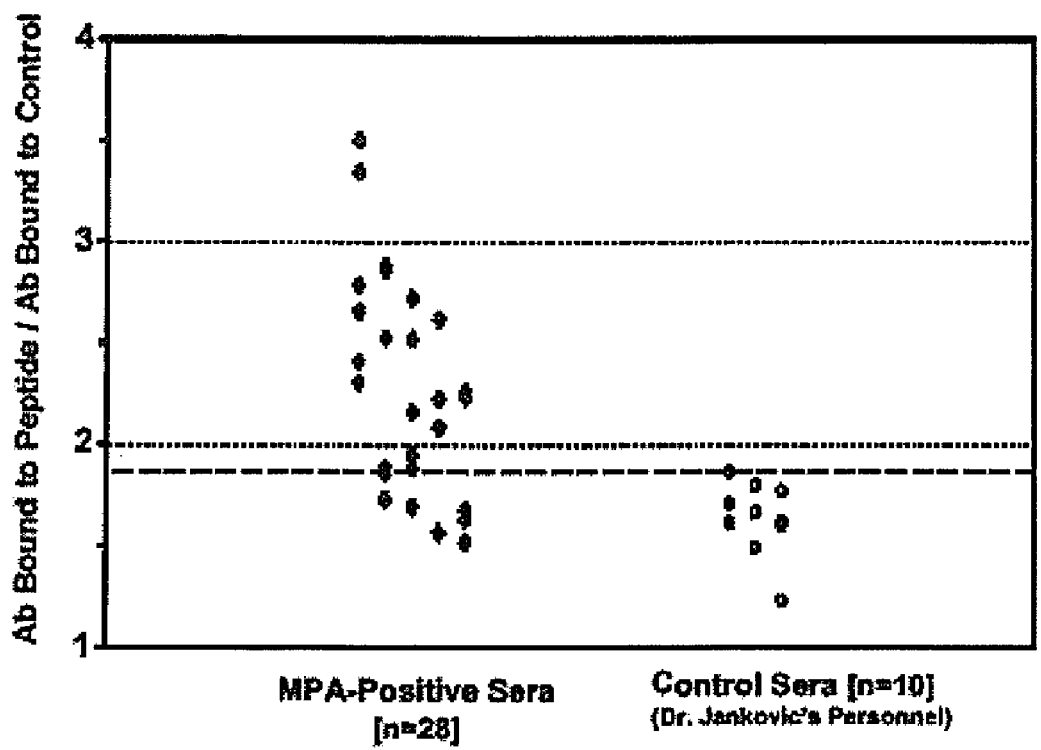
FIG. 29 shows binding to peptide C31 of antibodies in MPA-positive sera from CD patients (n=28) and in normal controls (n=10). Results are the average of four experiments and are expressed as a ratio of (antibodies bound to peptide C10)/(average of antibodies bound by negative control peptides N2, N12, C17 and C23).

D. Synthetic Peptide Assay for Analysis of Reactivity of MPA-Positive Patient Sera As disclosed above, MPA-positive cervical dystonia patient sera contained antibodies that bound to one or more of the peptides N25, C10, C15, C20 and C31, indicating that binding to one or more of these peptides can used to determine the presence of antibody responses in patient sera. FIGS. 27, 28, 29 and 30 show the ratio of the specific cpm bound in the same assay to non-binding peptides and to BSA. As shown in FIG. 26, analysis on the basis of peptide N25 was able to distinguish clearly 21 out of 28 (75%) of patient sera from unimmunized controls. Binding to peptide C10 was also able to distinguish 21 out of 28 sera from the controls, while binding to peptides C15 and C31 distinguished 18 (64.3%) and 20 (71.4%) out of 28 sera, respectively (FIG. 28 to 30).

Figure 31:
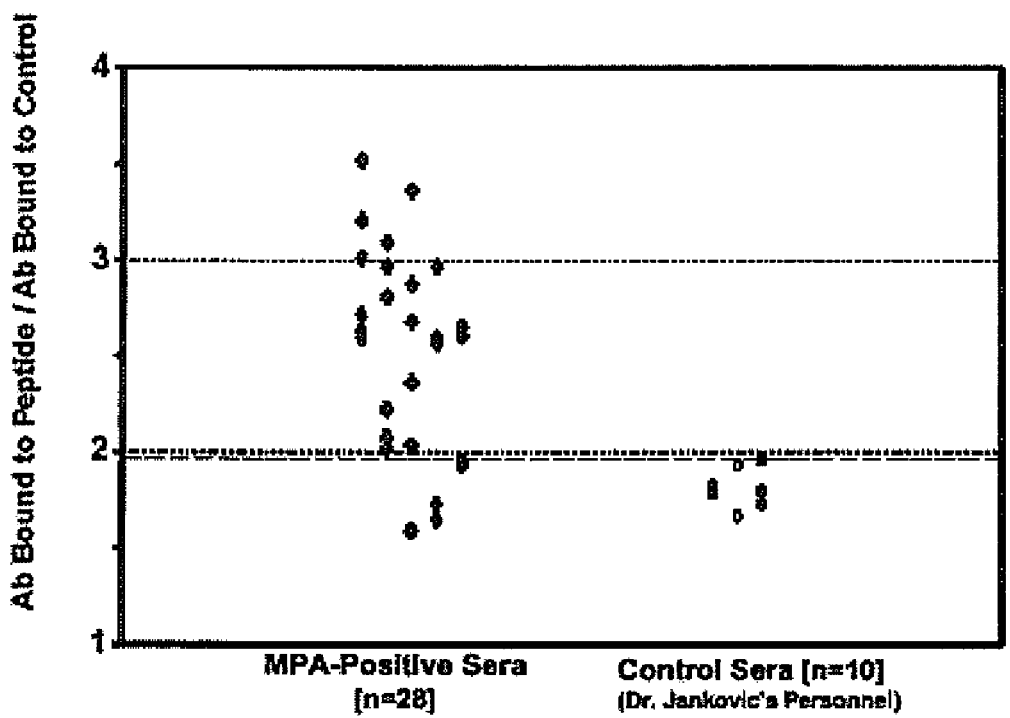
FIG. 31 shows binding peptides (N25+C10+C31) of antibodies in MPA-positive sera from CD patients (n=28) and in normal controls (n=10). Results, which are the average of four experiments, are expressed as a ratio of (antibodies bound to peptides N25+C10+C31)/(average of antibodies bound by negative control peptides N2, N12, C17 and C23).
Figure 33:
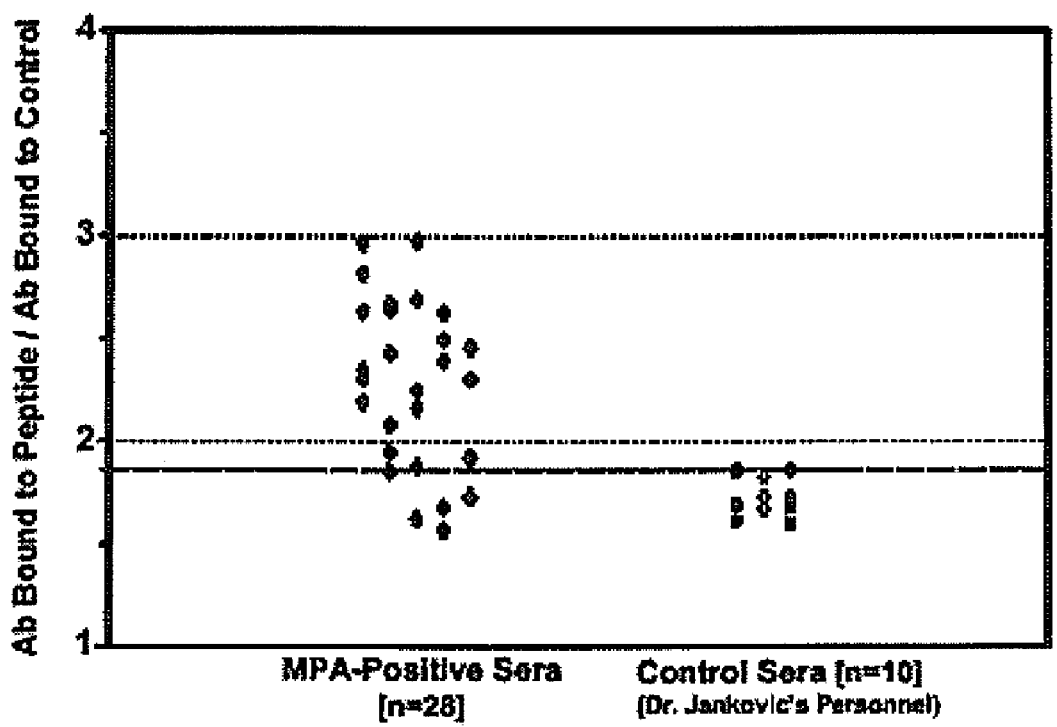
FIG. 33 shows binding to peptides (N25+C10+C15+C31) of antibodies in MPA-positive sera from CD patients (n=28) and in normal controls (n=10). Results, which are the average of four experiments, are expressed as a ratio of (antibodies bound to peptides N25+C10+C15+C31)/(average of antibodies bound by negative control peptides N2, N12, C17 and C23).

Combinations of two or more peptides were also assayed for their discriminatory capability. As shown in FIG. 30, when peptides N25 and C10 were combined in the assay, 25 out of 28 (89.3%) of the CD sera were discriminated from controls. The combination of peptides N25, C10 and C31 distinguished 24 out of 28 sera (85.7%; FIG. 31), and the combination of peptides N25, C10 and C15 distinguished 25 out of 28 (89.3%) of the MPA-positive CD sera from controls (see FIG. 32). Finally, a combination of four peptides (N25, C10, C15 and C31) distinguished 21 out of 28 sera (75%) from the controls, as shown in FIG. 33. These results demonstrate that a combination assay using peptides N25 and C10 or N25, C10 and C15 can be useful for detecting the presence of specific anti-toxin antibodies in BOTOX® treated patients.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

Example 11

Mapping of Synaptosome-Binding Regions of the Heavy Chain of Botulinum Neurotoxin A by Synthetic Overlapping Peptides Encompassing the Entire Chain A. Binding of $^{125}$I-Labeled BoNT/A to Synaptosomes To make radioactively-labeled active BoNT/A toxin, active BoNT/A (Metabiologics, Inc., Madison, Wis.) was labeled with $^{125}$Iodine using a chloramine T method as described in, e.g. W. M Hunter & F. C. Greenwood, *Preparation of Iodine-131-labeled human growth hormone of high specific activity*, 194 NATURE 495-496, (1962). A labeling reaction comprising 50 µl of 100 mM potassium phosphate, pH 8.0 containing 1.0 µg active BoNT/A toxin, 5 µl of 10 mCi/mL sodium $^{125}$Iodine, and 25 µl of 100 mM potassium phosphate, pH 8.0 containing 2 mg/mL chloramine T was incubated on ice for 5 minutes. To this labeling reaction, 50 µl of 100 mM potassium phosphate, pH 8.0 containing 20 mg/mL sodium metabisulfite was added to stop the reaction. Excess unlabeled radioactive iodine was removed from the $^{125}$Iodine-labeled toxin by applying the labeling mixture through a Sephadex G-25 gel filtration column equilibrated and eluted as a single fraction with a column solution comprising 10 mM phosphate-buffered saline, pH 7.2; 150 mM sodium chloride; and 0.1% bovine serum albumin (BSA). The level of $^{125}$Iodine incorporation was determined by measuring the radioactivity from a 1 µL aliquot using a gamma scintillation counter. The $^{125}$Iodine-labeled BoNT/A peptide containing eluent was adjusted to a radioactivity level suitable for synaptosome binding assays. The $^{125}$Iodine-labeled active BoNT/A toxin was stored at 4° C. and used within two days.

To determine the amount of synaptosome required to achieve saturation binding with a fixed amount of BoNT/A peptide, a synaptosome binding assay was conducted. Approximately 50,000 counts/minute of $^{125}$I-labeled active BoNT/A peptide was mixed with increasing volumes of a synaptosome preparation (from 0 to 8 µL) in 100 µL of Ringer's solution, pH 7.0 (120 mM sodium chloride, 2.5 mM potassium chloride, 2 mM calcium chloride, 4 mM magnesium chloride, 5 mM 2-amino-2-hydroxymethyl-1,3-propanediol hydrochloric acid (Tris-HCl, pH 7.0), 0.5% (w/v) bovine serum albumin). The reaction mixtures were incubated at 37° C. for 20 minutes in order to allow for the formation of any peptide-synaptosome complexes. The reaction mixtures were then microcentrifuged (23,000×g at 20° C. for 3 minutes) to pellet peptide-synaptosome complexes. The pellets were washed twice in 800 µL of Ringer's solution, pH 7.0 to remove any unbound toxin. The pellets containing peptide-synaptosome complexes were resuspended in 300 µL of Ringer's solution, pH 7.0, transferred to a glass scintillation tube, and the amount of radioactivity from these complexes measured using a gamma scintillation counter. The percent synaptosome binding inhibition of a synthetic peptide sample was calculated using the following formula: [1-(count of the sample/count of control)]×100. The experiment was carried out in triplicate.

Titration of a fixed amount of $^{125}$I-labeled BoNT/A (50,000 cpm) with increasing amounts of synaptosomes is shown in FIG. 34. The amount of labeled toxin bound increased until it reached a plateau of about 8% of the added labeled toxin at about 6 µl of synaptosomes. FIG. 35 shows an example of the inhibition of the binding of labeled BoNT/A by unlabeled toxin. It can be seen in FIG. 35a that the binding decreased steadily in the presence of increasing amounts of unlabeled BoNT/A. The binding was completely (100%) inhibited by unlabeled BoNT/A (FIG. 35b), but not by unrelated proteins indicating that the binding of $^{125}$I-labeled BoNT/A to synaptosomes was entirely specific. The 50% inhibition value ($IC_{50}$) was obtained at an inhibitor concentration of $1.2\times10^{-8}$ M. I also carried out titrations to determine inhibition of the binding of each of active BoNT/A or inactivated toxin (toxoid) to synaptosomes by the other. It was found that toxoid inhibited at maximum (2 µg) the synaptosome-binding of active toxin completely (98%) while maximum inhibition at plateau (2 µg) by active toxin of toxoid synaptosome-binding was 78%.

B. Inhibition by the Individual Peptides of the Binding of 125I-Labeled BoNT/A to Synaptosomes The regions of the H chain involved in the binding to synaptosomes were mapped by determining the ability of each peptide to inhibit the binding of $^{125}$I-labeled BoNT/A to synaptosomes. FIG. 36a shows an example of the inhibition curves obtained with the synthetic peptides. The values of maximum inhibition were obtained by plotting the inhibition values against the reciprocal of the different peptide concentrations used in the inhibition assay (see FIG. 36b). The maximum inhibitory activities of the 60 peptides are summarized in FIG. 37. The results showed that the synaptosome-binding regions were not only present on the $H_C$ domain, but a number of such regions were also found on the $H_N$ domain (FIG. 37). On the $H_N$ domain, inhibitory activities greater than 10% were exhibited, in decreasing order, by peptides N26 (33.4%), N21 (25.0%), N16 (23.2%), N7 (15.7%), N19 (14.4%), and N23 (10.3%). Five other peptides, N2, N5, N6, N12 and N15, possessed inhibitory activities between 5.6-8.7%. The remaining 18 $H_N$ peptides had little or no detectable inhibitory activity. In the $H_C$ domain, regions within peptides C16, C23 and C31 had the highest inhibitory activities (between 25-29%), followed in inhibitory activity (10-12%) by peptides C19, C25 and C28. Two other peptides, C17 and C24, had low inhibitory activities (5.8 and 4.9%, respectively). The remaining 23 $H_C$ peptides showed little or no detectable inhibitory activity.

C. Inhibition of the Binding of 125I-Labeled BoNT/A to Synaptosomes by Mixtures of Equimolar Quantities of the Active Peptides The competitive inhibitory activities were also determined for mixtures containing equimolar quantities of various $H_C$ and $H_N$ synthetic peptides. For example, the following peptide mixtures were used as the competitive inhibitor peptide source: (1) The six $H_N$ peptides N7, N16, N19, N21, N23 and N26 in a mixture containing 0.167 µg of each peptide in 100 µL of reaction mixture; (2) the five $H_C$ peptides C16, C19, C23, C28 and C31 in a mixture containing 0.200 µg of each peptide in 100 µL of reaction mixture; (3) all eleven $H_N/H_C$ peptides N7, N16, N19, N21, N23, N26, C16, C19, C23, C28 and C31 in a mixture containing 0.091 µg of each peptide. In these experiments the amounts of inhibiting peptide mixture used were increased up to 1 µg/100 µL of each reaction mixture. Under these conditions, the controls that did not have synaptosomes showed no non-specific binding of $^{125}$I-labeled BoNT/A to the peptides. When higher amounts of peptide mixture were used, some non-specific binding of $^{125}$I-labeled BoNT/A to the peptides was observed, which increased with the amount of peptide mixture and thus afforded unreliable inhibition values. In addition, the inhibitory capability of each peptide was determined individually FIG. 38 and Table 1 show the inhibitory activities of the three mixtures.

The mixture of the $H_N$ peptides contained at maximum amount 0.167 µg of each of the six peptides and exhibited a maximum inhibitory activity of 30.1%. At this excess, the sum of the inhibition of the six peptides is expected to be 31.2%. This compares very well with the inhibition exerted by a mixture containing similar amounts of peptides. The inhibition afforded by the mixture of the five $H_C$ peptides (37.4%) was significantly higher than the sum of the inhibition values by the same amount of the individual $H_C$ peptides (28.3%). Finally, the inhibition by the mixture of the 11 $H_N$ and $H_C$ peptides together (44.8%) was also substantially higher than the sum of inhibition values of similar amounts of the individual peptides (31.2%).

TABLE 7

Inhibitory activities of equimolar mixtures of the active peptides

| Inhibitor mixture | Percent inhibition[a] | |
|---|---|---|
| | Sum of individual peptide inhibition (%) | Peptide mixture inhibition (%) |
| $H_N$ peptides (0.167 µg/peptide) | 31.2 | 30.1 |
| $H_C$ peptides (0.200 µg/peptide) | 28.4 | 37.4 |
| $H_N/H_C$ peptides (0.091 µg/peptide) | 31.2 | 44.8 |

[a]The inhibition of the six $H_N$ peptides was determined individually at 0.167 µg or in a mixture containing 0.167 µg of each peptide in 100 µL of reaction mixture; the inhibition of the five $H_C$ peptides was determined individually at 0.200 µg or in a mixture containing 0.200 µg of each peptide in 100 µL of reaction mixture; and the inhibition of the six $H_N$ peptides and the five $H_C$ peptides was determined individually at 0.091 µg or in a mixture containing 0.091 µg of each peptide in 100 µL of reaction mixture.

Tables 8 and 9 compare the peptides that bind protecting mouse anti-BoNT/A Abs (see Tables 1 & 2) to the regions that bind to mouse synaptosomes. Interestingly, many of the synaptosome-binding peptides seem to flank antibody-binding peptides. In the $H_N$ domain, the major synaptosome-binding regions within peptides N16, N19, N21 and N23 as well as the minor regions within peptides N2, N12, and N15 did not correspond to binding regions of mouse antibodies. However, the major synaptosome-binding regions within the overlap N6/N7 coincided with an antibody-binding region. The major synaptosome-binding region within peptide N26 shared an overlap with the antibody-binding region within peptide N25 and it is very likely that the two binding regions are displaced relative to another by 2-4 residues. Therefore, antibodies binding to the peptides N6, N7, N8 and to peptide N25 most likely work by blocking the ability of regions N5, N6, N7 and region N26 respectively to bind to synaptosomes. In the $H_C$ domain, the major synaptosome-binding regions C16, C17, C19, C23, C24, C25 and C31 also correspond in the vicinity of antibody-binding regions C15, C24 and C31. The extensive correspondence between the synaptosome-binding and the antibody-binding regions on the $H_C$ domain can explain the high protective capacity of anti-BoNT/A antibodies (Middlebrook, 1995; Byrne and Smith, 2000; Woodward et al., 2003).

TABLE 8

| Peptide No. | Sequence Position (Residues of SEQ ID NO: 1) | Antibody Binding[a] | | | | Synaptosome Binding[b] |
|---|---|---|---|---|---|---|
| | | Human | Horse | Mouse | Chicken | |
| N1 | 449-467 | ++ | − | + | ± | − |
| N2 | 463-481 | − | +++++ | − | − | ++ |
| N3 | 477-495 | − | ± | − | − | − |
| N4 | 491-509 | ++ | + | ± | + | − |
| N5 | 505-523 | − | + | − | − | ++ |
| N6 | 519-537 | ++ | + | +++ | ++ | ++ |
| N7 | 533-551 | ++ | +++ | +++ | +++ | ++++ |
| N8 | 547-565 | +++++ | +++++ | +++++ | +++++ | − |
| N9 | 561-579 | + | ++++ | ++++ | ± | − |
| N10 | 575-593 | ± | ++ | + | ++ | − |
| N11 | 589-607 | +++ | + | − | + | − |
| N12 | 603-621 | + | − | − | − | ++ |
| N13 | 617-635 | − | ± | − | − | − |
| N14 | 631-649 | ++ | ± | ± | + | − |
| N15 | 645-663 | − | − | − | ± | ++ |
| N16 | 659-677 | ++++ | − | − | − | +++++ |
| N17 | 673-691 | ++ | − | ± | ++ | − |
| N18 | 687-705 | + | ± | − | − | − |
| N19 | 701-719 | ± | + | + | ++ | +++ |
| N20 | 715-733 | ++ | ++ | ± | ++ | − |
| N21 | 729-747 | ± | − | − | − | +++++ |
| N22 | 743-761 | ++++ | ++ | + | ++++ | − |
| N23 | 757-775 | − | + | − | − | +++ |
| N24 | 771-789 | ++ | ± | + | + | − |
| N25 | 785-803 | +++++ | +++ | +++++ | +++++ | − |
| N26 | 799-817 | − | − | − | − | +++++ |
| N27 | 813-831 | ++ | ++++ | +++ | ++++ | − |
| N28 | 827-845 | ++ | + | +++ | +++ | − |
| N29 | 841-859 | + | + | − | − | − |
| L-Peptide | 218-231 | − | − | − | − | − |
| Active BoNT/A | — | +++++ | +++++ | +++++ | +++++ | +++++ |

[a](+) or (−) signs are based on net cpm values and denote the following: (−), less than 1,500 cpm; (±), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm.
[b](+) or (−) signs are based on percent binding inhibition values of BoNT/A to a synaptosome preperation by a synthetic peptide and denote the following: (−), less than 2% inhibition; (+), 2-5% inhibition; (++), 5-10% inhibition; (+++), 10-15% inhibition; (++++), 15-20% inhibition; (+++++), greater than 20% inhibition.

TABLE 9

| Peptide No. | Sequence Position (Residues of SEQ ID NO: 1) | Antibody Binding[a] Human | Horse | Mouse | Chicken | Synaptosome Binding[b] |
|---|---|---|---|---|---|---|
| C1 | 855-873 | − | +++ | ± | − | − |
| C2 | 869-887 | +++ | − | +++ | +++ | − |
| C3 | 883-901 | − | + | + | +++++ | − |
| C4 | 897-915 | − | ± | − | ± | − |
| C5 | 911-929 | ++ | + | − | + | − |
| C6 | 925-943 | +++ | − | − | ++ | − |
| C7 | 939-957 | + | ++ | + | +++++ | − |
| C8 | 953-971 | − | − | − | − | − |
| C9 | 967-985 | + | − | ± | ++++ | − |
| C10 | 981-999 | +++ | ± | − | +++++ | − |
| C11 | 995-1013 | +++++ | + | + | +++++ | − |
| C12 | 1009-1027 | − | − | − | + | − |
| C13 | 1023-1041 | − | + | − | − | − |
| C14 | 1037-1055 | − | + | − | + | − |
| C15 | 1051-1069 | +++++ | ± | ++ | +++++ | − |
| C16 | 1065-1083 | − | − | − | − | +++++ |
| C17 | 1079-1097 | − | + | − | − | ++ |
| C18 | 1093-1111 | − | + | + | ++ | − |
| C19 | 1107-1125 | ± | − | − | − | +++ |
| C20 | 1121-1139 | + | + | ± | +++++ | − |
| C21 | 1135-1153 | ++ | ± | ± | +++ | − |
| C22 | 1149-1167 | ± | + | − | ++ | − |
| C23 | 1163-1181 | ± | − | − | − | +++++ |
| C24 | 1177-1195 | +++ | − | ++ | +++++ | + |
| C25 | 1191-1209 | ± | ++ | − | − | +++ |
| C26 | 1205-1223 | − | + | − | − | − |
| C27 | 1219-1237 | + | − | − | − | − |
| C28 | 1233-1251 | + | − | − | − | +++ |
| C29 | 1247-1265 | ++ | ± | − | ± | − |
| C30 | 1261-1279 | + | ++ | − | +++ | − |
| C31 | 1275-1296 | ++ | +++ | ++ | +++ | +++++ |
| L-Peptide | 218-231 | − | − | − | − | − |
| Active BoNT/A | — | +++++ | +++++ | +++++ | +++++ | +++++ |

[a](+) or (−) signs are based on net cpm values and denote the following: (−), less than 1,500 cpm; (±), 1,500-3,000 cpm; (+), 3,000-7,000 cpm; (++), 7,000-15,000 cpm; (+++), 15,000-25,000 cpm; (++++), 25,000-35,000 cpm; (+++++), exceeding 35,000 cpm.
[b](+) or (−) signs are based on percent binding inhibition values of BoNT/A to a synaptosome preperation by a synthetic peptide and denote the following: (−), less than 2% inhibition; (+), 2-5% inhibition; (++), 5-10% inhibition; (+++), 10-15% inhibition; (++++), 15-20% inhibition; (+++++), greater than 20% inhibition.

Example 12

BoNT/A Immunophereses in an Individual

This example illustrates an immunophereses method for treating blood in an individual using an anti-BoNT/A immunoaffinity column.

An individual is connected to an extracorporeal circulation circuit where blood is continuously drawn from an antecubital vein via a 15-gauge dialysis needle at a flow rate of approximately 50 to 80 mL/min. The total volume of blood removed from an individual is approximately 300 ml. The processed blood is returned back to the individual. To avoid thrombotic complications, heparin at an input rate of 20 units/min (not to exceed 5000 units per treatment) and anti-coagulant citrate dextrose formula A solution (ACD-A; Baxter Healthcare Corp, Deerfield, Ill.) is administered immediately prior to the procedure to prevent coagulation. The ratio of citrate to whole blood was kept at 1:22.

For primary plasma separation, an autopheresis-C™ Therapeutic Plasma System (TPS) is employed (Baxter Healthcare Corp, Deerfield, Ill.). Plasma is first separated from the cellular components using the Plasmacell-CR, a rotating cylindrical membrane housed in a plastic casting. The plasma is then directed to a first 150 ml anti-BoNT/B immunoaffinity column where anti-BoNT/A antibodies bind to the immobilized BoNT/A peptides disclosed in the present specification. The perfusion rate of plasma passing through the column is between 15 to 40 ml/min. A continuous flow operation is performed in which the TPS is connected with an adsorption-desorption-automate (ADA; Baxter Healthcare Corp, Deerfield, Ill.) controlling the flow of plasma and regeneration solutions. In general, a predetermined amount of plasma is processed through the first column and then the flow is directed to a second 150 ml anti-BoNT/A immunoaffinity column. While the second column is being loaded, the first column is regenerated using a suitable low pH buffer. Thus, the columns are alternately loaded and regenerated.

After passage though the anti-BoNT/A immunoaffinity column, the treated plasma is reconstituted with the cellular components of the blood and returned back into the individual. The blood can be pre-warmed to body temperature before being returned to the individual. This process is repeated until the desired amount of anti-BoNT/A antibodies is eliminated from the individual's blood.

---

What is claimed:

1. A method of determining immunoresistance to botulinum toxin therapy in an individual, the method comprising the steps of:
  a) combining a BoNT/A peptide with a test sample under conditions suitable for the selective binding of the BoNT/A peptide to an anti-BoNT antibody, the BoNT/A peptide having a length of at least six amino acids and at most 60 amino acids;
  wherein the BoNT/A peptide has a length of at least six amino acids and at most 60 amino acids and comprises amino acids 519-537 of SEQ ID NO: 1, a conservative BoNT/A amino acid sequence variant thereof, and an immunoreactive BoNT/A amino acid sequence fragment thereof;
  wherein the conservative BoNT/A amino acid sequence variant immunoreactive with the BoNT antibodies comprises 1-4 conservative amino acid substitutions to amino acids 519-537 of SEQ ID NO 1
  wherein the immunoreactive BoNT/A amino acid sequence fragment immunoreactive with the BoNT antibodies comprises at least six consecutive amino acids of 519-537 of SEQ ID NO: 1 and
  b) determining the presence of an anti-BoNT antibody-BoNT/A peptide complex, the antibody-peptide complex formed by the selective binding of an anti-BoNT antibody and the BoNT/A peptide; where the presence of the anti-BoNT antibody-BoNT/A peptide complex is indicative of immunoresistance to a BoNT therapy.

2. The immunoresistance method of claim 1, wherein the method comprises a further step of correlating the amount of an antibody-peptide complex formed from the test sample relative to the amount of an antibody-peptide complex formed by the BoNT/A peptide combined to a control sample.

3. The immunoresistance method of claim 1, wherein the test sample comprises blood.

4. The immunoresistance method of claim 1, wherein the test sample comprises serum.

5. The immunoresistance method of claim 4, wherein the test sample comprises IgG antibody component separated from the serum.

6. The immunoresistance method of claim 1, wherein the immunoresistance to botulinum toxin therapy is a BoNT/A immunoresistance.

7. The immunoresistance method of claim 1, wherein the individual is human.

8. The immunoresistance method of claim 1, wherein the presence of an anti-BoNT antibody-BoNT/A peptide complex is determined qualitatively or quantitatively.

9. The immunoresistance method of claim 1, wherein the presence of an anti-BoNT antibody-BoNT/A peptide complex is determined by a competitive assay or a non-competitive assay.

10. The immunoresistance method of claim 1, wherein the presence of an anti-BoNT antibody-BoNT/A peptide complex is determined by an assay format selected from the group consisting of a radioimmunoassay, an enzyme-linked immunosorbent assay, an enzyme immunoassay, a fluorescence immunoassay, and a luminescent immunoassay.

11. The immunoresistance method of claim 1, wherein the presence of at least 10% complex formation of an anti-BoNT antibody-BoNT/A peptide complex is indicative of a BoNT immunoresistance.

12. The immunoresistance method of claim 1, wherein the presence of at least 50% complex formation of an anti-BoNT antibody-BoNT/A peptide complex is indicative of a BoNT immunoresistance.

* * * * *

SEQUENCE LISTING

```
<160> NUMBER OF SEQ ID NOS: 5

<210> SEQ ID NO 1
<211> LENGTH: 1296
<212> TYPE: PRT
<213> ORGANISM: Clostridium botulinum serotype A

<400> SEQUENCE: 1

Met Pro Phe Val Asn Lys Gln Phe Asn Tyr Lys Asp Pro Val Asn Gly
 1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
```

```
                65                  70                  75                  80
Asp Asn Glu Lys Asp Asn Tyr Leu Lys Gly Val Thr Lys Leu Phe Glu
                    85                  90                  95

Arg Ile Tyr Ser Thr Asp Leu Gly Arg Met Leu Leu Thr Ser Ile Val
            100                 105                 110

Arg Gly Ile Pro Phe Trp Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495
```

```
Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Gly Gln Leu
        515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Tyr Val Lys
        580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
        660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
        850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
        900                 905                 910

Gln Ile Gln Leu Phe Asn Leu Glu Ser Ser Lys Ile Glu Val Ile Leu
        915                 920                 925
```

Lys Asn Ala Ile Val Tyr Asn Ser Met Tyr Glu Asn Phe Ser Thr Ser
            930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
            1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
    1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
            1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
            1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
            1285                1290                1295

<210> SEQ ID NO 2
<211> LENGTH: 1296
<212> TYPE: PRT
<213> ORGANISM: Clostridium botulinum serotype A

<400> SEQUENCE: 2

Met Pro Phe Val Asn Lys Gln Phe Asn Tyr Lys Asp Pro Val Asn Gly
1               5                   10                  15

-continued

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Asp Val Leu Asn Leu Thr
            165                 170                 175

Arg Asn Gly Tyr Gly Ser Thr Gln Tyr Ile Arg Phe Ser Pro Asp Phe
        180                 185                 190

Thr Phe Gly Phe Glu Glu Ser Leu Glu Val Asp Thr Asn Pro Leu Leu
    195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
        260                 265                 270

Phe Ile Asp Ser Leu Gln Glu Asn Glu Phe Arg Leu Tyr Tyr Tyr Asn
    275                 280                 285

Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Asn Phe Phe Lys Val Ile Asn Arg Lys Thr Tyr Leu Asn
    355                 360                 365

Phe Asp Lys Ala Val Phe Arg Ile Asn Ile Val Pro Asp Glu Asn Tyr
    370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
            405                 410                 415

Lys Asn Phe Thr Gly Leu Phe Glu Phe Tyr Lys Leu Leu Cys Val Arg
        420                 425                 430

Gly Ile Ile Pro Phe Lys Thr Lys Ser Leu Asp Glu Gly Tyr Asn Lys

```
                435             440             445
Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Asn Ile Ser Leu
                485                 490                 495

Asp Leu Ile Gln Gln Tyr Tyr Leu Thr Phe Asp Phe Asn Glu Pro
                500                 505                 510

Glu Asn Ile Ser Ile Glu Asn Leu Ser Ser Asp Ile Ile Gly Gln Leu
                515                 520                 525

Glu Pro Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
                580                 585                 590

Lys Ile Asn Lys Ala Val Glu Ala Phe Met Phe Leu Asn Trp Ala Glu
                595                 600                 605

Glu Leu Val Tyr Asp Phe Thr Asp Glu Thr Asn Glu Val Thr Thr Met
610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
                645                 650                 655

Ile Phe Thr Gly Val Val Ala Met Leu Glu Phe Ile Pro Glu Tyr Ala
                660                 665                 670

Leu Pro Val Phe Gly Thr Phe Ala Ile Val Ser Tyr Ile Ala Asn Lys
                675                 680                 685

Val Leu Thr Val Gln Thr Ile Asn Asn Ala Leu Ser Lys Arg Asn Glu
690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Glu Lys Asn Asn Ile Asn Phe Asn Ile Asp Asp
                755                 760                 765

Leu Ser Ser Lys Leu Asn Glu Ser Ile Asn Ser Ala Met Ile Asn Ile
770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Val Leu
                820                 825                 830

Gln Val Asp Arg Leu Lys Asp Glu Val Asn Asn Thr Leu Ser Ala Asp
                835                 840                 845

Ile Pro Phe Gln Leu Ser Lys Tyr Val Asp Asn Lys Lys Leu Leu Ser
850                 855                 860
```

```
Thr Phe Thr Glu Tyr Ile Lys Asn Ile Val Asn Thr Ser Ile Leu Ser
865                 870                 875                 880

Ile Val Tyr Lys Lys Asp Asp Leu Ile Asp Leu Ser Arg Tyr Gly Ala
                885                 890                 895

Lys Ile Asn Ile Gly Asp Arg Val Tyr Tyr Asp Ser Ile Asp Lys Asn
            900                 905                 910

Gln Ile Lys Leu Ile Asn Leu Glu Ser Ser Thr Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Lys Ile Pro Lys Tyr Phe Ser Lys Ile Asn Leu Asn Asn
945                 950                 955                 960

Glu Tyr Thr Ile Ile Asn Cys Ile Glu Asn Asn Ser Gly Trp Lys Val
                965                 970                 975

Ser Leu Asn Tyr Gly Glu Ile Ile Trp Thr Leu Gln Asp Asn Lys Gln
            980                 985                 990

Asn Ile Gln Arg Val Val Phe Lys Tyr Ser Gln Met Val Asn Ile Ser
            995                 1000                1005

Asp Tyr Ile Asn Arg Trp Ile Phe Val Thr Ile Thr Asn Asn Arg Leu
    1010                1015                1020

Thr Lys Ser Lys Ile Tyr Ile Asn Gly Arg Leu Ile Asp Gln Lys Pro
1025                1030                1035                1040

Ile Ser Asn Leu Gly Asn Ile His Ala Ser Asn Lys Ile Met Phe Lys
                1045                1050                1055

Leu Asp Gly Cys Arg Asp Pro Arg Arg Tyr Ile Met Ile Lys Tyr Phe
            1060                1065                1070

Asn Leu Phe Asp Lys Glu Leu Asn Glu Lys Glu Ile Lys Asp Leu Tyr
            1075                1080                1085

Asp Ser Gln Ser Asn Ser Gly Ile Leu Lys Asp Phe Trp Gly Asn Tyr
    1090                1095                1100

Leu Gln Tyr Asp Lys Pro Tyr Tyr Met Leu Asn Leu Phe Asp Pro Asn
1105                1110                1115                1120

Lys Tyr Val Asp Val Asn Asn Ile Gly Ile Arg Gly Tyr Met Tyr Leu
                1125                1130                1135

Lys Gly Pro Arg Gly Ser Val Val Thr Thr Asn Ile Tyr Leu Asn Ser
            1140                1145                1150

Thr Leu Tyr Glu Gly Thr Lys Phe Ile Ile Lys Lys Tyr Ala Ser Gly
            1155                1160                1165

Asn Glu Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asp Asp Gln Gly Ile Arg
            1220                1225                1230

Asn Lys Cys Lys Met Asn Leu Gln Asp Asn Asn Gly Asn Asp Ile Gly
            1235                1240                1245

Phe Ile Gly Phe His Leu Tyr Asp Asn Ile Ala Lys Leu Val Ala Ser
    1250                1255                1260

Asn Trp Tyr Asn Arg Gln Val Gly Lys Ala Ser Arg Thr Phe Gly Cys
1265                1270                1275                1280

Ser Trp Glu Phe Ile Pro Val Asp Asp Gly Trp Gly Glu Ser Ser Leu
                1285                1290                1295
```

<210> SEQ ID NO 3
<211> LENGTH: 1292
<212> TYPE: PRT
<213> ORGANISM: Clostridium botulinum serotype A

<400> SEQUENCE: 3

```
Met Pro Phe Val Asn Lys Pro Phe Asn Tyr Arg Asp Pro Gly Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125

Val Ile Asp Thr Asn Cys Ile Asn Val Ile Glu Pro Gly Gly Ser Tyr
    130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320

Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380
```

```
Thr Ile Asn Glu Gly Phe Asn Leu Glu Gly Ala Asn Ser Asn Gly Gln
385                 390                 395                 400

Asn Thr Glu Ile Asn Ser Arg Asn Phe Thr Arg Leu Lys Asn Phe Thr
            405                 410                 415

Gly Leu Phe Glu Phe Tyr Lys Leu Leu Cys Val Arg Gly Ile Ile Pro
        420                 425                 430

Phe Lys Thr Lys Ser Leu Asp Glu Gly Tyr Asn Lys Ala Leu Asn Tyr
    435                 440                 445

Leu Cys Ile Lys Val Asn Asn Trp Asp Leu Phe Phe Ser Pro Ser Glu
450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Gln Leu Glu Pro Met Pro
        515                 520                 525

Asn Ile Glu Arg Phe Pro Asn Gly Lys Lys Tyr Glu Leu Asp Lys Tyr
    530                 535                 540

Thr Met Phe His Tyr Leu Arg Ala Gln Glu Phe Glu His Gly Asp Ser
545                 550                 555                 560

Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Lys Ile Asn Lys
            580                 585                 590

Ala Val Glu Ala Val Ile Phe Leu Ser Trp Ala Glu Glu Leu Val Tyr
        595                 600                 605

Asp Phe Thr Asp Glu Thr Asn Glu Val Thr Thr Met Asp Lys Ile Ala
    610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
            660                 665                 670

Gly Thr Phe Ala Ile Val Ser Tyr Ile Ala Asn Lys Val Leu Thr Val
        675                 680                 685

Gln Thr Ile Asn Asn Ala Leu Ser Lys Arg Asn Glu Lys Trp Asp Glu
    690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
            740                 745                 750

Glu Glu Lys Asn Asn Ile Asn Phe Asn Ile Asp Asp Leu Ser Ser Lys
        755                 760                 765

Leu Asn Arg Ser Ile Asn Arg Ala Met Ile Asn Ile Asn Lys Phe Leu
    770                 775                 780

Asp Gln Cys Ser Val Ser Tyr Leu Met Asn Ser Met Ile Pro Tyr Ala
785                 790                 795                 800

Val Lys Arg Leu Lys Asp Phe Asp Ala Ser Val Arg Asp Val Leu Leu
```

-continued

```
                805                 810                 815
Lys Tyr Ile Tyr Asp Asn Arg Gly Thr Leu Ile Leu Gln Val Asp Arg
            820                 825                 830

Leu Lys Asp Glu Val Asn Asn Thr Leu Ser Ala Asp Ile Pro Phe Gln
            835                 840                 845

Leu Ser Lys Tyr Val Asn Asp Lys Lys Leu Leu Ser Thr Phe Thr Glu
            850                 855                 860

Tyr Ile Lys Asn Ile Val Asn Thr Ser Ile Leu Ser Ile Val Tyr Lys
865                 870                 875                 880

Lys Asp Asp Leu Ile Asp Leu Ser Arg Tyr Gly Ala Lys Ile Asn Ile
            885                 890                 895

Gly Asp Arg Val Tyr Tyr Asp Ser Ile Asp Lys Asn Gln Ile Lys Leu
            900                 905                 910

Ile Asn Leu Glu Ser Ser Thr Ile Glu Val Ile Leu Lys Asn Ala Ile
            915                 920                 925

Val Tyr Asn Ser Met Tyr Glu Asn Phe Ser Thr Ser Phe Trp Ile Lys
            930                 935                 940

Ile Pro Lys Tyr Phe Ser Lys Ile Asn Leu Asn Asn Glu Tyr Thr Ile
945                 950                 955                 960

Ile Asn Cys Ile Glu Asn Asn Ser Gly Trp Lys Val Ser Leu Asn Tyr
            965                 970                 975

Gly Glu Ile Ile Trp Thr Leu Gln Asp Asn Lys Gln Asn Ile Gln Arg
            980                 985                 990

Val Val Phe Lys Tyr Ser Gln Met Val Asn Ile Ser Asp Tyr Ile Asn
            995                 1000                1005

Arg Trp Met Phe Val Thr Ile Thr Asn Asn Arg Leu Thr Lys Ser Lys
            1010                1015                1020

Ile Tyr Ile Asn Gly Arg Leu Ile Asp Gln Lys Pro Ile Ser Asn Leu
1025                1030                1035                1040

Gly Asn Ile His Ala Ser Asn Lys Ile Met Phe Lys Leu Asp Gly Cys
            1045                1050                1055

Arg Asp Pro Arg Arg Tyr Ile Met Ile Lys Tyr Phe Asn Leu Phe Asp
            1060                1065                1070

Lys Glu Leu Asn Glu Lys Glu Ile Lys Asp Leu Tyr Asp Ser Gln Ser
            1075                1080                1085

Asn Pro Gly Ile Leu Lys Asp Phe Trp Gly Asn Tyr Leu Gln Tyr Asp
            1090                1095                1100

Lys Pro Tyr Tyr Met Leu Asn Leu Phe Asp Pro Asn Lys Tyr Val Asp
1105                1110                1115                1120

Val Asn Asn Ile Gly Ile Arg Gly Tyr Met Tyr Leu Lys Gly Pro Arg
            1125                1130                1135

Gly Ser Val Met Thr Thr Asn Ile Tyr Leu Asn Ser Thr Leu Tyr Met
            1140                1145                1150

Gly Thr Lys Phe Ile Ile Lys Lys Tyr Ala Ser Gly Asn Glu Asp Asn
            1155                1160                1165

Ile Val Arg Asn Asn Asp Arg Val Tyr Ile Asn Val Val Val Lys Asn
            1170                1175                1180

Lys Glu Tyr Arg Leu Ala Thr Asn Ala Ser Gln Ala Gly Val Glu Lys
1185                1190                1195                1200

Ile Leu Ser Ala Leu Glu Ile Pro Asp Val Gly Asn Leu Ser Gln Val
            1205                1210                1215

Val Val Met Lys Ser Lys Asp Asp Gln Gly Ile Arg Asn Lys Cys Lys
            1220                1225                1230
```

```
Met Asn Leu Gln Asp Asn Asn Gly Asn Asp Ile Gly Phe Val Gly Phe
        1235                1240                1245

His Leu Tyr Asp Asn Ile Ala Lys Leu Val Ala Ser Asn Trp Tyr Asn
        1250                1255                1260

Arg Gln Val Gly Lys Ala Ser Arg Thr Phe Gly Cys Ser Trp Glu Phe
1265                1270                1275                1280

Ile Pro Val Asp Asp Gly Trp Gly Glu Ser Ser Leu
                1285                1290

<210> SEQ ID NO 4
<211> LENGTH: 1296
<212> TYPE: PRT
<213> ORGANISM: Clostridium botulinum serotype A

<400> SEQUENCE: 4

Met Pro Leu Val Asn Gln Gln Ile Asn Tyr Tyr Asp Pro Val Asn Gly
 1                5                  10                  15

Val Asp Ile Ala Tyr Ile Lys Ile Pro Asn Ala Gly Lys Met Gln Pro
             20                  25                  30

Val Lys Ala Phe Lys Ile His Asn Lys Val Trp Val Ile Pro Glu Arg
         35                  40                  45

Asp Ile Phe Thr Asn Pro Glu Glu Val Asp Leu Asn Pro Pro Glu
 50                  55                  60

Ala Lys Gln Val Pro Ile Ser Tyr Tyr Asp Ser Ala Tyr Leu Ser Thr
 65                  70                  75                  80

Asp Asn Glu Lys Asp Asn Tyr Leu Lys Gly Val Ile Lys Leu Phe Glu
                 85                  90                  95

Arg Ile Tyr Ser Thr Asp Leu Gly Arg Met Leu Leu Ile Ser Ile Val
             100                 105                 110

Arg Gly Ile Pro Phe Trp Gly Gly Lys Ile Asp Thr Glu Leu Lys
         115                 120                 125

Val Ile Asp Thr Asn Cys Ile Asn Ile Ile Gln Leu Asp Asp Ser Tyr
         130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                 165                 170                 175

Arg Asn Gly Tyr Gly Ser Thr Gln Tyr Ile Arg Phe Ser Pro Asp Phe
             180                 185                 190

Thr Val Gly Phe Glu Glu Ser Leu Glu Val Asp Thr Asn Pro Leu Leu
         195                 200                 205

Gly Ala Gly Lys Phe Ala Gln Asp Pro Ala Val Ala Leu Ala His Glu
     210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                 245                 250                 255

Glu Val Ser Leu Glu Glu Leu Ile Thr Phe Gly Gly Asn Asp Ala Lys
             260                 265                 270

Phe Ile Asp Ser Leu Gln Lys Lys Glu Phe Ser Leu Tyr Tyr Tyr Asn
         275                 280                 285

Lys Phe Lys Asp Ile Ala Ser Thr Leu Asn Lys Ala Lys Ser Ile Val
     290                 295                 300

Gly Thr Thr Ala Ser Leu Gln Tyr Met Lys Asn Val Phe Lys Glu Lys
305                 310                 315                 320
```

```
Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Asp Val Asn Tyr
    370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Glu Leu Cys Ile Lys Val Asn Asn Trp Asp Leu Phe Phe
    450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
    530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
        595                 600                 605

Asn Leu Val Tyr Asp Phe Thr Asp Glu Thr Asn Glu Val Ser Thr Met
    610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
            660                 665                 670

Leu Pro Val Leu Gly Thr Phe Ala Leu Val Ser Tyr Val Ser Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750
```

```
Gln Tyr Thr Glu Glu Lys Asn Asn Ile Asn Phe Asn Ile Asp Asp
            755                 760                 765
Leu Ser Ser Lys Leu Asn Glu Ser Ile Asn Ser Ala Met Ile Asn Ile
    770                 775                 780
Asn Lys Phe Leu Asp Gln Cys Ser Val Ser Tyr Leu Met Asn Ser Met
785                 790                 795                 800
Ile Pro Tyr Ala Val Lys Arg Leu Lys Asp Phe Asp Ala Ser Val Arg
                805                 810                 815
Asp Val Leu Leu Lys Tyr Ile Tyr Asp Asn Arg Gly Thr Leu Ile Gly
                820                 825                 830
Gln Val Asn Arg Leu Lys Asp Lys Val Asn Asn Thr Leu Ser Ala Asp
            835                 840                 845
Ile Pro Phe Gln Leu Ser Lys Tyr Val Asp Asn Lys Lys Leu Leu Ser
    850                 855                 860
Thr Phe Thr Glu Tyr Ile Lys Asn Ile Thr Asn Ala Ser Ile Leu Ser
865                 870                 875                 880
Ile Val Tyr Lys Asp Asp Leu Ile Asp Leu Ser Arg Tyr Gly Ala
                885                 890                 895
Glu Ile Tyr Asn Gly Asp Lys Val Tyr Tyr Asn Ser Ile Asp Lys Asn
                900                 905                 910
Gln Ile Arg Leu Ile Asn Leu Glu Ser Ser Thr Ile Glu Val Ile Leu
            915                 920                 925
Lys Lys Ala Ile Val Tyr Asn Ser Met Tyr Glu Asn Phe Ser Thr Ser
    930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Phe Gln Asp Thr Gln Glu
            980                 985                 990
Ile Lys Gln Arg Val Val Phe Lys Tyr Ser Gln Met Ile Asn Ile Ser
        995                 1000                1005
Asp Tyr Ile Asn Arg Trp Ile Phe Val Thr Ile Thr Asn Asn Arg Ile
    1010                1015                1020
Thr Lys Ser Lys Ile Tyr Ile Asn Gly Arg Leu Ile Asp Gln Lys Pro
1025                1030                1035                1040
Ile Ser Asn Leu Gly Asn Ile His Ala Ser Asn Lys Ile Met Phe Lys
                1045                1050                1055
Leu Asp Gly Cys Arg Asp Pro His Arg Tyr Ile Val Ile Lys Tyr Phe
                1060                1065                1070
Asn Leu Phe Asp Lys Glu Leu Ser Glu Lys Glu Ile Lys Asp Leu Tyr
            1075                1080                1085
Asp Asn Gln Ser Asn Ser Gly Ile Leu Lys Asp Phe Trp Gly Asp Tyr
    1090                1095                1100
Leu Gln Tyr Asp Lys Ser Tyr Tyr Met Leu Asn Leu Tyr Asp Pro Asn
1105                1110                1115                1120
Lys Tyr Val Asp Val Asn Asn Val Gly Ile Arg Gly Tyr Met Tyr Leu
                1125                1130                1135
Lys Gly Pro Arg Asp Asn Val Met Thr Thr Asn Ile Tyr Leu Asn Ser
                1140                1145                1150
Ser Leu Tyr Met Gly Thr Lys Phe Ile Ile Lys Lys Tyr Ala Ser Gly
            1155                1160                1165
Asn Lys Asp Asn Ile Val Arg Asn Asn Asp Arg Val Tyr Ile Asn Val
```

```
                1170                1175                1180
Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Met Lys Ser Lys Asn Asp Gln Gly Ile Thr
                1220                1225                1230

Asn Lys Cys Lys Met Asn Leu Gln Asp Asn Asn Gly Asn Asp Ile Gly
                1235                1240                1245

Phe Ile Gly Phe His Gln Phe Asn Asn Ile Ala Lys Leu Val Ala Ser
                1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Arg Glu Arg Pro Leu
                1285                1290                1295

<210> SEQ ID NO 5
<211> LENGTH: 57
<212> TYPE: PRT
<213> ORGANISM: Clostridium botulinum serotype E

<400> SEQUENCE: 5

Lys Asn Glu Leu Thr Asn Lys Tyr Asp Ile Lys Gln Ile Glu Asn Glu
1               5                   10                  15

Leu Asn Gln Lys Val Ser Ile Ala Met Asn Asn Ile Asp Arg Phe Leu
            20                  25                  30

Thr Glu Ser Ser Ile Ser Tyr Leu Met Lys Leu Ile Asn Glu Val Lys
        35                  40                  45

Ile Asn Lys Leu Arg Glu Tyr Asp Glu
50                  55
```